US010435700B2

(12) United States Patent
Kudithipudi et al.

(10) Patent No.: US 10,435,700 B2
(45) Date of Patent: Oct. 8, 2019

(54) GENETIC CONTROL OF AXILLARY BUD GROWTH IN TOBACCO PLANTS

(71) Applicant: ALTRIA CLIENT SERVICES LLC, Richmond, VA (US)

(72) Inventors: Chengalrayan Kudithipudi, Midlothian, VA (US); Yanxin Shen, Glen Allen, VA (US); Dongmei Xu, Glen Allen, VA (US); Jesse Frederick, Richmond, VA (US); Jaemo Yang, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 568 days.

(21) Appl. No.: 14/875,928

(22) Filed: Oct. 6, 2015

(65) Prior Publication Data

US 2016/0281100 A1 Sep. 29, 2016

Related U.S. Application Data

(60) Provisional application No. 62/060,473, filed on Oct. 6, 2014.

(51) Int. Cl.

*C12N 15/82* (2006.01)
*C12N 15/31* (2006.01)
*C07K 14/415* (2006.01)

(52) U.S. Cl.

CPC ........ *C12N 15/8218* (2013.01); *C07K 14/415* (2013.01); *C12N 15/8229* (2013.01); *C12N 15/8261* (2013.01); *C12N 15/8295* (2013.01); *Y02A 40/146* (2018.01)

(58) Field of Classification Search

None
See application file for complete search history.

(56) References Cited

U.S. PATENT DOCUMENTS 4,091,823 A 5/1978 Kallianos et al.
4,516,590 A 5/1985 Teng
4,528,993 A 7/1985 Sensabaugh, Jr. et al.
4,638,816 A 1/1987 Cox et al.
4,660,577 A 4/1987 Sensabaugh, Jr. et al.
4,683,195 A 5/1987 Teng
4,683,202 A 7/1987 Mullis
4,732,856 A 3/1988 Fedoroff
4,761,373 A 8/1988 Anderson et al.
4,762,785 A 9/1988 Comai
4,769,061 A 9/1988 Comai
4,778,987 A 10/1988 Saaski et al.
4,800,159 A 1/1989 Mullis et al.
4,810,648 A 3/1989 Stalker
4,848,373 A 7/1989 Lenkey
4,940,835 A 7/1990 Shah et al.
4,945,050 A 7/1990 Sanford et al.
4,965,188 A 10/1990 Mullis et al.
4,975,374 A 12/1990 Goodman et al.
4,987,907 A 1/1991 Townsend
5,004,863 A 4/1991 Umbeck
5,013,658 A 5/1991 Dooner et al.
5,013,659 A 5/1991 Bedbrook et al.
5,085,325 A 2/1992 Jones et al.
5,104,310 A 4/1992 Saltin
5,141,131 A 8/1992 Miller, Jr. et al.
5,149,645 A 9/1992 Hoekema et al.
5,159,135 A 10/1992 Umbeck
5,162,602 A 11/1992 Somers et al.
5,164,180 A 11/1992 Payne et al.
5,177,010 A 1/1993 Goldman et al.
5,231,019 A 7/1993 Paszkowski et al.
5,276,268 A 1/1994 Strauch et al.
5,316,931 A 5/1994 Donson et al.
5,372,149 A 12/1994 Roth et al.
5,463,174 A 10/1995 Maloney et al.
5,464,763 A 11/1995 Schilperoort et al.
5,469,976 A 11/1995 Burchell
5,491,081 A 2/1996 Webb
5,545,565 A 8/1996 De Greve et al.
5,561,236 A 10/1996 Leemans et al.
5,563,055 A 10/1996 Townsend et al.
5,565,350 A 10/1996 Kmiec
5,589,367 A 12/1996 Donson et al.
5,659,026 A 8/1997 Baszczynski et al.
5,689,035 A 11/1997 Webb
5,731,181 A 3/1998 Kmiec (Continued)

FOREIGN PATENT DOCUMENTS

CN 1824774 8/2006
EP 0 242 246 10/1987

(Continued)

OTHER PUBLICATIONS

Tokuriki, et al. (Journal of molecular biology 369.5 (2007): 1318-1332). (Year: 2007).*
Guo et al. (2004, Proc. Natl. Acad. Sci. USA 101:9205-9210). (Year: 2004).*
Lännenpää et al. (Plant Cell Rep (2005) 24:69-78). (Year: 2005).*
Lemmetyinen et al. (Molecular Breeding 7: 341-350, 2001). (Year: 2001).*
Hartley (1988. J. Mol. Biol. 202: 913-915). (Year: 1988).*
GenBank Accession M14442 dated Feb. 1, 1996. (Year: 1996).*
Daub et al. (Phytopathology 79.5 (1989): 600-605). (Year: 1989).*
Crone et al., "The differential expression of a heat shock promoter in floral and reproductive tissues," Plant Cell Environ., 2001, 24:869-874.

(Continued)

*Primary Examiner* — Mykola V. Kovalenko
*Assistant Examiner* — Charles Logsdon
(74) *Attorney, Agent, or Firm* — Arnold & Porter Kaye Scholer LLP

(57) ABSTRACT

This disclosure provides a number of sequences involved in axillary bud growth in tobacco, methods of using such sequences, tobacco plants carrying modifications to such sequences or transgenes of such sequences, and tobacco products made from tobacco leaf harvested from such plants.

9 Claims, 27 Drawing Sheets

Specification includes a Sequence Listing.

(56) References Cited

U.S. PATENT DOCUMENTS

| | | | |
|---|---|---|---|
| 5,756,325 A | 5/1998 | Kmiec | |
| 5,760,012 A | 6/1998 | Kmiec et al. | |
| 5,767,366 A | 6/1998 | Sathasivan et al. | |
| 5,789,156 A | 8/1998 | Bujard et al. | |
| 5,795,972 A | 8/1998 | Kmiec | |
| 5,814,618 A | 9/1998 | Bujard et al. | |
| 5,866,785 A | 2/1999 | Donson et al. | |
| 5,871,984 A | 2/1999 | Kmiec | |
| 5,879,903 A | 3/1999 | Strauch et al. | |
| 5,879,918 A | 3/1999 | Tomes et al. | |
| 5,886,244 A | 3/1999 | Tomes et al. | |
| 5,889,190 A | 3/1999 | Donson et al. | |
| 5,889,191 A | 3/1999 | Turpen | |
| 5,928,937 A | 7/1999 | Kakefuda et al. | |
| 5,932,782 A | 8/1999 | Bidney | |
| 5,981,840 A | 11/1999 | Zhao et al. | |
| 6,072,050 A | 6/2000 | Bowen et al. | |
| 6,084,155 A | 7/2000 | Volrath et al. | |
| 6,166,302 A | 12/2000 | Merlo et al. | |
| 6,451,732 B1 | 9/2002 | Beckett et al. | |
| 6,451,735 B1 | 9/2002 | Ottway et al. | |
| 8,093,459 B2 * | 1/2012 | Thomas | C12N 15/8226 800/298 |
| 8,124,851 B2 | 2/2012 | Dewey et al. | |
| 8,319,011 B2 | 11/2012 | Xu et al. | |
| 9,187,759 B2 | 11/2015 | Dewey et al. | |
| 9,228,194 B2 | 1/2016 | Dewey et al. | |
| 9,228,195 B2 | 1/2016 | Dewey et al. | |
| 9,247,706 B2 | 2/2016 | Dewey et al. | |
| 2001/0016956 A1 | 8/2001 | Ward et al. | |
| 2002/0008055 A1 | 1/2002 | Campbell et al. | |
| 2004/0118422 A1 | 6/2004 | Lundin et al. | |
| 2005/0057263 A1 | 3/2005 | Moshe et al. | |
| 2005/0178398 A1 | 8/2005 | Breslin et al. | |
| 2005/0244521 A1 | 11/2005 | Strickland et al. | |
| 2006/0191548 A1 | 8/2006 | Strickland et al. | |
| 2006/0200878 A1 | 9/2006 | Lutfiyya et al. | |
| 2007/0083948 A1 | 4/2007 | McAvoy et al. | |
| 2012/0024301 A1 | 2/2012 | Carroll et al. | |
| 2012/0031414 A1 | 2/2012 | Atchley et al. | |
| 2012/0031416 A1 | 2/2012 | Atchley et al. | |
| 2016/0281100 A1 | 9/2016 | Kudithipudi et al. | |

FOREIGN PATENT DOCUMENTS

| | | |
|---|---|---|
| EP | 0821866 | 2/1998 |
| EP | 2 383 344 | 11/2011 |
| WO | WO 98/49350 | 11/1998 |
| WO | WO 99/07865 | 2/1999 |
| WO | WO 0058035 | 10/2000 |
| WO | WO 2003/050287 | 6/2003 |
| WO | WO 2004/041006 | 5/2004 |
| WO | WO 2006/035221 | 4/2006 |
| WO | WO 2008/133643 | 11/2008 |
| WO | WO 2011/027315 | 3/2011 |

OTHER PUBLICATIONS

Mayo et al., "Genetic transformation of tobacco NT1 cells with Agrobacterium tumefaciens," Nat Protoc. 2006;1(3):1105-11.

International Search Report and Written Opinion in International Application No. PCT/US2015/054247, dated Apr. 15, 2016, 20 pages.

International Preliminary Report on Patentability in International Application No. PCT/US2015/054247, dated Apr. 11, 2017, 11 pages.

Amaya et al., "Expression of Centroradialis (CEN) and CEN-like Genes in Tobacco Reveals a Conserved Mechanism Controlling Phase Change is Diverse Species," The Plant Cell, 1999, 11(8):1405-1417.

Gonzalez-Grandio et al., "Branched1 Promotes Axillary Bud Dormancy in Response to Shade in *Arabidopsis*," The Plant Cell, 2013, 25(3):834-850.

Liang et al., "Mediation of flowering by a calmodulin-dependent protein kinase," Science in China (Series C), 2001, 44(5):506-512.

Liu et al., "Overexpression of millet ZIP-like gene (Sipf40) affects lateral bud outgrowth in tobacco and millet," Plant Physiology and Biochemistry, 2009, 47(11-12):1051-1060.

Muller et al., "Auxin, cytokinin and the control of shoot branching," Annals of Botany, 2011, 107(7):1203-1212.

Sun et al., "Inhibition of tobacco axillary bud differentiation by silencing Cup-Shaped Cotyledon 3," African Journal of Biotechnology, 2012, 11(16):3919-3927.

Tadege et al., "Stenofolia Regulates Blade Outgrowth and Leaf Vascular Patterning in Medicago truncatula and Nicotiana sylvestris," The Plant Cell, 2011, 23(6):2125-2142, 33 pages [With Supplemental Data].

Invitation to Pay Additional Fees, in International Application PCT/US2015/054247, dated Feb. 10, 2016, 11 pages.

"2015-2016 Burley and Dark Tobacco Production Guide," Bob Pearce, editor (2014).

Boutros et al., "Genome-Wide RNAi Analysis of Growth and Viability in *Drosophila* Cells," *Science*, 303:832-835 (2004).

Dietzl et al., "A genome-wide transgenic RNAi library for conditional gene inactivation in *Drosophila," Nature*, 448:151-156 (2007).

Fisher et al., "2015 Flue Cured Production Guide," North Carolina State University (2014).

Lee et al., "A systematic RNAi screen identifies a critical role for mitochondria in *C. elegans* longevity," *Nature Genetics*, 33:40-48 (2003).

Long et al., "Initiation of Axillary and Floral Meristems in *Arabidopsis," Developmental Biology*, 218:341-353 (2000).

Serrano et al., "The Folding of an Enzyme. II. Substructure of Barnase and the Contribution of Different Interactions to Protein Stability," *Journal of Molecular Biology*, 224:783-804 (1992).

Akaba et al., "Production of Homo- and Hetero-Dimeric Isozymes from Two Aldehyde Oxidase Genes of *Arabidopsis thaliana," The Journal of Biochemistry*, 126:395-401 (1999).

Allen et al., "Evolution of microRNA genes by inverted duplication of target gene sequences in *Arabidopsis thaliana," Nature Genetics*, 36:1282-1290 (2004).

Allen et al., "microRNA-directed phasing during trans-acting siRNA biogenesis in plants," *Cell*, 121:207-221 (2005).

Altschul et al., "Basic local alignment search tool," *Journal of Molecular Biology*, 215:403-410 (1990).

Altschul et al., "Gapped Blast and PSI-Blast: a new generation of protein database search programs," *Nucleic Acids Research*, 25:3389-3402 (1997).

Amaya et al., "Expression of Centroradialis (CEN) and CEN-like genes in tobacco reveals a conserved mechanism controlling phase change in diverse species," *Plant Cell*, 11:1405-1418 (1999).

Avci et al., "Cysteine proteases XCP1 and XCP2 aid micro-autolysis within the intact central vacuole during xylogenesis in *Arabidopsis* roots," *Plant Journal*, 56:303-315 (2008).

Axtell et al., "A two-hit trigger for siRNA biogenesis in plants," *Cell*, 127:565-577 (2006).

Bartel, "MicroRNAs: genomics, biogenesis, mechanism, and function," *Cell*, 116:281-297 (2004).

Beetham et al., "A tool for functional plant genomics: Chimeric RNA/DNA oligonucleotides cause in vivo gene-specific mutations," *Proceedings of the National Academy of Sciences USA*, 96:8774-8778 (1999).

Bender et al., "Pseudomonas syringae phytotoxins: Mode of Action, Regulation, and Biosynthesis by Peptide and Polyketide Synthetases," *Microbiology and Molecular Biology Reviews*, 63:266-292 (1999).

The Bogdanove laboratory, "TAL Effector Nucleotide Targeter 2.0," Retrieved from https://tale-nt.cac.cornell.edu/about, *Cornell University*.

Bowman et al., "Revised North Carolina grade index for flue-cured tobacco," *Tobacco Science*, 32:39-40 (1988).

Canevascini et al., "Tissue-specific expression and promoter analysis of the tobacco LTP1 gene," *Plant Physiology*, 112:513-524 (1996).

Cermak et al., "Efficient design and assembly of custom TALEN and other TAL effector-based constructs for DNA targeting," *Nucleic Acids Research*, 39:e82 (2011).

(56) References Cited

OTHER PUBLICATIONS

Cheng et al., Auxin Synthesized by the YUCCA Flavin Monooxygenases Is Essential for Embryogenesis and Leaf Formation in *Arabidopsis, Plant Cell*, 19:2430-3439 (2007).
Christensen et al., "Sequence analysis and transcriptional regulation by heat shock of polyubiquitin transcripts from maize," *Plant Molecular Biology*, 12:619-632 (1989).
Christensen et al., "Maize polyubiquitin genes: structure, thermal perturbation of expression and transcript splicing, and promoter activity following transfer to protoplasts by electroporation," *Plant Molecular Biology*, 18:675-689 (1992).
Christou et al., "Stable Transformations of Soybean Callus by DNA-Coated Gold Particles," *Plant Physiology*, 87:671-674 (1988).
Crone et al., "The differential expression of a heat shock promoter in floral and reproductive tissues," *Plant, Cell and Environment*, 24:869-874 (2001).
Crossway et al., "Micromanipulation techniques in plant manipulation," *Biotechniques*, 4:320-334 (1986).
De Jong et al., "Chemical-induced apoptotic cell death in tomato cells: involvement of caspase-like proteases," *Planta*, 211:656-662, (2000).
Devarenne et al., "Adi3 is a Pdk1-interacting AGC kinase that negatively regulates plant cell death," *EMBO Journal*, 25:255-265 (2006).
De Wet et al., "Exogenous gene transfer in maize (*Zea mays*) using DNA-treated pollen," *The Experimental Manipulation of Ovule Tissues*, 197-209 (1985).
D'Halluin et al., "Transgenic Maize Plants by Tissue Electroporation," *The Plant Cell*, 4:1495-1505 (1992).
Doyle et al., "TAL effector-nucleotide targeter (TALE-NT) 2.0: tools for TAL effector design and target prediction effector," *Nucleic Acids Research*, 40:W117-122 (2012).
Dugas et al., "MicroRNA regulation of gene expression in plants," *Current Opinion in Plant Biology*, 7:512-520 (2004).
Escamez et al., "Programmes of cell death and autolysis in tracheary elements: when a suicidal cell arranges its own corpse removal," *Journal of Experimental Botany*, 65:1313-1321 (2014).
Estruch et al., "Transgenic plants: An emerging approach to pest control," *Nature Biotechnology*, 15:137 (1997).
Fedoroff et al., "Cloning of the bronze locus in maize by a simple and generalizable procedure using the transposable controlling element Activator (Ac)," *Proceeding of the National Academy of Sciences USA*, 81:3825-3829 (1984).
Finer et al., "Transformation of soybean via particle bombardment of embryogenic suspension culture tissue," *Vitro Cellular Developmental Biology*, 27P:175-182 (1991).
Fisher et al., "Topping, Managing Suckers, and Using Ethepon," *Flue-Cured Tobacco Information, North Carolina State University*, 96-117 (2016).
Franco-Zorilla et al., "Target mimicry provides a new mechanism for regulation of microRNA activity," *Nature Genetics*, 39:1033-1037 (2007).
Gälweiler et al., "Regulation of polar auxin transport by AtPIN1 in *Arabidopsis* vascular tissue," *Science*, 282:2226-2230 (1998).
Gatz et al., "Regulation of a modified CaMV 35S promoter by the Tn10-encoded Tet repressor in transgenic tobacco," *Molecular and General Genetics*, 227:229-237 (1991).
Goldman et al., "Female Sterile Tobacco Plants Are Produced by Stigma," *EMBO Journal*, 13:2976-2984 (1994).
Gonzalez-Grandio et al., "BRANCHED1 Promotes Axillary Bud Dormancy in Response to Shade in *Arabidopsis," Plant Cell*, 25:834-850 (2013).
Greb et al., "Molecular analysis of the Lateral Suppressor gene in *Arabidopsis* reveals a conserved control mechanism for axillary meristem formation," *Genes & Development*, 17:1175-1187 (2003).
Griffiths-Jones et al., "Rfam: an RNA family database," *Nucleic Acids Research*, 31:439-441 (2003).
Guevara-Garcia et al., "Tissue-specific and wound-inducible pattern of expression of the mannopine synthase promoter is determined by the interaction between positive and negative cis-regulatory elements," *Plant Journal*, 4:495-505 (1993).
Hansen et al., "Wound-inducible and organ-specific expression of ORF13 from Agrobacterium rhiZogenes 8196 T-DNA in transgenic tobacco plants," *Molecular and General Genetics*, 254:337-343 (1997).
Hartley, "Barnase and barstar: two small proteins to fold and fit together," *Trends in Biochemical Sciences*, 14:450-454 (1989).
Hildering et al., "The use of induced mutations in plant breeding," supplement to Radiation Botany, 5:317-320 (1965).
Hoekema et al., "A binary plant vector strategy based on separation of vir- and T-region of the *Agrobacterium tumefaciens* Ti-plasmid," *Nature*, 303:179-180 (1983).
Horsch et al., "A simple and general method for transferring genes into plants," *Science*, 227:1229-1231 (1985).
Jones-Rhoades et al., "Computational identification of plant microRNAs and their targets, including a stress-induced miRNA," *Molecular Cell*, 14:787-799 (2004).
Kaeppler et al., "Silicon carbide fiber-mediated DNA delivery into plant cells," *Plant Cell Reports*, 9:415-418 (1990).
Kaeppler et al., "Silicon carbide fiber-mediated stable transformation of plant cells," *Theoretical and Applied Genetics*, 84:560-566 (1992).
Katoh et al., "Specific residues at every third position of siRNA shape its efficient RNAi activity," *Nucleic Acids Research*, 35:e27 (2007).
Kawamata et al., "Temporal and spatial pattern of expression of the pea phenylalanine ammonia-lyase gene1 promoter in transgenic tobacco," *Plant and Cell Physiology*, 38:792-803 (1997).
Keller et al., "*Arabidopsis* Regulator of Axillary MERISTEMS1 Controls a Leaf Axil Stem Cell Niche and Modulates Vegetative Development," *Plant Cell*, 18:598-611 (2006).
Khvorova et al., "Functional siRNAs and miRNAs exhibit strand bias," *Cell*, 115:209-216 (2003).
Kim, "MicroRNA biogenesis: coordinated cropping and dicing," *Nature Reviews Molecular Cell Biology*, 6:376-385 (2005).
Lam, "Analysis of Tissue-Specific Elements in the CaMV 35S Promoter," *Results and Problems in Cell Differentiation*, 20:181-196 (1994).
Last et al., "pEMU: an improved promoter for gene expression in cereal cells," *Theoretical and Applied Genetics*, 81:581-588 (1991).
Long et al., "A member of the Knotted class of homeodomain proteins encoded by the STM gene of *Arabidopsis," Nature*, 379:66-69 (1996).
Matsuoka et al., "Tissue-specific light-regulated expression directed by the promoter of a C4 gene, maize pyruvate, orthophosphate dikinase, in a C3 plant, rice," *Proceedings of the National Academy of Sciences USA*, 90:9586-9590 (1993).
Mayo et al., "Genetic transformation of tobacco NT1 cells with *Agrobacterium tumefaciens," Nature Protocols*, 1:1105-11 (2006).
McCabe et al., "Stable transformation of soybean (*Glycine max*) by particle acceleration," *Biotechnology*, 6:923-926 (1988).
McCallum et al., "Targeted screening for induced mutations," *Nature Biotechnology*, 18:455-457 (2000).
McNellis et al., "Glucocorticoid-inducible expression of a bacterial avirulence gene in transgenic *Arabidopsis* induces hypersensitive cell death," *Plant Journal*, 14:247-257 (1998).
Miller, "Memorandum on the Proposed Burley Tobacco Grade Index," *Legacy Tobacco Document Library*, Bates Nos. 523267826-523267833 (1988).
Miller et al., "A grade index for type 22 and 23 fire-cured tobacco," *Tobacco International*, 192:55-57 (1990).
Murchison et al., "miRNAs on the move: miRNA biogenesis and the RNAi machinery," *Current Opinion in Cell Biology*, 16:223-229 (2004).
Neu et al., "*Arabidopsis amidase* 1, a member of the amidase signature family," *FEBS Journal*, 274:3440-3451 (2007).
Odell et al., "Identification of DNA sequences required for activity of the cauliflower mosaic virus 35S promoter," *Nature*, 313:810-812 (1985).
Orozco et al., "Localization of Light-Inducible and Tissue-Specific Regions of the Spinach Ribulose Bisphosphate Carboxylase/

(56) References Cited

OTHER PUBLICATIONS

Oxygenase (Rubisco) Activase Promoter in Transgenic Tobacco Plants," *Plant Molecular Biology*, 23:1129-1138 (1993).
Ortiz-Morea et al., "Global analysis of the sugarcane microtranscriptome reveals a unique composition of small RNAs associated with axillary bud outgrowth," *Journal of Experimental Botany*, 64:2307-2320 (2013).
Parizotto et al., "In vivo investigation of the transcription, processing, endonucleolytic activity, and functional relevance of the spatial distribution of a plant miRNA," *Genes & Development*, 18:2237-2242 (2004).
Paszkiwski et al., "Direct Gene Transfer to Plants," *EMBO Journal*, 3:2717-2722 (1984).
Porta et al., "Use of viral replicons for the expression of genes in plants," *Molecular Biotechnology*, 5:209-221 (1996).
Rajani et al., "The *Arabidopsis* myc/bHLH gene Alcatraz enables cell separation in fruit dehiscence," *Current Biology*, 11:1941-1922 (2001).
Reynolds et al., "Rational siRNA design for RNA interference," *Nature Biotechnology*, 22:326-330 (2004).
Rhoades et al., "Prediction of plant microRNA targets," *Cell*, 110:513-520 (2002).
Riggs et al., "Stable transformation of tobacco by electroporation: Evidence for plasmid concatenation," *Proceedings of the National Academy of Sciences USA*, 83:5602-5606 (1986).
Rinehart et al., "Tissue-specific and developmental regulation of cotton gene FbL2A," *Plant Physiology*, 112:1331-1341 (1996).
Russell et al., "Tissue-Specific Expression in Transgenic Maize of Four Endosperm Promoters From Maize and Rice," *Transgenic Research*, 6:157-168 (1997).
Schena et al., "A steroid-inducible gene expression system for plant cells," *Proceedings of the National Academy of Sciences USA*, 88:10421-10425 (1991).
Shillito et al., "Direct gene transfer to protoplasts of dicotyledonous and monocotyledonous plants by a number of methods, including electroporation," *Methods in Enzymology*, 153:313-336 (1987).
Singh et al., "Cytological characterization of transgenic soybean," *Theoretical and Applied Genetics*, 96:319-324 (1998).
Stepanova et al., "TAA1-Mediated Auxin Biosynthesis Is Essential for Hormone Crosstalk and Plant Development," *Cell*, 133:177-191 (2008).
Stirnberg et al., "MAX1 and MAX2 control shoot lateral branching in *Arabidopsis," Development*, 129:1131-1141 (2002).
Sunkar et al., "Novel and stress-regulated microRNAs and other small RNAs from *Arabidopsis," Plant Cell*, 16:2001-2019 (2004).
Suzuki Laboratory, "siExlporer," Retrieved from http://rna.chem.t.u-tokyo.ac.jp/cgi/siexplorer.htm, *Lab of RNA Biochemistry, The University of Tokyo* .
Tanaka, "Studies on Biological Effects of Ion Beams on Lethality, Molecular Nature of Mutation, Mutation Rate, and Spectrum of Mutation Phenotype for Mutation Breeding in Higher Plants," *Journal of Radiation Research*, 51:223-233 (2010).
Tanaka-Ueguchi et al., "Over-expression of a tobacco homeobox gene NTH15, decreases the expression of a gibberellin biosynthetic gene encoding GA 20-oxidase," *Plant Journal*, 15:391-400 (1998).
Tomes et al., "Direct DNA Transfer into Intact Plant Cells via Microprojectile Bombardment," *Plant Cell, Tissue, and Organ Culture: Fundamental Methods* (1995).
Trobacher et al., "Induction of a ricinosomal-protease and programmed cell death in tomato endosperm by gibberellic acid," *Planta*, 237:664-679 (2013).
Van Camp et al., "Tissue-Specific Activity of Two Manganese Superoxide Dismutase Promoters in Transgenic Tobacco," *Plant Physiology*, 112:525-535 (1996).
Velten et al., "Isolation of a dual plant promotor fragment from the Ti Plasmid of Agrobacterium tumefaciens," *EMBO Journal*, 3:2723-2730 (1984).
Verkerk, "Chimerism of the tomato plant after seed irradiation with fast neutrons," *Netherlands Journal of Agricultural Science*, 19:197-203 (1971).
Wang et al., "MicroRNA171c-targeted SCL6-II, SCL6-III, and SCL6-IV genes regulate shoot branching in *Arabidopsis," Molecular Plant*, 3:794-806 (2010).
Watanabe et al., "*Arabidopsis* metacaspase 2d is a positive mediator of cell death induced during biotic and abiotic stresses," *Plant Journal*, 66:969-982 (2011).
Weising et al., "Foreign Genes in Plants: Transfer, Structure, Expression, and Applications," *Annual Review of Genetics*, 22:421-477 (1988).
Wernsman et al., "Tobacco" Chapter 17, *Principles of Cultivar Development*, 669-698 (1987).
Yadav et al., "Wuschel protein movement mediates stem cell homeostasis in the *Arabidopsis* shoot apex," *Genes & Development*, 25:2025-2030 (2011).
Yamada et al., "The Transport Inhibitor Response2 Gene Is Required for Auxin Synthesis and Diverse Aspects of Plant Development," *Plant Phsiology*, 151:168-179 (2009).
Yamamoto et al., "The Promoter of a Pine Photosynthetic Gene Allows Expression of a jS-Glucuronidase Reporter Gene in Transgenic Rice Plants in a Light-Independent but Tissue-Specific manner," *Plant & Cell Physiology*, 35:773-778 (1994).
Yamamoto et al., "Light-Responsive Elements of the Tobacco PSI-D Gene Are Located Both Upstream and Within the Transcribed Region," *Plant Journal*, 12:255-265 (1997).
Zeng et al., "Both natural and designed micro RNAs can inhibit the expression of cognate mRNAs when expressed in human cells," *Molecular Cell*, 9:1327-1333 (2002).
Zhang et al., "Transcription activator-like effector nucleases enable efficient plant genome engineering," *Plant Physiology*, 161:20-27 (2013).

* cited by examiner

WT

Over expression of SEQ ID:81-line 6

Control plant

RNAi_26 Line 7

7 days after topping

GENETIC CONTROL OF AXILLARY BUD GROWTH IN TOBACCO PLANTS

CROSS REFERENCE TO RELATED APPLICATIONS

This application claims the benefit of priority under 35 U.S.C. § 119(e) to U.S. Application No. 62/060,473 filed Oct. 6, 2014. The prior application is incorporated herein by reference in its entirety.

TECHNICAL FIELD

This disclosure generally relates to tobacco plants.

BACKGROUND

Tobacco is a plant species that exhibits exceptionally strong apical dominance. Molecular signals from shoot apical meristem mediate a hormonal environment that effectively inhibits axillary bud growth. Upon removal of the apical meristem (also known as "topping"), the signal is lost, enabling the formation of new shoots (or "suckers") from axillary buds. Sucker growth results in loss of yield and leaf quality. Suckers have been controlled by manual removal and through the application of chemicals. Maleic hydrazide (MH) and flumetralin are routinely used on topped plants to inhibit axillary bud growth (suckering). However, labor and chemical agents to control suckers are very expensive. Control of axillary bud growth in tobacco through conventional breeding, mutation breeding, and transgenic approaches have been a major objective for several decades but, to date, successful inhibition has not been achieved through genetic approaches. Therefore, development of tobacco traits with limited or no axillary bud growth would result in a reduction of the use of chemical agents and would reduce costs and labor associated with tobacco production.

SUMMARY

A number of nucleotide and polypeptide sequences involved in the formation of axillary bud growth are described herein. Methods of using such sequences also are described. The methods described herein allow for tobacco plants to be produced that exhibit reduced axillary bud growth after topping.

In one aspect, a tobacco hybrid, variety, line, or cultivar is provided that includes plants having a mutation in one or more of the nucleic acids shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, the plants exhibit, and can be selected for, reduced axillary bud growth relative to a plant lacking the mutation.

In one aspect, seed produced by any of the tobacco hybrids, varieties, lines, or cultivars is provided, the seed includes the mutation in the one or more nucleic acids.

In another aspect, a method of making a tobacco plant is provided. Such a method generally includes the steps of inducing mutagenesis in *Nicotiana tabacum* cells to produce mutagenized cells; obtaining one or more plants from the mutagenized cells; and identifying at least one of the plants that comprises a mutation in one or more of the nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. Such a method can further include identifying at least one of the plants that exhibits reduced axillary bud growth relative to a plant lacking the mutation.

In some embodiments, mutagenesis is induced using a chemical mutagen or ionizing radiation. Representative chemical mutagens include, without limitation, nitrous acid, sodium azide, acridine orange, ethidium bromide, and ethyl methane sulfonate (EMS). Representative ionizing radiation includes, without limitation, x-rays, gamma rays, fast neutron irradiation, and UV irradiation. In some embodiments, mutagenesis is induced using TALEN. In some embodiments, mutagenesis is induced using zinc-finger technology.

In another aspect, a method for producing a tobacco plant is provided. Such a method generally includes the steps of: crossing at least one plant of a first tobacco line with at least one plant of a second tobacco line, and selecting for progeny tobacco plants that have the mutation. Typically, the plant of the first tobacco line has a mutation in one or more nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, such a method can further include selecting for progeny tobacco plants that exhibit reduced axillary bud growth relative to a plant lacking the mutation.

In still another aspect, a tobacco product is provided that includes cured leaf from a tobacco plant having a mutation in one or more nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, the tobacco plant exhibits reduced axillary bud growth relative to leaf from a plant lacking the mutation. In some embodiments, the tobacco plant exhibits reduced MH residue relative to leaf from a plant lacking the mutation.

In yet another aspect, a method of producing a tobacco product is provided. Such a method typically includes providing cured leaf from a tobacco plant having a mutation in one or more nucleic acids having a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77; and manufacturing a tobacco product using the cured leaves. In some embodiments, the tobacco plant exhibits reduced axillary bud growth relative to cured leaf from a plant lacking the mutation.

As used herein, a mutation can be a point mutation, an insertion, a deletion, and a substitution.

In one aspect, a transgenic tobacco plant is provided that includes a plant expression vector having a nucleic acid molecule at least 25 nucleotides in length and at least 91% sequence identity to a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, the nucleic acid molecule has at least 91% sequence identity to a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, expression of the nucleic acid molecule results in a plant exhibiting reduced axillary bud growth relative to a tobacco plant not expressing the nucleic acid molecule.

In another aspect, seed produced by any of the transgenic tobacco plants described herein is provided, wherein the seed comprises the expression vector.

In another aspect, a transgenic tobacco plant is provided that includes a heterologous nucleic acid molecule of at least 25 nucleotides in length that hybridizes under stringent conditions to a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, the heterologous nucleic acid molecule hybridizes under stringent conditions to a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, expression of the heterologous nucleic acid molecule results in a plant exhibiting reduced axillary bud growth relative to a tobacco plant not expressing the nucleic acid molecule.

In some aspects, seed produced by any of the transgenic tobacco plants described herein is provided, where the seed comprises the heterologous nucleic acid molecule.

In still another aspect, a method of making a transgenic plant is provided. Such a method typically includes expressing a transgene encoding a double-stranded RNA molecule that inhibits expression from a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77, wherein the double-stranded RNA molecule comprises at least 25 consecutive nucleotides having 91% or greater sequence identity to a sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77. In some embodiments, wherein expression of the transgene results in the plant exhibiting reduced axillary bud growth relative to a plant not expressing the transgene.

In another aspect, a tobacco product is provided that includes cured leaf from any of the transgenic tobacco plants described herein.

In still another aspect, a method of producing a tobacco product is provided, the method including providing cured leaf from any of the transgenic tobacco plants described herein; and manufacturing a tobacco product using the cured leaf.

In yet another aspect, a method of reducing axillary bud growth in a tobacco plant is provided. Such a method generally includes introducing a heterologous nucleic acid molecule operably linked to a promoter into tobacco cells to produce transgenic tobacco cells, and regenerating transgenic tobacco plants from the transgenic tobacco cells. Typically, the heterologous nucleic acid molecule includes at least 25 nucleotides in length and has at least 91% sequence identity to a nucleic acid sequence shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. Such transgenic tobacco plants exhibit reduced axillary bud growth. In some embodiments, the heterologous nucleic acid molecule has at least 91% sequence identity to a nucleic acid sequence as shown in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, expression of the nucleic acid molecule results in a plant exhibiting reduced axillary bud growth relative to a tobacco plant not expressing the nucleic acid molecule. Such a method further can include selecting at least one of the transgenic tobacco plants that exhibits reduced axillary bud growth relative to a tobacco plant not expressing the heterologous nucleic acid molecule.

In one embodiment, the nucleic acid is in sense orientation. In some embodiments, the nucleic acid is in antisense orientation. In some embodiments, the nucleic acid molecule is introduced into the tobacco cells using particle bombardment, *Agrobacterium*-mediated transformation, microinjection, polyethylene glycol-mediated transformation, liposome-mediated DNA uptake, or electroporation. In some embodiments, the tobacco plant is a Burley type, a dark type, a flue-cured type, a Maryland type, or an Oriental type. In some embodiments, the tobacco plant is a variety selected from the group consisting of BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14xL8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVHSO, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN9OLC, TN 97, TN97LC, TN D94, TN D950, TR (Tom Rosson) Madole, VA 309, or VA359.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

ML: mature leaf; MID midrib; SK0: stalk before topping; SK24: stalk 24 hr post-topping; SAM: shoot apical meristem and SCL: senescent leaf.

Figure 1A:
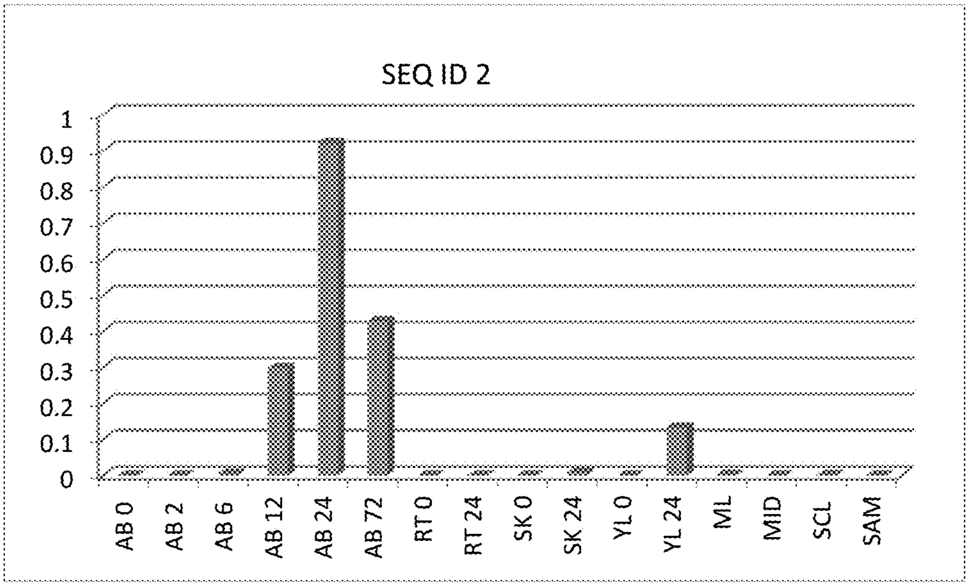
FIG. 1A is a graph showing gene expression verification of SEQ ID NO:2 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.
Figure 1B:
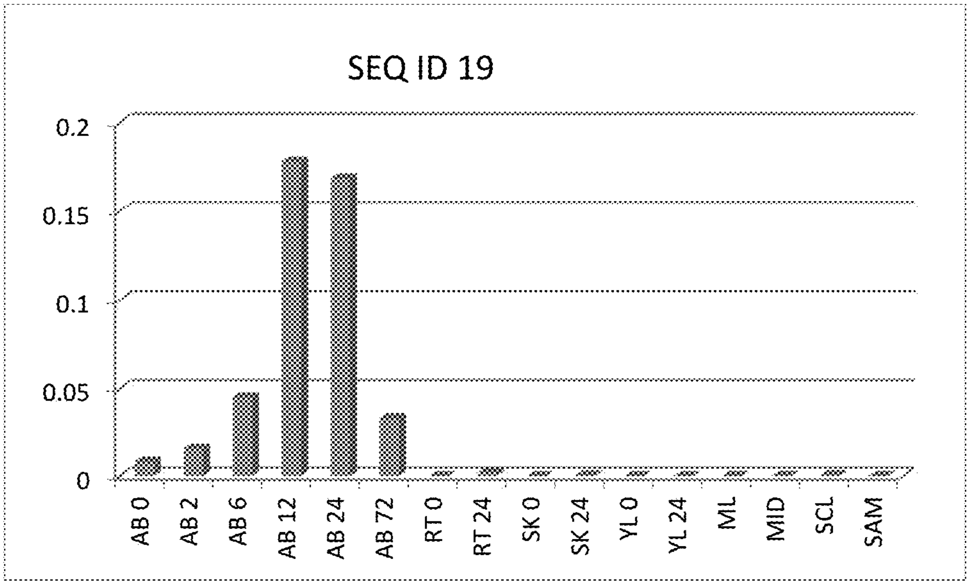
FIG. 1B is a graph showing gene expression verification of SEQ ID NO:19 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping.
Figure 1C:
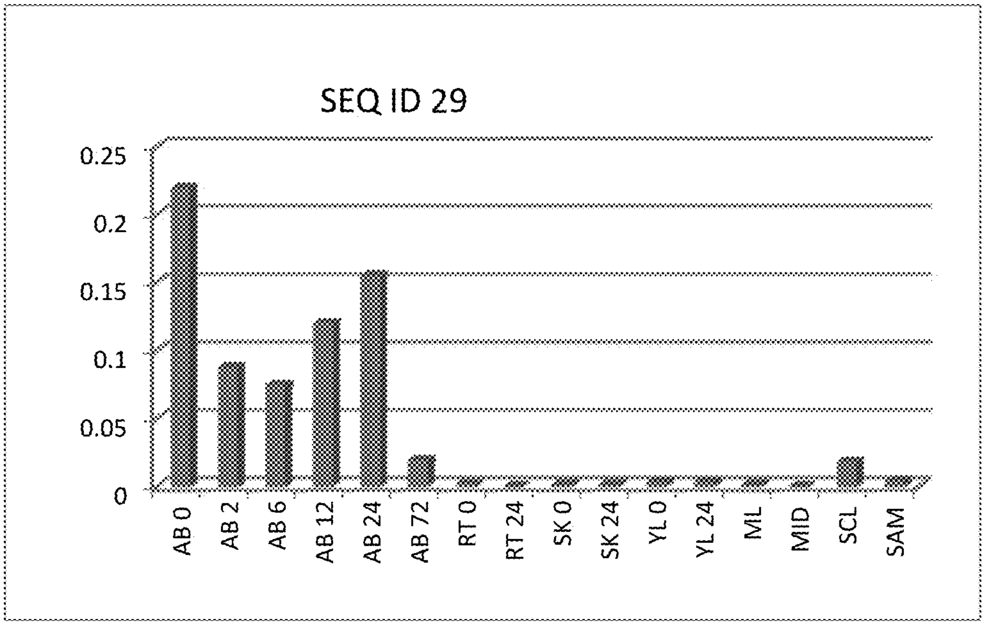

FIG. 1C is a graph showing gene expression verification of SEQ ID NO:29 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.

Figure 1D:
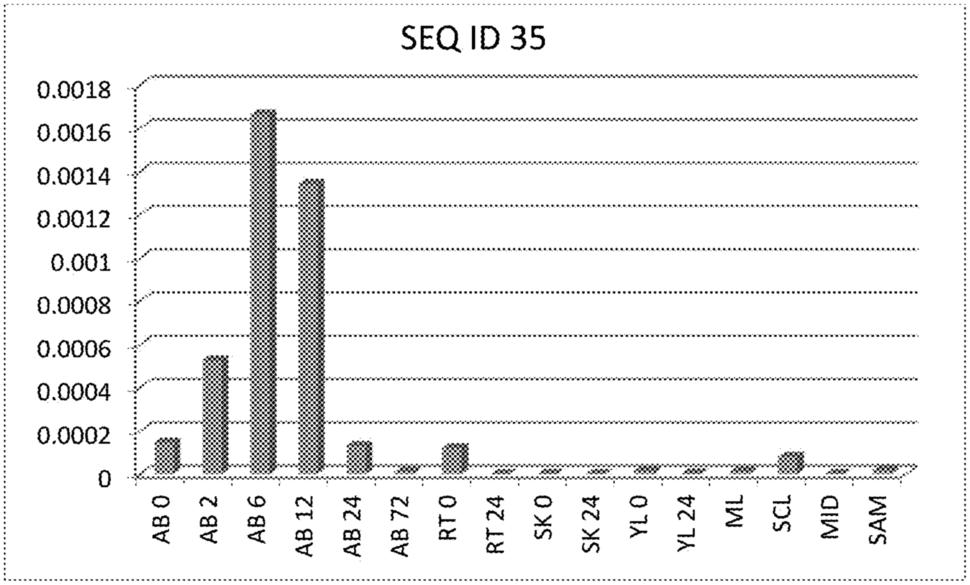

FIG. 1D is a graph showing gene expression verification of SEQ ID NO:35 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.

Figure 1E:
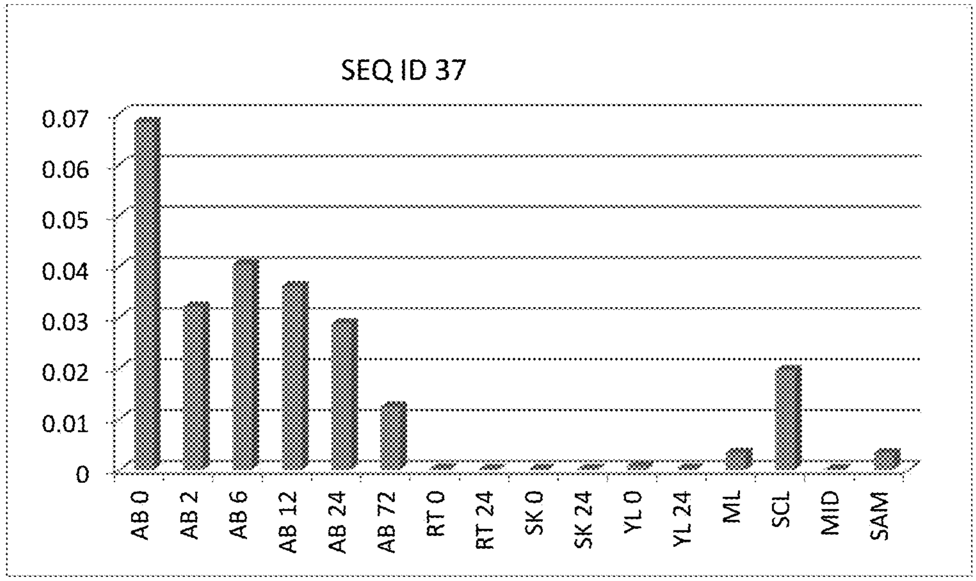

FIG. 1E is a graph showing gene expression verification of SEQ ID NO:37 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.

Figure 1F:
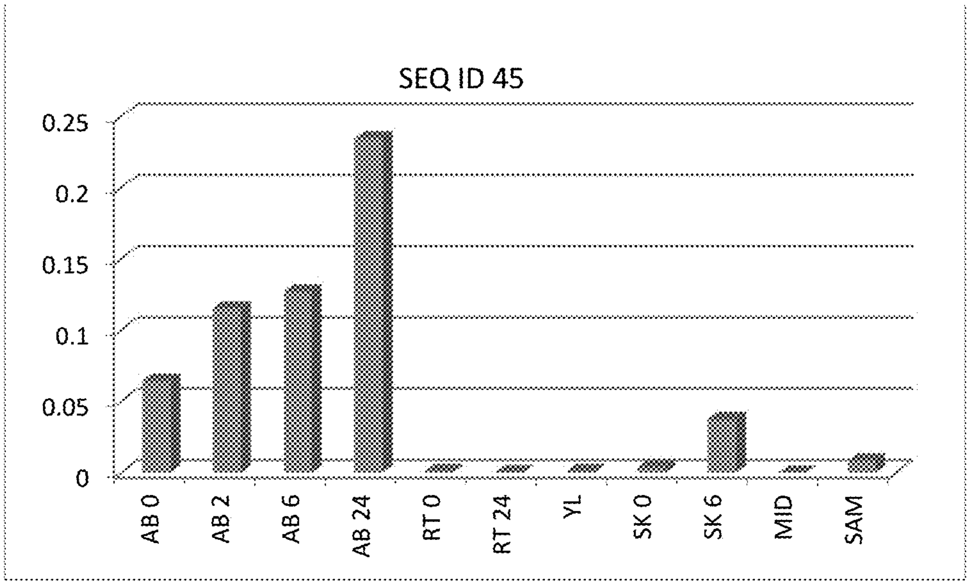

FIG. 1F is a graph showing gene expression verification of SEQ ID NO:45 using real time PCR analysis. AB0: axillary bud before topping; AB2: axillary bud 2 hr post-topping; AB6: axillary bud 6 hr post-topping; AB12: axillary bud 12 hr post-topping; AB48: axillary bud 48 hr post-topping; AB72: axillary bud 72 hr post-topping; RT0: roots before topping; RT24: roots 24 hr post-topping; YL0: young leaf before topping; YL24: young leaf 24 hr post-topping; ML: mature leaf; MID midrib; SK0: stalk before topping; SK24: stalk 24 hr post-topping; SAM: shoot apical meristem and SCL: senescent leaf.

Figure 2:
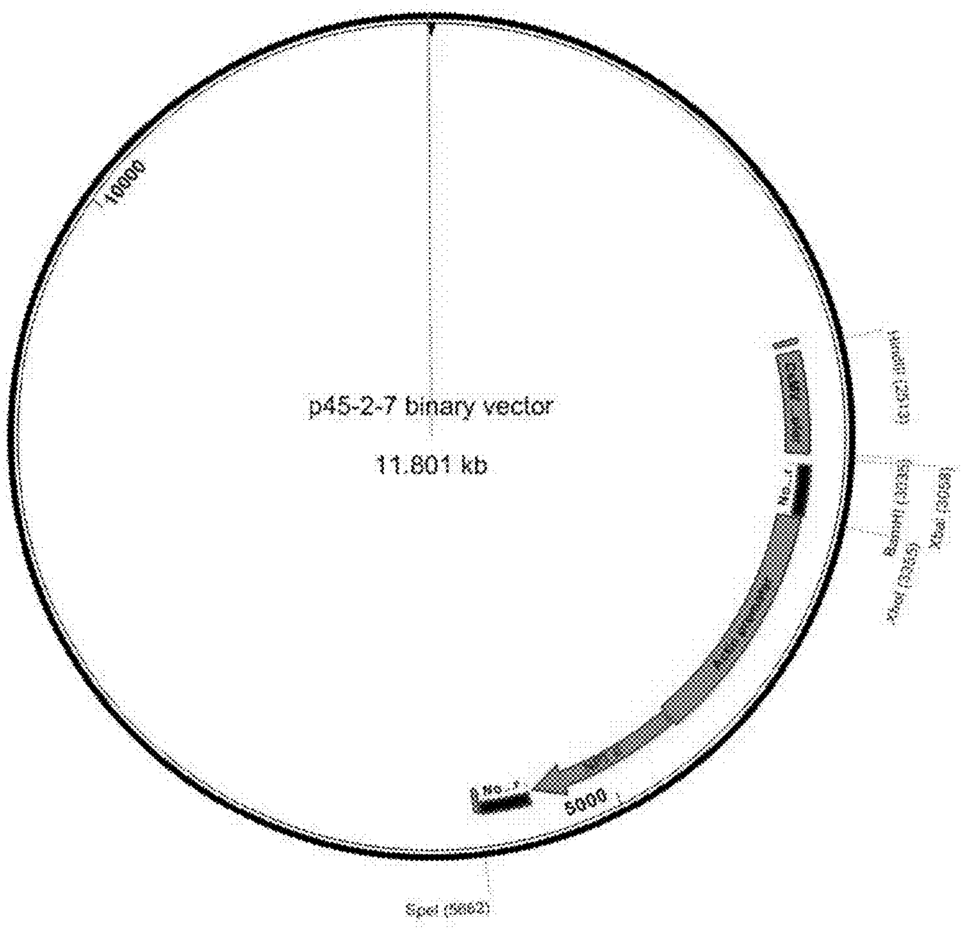

FIG. 2 is a schematic of the map of the Agrobacterium transformation vector, p45-2-7.

Figure 3A:
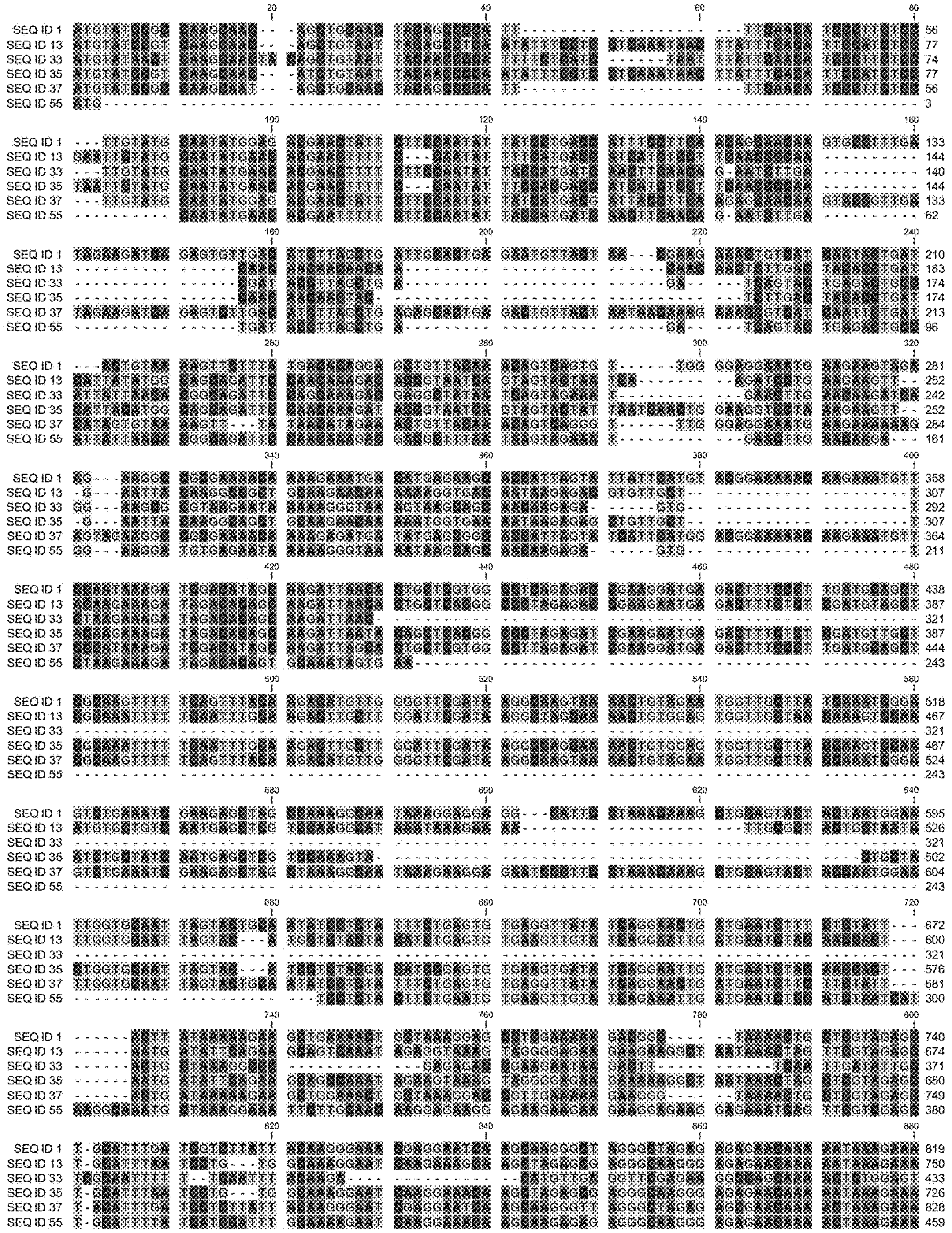

FIG. 3A shows various nucleic acid alignments (SEQ ID NOs: 1, 13, 33, 35, 37, and 55, top to bottom).

Figure 3A:
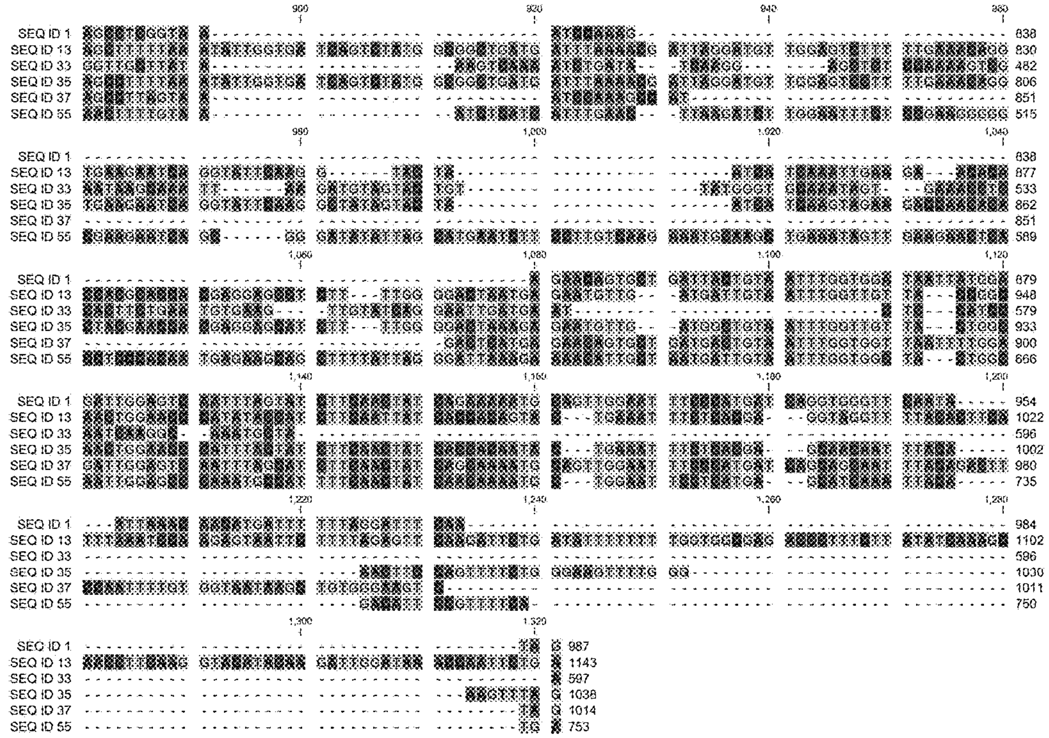
Figure 3B:
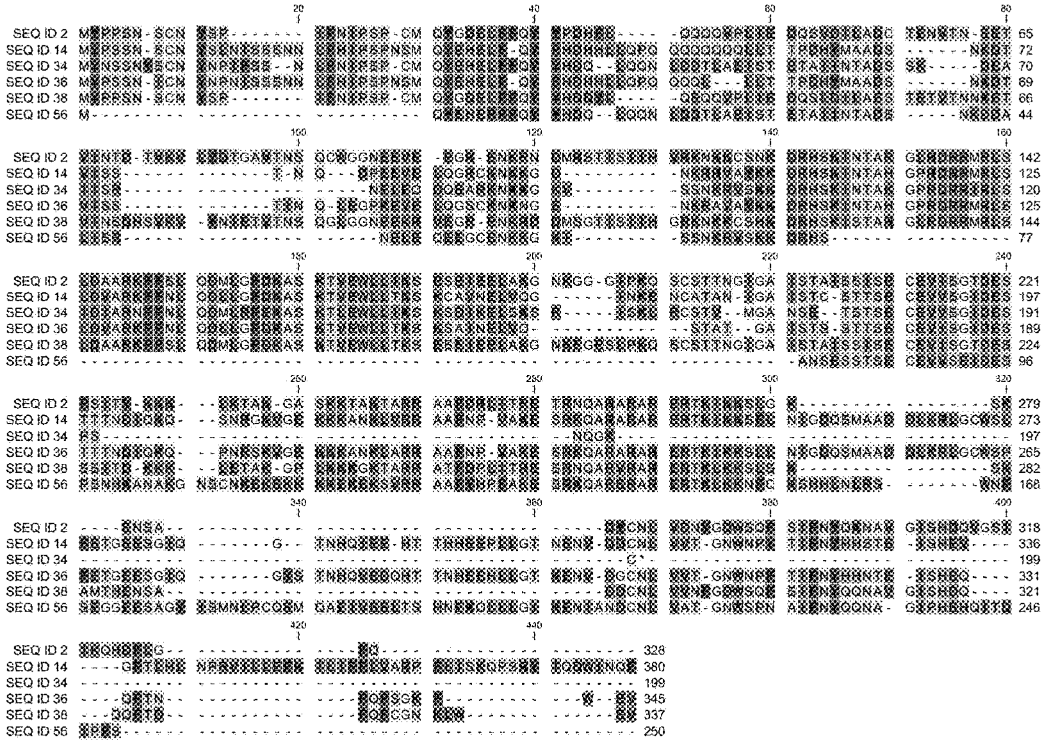

FIG. 3B shows various protein alignments (SEQ ID NOs: 2, 14, 34, 36, 38, and 56, top to bottom).

Figure 4A:
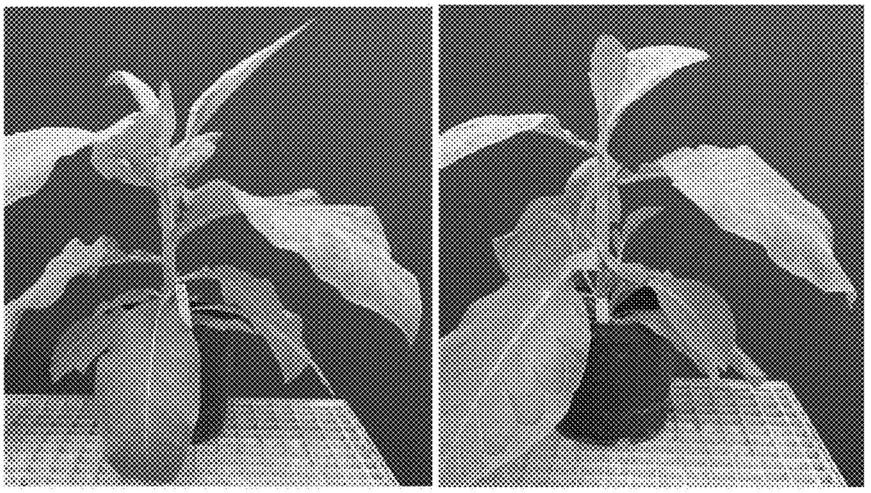

FIG. 4A are photographs of a wild type tobacco plant (left) and a tobacco plant transformed with RNA construct #1 (SEQ ID NO:29; right) before topping.

Figure 4B:
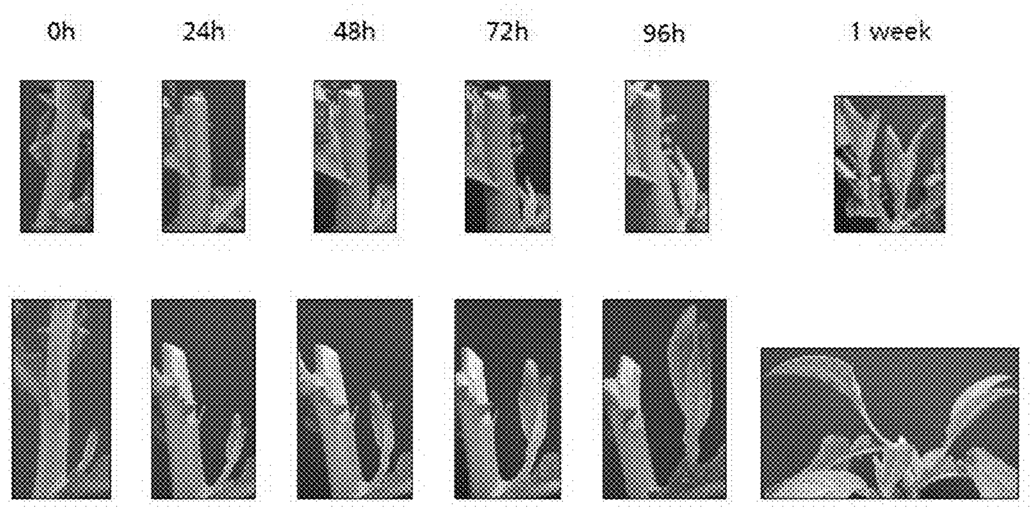

FIG. 4B are photographs of the wild type plant (top) and the plant transformed with RNA construct #1 (bottom) at the indicated time after topping.

Figure 4C:
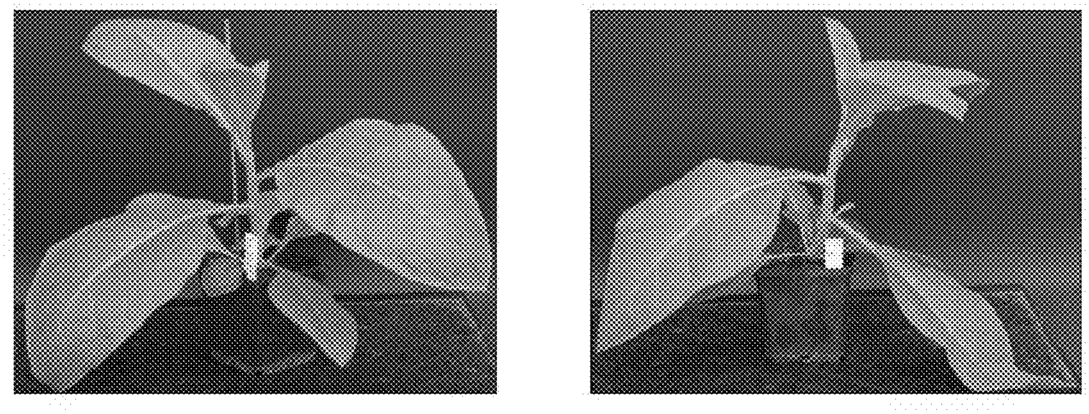

FIG. 4C are photographs showing the T1 generation produced from the wild-type plant (left) and the plant transformed with RNA construct #1 (right).

Figure 5A:
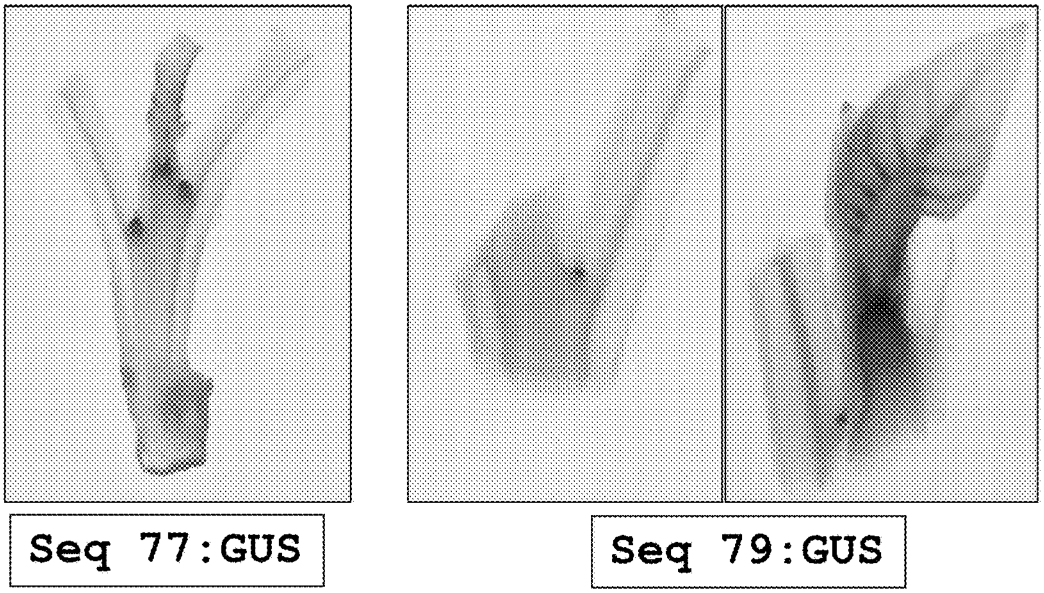

FIG. 5A shows GUS staining of expression from an axillary meristem-specific promoter P1 (the promoter from the sequence shown in SEQ ID NO:31) and promoter P7 (SEQ ID NO:32).

Figure 5B:
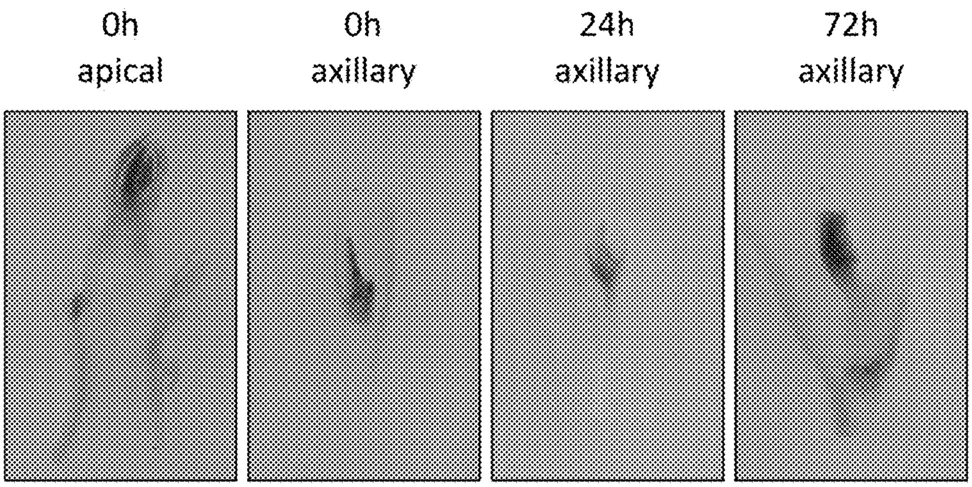

FIG. 5B shows GUS staining of expression from promoter P1 (P1:GUS expression vector) before topping (0 hour) and after topping (24 hr, 48 hr and 144 hr).

Figure 6A:
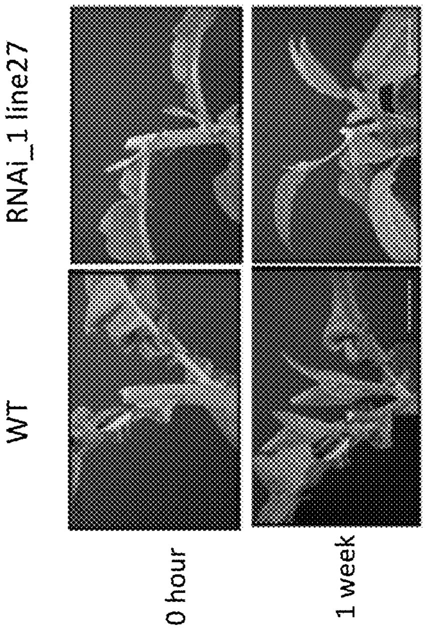

FIG. 6A are photographs that show the phenotype of the T0 generation for a transgenic line (RNAi_1 (SEQ ID NO:83 against the BRANCH tobacco homolog); right) in comparison to a wild type plant (left) at 0 h (top) and 1 week after topping (bottom).

Figure 6B:
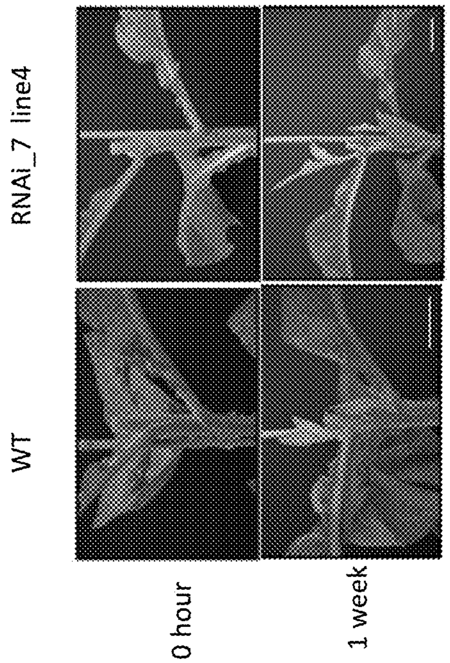

FIG. 6B are photographs that show the phenotype of the T0 generation for a transgenic line (RNAi_7 (SEQ ID NO:86 against the BRANCH tobacco homolog); right) in comparison to a wild type plant (left) at 0 h (top) and 1 week after topping (bottom).

Figure 6C:
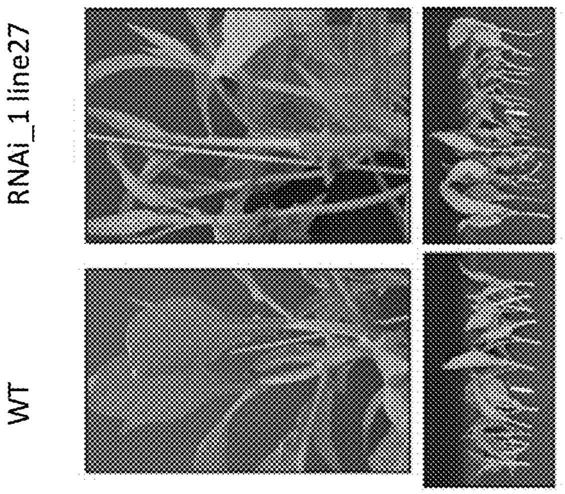

FIG. 6C are photographs that show the phenotype of T1 transgenic plants (RNAi_1; top right, bottom right) in comparison to wild type plants (top left and bottom left) two weeks after topping.

Figure 6D:
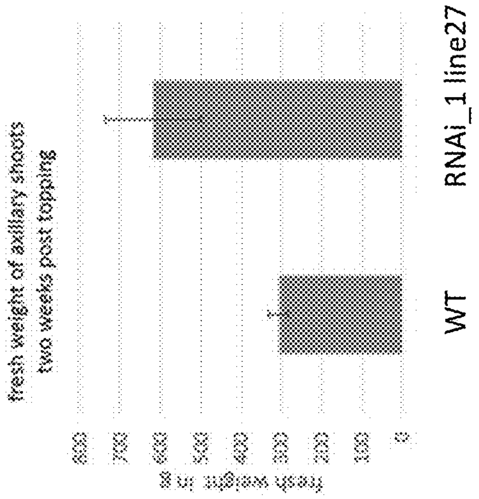

FIG. 6D is a graph showing that the fresh weight of axillary shoots of RNAi_1 plants was twice as much as that of wild type plant, indicating that silencing the BRANCH1 homolog in tobacco resulted in enhanced bud outgrowth.

Figure 7A:
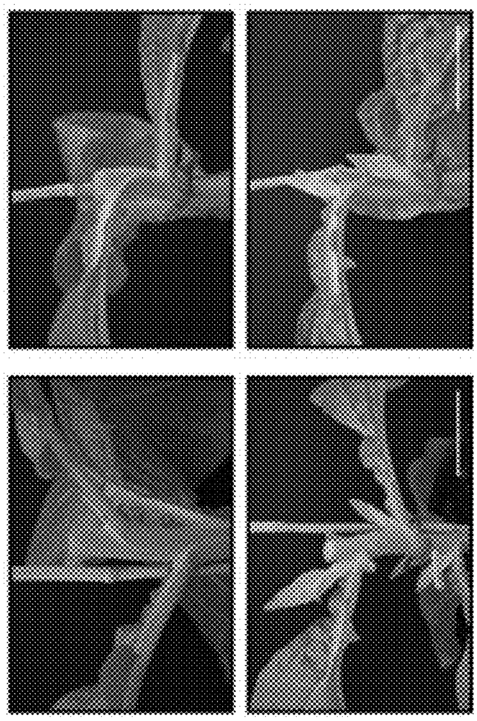

FIG. 7A are photographs that show that overexpression of the Arabidopsis BRANCH1 nucleic acid leads to reduced bud outgrowth (right) relative to wild type plants (left) within 1 week after topping (bottom).

Figure 7B:
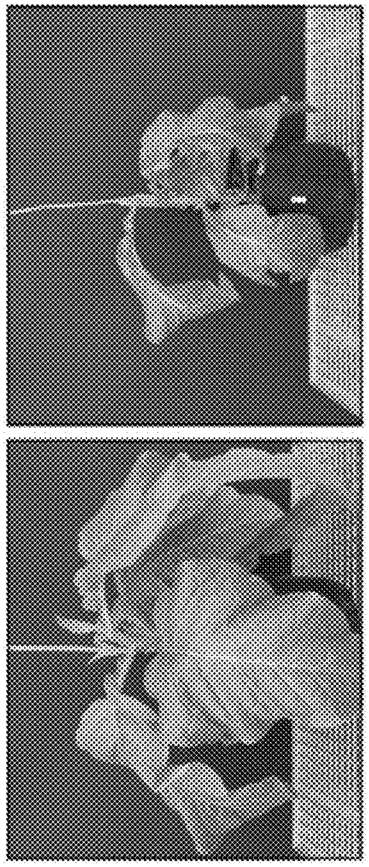

FIG. 7B are photographs that show that overexpression of the Arabidopsis BRANCH1 nucleic acid influences plant growth in general (right) relative to wild type plants (left).

Figure 8:
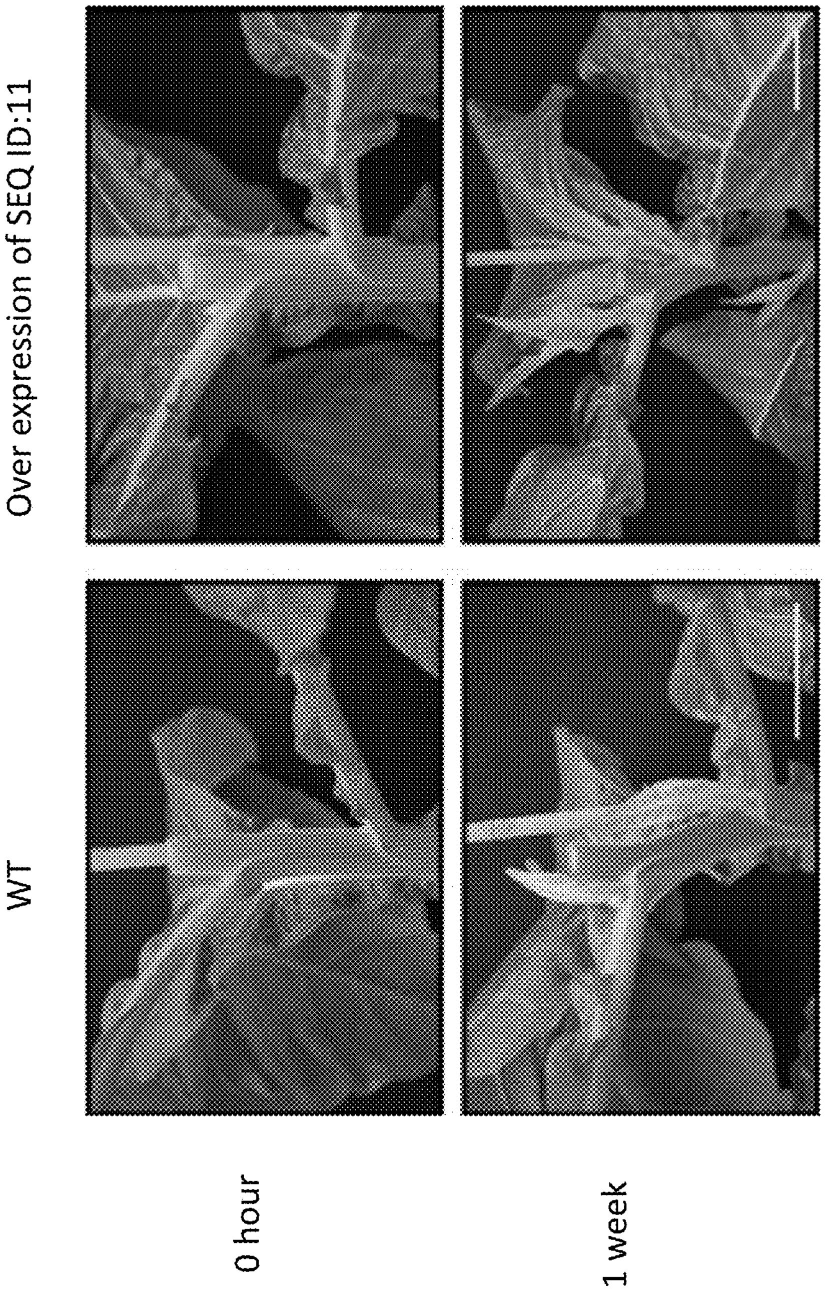

FIG. 8 are photographs that show that overexpression of the nucleic acid sequence shown in SEQ ID NO:11 leads to enhanced bud outgrowth after topping (right). The phenotype is exemplarily for one transgenic line in comparison to a wild type plant (left) 0 h (top) and 1 week after topping (bottom).

Figure 9:
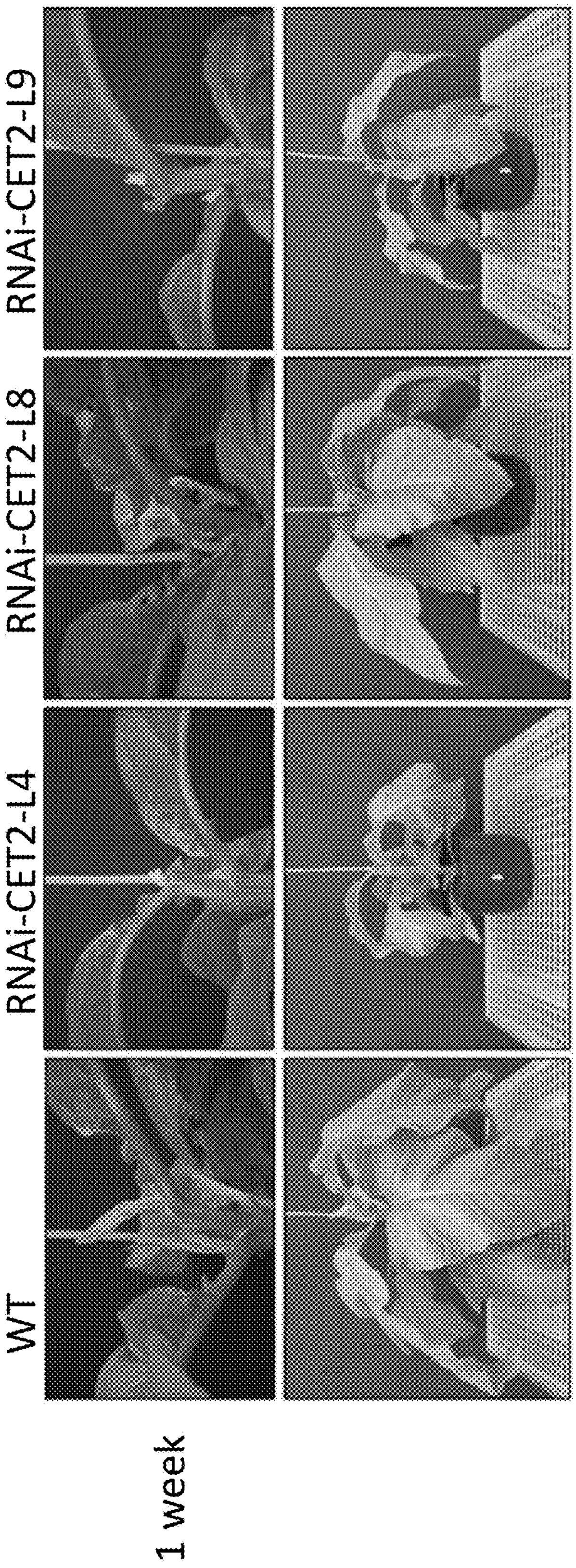

FIG. 9 are photographs (close-up, top; entire plant, bottom) that show that overexpression of RNAi_CET2 in three different transgenic lines down regulated sucker growth and resulted in reduced bud outgrowth. The phenotype of three lines transgenic for RNAi_CET2 in comparison to a wild type plant (left) 1 week after topping is shown.

Figure 10:
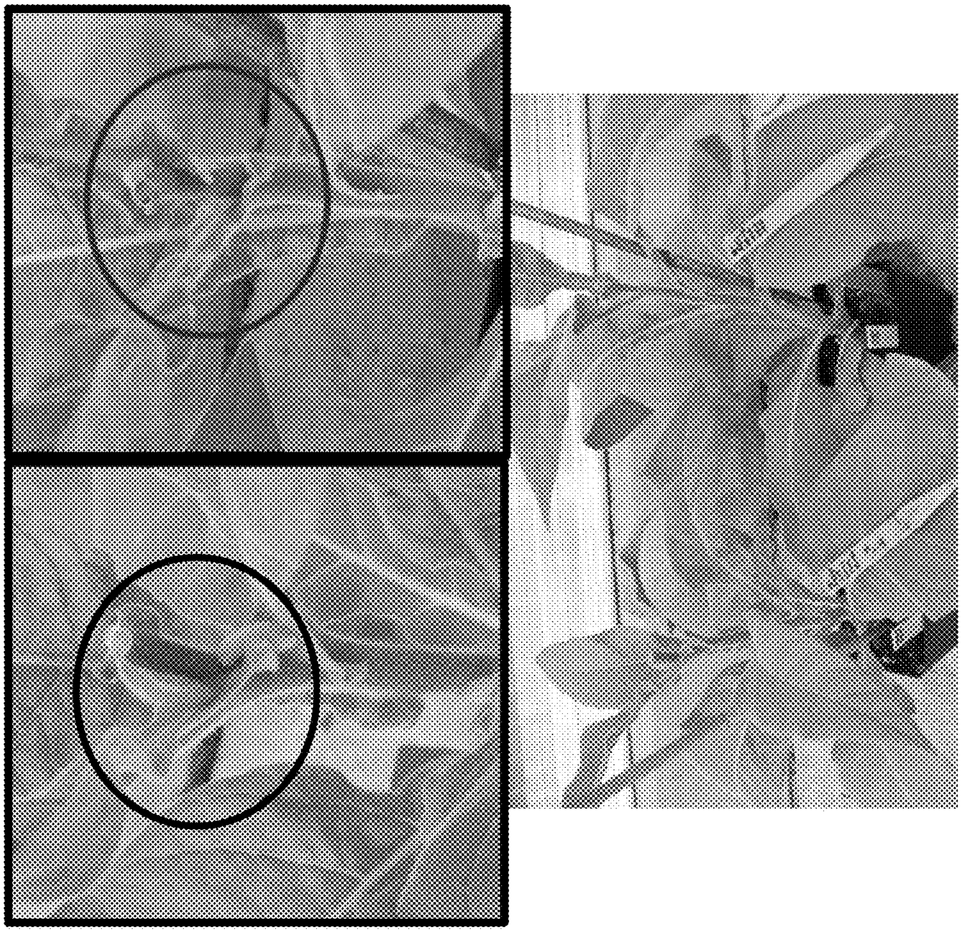

FIG. 10 are photographs taken 7 days after topping that show that expression of RNAi_26 reduced sucker growth (close-up, top right; entire plant, bottom) relative to a wild type plant (top left).

Figure 11:
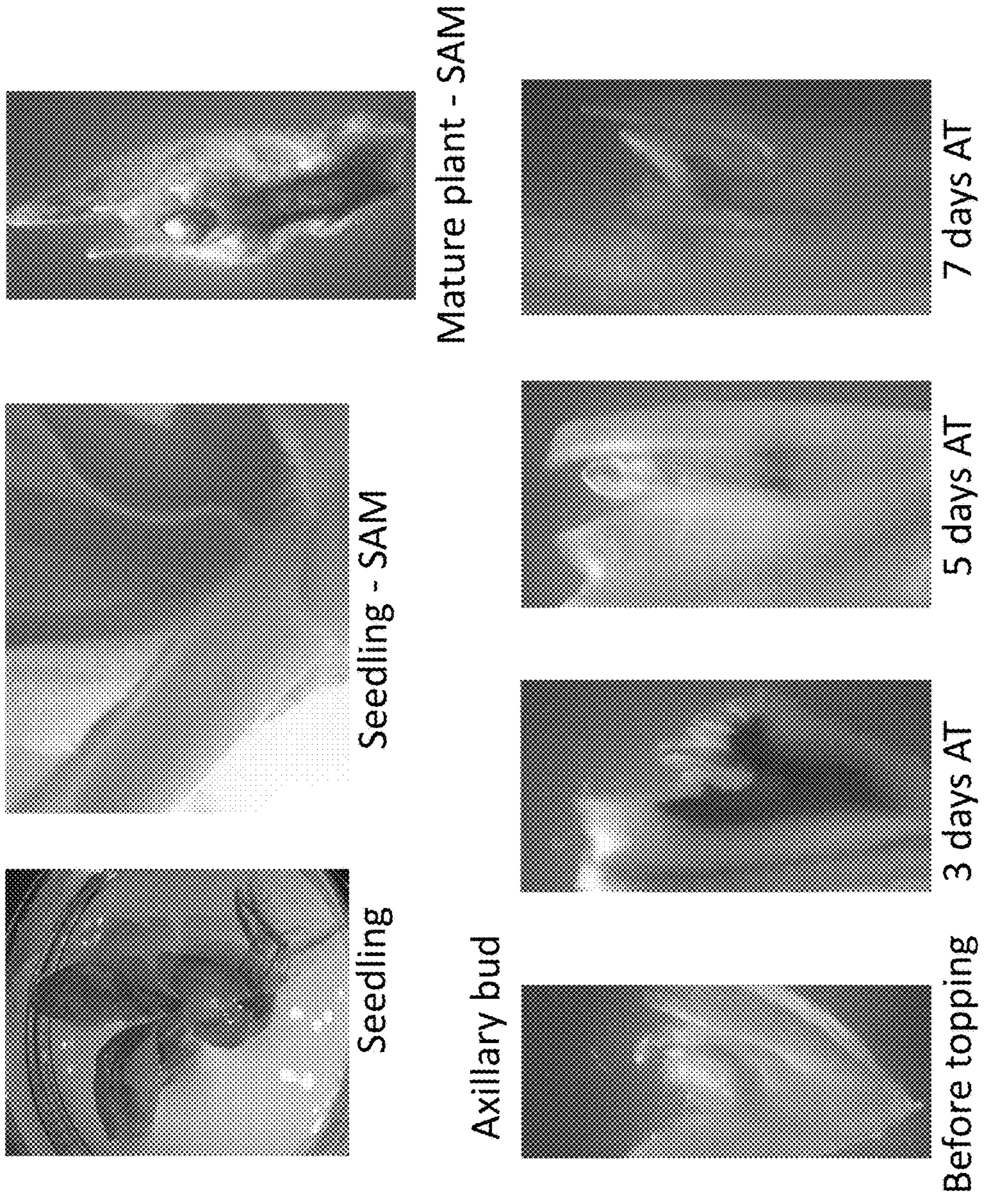

FIG. 11 are photographs showing the meristem-specific expression of GUS under control of the promoter having the sequence shown in SEQ ID NO:116. As labeled: no expression was observed in the seedling in the absence of SAM; in the seedling in the presence of SAM, blue color can be seen; weak expression on axillary buds was seen before topping; strong expression was observed 3 days after topping; GUS expression faded out within 5 days after topping; and GUS expression was absent by 7 days after topping.

Figure 12:
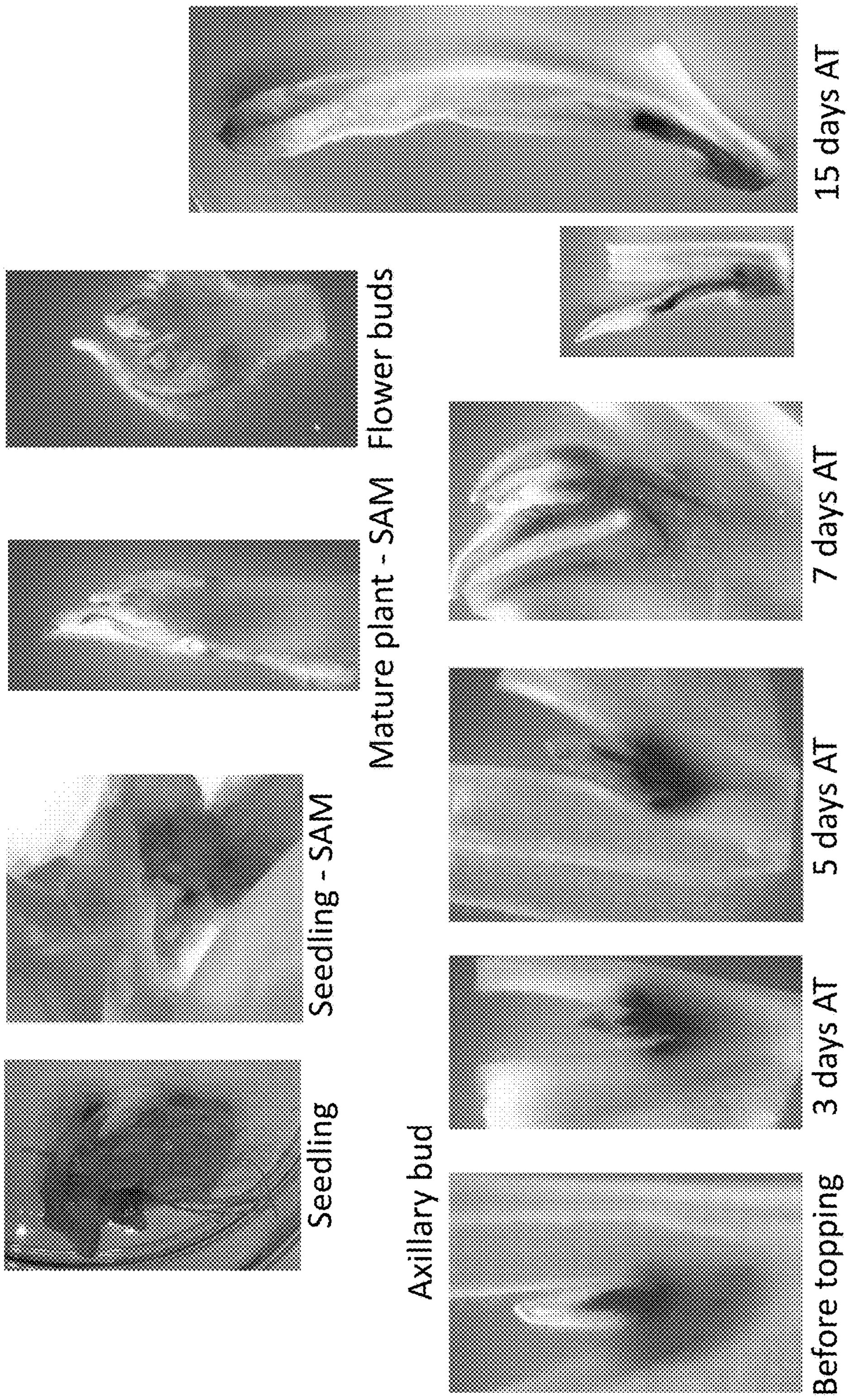

FIG. 12 are photographs showing the axillary bud-specific expression of GUS under control of the promoter having the sequence shown in SEQ ID NO:117. As labeled: no expression was observed in the seedling in the absence of SAM; GUS expression was observed in the axillary buds in the presence of SAM; in the mature plant, GUS expression was observed at the base and in the side buds; no GUS expression was observed in the flower buds; and strong GUS expression was observed in the axillary bud before topping and for up to 15 days after topping.

Figure 13:
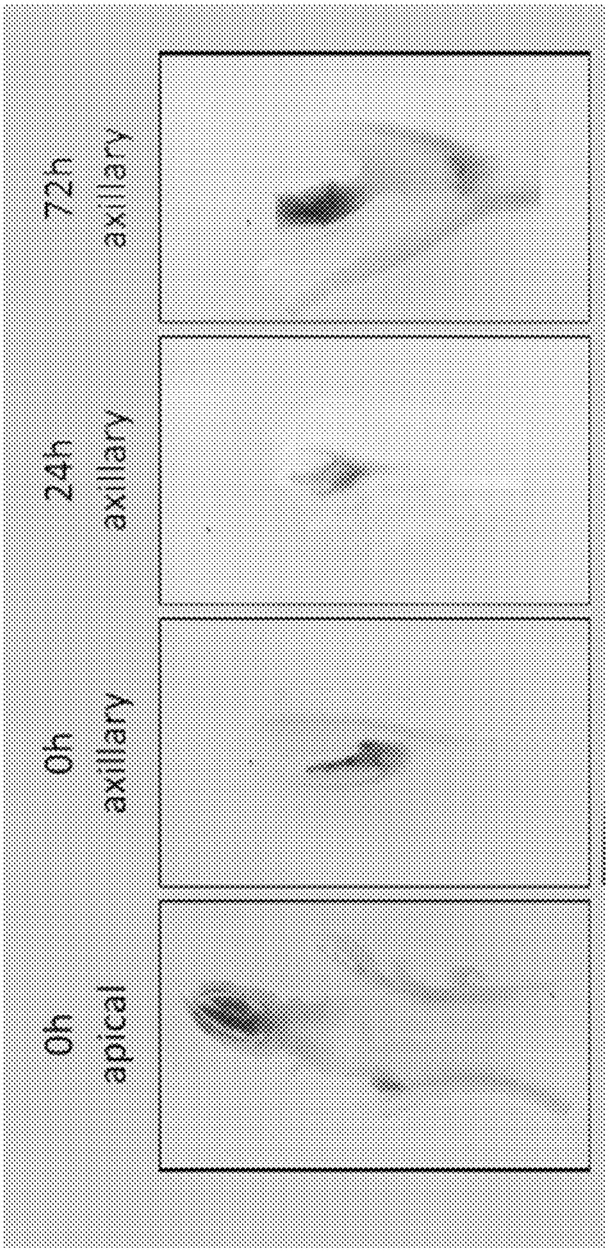

FIG. 13 are photographs showing meristem-specific GUS expression under control of the P1 promoter. GUS expression is observed, but is down-regulated after topping (at 0 hr).

DETAILED DESCRIPTION

This application describes approaches to produce tobacco with no or reduced sucker growth. For example, the description includes: axillary bud growth gene profiling to discover genes that are critical for axillary bud development; up regulation of axillary bud growth and/or sucker suppressor genes; down-regulation of axillary bud and/or sucker activator genes; and modulation of regulatory components of sucker growth; or initiation or induction of cell death mechanisms in axillary buds using axillary bud-specific promoters.

This disclosure is based on the discovery of nucleic acids encoding polypeptides from *N. tabacum, Arabidopsis thaliana* and *Bacillus amyloliquefaciens* that are involved in axillary bud growth and the regulation thereof. Such nucleic acids, SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and the polypeptides encoded thereby, SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82, are described and characterized herein. Based on this discovery, the level of expression of such nucleic acid sequences and/or the function of such polypeptides can be modulated in *Nicotiana* species, specifically, for example, *N. tabacum*. Modulating polypeptide function and/or gene expression can permit improved control of axillary bud growth.

Nucleic Acids and Polypeptides

Nucleic acids are provided herein (see, for example, SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81). As used herein, nucleic acids can include DNA and RNA, and includes nucleic acids that contain one or more nucleotide analogs or backbone modifications. A nucleic acid can be single stranded or double stranded, which usually depends upon its intended use. The nucleic acids provided herein encode polypeptides (see, for example, SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82).

Also provided are nucleic acids and polypeptides that differ from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82, respectively. Nucleic acids and polypeptides that differ in sequence from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and SEQ ID NOs: 2, 4, 6, 8, 10, 12, 14, 16, 18, 20, 22, 24, 26, 28, 30, 32, 34, 36, 38, 40, 42, 44, 46, 48, 50, 52, or 54, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, and SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81), thereby leading to changes in the amino acid sequence of the encoded polypeptide (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, or 82). For example, changes can be introduced into nucleic acid coding sequences using mutagenesis (e.g., site-directed mutagenesis, transcription activator-like effector nuclease (TALEN), PCR-mediated mutagenesis, clustered regularly interspaced short palindromic repeats (CRISPR) mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Additionally or alternatively, a vector can include sequences to direct homologous recombination of a nucleic acid (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81) into a genome. Representative sequences that can direct homologous recombination of a nucleic acid into a genome are known in the art and include TALEN sequences (e.g., Cermak et al., 2011, Nuc. Acids Res., 39:e82), CRISPR sequences (Jiang et al., 2013, Nuc. Acids Res., 41:e188), or zinc-finger nucleases (Guo et al., 2010, J. Mol. Biol., 400: 96).

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art and include plant cells. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally disclose Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Plants Having Reduced Axillary Bud Growth and Methods of Making

Tobacco hybrids, varieties, lines, or cultivars are provided that have a mutation in one or more nucleic acids described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). As described herein, stalks of plants having a mutation in one or more of the nucleic acids (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) can exhibit reduced axillary bud growth (e.g., compared to stalks of a plant that lacks the mutation). In some instances, the nucleic acid having the mutation can be an endogenous nucleic acid; in some instances, the nucleic acid having the mutation can be introduced recombinantly.

As used herein, axillary bud growth (or "suckering") describes the production of lateral buds (or "suckers") that grow between the leaf and the stalk after a tobacco plant is topped, as commonly understood in the art. Topping refers to the removal of the stalk apex, including the flowers and up to several adjacent leaves, when the plant is near maturity, and results in the loss of apical dominance. Provided axillary bud growth is sufficiently controlled, topping increases the yield and the value-per-acre as well as results in desirable modifications to physical and chemical properties of the leaf.

Methods of making a tobacco plant having a mutation are known in the art. Mutations can be random mutations or targeted mutations. For random mutagenesis, cells (e.g., *Nicotiana tabacum* cells) can be mutagenized using, for example, a chemical mutagen, ionizing radiation, or fast neutron bombardment (see, e.g., Li et al., 2001, *Plant J.,* 27:235-42). Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.,* 39(14):6315-25) or the use of zinc-finger nucleases (see, for example, Wright et al., 2005, *The Plant J.,* 44:693-705). Whether random or targeted, a mutation can be a point mutation, an insertion, a deletion, a substitution, or combinations thereof.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those conserved regions would likely have little to no effect on polypeptide function. In addition, a mutation in a single nucleotide can create a stop codon, which would result in a truncated polypeptide and, depending on the extent of truncation, loss of function.

Preferably, a mutation in one of the novel nucleic acids disclosed herein results in reduced or even complete elimination of axillary bud growth after topping in a tobacco plant comprising the mutation. Suitable types of mutations in a coding sequence include, without limitation, insertions of nucleotides, deletions of nucleotides, or transitions or transversions in the wild-type coding sequence. Mutations in the coding sequence can result in insertions of one or more amino acids, deletions of one or more amino acids, and/or non-conservative amino acid substitutions in the encoded polypeptide. In some cases, the coding sequence comprises more than one mutation or more than one type of mutation.

Insertion or deletion of amino acids in a coding sequence, for example, can disrupt the conformation of the encoded polypeptide. Amino acid insertions or deletions also can disrupt sites important for recognition of a binding ligand or for activity of the polypeptide. It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the polypeptide, introduce a stop codon to produce a truncated polypeptide, or disrupt an active site or domain (e.g., a catalytic site or domain, a binding site or domain) within the polypeptide. In addition, a target or signal sequence can be mutated, thereby disrupting or altering the placement of the protein in the cell.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Following mutagenesis, Mo plants are regenerated from the mutagenized cells and those plants, or a subsequent generation of that population (e.g., $M_1$, $M_2$, $M_3$, etc.), can be screened for a mutation in a sequence of interest (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). Screening for plants carrying a mutation in a sequence of interest can be performed using methods routine in the art (e.g., hybridization, amplification, combinations thereof) or by evaluating the phenotype (e.g., detecting and/or determining axillary bud growth). Generally, the presence of a mutation in one or more of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) results in a reduction of axillary bud growth in the mutant plants compared to a corresponding plant (e.g., having the same varietal background) lacking the mutation.

As used herein, reduced axillary bud growth, also referred to as reduced sucker growth, refers to a reduction (e.g., a statistically significant reduction) in the number of axillary buds, a reduction (e.g., a statistically significant reduction) in the size of the axillary buds (e.g., biomass), and/or a reduction (e.g., a statistically significant reduction) of the impact the axillary buds have on agronomic performance (e.g., yield, quality and overall productivity of the plant) compared to a control plant. The effects can be demonstrated as impeding and/or eliminating axillary bud growth after topping, or reducing and/or eliminating the need for application of chemicals (e.g., MH and/or flumetralin) after topping. As used herein, statistically significant refers to a p-value of less than 0.05, e.g., a p-value of less than 0.025 or a p-value of less than 0.01, using an appropriate measure of statistical significance, e.g., a one-tailed two sample t-test.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype. Such plants may be heterozygous and exhibit a mutant phenotype due to phenomena such as dominant negative suppression, despite the presence of the wild type allele, or such plants may be heterozygous due to different independently induced mutations in different alleles.

A tobacco plant carrying a mutant allele can be used in a plant breeding program to create novel and useful cultivars, lines, varieties and hybrids. Thus, in some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Breeding is carried out using known procedures. DNA fingerprinting, SNP or similar technologies may be used in a marker-assisted selection (MAS) breeding program to transfer or breed mutant alleles into other tobaccos, as described herein. Progeny of the cross can be screened for a mutation using methods described herein, and plants having a mutation in a nucleic acid sequence disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) can be selected. For example, plants in the $F_2$ or backcross generations can be screened using a marker developed from a sequence described herein or a fragment thereof, using one of the techniques listed herein. Progeny plants also can be screened for axillary bud growth, and those plants having reduced axillary bud growth, compared to a corresponding plant that lacks the mutation, can be selected. Plants identified as possessing the mutant allele and/or the mutant phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with a parent line if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, confirmation of the null condition, and/or planting to evaluate axillary bud growth.

The result of a plant breeding program using the mutant tobacco plants described herein are novel and useful cultivars, varieties, lines, and hybrids. As used herein, the term "variety" refers to a population of plants that share characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Tobacco hybrids can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties, lines and cultivars described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The tobacco plants used in the methods described herein can be a Burley type, a dark type, a flue-cured type, a Maryland type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14xL8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVHSO, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN9OLC, TN 97, TN97LC, TN D94, TN D950, TR (Tom Rosson) Madole, VA 309, or VA359.

In addition to mutation, another way in which axillary bud growth in tobacco can be reduced is to use inhibitory RNAs (e.g., RNAi). Therefore, transgenic tobacco plants are provided that contain a transgene encoding at least one RNAi molecule, which, when expressed, silences at least one of the endogenous nucleic acids described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). As described herein, such transgenic plants exhibit reduced axillary bud growth (e.g., compared to a plant lacking or not expressing the RNAi).

RNAi technology is known in the art and is a very effective form of post-transcriptional gene silencing. RNAi molecules typically contain a nucleotide sequence (e.g., from about 18 nucleotides in length (e.g., about 19 or 20 nucleotides in length) up to about 700 nucleotides in length) that is complementary to the target gene in both the sense and antisense orientations. The sense and antisense strands can be connected by a short "loop" sequence (e.g., about 5 nucleotides in length up to about 800 nucleotides in length) and expressed in a single transcript, or the sense and antisense strands can be delivered to and expressed in the target cells on separate vectors or constructs. A number of companies offer RNAi design and synthesis services (e.g., Life Technologies, Applied Biosystems).

The RNAi molecule can be expressed using a plant expression vector. The RNAi molecule typically is at least 25 nucleotides in length and has at least 91% sequence identity (e.g., at least 95%, 96%, 97%, 98% or 99% sequence identity) to one of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77) or hybridizes under stringent conditions to one of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 57, 59, 61, 63, 65, 69, 71, 73, 75, or 77). Hybridization under stringent conditions is described above.

Further, certain of the sequences described herein can be overexpressed in plants to reduce axillary bud growth. Accordingly, transgenic tobacco plants are provided that are transformed with a nucleic acid molecule described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81) or a functional fragment thereof under control of a promoter that is able to drive expression in plants. As discussed herein, a nucleic acid molecule used in a plant expression vector can have a different sequence than a sequence described herein, which can be expressed as a percent sequence identity (e.g., relative to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81) or based on the conditions under which the sequence hybridizes to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein and the alignments shown in FIG. 3, one of skill in the art can predict the portion(s) of a polypeptide (e.g., one or more domains) that may impart the desired functionality.

Promoters that drive expression of a coding sequence in plants are known in the art. Representative promoters include, for example, the CaMV 35S promoter, the actin promoter, the ubiquitin promoter, the phaseolin promoter, a rubisco promoter, the zein promoter, an ACEI system promoter, the In2 promoter, or the H3 histone promoter. In addition, tissue- or developmentally-specific promoter sequences related to axillary bud growth are described herein and can be used to express or overexpress a nucleic acid coding sequence. Representative tissue- or developmentally-specific promoter sequences related to axillary bud growth are shown in SEQ ID NOs: 113, 114, 115, 116, 117, or 118. As described herein, the coding sequence can be any of the nucleic acid coding sequences described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81); alternatively, a coding sequence can be derived from a gene that results in programmed cell death (e.g., nucleic acid molecules that encode a ribosome inactivating protein, nucleic acid molecules that encode proteins involved in the hypersensitive response plants initiate when confronted with a pathogen (e.g., a fungus or a bacteria)). Simply by way of example, a tissue- or developmentally-specific promoter sequence related to axillary bud growth as described herein can be used to express or overexpress a coding sequence whose expression is decreased after topping or a coding sequence involved in apoptosis.

Methods of introducing a nucleic acid (e.g., a heterologous nucleic acid) into plant cells are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols,* 2(7):1565-72)), liposome-mediated DNA uptake, or electroporation. Following transformation, the transgenic plant cells can be regenerated into transgenic tobacco plants. As described herein, expression of the transgene results in a plant that exhibits reduced axillary bud growth relative to a plant not expressing the transgene. The regenerated transgenic plants can be screened for axillary bud growth, and plants having reduced axillary bud growth, compared to a corresponding non-transgenic plant, can be selected for use in, for example, a breeding program as discussed herein. In addition to over-expression or downregulation of axillary bud growth-related coding sequences, axillary bud growth can be controlled using any of the following approaches:

a. altering the expression of axillary bud growth-related regulatory genes that are critical for axillary bud development (as described in Examples 7 and 8);
b. altering meristem development-specific genes using axillary bud-specific promoters;
c. altering the hormonal signaling leading to axillary shoot growth inhibition. This can be accomplished through overexpression or downregulation of hormonal synthesis or transport genes driven by tissue specific or timing specific (e.g., after topping) promoters; and
d. initiating cell death mechanisms in axillary buds using axillary bud specific promoters driving cell suicide or toxicity genes.

Nucleic acids that confer traits such as herbicide resistance (sometimes referred to as herbicide tolerance), insect resistance, or stress tolerance, can also be present in the novel tobacco plants described herein. Genes conferring resistance to a herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 20010016956.

A number of genes are available that confer resistance to insects, for example, insects in the order Lepidoptera. Exemplary genes include those that encode truncated Cry1A(b)

and Cry1A(c) toxins. See, e.g., genes described in U.S. Pat. Nos. 5,545,565; 6,166,302; and 5,164,180. See also, Vaeck et al., 1997, *Nature,* 328:33-37 and Fischhoff et al., 1987, *Nature Biotechnology,* 5:807-813. Particularly useful are genes encoding toxins that exhibit insecticidal activity against *Manduca sexta* (tobacco hornworm); *Heliothis virescens* Fabricius (tobacco budworm) and/or *S. litura* Fabricius (tobacco cutworm).

Tobacco Products and Methods of Making

Leaf from tobacco plants having reduced axillary bud growth can be cured, aged, conditioned, and/or fermented. Methods of curing tobacco are well known and include, for example, air curing, fire curing, flue curing and sun curing. Aging also is known and typically is carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993, 4,660,577, 4,848,373 and 5,372,149. The tobacco also can be further processed (e.g., cut, expanded, blended, milled or comminuted), if desired, and used in a tobacco product.

Tobacco products are known in the art and include products made or derived from tobacco that are intended for human consumption, including any component, part, or accessory of a tobacco product. Representative tobacco products include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco. Representative smokeless tobacco products include, for example, chewing tobacco, snuff, long-cut moist smokeless tobacco, snus, pouches, films, tablets, coated dowels, rods, and the like.

Representative cigarettes and other smoking articles include, for example, smoking articles that include filter elements or rod elements, where the rod element of a smokeable material can include cured tobacco within a tobacco blend. In addition to the tobacco described herein, tobacco products also can include other ingredients such as, without limitation, binders, plasticizers, stabilizers, and/or flavorings. See, for example, US 2005/0244521; US 2006/0191548; US 2012/0024301; US 2012/0031414; and US 2012/0031416 for examples of tobacco products.

The invention will be further described in the following examples, which do not limit the scope of the methods and compositions of matter described in the claims.

EXAMPLES

Example 1

Sampling, RNA Preparation and Sequencing

Tobacco seeds from TN90, a Burley variety, were germinated. After 4 weeks, seedlings were transferred onto 4 inch pots. At layby stage (8-10 fully expanded leaves), a total of 10 different samples including axillary buds before topping (Aa), axillary buds after topping (Ab, Ac, Ad and Ae (2 h, 6 h, 24 h and 72 h, respectively), roots before topping (Ra), roots after topping (Rb, Rc (24 h and 72 h)), young leaf at the time of topping (YL), and shoot apical meristem (ST) were collected for next generation sequencing analysis. Each of the time points were represented by three independently collected samples. These three samples served as biological replicates.

RNA from the samples described above was isolated using RNeasy Plant Mini Kit (Qiagen, MA) and quality was tested using Agilent Plant RNA Nano Kit and a 2100 Bioanalyzer (Agilent Technologies, Calif.). Thirty cDNA libraries were constructed, with indexing using a TrueSeq RNA Library Prep Kit v.2 (Illumina). cDNA libraries made from the same biological replicates were pooled together, and each pooled replicate was analyzed on an Illumina HiSeq 2000, 100 bp single reads with a minimum of 30 million reads per sample. Two samples were tagged per lane for a total of 15 sequencing lanes. Axillary bud specific gene expression in TN90 tobacco was determined by RNA deep sequencing performed by ArrayXpress (Raleigh, N.C.).

Example 2

RNA Sequence Analysis

Gene expression data from five axillary buds, 3 roots, and one each of young leaf and shoot apical meristem samples were analyzed to identify axillary bud development-related genes compared to other tissues. Gene reads were mapped to our in-house tobaccopedia genome database (Table 1). EdgeR in CLC genomic workbench was used to perform differential gene expression. Gene expression data was filtered for axillary bud specific expression from other tissues. FDR adjustment was performed on all p-values and a cut-off of an FDR corrected p-value<0.05 was used. Results were then filtered for high axillary bud expression. The list of differentially expressed candidate genes for sucker control are listed in Table 2.

TABLE 1

Mapping of Next Generation Sequencing Reads Using In-House Tobaccopedia Database

| Samples | Reads Mapped | % mapped |
|---|---|---|
| Aa1 | 23,920,938 | 92.03 |
| Aa2 | 49,392,444 | 91.21 |
| Aa3 | 28,288,803 | 86.23 |
| Ab1 | 24,848,558 | 92.2 |
| Ab2 | 35,727,478 | 92.23 |
| Ab3 | 34,000,094 | 92.25 |
| Ac1 | 45,951,075 | 92.04 |
| Ac2 | 48,242,863 | 92.15 |
| Ac3 | 41,733,418 | 91.67 |
| Ad1 | 33,474,960 | 92.08 |
| Ad2 | 31,891,377 | 92.35 |
| Ad3 | 40,791,919 | 92.23 |
| Ae1 | 28,758,337 | 92.04 |
| Ae2 | 38,369,793 | 92.26 |
| Ae3 | 40,552,134 | 92.45 |
| Ra1 | 39,732,686 | 92.02 |
| Ra2 | 40,262,611 | 91.16 |
| Ra3 | 33,248,092 | 92.13 |
| Rb1 | 35,937,062 | 93.06 |
| Rb2 | 40,036,265 | 92.43 |
| Rb3 | 46,268,788 | 92.34 |
| Rc1 | 35,595,122 | 92.84 |
| Rc2 | 37,925,157 | 92.25 |
| Rc3 | 34,832,062 | 92.18 |
| ST1 | 48,115,555 | 92.45 |
| ST2 | 41,373,361 | 92.41 |
| ST3 | 31,760,672 | 91.85 |
| YL1 | 41,811,850 | 92.63 |
| YL2 | 51,356,432 | 91.82 |
| YL3 | 40,252,190 | 91.95 |

TABLE 2

Differential gene expression of selected candidate genes

| Contig Number | Axillary Buds Before Topping (AB0) | Axillary Buds After Topping 2 hr (AB2) | 6 hr (AB6) | 24 hr (AB24) | 72 hr (AB72) | Roots Before Topping (RT0) | Roots After Topping 24 hr (RT24) | 72 hr (RT72) | Shoot Apical Meristem | Young Leaf |
|---|---|---|---|---|---|---|---|---|---|---|
| C5787 | 1,072 | 998 | 1,346 | 663 | 652 | 7 | 9 | 11 | 180 | 47 |
| C16249 | 1,387 | 927 | 3,527 | 44,790 | 23,270 | 108 | 90 | 128 | 8,913 | 72 |
| C3898 | 763 | 1,132 | 1,852 | 5,559 | 2,644 | 110 | 156 | 80 | 513 | 7 |
| C2231 | 115 | 532 | 446 | 252 | 496 | 27 | 7 | 11 | 23 | 14 |
| C49345 | 2,342 | 2,357 | 2,992 | 3,143 | 2,190 | 38 | 28 | 27 | 26 | 103 |
| C64393 | 47 | 29 | 54 | 18 | 17 | 1 | 0 | 0 | 23 | 1 |
| C26207 | 128 | 131 | 187 | 69 | 54 | 0 | 1 | 1 | 13 | 0 |
| C83090 | 124 | 308 | 1,619 | 337 | 136 | 217 | 143 | 160 | 88 | 234 |
| C29909 | 3 | 162 | 186 | 9 | 9 | 22 | 22 | 29 | 6 | 2 |
| C82570 | 41 | 98 | 334 | 136 | 101 | 1 | 0 | 0 | 50 | 0 |
| C12866 | 1,479 | 1,486 | 4,216 | 16,176 | 12,228 | 46 | 36 | 33 | 2,144 | 839 |
| C34805 | 52 | 27 | 81 | 13 | 9 | 2 | 1 | 3 | 5 | 1 |
| C47069 | 152 | 114 | 135 | 46 | 45 | 2 | 2 | 2 | 1 | 0 |
| C73141 | 60 | 34 | 22 | 17 | 13 | 2 | 4 | 1 | 30 | 1 |
| C41568 | 176 | 131 | 385 | 48 | 43 | 14 | 12 | 15 | 19 | 10 |
| C50303 | 624 | 583 | 1,279 | 300 | 215 | 14 | 9 | 18 | 71 | 9 |
| C58496 | 176 | 121 | 253 | 95 | 70 | 7 | 1 | 1 | 69 | 27 |
| C68375 | 268 | 279 | 410 | 231 | 207 | 1 | 1 | 1 | 22 | 11 |
| C55919 | 193 | 241 | 366 | 117 | 123 | 2 | 2 | 2 | 13 | 1 |
| C40016 | 394 | 353 | 505 | 207 | 204 | 2 | 2 | 1 | 34 | 2 |
| C145337 | 2,110 | 2,953 | 8,542 | 1,362 | 2,095 | 337 | 181 | 337 | 305 | 131 |
| C348 | 1,022 | 1,253 | 2,580 | 715 | 762 | 79 | 53 | 59 | 164 | 13 |
| C131180 | 1,517 | 2,212 | 5,081 | 2,402 | 1,059 | 1,109 | 488 | 332 | 558 | 351 |
| C22266 | 222 | 265 | 479 | 290 | 187 | 2 | 3 | 1 | 20 | 3 |
| C53803 | 1,796 | 1,308 | 3,662 | 777 | 968 | 23 | 21 | 22 | 475 | 11 |
| C21860 | 104 | 75 | 68 | 107 | 46 | 0 | 1 | 0 | 3 | 0 |
| C11320 | 486 | 309 | 1,297 | 291 | 395 | 146 | 56 | 42 | 84 | 8 |
| C1838 | 364 | 175 | 126 | 152 | 97 | 1 | 0 | 0 | 36 | 14 |

Example 3

Confirmation of Selected Candidate Gene Expression

To confirm the expression pattern of selected candidate genes, the relative changes in transcripts from 10-16 different tissue samples (6 axillary bud samples (before topping and 2 hr, 6 hr, 12 hr, 24 hr and 72 hr after topping), young leaf 24 hr after topping, mature leaf, senescence leaf, midrib, stalk before topping, stalk 24 hr after topping, shoot apical meristem, root before topping and 24 hr after topping) were measured. In brief, total RNA was isolated using TRI Reagent (Sigma-Aldritch, St. Louis, Mo.). To remove DNA impurities, purified RNA was treated with RNase-free DNase (Turbo DNA-free, Ambion, Austin, Tex.). To synthesize the first cDNA strand, approximately 10 μg of total RNA was transcribed utilizing the High Capacity cDNA Kit (Applied Biosystems, Foster City, Calif.). To measure the level of selected gene transcripts in the samples, RT-PCR was performed using SYBR Green PCR Master Mix (Applied Biosystems, Foster City, Calif.) and the gene specific primers listed in Table 3. Real time gene expression verification of representative candidate genes are listed in FIGS. 1A-1G.

TABLE 3

Real time PCR Primers used for the confirmation of gene expression

| Primer Name | Forward primer | SEQ ID NO | Reverse primer | SEQ ID NO | Amplicon size |
|---|---|---|---|---|---|
| SCRT1 | TTTTCGAGGCTCCTTTAGCA | 123 | CATGTTGGGGTTCGATAAGG | 124 | 250 |
| SCRT2 | CCTTTTTTACTCATTCAGAGAAACGA | 125 | GTGTGACACTGAATTAATCCTTTCC | 126 | 380 |
| SCRT3 | AGGCTTGCTGAAGCAAAAGA | 127 | TCGGCGAAATTACAGTCTCA | 128 | 211 |
| SCRT4 | TTGTGTCATGGTGCAATCAA | 129 | TCCAACTTAGGCCTCACACC | 130 | 199 |
| SCRT5 | TTGCAATGCTTCTGTTTTCG | 131 | ATATTGGCCGCATCTTGGT | 132 | 193 |
| SCRT6 | TTCTCTTCCCGAGAAACAGTG | 133 | CGGAGTTGGAGATGAAGATGA | 134 | 217 |
| SCRT7 | CCTGTGGCAAAGGAATCAAG | 135 | TGCGTGGTGTGTTCTTCAAT | 136 | 200 |
| SCRT8 | GGGTGCTTTGAAGTCCCTTT | 137 | GAATCCTGCTCCAAACAAGC | 138 | 211 |

TABLE 3-continued

| Real time PCR Primers used for the confirmation of gene expression | | | | | |
|---|---|---|---|---|---|
| Primer Name | Forward primer | SEQ ID NO | Reverse primer | SEQ ID NO | Amplicon size |
| SCRT9 | TGGGCAGCAGAAATAAGAGA | 139 | GCTGATCTTGTTGTGGCTTG | 140 | 200 |
| SCRT10 | CACCATAAGCACAGGTGCAA | 141 | TCCGCCTTGCTTTATGAAAA | 142 | 205 |
| SCRT11 | TCCTCTTTGCCATTTCTCTCA | 143 | GGCCAGAAAAAGAATGACCA | 144 | 201 |
| SCRT12 | GGGTCCCTCTAAATCCCAAG | 145 | CCGGAAGTCAAGAATCCAGT | 146 | 201 |
| SCRT13 | TGGACATGAGGCATTTGCTA | 147 | GCATCGCGAGATCAAGAGTT | 148 | 183 |
| SCRT14 | AAGCCCGCCTTTCTACCTTA | 149 | TCTTGATCATCGAACGAATCAC | 150 | 196 |
| SCRT15 | CCAATTCCCTCTTCCTTCCT | 151 | ATCCATCCAAGTCAGCCTTC | 152 | 203 |
| SCRT16 | TGGTTGAGGCCCCAATATAC | 153 | CCCCGCTATCGACTTGATTA | 154 | 198 |
| SCRT17 | CGGAAGAGCCTGTGGTATGA | 155 | TGAAATCAGATTCAGGCATCA | 156 | 203 |
| SCRT18 | AGATCAGGAAGCGCGTAAGA | 157 | CAGAGTTTTGCTGGCCTTCT | 158 | 193 |
| SCRT19 | GTGGCAAAGGAATCAAGGAA | 159 | ATGGGTTCCAGTTGCCAGTA | 160 | 283 |
| SCRT20 | CGGTCCTTTAGCAGTTTCCA | 161 | CATGTTGGGGTTCGATAAGG | 162 | 250 |
| SCRT21 | ATCTGGAGTATTTCTTCTACCT | 163 | CTTAAACTCTCTGCCGAATAAA | 164 | 111 |
| SCRT22 | TCCTTCTTTCTGTCTGTTTCTCTT | 165 | GTCCTCACTGCTGTCTTTCTC | 166 | 110 |
| SCRT23 | GCACTTCTGGTGGTGAAAGA | 167 | GTCATTCTCAGTTATGTTACGGAAAG | 168 | 102 |
| SCRT24 | AGCTGCTCCATAACCGAAAT | 169 | CGACCCTGAATTTCCTCTAGTT | 170 | 108 |
| SCRT25 | GGATGTAAGGCATTGGACATAGA | 171 | GAGTTCCCTATCAACCGAAACA | 172 | 96 |
| SCRT26 | GGCGAGTCATTAACCTCCTATTT | 173 | GTCTTAGCGTCCAAGTGCTAAT | 174 | 117 |
| SCRT27 | GCTGAAGAACCTTTGCCTTTAC | 175 | GCCGATTTCTCAACACAAAGAA | 176 | 106 |

Example 4

Full Length Candidate Genes Cloning, Analysis and Selected Real Time PCR for Verification The candidate genes predicted to be involved in axillary bud initiation and growth were identified and annotated (Table 4), and RNAs from axillary bud tissues of TN90 plants, from before topping, and 12 hr, 24 hr and 48 hr after topping, were collected. cDNA libraries were created from the RNAs using the In-Fusion SMARTER Directional cDNA Library Construction Kit from Clontech (Cat #634933). Full length candidate genes were cloned using the gene specific primers designed from predicted full-length cDNA sequences. The full length coding sequences were confirmed by sequencing and are shown in SEQ ID NOs:1, 3, 5, 7, 9, 11, 13, 15, 17, 19, 21, 23, 25, 27, 29, 31, 33, 35, 37, 57, 59, or 69. The predicted protein sequences are shown in SEQ ID NOs:2, 4, 6, 8, 10, 12, 14, 16, 18, 20, 22, 24, 26, 28, 30, 32, 34, 36, 38, 58, 60, or 70.

TABLE 4

| Selected Candidate Genes | | | | |
|---|---|---|---|---|
| Contig Number | Coding Sequence | Nucleotide (bp) | Protein (aa) | SEQ ID NO (DNA/protein) |
| C5787 | Full length confirmed | 987 | 328 | 1/2 |
| C16249 | Full length confirmed | 318 | 105 | 3/4 |
| C3898 | Full length confirmed | 1797 | 598 | 5/6 |
| C7651 | Full length confirmed | 1392 | 463 | 7/8 |
| C49345 | Full length confirmed | 405 | 134 | 9/10 |
| C64393 | Full length confirmed | 630 | 209 | 11/12 |
| C26207 | Full length confirmed | 1143 | 380 | 13/14 |
| C83090 | Full length confirmed | 915 | 304 | 15/16 |
| C29909 | Full length confirmed | 1353 | 450 | 17/18 |
| C82570 | Full length confirmed | 732 | 243 | 19/20 |
| C12866 | Pseudo gene | — | — | — |
| C34805 | Full length confirmed | 471 | 156 | 21/22 |
| C47069 | Full length confirmed | 1437 | 478 | 23/24 |
| C73141 | Full length confirmed | 645 | 214 | 25/26 |
| C41568 | Full length confirmed | 2205 | 734 | 27/28 |
| C50303 | Full length confirmed | 1302 | 433 | 29/30 |
| C58496 | Full length confirmed | 1266 | 421 | 31/32 |
| C68375 | Full length confirmed | 597 | 198 | 33/34 |
| C55919 | Full length confirmed | 1038 | 345 | 35/36 |
| C40016 | Full length confirmed | 1014 | 337 | 37/38 |
| G47965 | Full length confirmed | 1659 | 553 | 57/58 |
| G88345 | Full length confirmed | 1632 | 544 | 59/60 |
| S10610 | Full length confirmed | 396 | 132 | 69/70 |

From RNA sequence analysis and RT-PCR confirmation, candidate putative full length gene sequences were selected for RNAi and full length *Agrobacterium* transformation analysis. The candidate sequences are listed in Table 5 and are shown in SEQ ID NOs:39, 41, 43, 45, 47, 49, 51, 53, 61, 63, 65, 71, 73, 75, or 77. The predicted protein sequences are shown in SEQ ID NOs:40, 42, 44, 46, 48, 50, 52, 54, 62, 64, 66, 72, 74, 76, or 78.

Six of the candidate genes are members of a transcription factor gene family based on the presence of a conserved domain (TCP domain). The nucleotide and protein sequence alignments are shown in FIG. 3. Members of this family are implicated in plant growth and development regulation. The conserved domain is thought to be responsible for DNA binding to cis-elements in promoters in order to regulate downstream genes.

TABLE 5

Selected candidate putative gene sequences

| Contig Number | Coding Sequence | Nucleotide (bp) | Protein (aa) | SEQ ID NO (DNA/protein) |
|---|---|---|---|---|
| C145337 | Predicted | 867 | 288 | 39/40 |
| C348 | Predicted | 2562 | 853 | 41/42 |
| C131180 | Predicted | 2790 | 929 | 43/44 |
| C22266 | Predicted | 2478 | 825 | 45/46 |
| C21860 | Confirmed | 1152 | 383 | 47/48 |
| C75660 | Predicted | 813 | 270 | 49/50 |
| C11320 | Predicted | 762 | 253 | 51/52 |
| C1838 | Predicted | 753 | 250 | 53/54 |
| G120126 | Predicted | 960 | 320 | 61/62 |
| G151887 | Predicted | 930 | 310 | 63/64 |
| G135280 | Predicted | 822 | 274 | 65/66 |
| G56830 | Predicted | 1158 | 386 | 71/72 |
| S4261 | Predicted | 1224 | 408 | 73/74 |
| S950 | Predicted | 1014 | 338 | 75/76 |
| S1904 | Predicted | 1011 | 337 | 77/78 |

Example 5

Development of Transgenic Plants Containing RNAi or Over-Expression Constructs and Efficacy Testing To investigate the function of the candidate genes, three sets of transgenic plants were generated; a first using the full length coding sequence from tobacco (Table 4, SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 69), a second using non-tobacco origin full length genes (Table 4, SEQ ID NOs: 55, 67, 79, or 81); and a third using a RNAi sequence (SEQ ID NO: 83, 84, 85, 86, 87, 88, 89, 90, 91, 92, 93, 94, 95, 96, 97, 98, 99, 100, or 101). An expression vector, p45-2-7 (SEQ ID NO:112; FIG. 2), was used, which has a CsVMV promoter and a NOS terminator, as well as a cassette having a kanamycin selection marker (NPT II) under direction of the actin2 promoter and a NOS terminator. The nucleic acid constructs carrying the transgenes of interest were introduced into tobacco leaf discs using an *Agrobacterium* transformation approach. See, for example, Mayo et al., 2006, Nat Protoc., 1(3):1105-11 and Horsch et al., 1985, Science 227:1229-1231.

Briefly, tobacco plants (Narrow Leaf Madole (NLM)) were grown from magenta boxes, and leaf disks were cut into 15×150 mm plates. *Agrobacterium tumefaciens* containing the target plasmid were collected by centrifugation of 20 ml cell suspension in 50 ml centrifuge tube at 3500 rpm for 10 minutes. Supernatant was removed and *Agrobacterium* cell pellet was resuspended in 40 ml liquid resuspension medium. About 25 ml of the solution was transferred to each 15×100 mm Petri plates. In those 15×150 mm plates, tobacco leaves, avoiding the midrib, were cut into 0.6 cm disk. Leaf disks were placed upside down, a thin layer of MS/B5 liquid resuspension medium was added, and slices were made with a #15 razor blade. The leaf discs were poked uniformly with a fine point needle. Eight disks were placed, upside down, in each regeneration plate (15×100 mm). *Agrobacterium tumefaciens* suspension was added and the leaf discs were incubated for 10 minutes.

Leaf disks were transferred to co-cultivation plates (1/2 MS medium) and disks were placed upside down in contact with filter paper overlaid on the co-cultivation TOM medium (MS medium with 20 g sucrose/L; 1 mg/L IAA and 2.5 mg/L BAP). The plate was sealed with parafilm and labeled appropriately. Plates were incubated in dim light (60-80 mE/ms) and 18/6 photoperiods at 24° C. for three days. Leaf disks were transferred to regeneration/selection TOM K medium plates (TOM medium with 300 mg/l Kanamycin) and subculture bi-weekly to the same fresh medium in dim light at 24° C. until shoots become excisable. Shoots from leaves were removed with forceps and inserted in MS basal medium with 100 mg/L kanamycin at 24° C. and 18/6 photoperiods with light intensity of 6080 mE/ms for rooting.

When plantlets with both shoots and roots grew large enough (e.g., reach over half of a GA7 box), they were transferred to soil for acclimatization. During the transfer, the gel was washed from the root tissue with tap water. Established seedlings were transferred to the greenhouse for further analysis and to set seed.

Efficacy testing for sucker growth phenotypes were conducted by growing plants to laybe stage. These plants were topped and axillary bud growth was observed at specific time points after topping.

FIG. 4A show a wild type plant (left) and a plant transformed with RNA construct #1 (SEQ ID NO:55; right) before topping, and FIG. 4B show the wild type plant (top) and the plant transformed with RNA construct #1 (bottom) at the indicated times after topping. FIG. 4C shows the T1 generation of wild type plants (left) and plants transformed with RNA construct #1 (right). The growth of the axillary buds after topping was increased substantially in the transgenic plants relative to the wild type plants. Initiation of axillary bud growth in the transgenic plants was already beginning even before the plant was topped, and the rate of growth was increased for up to 1 week after topping. These results demonstrated that the expression of RNA construct #1 is likely responsible for bud dormancy, and down-regulation of the gene is a factor in sucker initiation and growth.

The sequence of the expression cassette is shown in SEQ ID NO:111, with the relevant portions indicated to the left.

Example 6

Promoter Cloning, Transformation and Analysis

The expression pattern of the 41 candidate genes were analyzed, promoters of the genes with high level expression in axillary bud, but low expression levels in other tissues, were selected (Table 6). Expression pattern of these clones were confirmed by real-time PCR analysis (FIG. 1). Six axillary meristem-specific promoters were cloned by PCR methods from TN90 genomic DNA using gene-specific primers. The sequences of the promoters are shown in SEQ ID NO:113-118.

Expressions of candidate promoters were analyzed by transformation of tobacco with a chimeric candidate promoter::beta-glucuronidase (GUS) reporter gene with the same cassette described in Example 5. The chimeric gene was introduced via *Agrobacterium*-mediated transformation into a NLM line. Gus staining was used to locate promoter expression following the method of Crone et al., 2001, *Plant Cell Environ.,* 24:869-874. Transgenic tobacco tissue was placed in cold 90% Acetone on ice. When all samples were harvested, samples were placed at room temperature for 20 minutes. Acetone was removed from the samples, and staining buffer (0.2% Triton X-100; 50mM NaHPO4 Buffer, pH7.2; 2mM Potassium Ferrocyanide) was added to samples, all the while keeping the samples on ice. X-Gluc was added to the staining buffer to a final concentration of 2mM—from a 100 mM stock solution of X-Gluc in DMF, which must be kept in the dark at −20° C. Staining buffer was removed from samples and fresh staining buffer with X-Gluc was added. The samples were infiltrated under vacuum, on ice, for 15 to 20 minutes. The samples were incubated at 37° C. from 2 hours to overnight. The samples were removed from the incubator and the staining buffer was removed. Samples were washed through an ethanol series (i.e., from 10%, 30%, 50%, 70%; the sample can be heated to 60° C. to get rid of chloroplasts, if desired), to 95%, avoiding light, for 30 min each step. Finally, samples were kept in 100% ethanol.

The GUS-positive plant tissues were examined with a bright field microscope (Leica Q500MC, Cambridge, England) at a low magnification and photographed with a digital camera. See FIGS. 5A and 5B. Results of experiments using two different promoters described herein (SEQ ID NOs:113 and 115) are shown in FIG. 5. Young seedlings were stained. The GUS expression, indicated by the blue staining, is concentrated in the axillary bud, indicating that these two promoters are active in the axillary bud, but not in the stem or leaves (FIG. 5A). The expression of GUS under the direction of the SEQ ID NO:113 promoter also decreased after topping, which coincides with the gene expression pattern that was observed for the endogenous gene that is normally regulated by this promoter (FIG. 5B). These promoter sequences can be used to express genes only or predominantly in the axillary bud while limiting expression in the rest of the plant.

TABLE 6

Selected clones for the promoter analysis

| Contig Number | Length of Promoter | SEQ ID NO |
|---|---|---|
| C5787 | 2248 | 113 |
| C7651 | 2800 | 114 |
| C26207 | 3356 | 115 |
| C12866 | 3150 | 116 |
| C41568 | 2964 | 117 |
| C16249 | 941 | 118 |

Example 7

Efficacy Test of Promoter and Gene Combinations

After testing of the tissue-specific expression patterns of candidate promoters using promoter::GUS fusion analysis in transgenic plants, we constructed serial vectors to express the candidate genes only in the axillary bud. Using *Agrobacterium*-mediated transformation, transgenic plants containing these constructs are generated. The expression of the candidate gene(s) in the transgenic plants can result in the plants suppressing axillary bud growth, resulting from either suppression or over-expression of candidate gene(s).

Some examples are shown as bellow:

Construct 1: Promoter (SEQ ID NO:113) and gene (SEQ ID NO: 17)

Construct 2: Promoter (SEQ ID NO:113) and gene (SEQ ID NO:104)

Construct 3: Promoter (SEQ ID NO:113) and gene (SEQ ID NO: 7)

Construct 4: Promoter (SEQ ID NO:113) and gene (SEQ ID NO: 41)

Construct 5: Promoter (SEQ ID NO:113) and gene (SEQ ID NO: 5)

Construct 6: Promoter (SEQ ID NO:118) and gene (SEQ ID NO: 17)

Construct 7: Promoter (SEQ ID NO:118) and gene (SEQ ID NO:104)

Construct 8: Promoter (SEQ ID NO:118) and gene (SEQ ID NO: 7)

Construct 9: Promoter (SEQ ID NO:118) and gene (SEQ ID NO: 41)

Construct 10: Promoter (SEQ ID NO:118) and gene (SEQ ID NO: 5)

Construct 11: Promoter (SEQ ID NO:115) and gene (SEQ ID NO: 17)

Construct 12: Promoter (SEQ ID NO:115) and gene (SEQ ID NO:104)

Construct 13: Promoter (SEQ ID NO:115) and gene (SEQ ID NO: 7)

Construct 14: Promoter (SEQ ID NO:115) and gene (SEQ ID NO: 41)

Construct 15: Promoter (SEQ ID NO:115) and gene (SEQ ID NO: 5)

Construct 16: Promoter (SEQ ID NO:117) and gene (SEQ ID NO: 17)

Construct 17: Promoter (SEQ ID NO:117) and gene (SEQ ID NO:104)

Construct 18: Promoter (SEQ ID NO:117) and gene (SEQ ID NO: 7)

Construct 19: Promoter (SEQ ID NO:117) and gene (SEQ ID NO: 41)

Construct 20: Promoter (SEQ ID NO:117) and gene (SEQ ID NO: 5)

Efficacy testing for the impact of constructs 1-20 will be carried out under greenhouse and field conditions. Transgenic plants and matched wild type controls will be grown to layby stage and topped. Sucker growth will be quantified with a metric including the total number of suckers, the rate of sucker growth, and the emergence of new suckers after sucker removal. These measurements will be conducted by hand or by digital imaging technology. Field efficacy testing will also determine the type and extent of sucker control chemical application needed under normal agronomical practices. With this metric the effect of gene expression constructs on axillary bud initiation and growth will be compared with wild type plants of the same variety. At the same time, the impact of this technology on costs related to sucker control and any changes in chemical residues found in the final cured leaf will be quantified.

Example 8

TALEN-Mediated Mutagenesis

Transcription activator-like effector nucleases (TALENs) technology was used to carry out genome modification in commercial tobacco varieties such as TN90, K326 and Narrow Leaf Madole. TALENs enable genetic modification through induction of a double strand break (DSB) in a DNA target sequence. The ensuing DNA break repair by either non-homologous end joining (NHEJ) or homology-directed repair (HDR)-mediated pathway can be exploited to introduce the desired modification (e.g. gene disruption, gene correction or gene insertion).

To introduce TALENs and a donor DNA into a plant cell, PEG-mediated protoplast transformation was used. Tobacco leaves of 4-8 weeks old tobacco plants from sterile culture were cut into small pieces and transferred in a petri dish containing filter-sterilized enzyme solution with 1.0% Cellulase onuzuka R10 and 0.5% Macerozym. The leaf strips in the petri dish were vacuum infiltrated for 30 min in the dark using a desiccator. After incubation, the digested leaves were resuspended by shaking at 45 rpm for 230 minutes and then filtered through a sterilized nylon filter (100 μm pore size) by collecting in a 50 ml centrifuge tube. The solution laid on Lymphoprep was separated with the centrifugation at 100 g for 10 min. The protoplast bands were collected using a Pasteur pipette, and purified protoplasts were washed with an equal volume of W5n solution containing with NaCl, $CaCl_2$, KCl, MES and Glucose, and centrifuged for 5 min at 2000 rpm. The protoplast pellets were resuspended at $2\times10^5$/ml in W5n solution, and left on ice for 30 mins. Afterwards, the supernatant was removed and the protoplast pellet was resuspended in filter-sterilized MMM solution containing mannitol, $MgCl_2$ and MES.

The PEG transfection of tobacco protoplasts was performed according to the method described by Zhang et al. (2012) with some modifications. A 500 μl aliquot of the protoplast suspension was transferred into 10 ml culture tube and 25 μl (10 μg) of plasmid DNA was added slowly to the protoplasts suspension. In the protoplast-DNA solution, 525 μl PEG solution was added, and mixed carefully by tapping the tube. The tube was incubated for 20 minutes, then 2.5 ml W5n solution was added to stop the reaction. The solution was centrifuged at 100 g for 5 min, and washed with protoplast culture media. The PEG-treated protoplasts were resuspended in 1 ml culture media containing with 0.1 mg/l NAA and 0.5 mg/l BAP, and mixed with 1 ml low-melting agar to make protoplast beads. The protoplast beads were cultured in liquid media, and calli growing from the protoplast beads were transferred onto solid shooting media. When shoots were well developed, the shoots were transferred in a magenta box for root formation. When root systems were fully developed and shoot growth had resumed, plants were transplanted into soil.

TALEN approaches that can be used to prevent or reduce sucker growth include: (1) for targeted genomic integration in tobacco varieties, gene-specific TALENs and a donor DNA with homology-derived recombination (HDR) are designed; (2) for sucker-specific promoter and target gene insertion in the tobacco genome; and (3) for target gene disruption, gene-specific TALENs with, e.g., non-homologous end joining (NHEJ) are used to direct the TALENs to the target gene disruption.

(1) Targeted Genomic Integration:

(A) Targeted genomic integration of a coding sequence into the promoter region of a gene with highly specific expression in axillary bud:

Instead of random gene insertion using conventional transformation methods, the targeted genomic integration of a coding sequence into the promoter region of a gene with highly specific expression in axillary bud can be used to control the expression of the coding sequence by the endogenous promoter activity. One example of the targeted genomic integration approach is the combination of a promoter (SEQ ID NO:118) and a coding sequence (SEQ ID NO:1). Using such a construct, a coding sequence (or more than one coding sequence) is homologously recombined into the genomic region of the promoter sequence and controlled by the promoter.

A TALEN donor sequence is shown in SEQ ID NO:119 (the promoter and target sequences are underlined, and the target gene sequence is in bold), and a TALEN target sequence is shown in SEQ ID NO:120 (the target sequences are underlined).

(B) Targeted genomic integration of a promoter and a coding sequence into the promoter region of a gene with highly specific expression in axillary bud:

To effectively provide a double dose of promoter control, a sucker-specific promoter and a coding sequence can be inserted into the promoter region of a gene highly expressed in axillary bud. In this approach, two promoters work together to control the coding sequence (or coding sequences). For example, in one end of a promoter (SEQ ID NO:118), a construct including a promoter (SEQ ID NO:113) and a coding sequence (SEQ ID NO:13) is inserted using TALEN technology, thereby directing expression of the coding sequence by both promoters (SEQ ID NO:118 and 113).

A TALEN donor sequence is shown in SEQ ID NO:121 (the endogenous promoter is underlined, the exogenous promoter is italicized, and the target gene is in bold).

(C) Sucker-specific promoter and coding sequence insertion

Another option of targeted gene integration is to insert a selected tobacco promoter and coding sequence into an effective location of the tobacco genome by TALEN.

(2) Target Gene Disruption

To disrupt the function of candidate genes without using RNAi constructs, gene-specific TALENs were designed and introduced into tobacco cells, resulting in deletions or insertions to knockout the endogenous gene (or genes). For example, potential TALEN target sites in a coding sequence (SEQ ID NO:104) were identified, and homologous recombination sites within the coding sequence of the gene were selected.

A TALEN target sequence is shown in SEQ ID NO:122 (the target sequences are underlined).

Example 9

Additional Transgenic Strategies

The following strategies to regulate sucker outgrowth are described herein.

The first strategy applied was to regulate axillary bud outgrowth gene expression. Mutant studies in *Arabidopsis,* rice, and barley suggest that the genetic pathways that regulate branching are complex. There are two general classes of genes that regulate branching. One class of genes restricts the out-growth of buds and is defined by mutants with increased branching. See, for example, the *Arabidopsis* BRANCHED1 gene (e.g., SEQ ID NO:81 and the possible tobacco homologs shown in SEQ ID NOs: 1, 13, 35, 37, 39) and the *Arabidopsis* More Axillary Branching (MAX) gene. The other class of genes promotes axillary meristem development and is defined by mutants with decreased branching. See, for example, the *Arabidopsis* Lateral Suppressor (LAS) gene and the possible homologues in tobacco (e.g., SEQ ID NOs: 71 or 73) as well as the *Arabidopsis* Regulator of Axillary Meristems (RAX) and the possible tobacco homologous (e.g., SEQ ID NOs: 75 and 77).

The second strategy applied was to regulate tobacco cytokinin synthesis and distribution. As a plant hormone, cytokinin plays many regulatory roles in shoot growth, retardation of leaf senescence, inhibition of root growth, seed germination, and stress responses. It is well-known that cytokinin promotes axillary bud outgrowth. When cytokinin is applied directly to axillary buds or supplied via the xylem stream, side branches are increased. Cytokinin oxidase/dehydrogenase (CKX) is an enzyme that degrades cytokinin. Overexpression of individual CKX genes established cytokinin deficient plants and revealed that cytokinin is a positive regulator of the shoot meristem activity. On the other hand, reduced expression of CKX in rice causes cytokinin accumulation in shoot meristems, which increases the number of buds such as floral buds, ultimately resulting in enhanced grain yield. Based on these results, CKX expression in axillary buds can inhibit or delay axillary bud outgrowth in tobacco after the shoot apical meristem has been topped.

Decapitation of the shoot apex releases axillary buds from their dormancy and they begin to grow out. Auxin derived from an intact shoot apex suppresses axillary bud outgrowth, whereas cytokinin induced by decapitation of the shoot apex stimulates axillary bud outgrowth. Depletion of cytokinin in the axillary bud region by overexpression of the relevant enzymes under control of an axillary bud specific promoter can be used to inhibit axillary meristem outgrowth. The candidate genes involved in this strategy are Arabidopsis cytokinin oxidase (CKX; SEQ ID NO:55 encoding SEQ ID NO:56); tobacco CKXs (SEQ ID NOs:57, 59, or 61); and tobacco adenosine phosphate-isopentenyltransferase (IPT) (SEQ ID NO: 61).

The third strategy applied was to control axillary bud outgrowth by destroying axillary apical meristem development. There are two types of the expression of transgenes in transgenic plants: constitutive expression and tissue specific expression. The constitutive gene expression can result in unexpected problems if a gene of critical importance in a certain tissue is miss-expressed in other tissues. Unlike constitutive expression of genes, tissue-specific expression is the result of gene regulation in a target tissue. For tissue-specific expression, promoters can control the expression of given genes in a tissue-dependent manner and according to the developmental stage of the plant. In our case, the promoters were obtained from genes specifically expressed in axillary buds, and the promoters were defined to regulate gene expression in buds. To control sucker growth after topping of a shoot apical meristem, the promoters (or modified promoters) can be used to direct expression of a heterologous gene in tobacco plants. As a result of axillary bud-specific expression, the heterologous gene (or the transgene) operably linked to the promoter is expressed in axillary buds where expression of the transgene is desired, leaving the rest of the plant unaffected by transgene expression.

Shoot meristems of plants are composed of stem cells that are continuously replenished through a classical feedback circuit involving the homeobox WUSCHEL (WUS) gene and the CLAVATA (CLV) gene signaling pathway. Targeting of the WUSHEL sequence or overexpression of the CLAVATA gene in axillary buds alters the pathway and causes a defect in shoot meristem development and inhibits shoot outgrowth. The candidate genes are WUS (SEQ ID NOs: 63 and 65) and CLV3 (SEQ ID NO: 67).

The CENTRORADIALIS (CEN) gene, which is required for indeterminate growth of the shoot meristem in Antirrhinum, was cloned and characterized. When the gene is expressed in tobacco, the tobacco plants showed an extended vegetative phase, delaying the switch to flowering. In tobacco, the CET genes (from "CEN-like genes from tobacco") are not expressed in the main shoot meristem; their expression is restricted to vegetative axillary meristems. It is clear that CET genes play a role in the development of vegetative axillary meristems to axillary bud growth, however, their actual function remains unknown. When their expression is silenced using an RNAi_CET construct, the transgenic plants show bud growth retardation after topping.

Example 10

Experimental Data

Plant tissues were stained for GUS by immersion in a staining solution (50 mM sodium phosphate buffer, pH 7.0, 1 mM EDTA, 0.5 mg/mL 5-bromo-4-chloro-3-indolyl -D GlcUA [X-Gluc; Biosynth AG], 0.4% Triton X-100, and 5 mM each of potassium ferri/ferrocyanide), and incubated at 37 ° C. for 6-24 h.

The promoter shown in SEQ ID NO:117 has been shown to be a good candidate for specific expression in the axillary bud before topping and for 15 days after topping. There was no expression in the shoot apical meristem region before topping. The promoter shown in SEQ ID NO:117 (about 2.5 kb) is the 5'end upstream of sequence of SEQ ID NO: 27, which encodes eukaryotic translation initiation factor 3, subunit A (eIF-3A), a component of the eukaryotic translation initiation factor 3 (eIF-3) complex, which is required for several steps in the initiation of protein synthesis.

Several genes were stacked by co-transformation to overexpress and/or knock down using, for example, RNAi, under the control of the promoter shown in SEQ ID NO:117. The following are the constructs and genes that were stacked together by co-transformation.

a) Promoter SEQ ID NO:117—RNAi_CET2-26-6, which targets CET2, SEQ ID NO: 11 and SEQ ID NO:49;

b) Promoter SEQ ID NO:117—RNAi_CET2-26-6, co-transformed with Promoter SEQ ID NO:117—AtBRC$_1$ (SEQ ID NO:81);

c) Promoter SEQ ID NO:117—RNAi_CET2-26-6, co-transformed with Promoter SEQ ID NO:117—SEQ ID NO: 1; and d) Promoter SEQ ID NO:117—SEQ ID NO: 1, co-transformed with Promoter SEQ ID NO:117—AtBRC$_1$ (SEQ ID NO:81).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

What is claimed is:

1. A method of reducing axillary bud growth in a tobacco plant, comprising introducing a heterologous nucleic acid molecule operably linked to a promoter comprising a sequence selected from the group consisting of SEQ ID NOs: 113-118 into tobacco cells to produce transgenic tobacco cells, and regenerating transgenic tobacco plants from the transgenic tobacco cells, the heterologous nucleic acid molecule comprising a nucleic acid sequence encoding a polypeptide having at least 95% sequence identity to the amino acid sequence encoded by SEQ ID NO: 79, wherein the transgenic tobacco plants exhibit reduced axillary bud growth after topping as compared to control tobacco plants not expressing said heterologous nucleic acid molecule.

2. The method of claim 1, wherein the heterologous nucleic acid molecule has 100% sequence identity to SEQ ID NO: 79.

3. The method of claim 1, further comprising selecting at least one of the transgenic tobacco plants that exhibits reduced axillary bud growth relative to a control tobacco plant not expressing the heterologous nucleic acid molecule.

4. The method of claim 1, wherein the nucleic acid molecule is introduced into the tobacco cells using particle bombardment, Agrobacterium-mediated transformation, microinjection, polyethylene glycol-mediated transformation, liposome-mediated DNA uptake, or electroporation.

5. The method of claim 1, wherein the tobacco plant is selected from the group consisting of a Burley type, a dark type, a flue-cured type, a Maryland type, and an Oriental type.

6. The method of claim 1, wherein the tobacco plant is a variety selected from the group consisting of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight 1-120, Speight NF3, TI 1406, TI 1269, TN 86, TN86LC, TN 90, TN90LC, TN 97, TN97LC, TN D94, TN D950, TR (Tom Rosson) Madole, VA 309, or VA359.

7. The method of claim 1, wherein said nucleic acid molecule encodes a polypeptide having at least 98% amino acid sequence identity to SEQ ID NO: 80.

8. The method of claim 1, wherein said nucleic acid molecule encodes a polypeptide having at least 99% amino acid sequence identity to SEQ ID NO: 80.

9. The method of claim 1, wherein said nucleic acid molecule encodes a polypeptide having 100% amino acid sequence identity to SEQ ID NO: 80.

* * * * *

SEQUENCE LISTING

<160> NUMBER OF SEQ ID NOS: 196

<210> SEQ ID NO 1
<211> LENGTH: 987
<212> TYPE: DNA
<213> ORGANISM: Nicotiana tabacum

<400> SEQUENCE: 1
atgtatccgc caagcaacag ctgcaactac agccccattt tcaacatccc ttctccttgt 60
atgcaatatg gagacgaact attcttccaa tattatcctg accatttcct tcaacagcaa 120
caagtgcctt tgatagaaga tcagagtgtt gacatcttag ctgattgcac tgagaatgtt 180
actaacgaag aaactgtcat caatactgat actgtaaaag ttctttatga cacaggagct 240
gttacaaaca gtcagtgttg gggaggaaat gaagaagtag aagaaggccg cgaaaacaaa 300
agaaatgaca tgagaagcac cattagtatt attcatgtac ggaaaaacaa gaaatgttcc 360
aataaagatc gacatagcaa gattaacact gctcgtggcc tcagagaccg aaggatgaga 420
ctttcccttg atgcagctcg caagtttttc agtttacaag acatgttggg gttcgataag 480
gcaagtaaaa ctgtagaatg gttgcttatc aaatcggagt ctgaaatcga agagctagcc 540
aaaggcaata aaggaggagg cattcctaaa caaagctgca gtactactaa tggaattggt 600
gcaattagta ctgcaatatc ctctatttct gagtgtgagg ttatatcagg aactgatgaa 660
tctttctcta ttacttataa aaagaagctg aaaactgcta aaggagcctc gaaaaagacg 720
gctaaaactg ctcgtagagc tgcatttgat cgtcttatta caagggaaac gaggaatcaa 780
gcaagggcta gggctagaga gagaacaaaa ataaagaaaa gcctcggtaa atccaaagag 840
aacagtgctg attactgtaa tttggtggat aattatggag attggagtca atttagtatc 900
ttcaactatc agaaaaatgc agttggaatt tcccatgatc aggtgggttc aataattaaa 960
caacatgatt ttttaggatt tcaatag 987

<210> SEQ ID NO 2
<211> LENGTH: 328
<212> TYPE: PRT
<213> ORGANISM: Nicotiana tabacum

<400> SEQUENCE: 2

Met Tyr Pro Pro Ser Asn Ser Cys Asn Tyr Ser Pro Ile Phe Asn Ile
1 5 10 15

Pro Ser Pro Cys Met Gln Tyr Gly Asp Glu Leu Phe Phe Gln Tyr Tyr
20 25 30

Pro Asp His Phe Leu Gln Gln Gln Gln Val Pro Leu Ile Glu Asp Gln
35 40 45

Ser Val Asp Ile Leu Ala Asp Cys Thr Glu Asn Val Thr Asn Glu Glu
50 55 60

Thr Val Ile Asn Thr Asp Thr Val Lys Val Leu Tyr Asp Thr Gly Ala
65 70 75 80

Val Thr Asn Ser Gln Cys Trp Gly Gly Asn Glu Glu Val Glu Glu Gly
85 90 95

Arg Glu Asn Lys Arg Asn Asp Met Arg Ser Thr Ile Ser Ile Ile His
100 105 110

Val Arg Lys Asn Lys Lys Cys Ser Asn Lys Asp Arg His Ser Lys Ile
115 120 125

Asn Thr Ala Arg Gly Leu Arg Asp Arg Arg Met Arg Leu Ser Leu Asp
130 135 140

-continued

```
Ala Ala Arg Lys Phe Phe Ser Leu Gln Asp Met Leu Gly Phe Asp Lys
145                 150                 155                 160

Ala Ser Lys Thr Val Glu Trp Leu Leu Ile Lys Ser Glu Ser Glu Ile
                165                 170                 175

Glu Glu Leu Ala Lys Gly Asn Lys Gly Gly Gly Ile Pro Lys Gln Ser
            180                 185                 190

Cys Ser Thr Thr Asn Gly Ile Gly Ala Ile Ser Thr Ala Ile Ser Ser
        195                 200                 205

Ile Ser Glu Cys Glu Val Ile Ser Gly Thr Asp Glu Ser Phe Ser Ile
    210                 215                 220

Thr Tyr Lys Lys Lys Leu Lys Thr Ala Lys Gly Ala Ser Lys Lys Thr
225                 230                 235                 240

Ala Lys Thr Ala Arg Arg Ala Ala Phe Asp Arg Leu Ile Thr Arg Glu
                245                 250                 255

Thr Arg Asn Gln Ala Arg Ala Arg Ala Arg Glu Arg Thr Lys Ile Lys
            260                 265                 270

Lys Ser Leu Gly Lys Ser Lys Glu Asn Ser Ala Asp Tyr Cys Asn Leu
        275                 280                 285

Val Asp Asn Tyr Gly Asp Trp Ser Gln Phe Ser Ile Phe Asn Tyr Gln
    290                 295                 300

Lys Asn Ala Val Gly Ile Ser His Asp Gln Val Gly Ser Ile Ile Lys
305                 310                 315                 320

Gln His Asp Phe Leu Gly Phe Gln
                325
```

<210> SEQ ID NO 3
<211> LENGTH: 318
<212> TYPE: DNA
<213> ORGANISM: Nicotiana tabacum

<400> SEQUENCE: 3

```
atggctcgct ccttgtgttt catggcattt gcagtcttgg caatgatgct ctttgttgcc     60

tatgaggttc aagctagaga atgcaaaaca gaaagcaata cattccctgg attatgcatt    120

accaaaccac catgcagaaa agcttgtatc agtgagggat ttactgatgg tcattgtagc    180

aaaatcctca gaaggtgcct atgcactaag ccatgtgtgt tcgatgagaa gatgatcaaa    240

acaggagctg aaactttgc tgaggaagca aaaactttgg ctgcagcttt gcttgaagaa    300

gagataatgg ataactaa                                                   318
```

<210> SEQ ID NO 4
<211> LENGTH: 105
<212> TYPE: PRT
<213> ORGANISM: Nicotiana tabacum

<400> SEQUENCE: 4

```
Met Ala Arg Ser Leu Cys Phe Met Ala Phe Ala Val Leu Ala Met Met
1               5                   10                  15

Leu Phe Val Ala Tyr Glu Val Gln Ala Arg Glu Cys Lys Thr Glu Ser
            20                  25                  30

Asn Thr Phe Pro Gly Leu Cys Ile Thr Lys Pro Pro Cys Arg Lys Ala
        35                  40                  45

Cys Ile Ser Glu Gly Phe Thr Asp Gly His Cys Ser Lys Ile Leu Arg
    50                  55                  60

Arg Cys Leu Cys Thr Lys Pro Cys Val Phe Asp Glu Lys Met Ile Lys
65                  70                  75                  80
```

-continued

```
Thr Gly Ala Glu Thr Phe Ala Glu Glu Ala Lys Thr Leu Ala Ala Ala
                85                  90                  95

Leu Leu Glu Glu Glu Ile Met Asp Asn
            100                 105


<210> SEQ ID NO 5
<211> LENGTH: 1797
<212> TYPE: DNA
<213> ORGANISM: Nicotiana tabacum

<400> SEQUENCE: 5

atggcttctc ttccccttct caccaccaat gccatctctt catcagcttc ttctttaacc      60

accacacctc tttccaattt gcattcttct cctttcttta caaagacatc aaaagtttcc     120

actatagata agtgcagtaa ctatcgtttc caagtttcat gcaagggtac agaagatgac     180

caaaccatca acacttccaa atcttctgat tcttcaaaca ataagatcat tgatagaaga     240

aacatgctac ttggattagg aggcatttat ggtgctgcta ctcttgttgg tggtcatccc     300

tttgccttcg cggctcctgt gcccggacct gacgtttcca aatgtggtcc tgcagatttg     360

ccaccaggtg cagcaccagt caactgttgt cctccgacaa cggcgaacat catcgacttc     420

caacttccac caccgtcaac caccctccgt acacggccag cagctcattc cgccgatagt     480

gcctatatag agaaattcaa cagagctatt cagctcatga aacaacttcc agataacgat     540

ccacgtagct tcaagcaaca agcaaatgtt cattgtgctt actgtgatgg agcttatgga     600

caactaggtt tcccaagttc tgaactccaa gttcattcct cttggctttt cttccctttc     660

catcgttgtt atctctactt cttcgaaaaa atcttgggaa gtttaataaa tgaccctact     720

ttcgctatcc cattttggaa ctgggatcat cctgatggca tgagacttcc ggccatgtat     780

gcgaaccgta gttcttctct cttcgatcct ctccgtgatc agaagcatca gcctccggtc     840

attgttgatc tcgacttcaa tggagcggat cctaacataa gtaacgctca acaaacttcc     900

cagaatctga caatcatgta taggcaaatg gtctctctag gaagtactcc ggcagctttc     960

ctcggagacc cttaccgtgc cggtggcgaa ccgggtggtg ctgggtccct cgagaacatt    1020

ccacatggaa cggtccatgt ttggaccggt gatagaaccc aacctaattt tgaaaatatg    1080

ggagtttttt atgcagctgg tagagaccct attttctatg ctcatcattc taatattgat    1140

agattgtgga gtgtttggaa aaccctaggt ggaagacgtc aagattttac tgaccctgat    1200

tttttaaatt cttcgttttt gttttacgat gagaaagcac aaatggtacg tattagggta    1260

cgtgactgtt tggatacaac aagacttgga tacgtttatc aaggtgtagt taatccgtgg    1320

ataaattctc gtccaagggc tagggtttca agtgctttga gtagcgtaag gaggcttgct    1380

gaagcaaaag attatttccc aacaaaactt ggccatgtga taagagtaat ggtgaaaagg    1440

ccaaataata aaaagagaaa caaggaggag aaagatgcaa aagaggagtt tttagtggtt    1500

gaagggatag agctggaaac tgatgttttt gtcaagtttg atgtgttgat taatgatgaa    1560

gatgagactg taatttcgcc gaataatgct gagtttgcag gtagttttgt gaacgtgcca    1620

catcttagtc atggtaagag tgacgagaaa cgtaagacta agttgaagtt ggctataact    1680

gagctgctgg aagatttaga tgctgaggat gatgatcatg tggtggtgac ttttgttcca    1740

aagaatggtt ctggtgctgt gaaaattgga ggtgtcaaga ttgtgcttga ggattga       1797


<210> SEQ ID NO 6
<211> LENGTH: 598
<212> TYPE: PRT
<213> ORGANISM: Nicotiana tabacum
```

-continued

```
<400> SEQUENCE: 6

Met Ala Ser Leu Pro Leu Leu Thr Thr Asn Ala Ile Ser Ser Ser Ala
1               5                   10                  15

Ser Ser Leu Thr Thr Thr Pro Leu Ser Asn Leu His Ser Ser Pro Phe
            20                  25                  30

Phe Thr Lys Thr Ser Lys Val Ser Thr Ile Asp Lys Cys Ser Asn Tyr
        35                  40                  45

Arg Phe Gln Val Ser Cys Lys Gly Thr Glu Asp Asp Gln Thr Ile Asn
    50                  55                  60

Thr Ser Lys Ser Ser Asp Ser Ser Asn Asn Lys Ile Ile Asp Arg Arg
65                  70                  75                  80

Asn Met Leu Leu Gly Leu Gly Gly Ile Tyr Gly Ala Ala Thr Leu Val
                85                  90                  95

Gly Gly His Pro Phe Ala Phe Ala Ala Pro Val Pro Gly Pro Asp Val
            100                 105                 110

Ser Lys Cys Gly Pro Ala Asp Leu Pro Pro Gly Ala Ala Pro Val Asn
        115                 120                 125

Cys Cys Pro Pro Thr Thr Ala Asn Ile Ile Asp Phe Gln Leu Pro Pro
    130                 135                 140

Pro Ser Thr Thr Leu Arg Thr Arg Pro Ala Ala His Ser Ala Asp Ser
145                 150                 155                 160

Ala Tyr Ile Glu Lys Phe Asn Arg Ala Ile Gln Leu Met Lys Gln Leu
                165                 170                 175

Pro Asp Asn Asp Pro Arg Ser Phe Lys Gln Gln Ala Asn Val His Cys
            180                 185                 190

Ala Tyr Cys Asp Gly Ala Tyr Gly Gln Leu Gly Phe Pro Ser Ser Glu
        195                 200                 205

Leu Gln Val His Ser Ser Trp Leu Phe Phe Pro Phe His Arg Cys Tyr
    210                 215                 220

Leu Tyr Phe Phe Glu Lys Ile Leu Gly Ser Leu Ile Asn Asp Pro Thr
225                 230                 235                 240

Phe Ala Ile Pro Phe Trp Asn Trp Asp His Pro Asp Gly Met Arg Leu
                245                 250                 255

Pro Ala Met Tyr Ala Asn Arg Ser Ser Ser Leu Phe Asp Pro Leu Arg
            260                 265                 270

Asp Gln Lys His Gln Pro Pro Val Ile Val Asp Leu Asp Phe Asn Gly
        275                 280                 285

Ala Asp Pro Asn Ile Ser Asn Ala Gln Gln Thr Ser Gln Asn Leu Thr
    290                 295                 300

Ile Met Tyr Arg Gln Met Val Ser Leu Gly Ser Thr Pro Ala Ala Phe
305                 310                 315                 320

Leu Gly Asp Pro Tyr Arg Ala Gly Gly Glu Pro Gly Gly Ala Gly Ser
                325                 330                 335

Leu Glu Asn Ile Pro His Gly Thr Val His Val Trp Thr Gly Asp Arg
            340                 345                 350

Thr Gln Pro Asn Phe Glu Asn Met Gly Val Phe Tyr Ala Ala Gly Arg
        355                 360                 365

Asp Pro Ile Phe Tyr Ala His His Ser Asn Ile Asp Arg Leu Trp Ser
    370                 375                 380

Val Trp Lys Thr Leu Gly Gly Arg Arg Gln Asp Phe Thr Asp Pro Asp
385                 390                 395                 400

Phe Leu Asn Ser Ser Phe Leu Phe Tyr Asp Glu Lys Ala Gln Met Val
```

-continued

```
                405                 410                 415

Arg Ile Arg Val Arg Asp Cys Leu Asp Thr Thr Arg Leu Gly Tyr Val
            420                 425                 430

Tyr Gln Gly Val Val Asn Pro Trp Ile Asn Ser Arg Pro Arg Ala Arg
        435                 440                 445

Val Ser Ser Ala Leu Ser Ser Val Arg Arg Leu Ala Glu Ala Lys Asp
    450                 455                 460

Tyr Phe Pro Thr Lys Leu Gly His Val Ile Arg Val Met Val Lys Arg
465                 470                 475                 480

Pro Asn Asn Lys Lys Arg Asn Lys Glu Glu Lys Asp Ala Lys Glu Glu
                485                 490                 495

Phe Leu Val Val Glu Gly Ile Glu Leu Glu Thr Asp Val Phe Val Lys
            500                 505                 510

Phe Asp Val Leu Ile Asn Asp Glu Asp Glu Thr Val Ile Ser Pro Asn
        515                 520                 525

Asn Ala Glu Phe Ala Gly Ser Phe Val Asn Val Pro His Leu Ser His
    530                 535                 540

Gly Lys Ser Asp Glu Lys Arg Lys Thr Lys Leu Lys Leu Ala Ile Thr
545                 550                 555                 560

Glu Leu Leu Glu Asp Leu Asp Ala Glu Asp Asp Asp His Val Val Val
                565                 570                 575

Thr Phe Val Pro Lys Asn Gly Ser Gly Ala Val Lys Ile Gly Gly Val
            580                 585                 590

Lys Ile Val Leu Glu Asp
        595


<210> SEQ ID NO 7
<211> LENGTH: 1392
<212> TYPE: DNA
<213> ORGANISM: Nicotiana tabacum

<400> SEQUENCE: 7

atggtaggca aaagaaatga gcctcatgtc atatttgtac cttacccaag ccaaggtcac      60

attaaccctc ttctccaatt tgcaaaacgc ttatactcca aaggtgtaaa agcaacttta     120

gccactacta aatacacagt caagtctatt aattcaccca acatttcagt tgaagcaatt     180

tctgatggat ttgacgaaag tggtttttcc caagcccaaa aagcagatat atatctcaaa     240

tcattcaaag aaaatggttc aacaactcta tcagaaataa taaaaaatta cgagaattcg     300

acacatccga taagttgcat tgtttatgat tcgtttttac catgggctct tgatgtggct     360

aaaaaacatg ggatttatgg agctgcgttt tttacaaatt cagccactgt ttgtgtagtt     420

tttgctcaca ttcattataa aacattttca ttgccggcga agattgaaga aaatgagcca     480

ttgttattgc ctggattgcc tagtttgtac ccaattgatg ttcctggatt tattagggag     540

cctgaaagtt accctgctta cttagccatg aaaatgagtc aattctctaa tttggaaaat     600

gctgattggg tttttgataa ctcctttcaa gaactagaag gagagatagc aagtggagtt     660

tcaaatattt ggccagcaag gttaattgga ccaatggtgc catcatccta tttagatgac     720

ataatagaag gtgacaaagg gtacggagca agtctatgga aaccacttag tgaagaatgt     780

ctcaaatggc taaaaacaaa gccaaatcaa tcagtaatct acatttcttt tggcagcatg     840

gtatcactca caccacaaca aatggaagaa atggcaaatg ctttaataga cagcaacatg     900

aatttccttt gggttgtaag agaaaccgaa aaaggcaaat tgccaaaaaa attcatagaa     960

tccacaattg gaaaagggtt aattgtgtca tggtgcaatc aattagaaat gctagcaaat    1020
```

-continued

```
caagccattg gttgttttgt gactcattgt ggatggaatt cgactcttga aggattgagc   1080

cttggcgtgc caatggtggc aatgccacaa tggtctgatc aaatgacgga tgctaaattt   1140

ataggtgaga tttgggaaat tggtgtgagg cctaagttgg ataagtttgg gattgttaga   1200

agagaagagc tattgttttg tttaaaggaa gtaatgggag ggaagaggag ttatgagatt   1260

aggagaaatg ctggaaaatg gaagaacttg gctaagaaag caattagtga aggaggtagc   1320

tcggacaagt ctattaatgt atttgtgaac agtcttagtc tagcatgcca gatgaagaag   1380

tacaagaaat aa                                                        1392
```

```
<210> SEQ ID NO 8
<211> LENGTH: 463
<212> TYPE: PRT
<213> ORGANISM: Nicotiana tabacum

<400> SEQUENCE: 8

Met Val Gly Lys Arg Asn Glu Pro His Val Ile Phe Val Pro Tyr Pro
1               5                   10                  15

Ser Gln Gly His Ile Asn Pro Leu Leu Gln Phe Ala Lys Arg Leu Tyr
            20                  25                  30

Ser Lys Gly Val Lys Ala Thr Leu Ala Thr Thr Lys Tyr Thr Val Lys
        35                  40                  45

Ser Ile Asn Ser Pro Asn Ile Ser Val Glu Ala Ile Ser Asp Gly Phe
    50                  55                  60

Asp Glu Ser Gly Phe Ser Gln Ala Gln Lys Ala Asp Ile Tyr Leu Lys
65                  70                  75                  80

Ser Phe Lys Glu Asn Gly Ser Thr Thr Leu Ser Glu Ile Ile Lys Asn
                85                  90                  95

Tyr Glu Asn Ser Thr His Pro Ile Ser Cys Ile Val Tyr Asp Ser Phe
            100                 105                 110

Leu Pro Trp Ala Leu Asp Val Ala Lys Lys His Gly Ile Tyr Gly Ala
        115                 120                 125

Ala Phe Phe Thr Asn Ser Ala Thr Val Cys Val Val Phe Ala His Ile
    130                 135                 140

His Tyr Lys Thr Phe Ser Leu Pro Ala Lys Ile Glu Glu Asn Glu Pro
145                 150                 155                 160

Leu Leu Leu Pro Gly Leu Pro Ser Leu Tyr Pro Ile Asp Val Pro Gly
                165                 170                 175

Phe Ile Arg Glu Pro Glu Ser Tyr Pro Ala Tyr Leu Ala Met Lys Met
            180                 185                 190

Ser Gln Phe Ser Asn Leu Glu Asn Ala Asp Trp Val Phe Asp Asn Ser
        195                 200                 205

Phe Gln Glu Leu Glu Gly Glu Ile Ala Ser Gly Val Ser Asn Ile Trp
    210                 215                 220

Pro Ala Arg Leu Ile Gly Pro Met Val Pro Ser Ser Tyr Leu Asp Asp
225                 230                 235                 240

Ile Ile Glu Gly Asp Lys Gly Tyr Gly Ala Ser Leu Trp Lys Pro Leu
                245                 250                 255

Ser Glu Glu Cys Leu Lys Trp Leu Lys Thr Lys Pro Asn Gln Ser Val
            260                 265                 270

Ile Tyr Ile Ser Phe Gly Ser Met Val Ser Leu Thr Pro Gln Gln Met
        275                 280                 285

Glu Glu Met Ala Asn Ala Leu Ile Asp Ser Asn Met Asn Phe Leu Trp
    290                 295                 300
```

Val Val Arg Glu Thr Glu Lys Gly Lys Leu Pro Lys Lys Phe Ile Glu
305 310 315 320

Ser Thr Ile Gly Lys Gly Leu Ile Val Ser Trp Cys Asn Gln Leu Glu
325 330 335

Met Leu Ala Asn Gln Ala Ile Gly Cys Phe Val Thr His Cys Gly Trp
340 345 350

Asn Ser Thr Leu Glu Gly Leu Ser Leu Gly Val Pro Met Val Ala Met
355 360 365

Pro Gln Trp Ser Asp Gln Met Thr Asp Ala Lys Phe Ile Gly Glu Ile
370 375 380

Trp Glu Ile Gly Val Arg Pro Lys Leu Asp Lys Phe Gly Ile Val Arg
385 390 395 400

Arg Glu Glu Leu Leu Phe Cys Leu Lys Glu Val Met Gly Gly Lys Arg
405 410 415

Ser Tyr Glu Ile Arg Arg Asn Ala Gly Lys Trp Lys Asn Leu Ala Lys
420 425 430

Lys Ala Ile Ser Glu Gly Gly Ser Ser Asp Lys Ser Ile Asn Val Phe
435 440 445

Val Asn Ser Leu Ser Leu Ala Cys Gln Met Lys Lys Tyr Lys Lys
450 455 460

<210> SEQ ID NO 9
<211> LENGTH: 405
<212> TYPE: DNA
<213> ORGANISM: Nicotiana tabacum

<400> SEQUENCE: 9
atggcaggga aggttgagaa agtgcttgca gtagtgatgc ttgcaatgct tctgttttcg 60
gagcatttaa tggctgctaa tcatgaaatt aaaacaactg aagataactc tactattagc 120
cctttctgct tagtaaaatg tttatttgga tgtagggggt tgccacctgt acaagcatcc 180
atttgtgctg ctcaatgtta tttaaagtgc cgtgaccaag atgcggccaa tattgctgaa 240
actaagggca taattggtga gactgcatac aaccagtatg atgttggatg tgcccttggc 300
tactgctctg agttcctgtt gaattatgat gagaagaggt tcaagtgctg catggaatac 360
tgccgcgagg acaaaatgat ttgtcctgtt gaggctgcag cttga 405

<210> SEQ ID NO 10
<211> LENGTH: 134
<212> TYPE: PRT
<213> ORGANISM: Nicotiana tabacum

<400> SEQUENCE: 10

Met Ala Gly Lys Val Glu Lys Val Leu Ala Val Val Met Leu Ala Met
1 5 10 15

Leu Leu Phe Ser Glu His Leu Met Ala Ala Asn His Glu Ile Lys Thr
20 25 30

Thr Glu Asp Asn Ser Thr Ile Ser Pro Phe Cys Leu Val Lys Cys Leu
35 40 45

Phe Gly Cys Arg Gly Leu Pro Pro Val Gln Ala Ser Ile Cys Ala Ala
50 55 60

Gln Cys Tyr Leu Lys Cys Arg Asp Gln Asp Ala Ala Asn Ile Ala Glu
65 70 75 80

Thr Lys Gly Ile Ile Gly Glu Thr Ala Tyr Asn Gln Tyr Asp Val Gly
85 90 95

```
Cys Ala Leu Gly Tyr Cys Ser Glu Phe Leu Leu Asn Tyr Asp Glu Lys
            100                 105                 110

Arg Phe Lys Cys Cys Met Glu Tyr Cys Arg Glu Asp Lys Met Ile Cys
        115                 120                 125

Pro Val Glu Ala Ala Ala
    130


<210> SEQ ID NO 11
<211> LENGTH: 630
<212> TYPE: DNA
<213> ORGANISM: Nicotiana tabacum

<400> SEQUENCE: 11

atgaattcaa agaaaaacaa ctcaccaaga aaaaggttga gaaaatatca tacaagaaaa      60

gctcctatta ttagctctta tatggacatg gctgaagcta gaagagaaat tgttcatgct     120

ttacaacttc atcgatcttc atcttcatct ccaactccgt ctattaatag cccaaagaag     180

tacacattat tgggtcaagg agttgtaagc tctcaacaat attactatta ctcaatagtg     240

gaatctatgc ctattcctga accaacatgg tctacaacgg ctccggcaat acttaatgca     300

ctgccaccgc tgccgctgcc gctgccgcca cctccgccgc tgtcttcttc ttccggtgaa     360

gttccagagt ttgaatggtg gatagggttt ttgaagtcgt tggacggcaa gaagagtgct     420

aacaatggtg aagtagtcat agaaaaatat tttcctctag aagaaaatgt tttgatggaa     480

aattcaaaga caggttttgg tcaattagaa catggattaa acagtgagtc tcctaattgt     540

atagataaga atgatgatcc taattaccaa tttccagatg agtggttgat tatccctaca     600

gctgatgatg attatgtact tgagctttaa                                      630


<210> SEQ ID NO 12
<211> LENGTH: 209
<212> TYPE: PRT
<213> ORGANISM: Nicotiana tabacum

<400> SEQUENCE: 12

Met Asn Ser Lys Lys Asn Asn Ser Pro Arg Lys Arg Leu Arg Lys Tyr
1               5                   10                  15

His Thr Arg Lys Ala Pro Ile Ile Ser Ser Tyr Met Asp Met Ala Glu
            20                  25                  30

Ala Arg Arg Glu Ile Val His Ala Leu Gln Leu His Arg Ser Ser Ser
        35                  40                  45

Ser Ser Pro Thr Pro Ser Ile Asn Ser Pro Lys Lys Tyr Thr Leu Leu
    50                  55                  60

Gly Gln Gly Val Val Ser Ser Gln Gln Tyr Tyr Tyr Tyr Ser Ile Val
65                  70                  75                  80

Glu Ser Met Pro Ile Pro Glu Pro Thr Trp Ser Thr Thr Ala Pro Ala
                85                  90                  95

Ile Leu Asn Ala Leu Pro Pro Leu Pro Leu Pro Leu Pro Pro Pro Pro
            100                 105                 110

Pro Leu Ser Ser Ser Ser Gly Glu Val Pro Glu Phe Glu Trp Trp Ile
        115                 120                 125

Gly Phe Leu Lys Ser Leu Asp Gly Lys Lys Ser Ala Asn Asn Gly Glu
    130                 135                 140

Val Val Ile Glu Lys Tyr Phe Pro Leu Glu Glu Asn Val Leu Met Glu
145                 150                 155                 160

Asn Ser Lys Thr Gly Phe Gly Gln Leu Glu His Gly Leu Asn Ser Glu
                165                 170                 175
```

```
Ser Pro Asn Cys Ile Asp Lys Asn Asp Asp Pro Asn Tyr Gln Phe Pro
            180                 185                 190

Asp Glu Trp Leu Ile Ile Pro Thr Ala Asp Asp Asp Tyr Val Leu Glu
        195                 200                 205

Leu

<210> SEQ ID NO 13
<211> LENGTH: 1143
<212> TYPE: DNA
<213> ORGANISM: Nicotiana tabacum

<400> SEQUENCE: 13

atgtatccgt caagcaacag ctgtaattac agcctcaata tttcctcctc aaataactta     60

tttcacattc catctccgaa ttctatgcaa tatgaacacg aacttttcca atattttcat    120

gaccatcatc tccttcaacc ccaacaacaa caacaacaac aacaactctt gactacacct    180

gatcattata tggcagcaga ttccaacaaa gacaccgtaa tcagtagtac taatcaagat    240

cctgaagaag ttgaattaca aggccgctgc aagaacaaaa aaggtgacaa taagagacgt    300

gttgcttaca agaaagatag acacagcaag attaacactg ctcacggccc tagagaccga    360

agaatgagac tttctctcga tgtagctcgc aaatttttca atttgcaaga cttgcttgga    420

ttcgataagg ctagcaaaac tgtggagtgg ttgctaacaa agtccaaatg tgctgtcaat    480

gagctcgtcc aaggcataaa taaagaaaat tgcgctactg ctaatattgg tgcaattagt    540

acatgctcta ctacatctga gtgtgaagtt gtatcaggaa ttgatgaatc tacaaccact    600

aatgatattc agaagcagtc aaatagaggt aaagtagggg agaagaagaa ggctaataaa    660

ctagttcgta gagctgcatt taatcctgtg gcaaaggaat caagaaagca agctagagcg    720

agggcaaggg agagaacaaa aataaagaaa agctttttaa atattggtga tcagtctatg    780

gcggctgatg atttaaaacg attaggatgt tggagtcttt ttgaaacagg tgaagaatca    840

ggtattcaag gtactaatca tcaaattgaa gaacacacca cgcaccacga ggagcctctt    900

ttggggacta atgagaatgt tgatgattgt aatttggttg ttaccggcaa ctggaaccca    960

tataccatct tcaattatca ccacagtact gaaatttctc acgaggtagg ttttacactt   1020

catttaaatc caagagtaat tcttttagag ttcaagattc tgatattttt tttggtggcg   1080

agaccctttc ttatatcaaa gcaaccttca aggtacatac aagattggat aaaccaattc   1140

tga                                                                 1143

<210> SEQ ID NO 14
<211> LENGTH: 380
<212> TYPE: PRT
<213> ORGANISM: Nicotiana tabacum

<400> SEQUENCE: 14

Met Tyr Pro Ser Ser Asn Ser Cys Asn Tyr Ser Leu Asn Ile Ser Ser
1               5                   10                  15

Ser Asn Asn Leu Phe His Ile Pro Ser Pro Asn Ser Met Gln Tyr Glu
            20                  25                  30

His Glu Leu Phe Gln Tyr Phe His Asp His His Leu Leu Gln Pro Gln
        35                  40                  45

Gln Gln Gln Gln Gln Gln Gln Leu Leu Thr Thr Pro Asp His Tyr Met
    50                  55                  60

Ala Ala Asp Ser Asn Lys Asp Thr Val Ile Ser Ser Thr Asn Gln Asp
65                  70                  75                  80
```

-continued

```
Pro Glu Glu Val Glu Leu Gln Gly Arg Cys Lys Asn Lys Lys Gly Asp
                85                  90                  95

Asn Lys Arg Arg Val Ala Tyr Lys Lys Asp Arg His Ser Lys Ile Asn
            100                 105                 110

Thr Ala His Gly Pro Arg Asp Arg Arg Met Arg Leu Ser Leu Asp Val
        115                 120                 125

Ala Arg Lys Phe Phe Asn Leu Gln Asp Leu Leu Gly Phe Asp Lys Ala
    130                 135                 140

Ser Lys Thr Val Glu Trp Leu Leu Thr Lys Ser Lys Cys Ala Val Asn
145                 150                 155                 160

Glu Leu Val Gln Gly Ile Asn Lys Glu Asn Cys Ala Thr Ala Asn Ile
                165                 170                 175

Gly Ala Ile Ser Thr Cys Ser Thr Thr Ser Glu Cys Glu Val Val Ser
            180                 185                 190

Gly Ile Asp Glu Ser Thr Thr Thr Asn Asp Ile Gln Lys Gln Ser Asn
        195                 200                 205

Arg Gly Lys Val Gly Glu Lys Lys Lys Ala Asn Lys Leu Val Arg Arg
    210                 215                 220

Ala Ala Phe Asn Pro Val Ala Lys Glu Ser Arg Lys Gln Ala Arg Ala
225                 230                 235                 240

Arg Ala Arg Glu Arg Thr Lys Ile Lys Lys Ser Phe Leu Asn Ile Gly
                245                 250                 255

Asp Gln Ser Met Ala Ala Asp Asp Leu Lys Arg Leu Gly Cys Trp Ser
            260                 265                 270

Leu Phe Glu Thr Gly Glu Glu Ser Gly Ile Gln Gly Thr Asn His Gln
        275                 280                 285

Ile Glu Glu His Thr Thr His His Glu Glu Pro Leu Leu Gly Thr Asn
    290                 295                 300

Glu Asn Val Asp Asp Cys Asn Leu Val Val Thr Gly Asn Trp Asn Pro
305                 310                 315                 320

Tyr Thr Ile Phe Asn Tyr His His Ser Thr Glu Ile Ser His Glu Val
                325                 330                 335

Gly Phe Thr Leu His Leu Asn Pro Arg Val Ile Leu Leu Glu Phe Lys
            340                 345                 350

Ile Leu Ile Phe Phe Leu Val Ala Arg Pro Phe Leu Ile Ser Lys Gln
        355                 360                 365

Pro Ser Arg Tyr Ile Gln Asp Trp Ile Asn Gln Phe
    370                 375                 380

<210> SEQ ID NO 15
<211> LENGTH: 915
<212> TYPE: DNA
<213> ORGANISM: Nicotiana tabacum

<400> SEQUENCE: 15

atggaaaagg ttcatgagaa accgctatct ctttataatg gatcattatc tgtttttaga     60

ttaggagatt tggctgtgaa aataacaaag gtgaaaaagg gatcattaaa taatgataat    120

ctttcacccc caacttcatt gttagttgtt tcaccaatca taccaggaac ttatccagtt    180

ttactctttt ttcatggctt cgttctcaag cctatatggt acaagtctct ccttcaacat    240

atttcttccc acggctatat agttgttgct ccacaggttt ctcaaagcga agaagtgaaa    300

aaagcagcca aagttacaga atggttaagt aaagccctcg aatccgtact gccggagaaa    360

gtacagccgg atctactcca gctcgccgtc tccggccaca gcagaggtgg taaaatagca    420
```

-continued

```
tttgcactag ctttaggata tggcatcaaa tttcaagcac ttctaggaat tgatccagtt    480

gcaggttttt ctccgtccaa ccgatctgct ccaaaaattc ttaaatatat tcctcgtatt    540

ttcgatcaga cggtccctgt ggcggtgatc ggcgctggct tgtcaaacca aagtgcgaat    600

tgtatctttc cacccttcgc accaaacggt gtcaaccatt cggagttttt taacgagtcc    660

aaaccacctt gctgttattt tctggctaaa aattatggac atactgatat gttagatgac    720

agaattgctg caattgcgag ttggatttca aagagtggga agggacccaa ggaccttatg    780

agaaaggctg ttggagggat tgttgtggct tttcttgagg ctaaattggg agagaaagtg    840

gataatctaa atgccattgt tcaagaacct tctcttgctc ccatcatcct tgacccagtc    900

atatctgtca aataa                                                     915
```

```
<210> SEQ ID NO 16
<211> LENGTH: 304
<212> TYPE: PRT
<213> ORGANISM: Nicotiana tabacum

<400> SEQUENCE: 16

Met Glu Lys Val His Glu Lys Pro Leu Ser Leu Tyr Asn Gly Ser Leu
1               5                   10                  15

Ser Val Phe Arg Leu Gly Asp Leu Ala Val Lys Ile Thr Lys Val Lys
            20                  25                  30

Lys Gly Ser Leu Asn Asn Asp Asn Leu Ser Pro Pro Thr Ser Leu Leu
        35                  40                  45

Val Val Ser Pro Ile Ile Pro Gly Thr Tyr Pro Val Leu Leu Phe Phe
    50                  55                  60

His Gly Phe Val Leu Lys Pro Ile Trp Tyr Lys Ser Leu Leu Gln His
65                  70                  75                  80

Ile Ser Ser His Gly Tyr Ile Val Val Ala Pro Gln Val Ser Gln Ser
                85                  90                  95

Glu Glu Val Lys Lys Ala Ala Lys Val Thr Glu Trp Leu Ser Lys Ala
            100                 105                 110

Leu Glu Ser Val Leu Pro Glu Lys Val Gln Pro Asp Leu Leu Gln Leu
        115                 120                 125

Ala Val Ser Gly His Ser Arg Gly Gly Lys Ile Ala Phe Ala Leu Ala
    130                 135                 140

Leu Gly Tyr Gly Ile Lys Phe Gln Ala Leu Leu Gly Ile Asp Pro Val
145                 150                 155                 160

Ala Gly Phe Ser Pro Ser Asn Arg Ser Ala Pro Lys Ile Leu Lys Tyr
                165                 170                 175

Ile Pro Arg Ile Phe Asp Gln Thr Val Pro Val Ala Val Ile Gly Ala
            180                 185                 190

Gly Leu Ser Asn Gln Ser Ala Asn Cys Ile Phe Pro Pro Phe Ala Pro
        195                 200                 205

Asn Gly Val Asn His Ser Glu Phe Phe Asn Glu Ser Lys Pro Pro Cys
    210                 215                 220

Cys Tyr Phe Leu Ala Lys Asn Tyr Gly His Thr Asp Met Leu Asp Asp
225                 230                 235                 240

Arg Ile Ala Ala Ile Ala Ser Trp Ile Ser Lys Ser Gly Lys Gly Pro
                245                 250                 255

Lys Asp Leu Met Arg Lys Ala Val Gly Gly Ile Val Val Ala Phe Leu
            260                 265                 270

Glu Ala Lys Leu Gly Glu Lys Val Asp Asn Leu Asn Ala Ile Val Gln
```

-continued

```
        275                 280                 285

Glu Pro Ser Leu Ala Pro Ile Ile Leu Asp Pro Val Ile Ser Val Lys
    290                 295                 300
```

<210> SEQ ID NO 17
<211> LENGTH: 1353
<212> TYPE: DNA
<213> ORGANISM: Nicotiana tabacum

<400> SEQUENCE: 17

```
atgtgtttgt taataaaggt ggcgaatcca ggagaatccg gcgagcatga cagaattcca      60

tcaacgggag gtgattcaga aagtacaact actaccacag aaggaggaat tccgcagcta     120

tatgaacaat tacaatcaca atcacaatca tttgaagaaa tgttgcggca acaaatacaa     180

caagaaacag agtatttgat gtcttcatct gcaactccta tgttttcacg gtatagtcag     240

acaagggaga tgtcggcaat ggtaacggcg ttaacgcatg tggtatcagg acggagagag     300

ggagagtgga cttacaggcc ggatattagt gccggcgctg ttacgacgtc gtttgctggt     360

ggttcgagta tttattcggc gagttcgccg tcgtcttcaa gttcagggtc atgggctgga     420

cagaagagaa gacgtgatca agaagaaagt gttgctgcag agcaagttca aagggtttat     480

ggagcttttg gtgaatttag aggtggagaa tcatcttcct ctgttaaaac tgaagaagct     540

tcaagcatgg tagcaccacc aaccaccacc agcactacca ccacaaccac cacggcggcg     600

caaacaccac cagaaccagc ggaaggagga ggagctgaag aaacagggga aaggaggagg     660

agatacagag gagtaagaca aaggccatgg ggaaaatggg cagcagaaat aagagatcca     720

cacaaagcag ctagagtttg gttaggcaca tttgatacag ctgaagctgc tgctagagct     780

tatgatgaag ctgcccttag attcagagga aacagagcta aactcaattt ccccgaaaat     840

gtccgcatat taccacaaca acaacagcaa caacctcaag ccacaacaag atcagccatt     900

tccagctcct ccgcagcttc acaattccca ttaatggctg cagcaacaac tccatcacca     960

tttttccaaa cttatcaacc tcagcagcag cagctgcctt ttcagagttc agaaatggtt    1020

agagattatt gggaatactc acagttactt caaaatccag gagagtttca tttacaacaa    1080

cagccttcag ccttgttaga gcaaatgttg tttgcttctt catcaatggg tcttttgcaa    1140

tcacacacat tcccttctta ttcttcatct tcctcattag ctacttcctc tgcagcttct    1200

tcccctgcat atcccctgtt ttactctgct caacaatcac gtttctttca gcccccacaa    1260

agtactcatc aaaatcaaac tagtagcagc agctccagtt ttcctgcacc attttggact    1320

agttcaaccc actacccacc ttcttctagt taa                                1353
```

<210> SEQ ID NO 18
<211> LENGTH: 450
<212> TYPE: PRT
<213> ORGANISM: Nicotiana tabacum

<400> SEQUENCE: 18

```
Met Cys Leu Leu Ile Lys Val Ala Asn Pro Gly Glu Ser Gly Glu His
1               5                   10                  15

Asp Arg Ile Pro Ser Thr Gly Gly Asp Ser Glu Ser Thr Thr Thr Thr
            20                  25                  30

Thr Glu Gly Gly Ile Pro Gln Leu Tyr Glu Gln Leu Gln Ser Gln Ser
        35                  40                  45

Gln Ser Phe Glu Glu Met Leu Arg Gln Gln Ile Gln Gln Glu Thr Glu
    50                  55                  60
```

```
Tyr Leu Met Ser Ser Ser Ala Thr Pro Met Phe Ser Arg Tyr Ser Gln
65                  70                  75                  80

Thr Arg Glu Met Ser Ala Met Val Thr Ala Leu Thr His Val Val Ser
                85                  90                  95

Gly Arg Arg Glu Gly Glu Trp Thr Tyr Arg Pro Asp Ile Ser Ala Gly
            100                 105                 110

Ala Val Thr Thr Ser Phe Ala Gly Gly Ser Ser Ile Tyr Ser Ala Ser
        115                 120                 125

Ser Pro Ser Ser Ser Ser Ser Gly Ser Trp Ala Gly Gln Lys Arg Arg
    130                 135                 140

Arg Asp Gln Glu Glu Ser Val Ala Ala Glu Gln Val Gln Arg Val Tyr
145                 150                 155                 160

Gly Ala Phe Gly Glu Phe Arg Gly Gly Glu Ser Ser Ser Ser Val Lys
                165                 170                 175

Thr Glu Glu Ala Ser Ser Met Val Ala Pro Pro Thr Thr Thr Ser Thr
            180                 185                 190

Thr Thr Thr Thr Thr Thr Ala Ala Gln Thr Pro Pro Glu Pro Ala Glu
        195                 200                 205

Gly Gly Gly Ala Glu Glu Thr Gly Glu Arg Arg Arg Arg Tyr Arg Gly
    210                 215                 220

Val Arg Gln Arg Pro Trp Gly Lys Trp Ala Ala Glu Ile Arg Asp Pro
225                 230                 235                 240

His Lys Ala Ala Arg Val Trp Leu Gly Thr Phe Asp Thr Ala Glu Ala
                245                 250                 255

Ala Ala Arg Ala Tyr Asp Glu Ala Ala Leu Arg Phe Arg Gly Asn Arg
            260                 265                 270

Ala Lys Leu Asn Phe Pro Glu Asn Val Arg Ile Leu Pro Gln Gln Gln
        275                 280                 285

Gln Gln Gln Pro Gln Ala Thr Thr Arg Ser Ala Ile Ser Ser Ser Ser
    290                 295                 300

Ala Ala Ser Gln Phe Pro Leu Met Ala Ala Ala Thr Thr Pro Ser Pro
305                 310                 315                 320

Phe Phe Gln Thr Tyr Gln Pro Gln Gln Gln Gln Leu Pro Phe Gln Ser
                325                 330                 335

Ser Glu Met Val Arg Asp Tyr Trp Glu Tyr Ser Gln Leu Leu Gln Asn
            340                 345                 350

Pro Gly Glu Phe His Leu Gln Gln Gln Pro Ser Ala Leu Leu Glu Gln
        355                 360                 365

Met Leu Phe Ala Ser Ser Ser Met Gly Leu Leu Gln Ser His Thr Phe
    370                 375                 380

Pro Ser Tyr Ser Ser Ser Ser Ser Leu Ala Thr Ser Ser Ala Ala Ser
385                 390                 395                 400

Ser Pro Ala Tyr Pro Leu Phe Tyr Ser Ala Gln Gln Ser Arg Phe Phe
                405                 410                 415

Gln Pro Pro Gln Ser Thr His Gln Asn Gln Thr Ser Ser Ser Ser Ser
            420                 425                 430

Ser Phe Pro Ala Pro Phe Trp Thr Ser Ser Thr His Tyr Pro Pro Ser
        435                 440                 445

Ser Ser
    450
```

<210> SEQ ID NO 19
<211> LENGTH: 732
<212> TYPE: DNA

<213> ORGANISM: Nicotiana tabacum

<400> SEQUENCE: 19

```
atggcacatt tcttctctat aaattcaacg ttagcaggaa cgaataaagc atccaaaaca      60

aatttcacat attcaactca agaaacagaa aaaccaaaaa taaagatcat cttactcttg     120

ttttctcttg cattagttcc cttgtcagcg atggcaactt gcaccactga tactccaaac     180

caagcactat tgagggatgt acacgatata gatggtaacc cccttcaagt aaaagccagg     240

tacttcatat ttccagttat tggcggtggt ggtgtacggc ttgctaatct tggagatcaa     300

gacgaaaacg cttgtgccac agcggtggtg ctatcacgca gtgaagttga caaaggtaaa     360

gcagtcaact tcatacctaa agaccccaaa catgagaaga ttgtggaggc ctcttcagta     420

aacatccagt tttatcttga ttattataag tgtgctaacc taactgtgtg gaaagtagac     480

aactacccta cacttccaag tcgctacacc ataagcacag gtgcaacgcc gggaaatccc     540

ctagagttga atagctggtt tcaaattatg tctcttggtg gctcgacgta taagatagtc     600

ttctgtccct ttggagaatg ccaaaatgtt ggcattgccg aggaaaatgg atataatcgt     660

ttggttctcg cagagaatgc aaaggccttt gttttcataa agcaaggcgg atatggaaag     720

gccgaagcat ga                                                         732
```

<210> SEQ ID NO 20
<211> LENGTH: 243
<212> TYPE: PRT
<213> ORGANISM: Nicotiana tabacum

<400> SEQUENCE: 20

```
Met Ala His Phe Phe Ser Ile Asn Ser Thr Leu Ala Gly Thr Asn Lys
1               5                   10                  15

Ala Ser Lys Thr Asn Phe Thr Tyr Ser Thr Gln Glu Thr Glu Lys Pro
            20                  25                  30

Lys Ile Lys Ile Ile Leu Leu Leu Phe Ser Leu Ala Leu Val Pro Leu
        35                  40                  45

Ser Ala Met Ala Thr Cys Thr Thr Asp Thr Pro Asn Gln Ala Leu Leu
    50                  55                  60

Arg Asp Val His Asp Ile Asp Gly Asn Pro Leu Gln Val Lys Ala Arg
65                  70                  75                  80

Tyr Phe Ile Phe Pro Val Ile Gly Gly Gly Gly Val Arg Leu Ala Asn
                85                  90                  95

Leu Gly Asp Gln Asp Glu Asn Ala Cys Ala Thr Ala Val Val Leu Ser
            100                 105                 110

Arg Ser Glu Val Asp Lys Gly Lys Ala Val Asn Phe Ile Pro Lys Asp
        115                 120                 125

Pro Lys His Glu Lys Ile Val Glu Ala Ser Ser Val Asn Ile Gln Phe
    130                 135                 140

Tyr Leu Asp Tyr Tyr Lys Cys Ala Asn Leu Thr Val Trp Lys Val Asp
145                 150                 155                 160

Asn Tyr Pro Thr Leu Pro Ser Arg Tyr Thr Ile Ser Thr Gly Ala Thr
                165                 170                 175

Pro Gly Asn Pro Leu Glu Leu Asn Ser Trp Phe Gln Ile Met Ser Leu
            180                 185                 190

Gly Gly Ser Thr Tyr Lys Ile Val Phe Cys Pro Phe Gly Glu Cys Gln
        195                 200                 205

Asn Val Gly Ile Ala Glu Glu Asn Gly Tyr Asn Arg Leu Val Leu Ala
    210                 215                 220
```

-continued

```
Glu Asn Ala Lys Ala Phe Val Phe Ile Lys Gln Gly Gly Tyr Gly Lys
225                 230                 235                 240

Ala Glu Ala


<210> SEQ ID NO 21
<211> LENGTH: 471
<212> TYPE: DNA
<213> ORGANISM: Nicotiana tabacum

<400> SEQUENCE: 21

atggctgagc aacaccagcg ccaccagcaa cagcagcagc agcagcagat gcaagtgggc      60

cacccgacgg aggcaatcaa gagccttctt cctcaaaggg gtccctctaa atcccaagtc     120

cttgctgtcg tcactctctt ccctgttggt ggggccctcc tctgccttgc tggactgacg     180

ctcgccggaa ctctgatcgg gcttgcagtc gctacgccgg ttttcttact gttcagcccg     240

gttttggtcc ccgctgccct gacaatcgcg ttggccgtca ctggattctt gacttccggc     300

gcctttggaa taacggcgct gtcgtcgctc tcgtggatca ttaactatat gaggagaatc     360

acaggtccag cagcagagca gatggagcat gcaaagcgga gggtgcagga cactgctggt     420

catatgggac agagaggtgg acagaagatt caagaaactg ctagaacttg a              471


<210> SEQ ID NO 22
<211> LENGTH: 156
<212> TYPE: PRT
<213> ORGANISM: Nicotiana tabacum

<400> SEQUENCE: 22

Met Ala Glu Gln His Gln Arg His Gln Gln Gln Gln Gln Gln Gln Gln
1               5                   10                  15

Met Gln Val Gly His Pro Thr Glu Ala Ile Lys Ser Leu Leu Pro Gln
            20                  25                  30

Arg Gly Pro Ser Lys Ser Gln Val Leu Ala Val Val Thr Leu Phe Pro
        35                  40                  45

Val Gly Gly Ala Leu Leu Cys Leu Ala Gly Leu Thr Leu Ala Gly Thr
    50                  55                  60

Leu Ile Gly Leu Ala Val Ala Thr Pro Val Phe Leu Leu Phe Ser Pro
65                  70                  75                  80

Val Leu Val Pro Ala Ala Leu Thr Ile Ala Leu Ala Val Thr Gly Phe
                85                  90                  95

Leu Thr Ser Gly Ala Phe Gly Ile Thr Ala Leu Ser Ser Leu Ser Trp
            100                 105                 110

Ile Ile Asn Tyr Met Arg Arg Ile Thr Gly Pro Ala Ala Glu Gln Met
        115                 120                 125

Glu His Ala Lys Arg Arg Val Gln Asp Thr Ala Gly His Met Gly Gln
    130                 135                 140

Arg Gly Gly Gln Lys Ile Gln Glu Thr Ala Arg Thr
145                 150                 155


<210> SEQ ID NO 23
<211> LENGTH: 1437
<212> TYPE: DNA
<213> ORGANISM: Nicotiana tabacum

<400> SEQUENCE: 23

atggatagtg ataggaggga ttgccacttg aacatgttgt ccaaaatggc tatgtgcaaa      60

tcacacgggc aagactcttc ctatttcata ggatggcaag aatatgagaa gaacccttat     120
```

```
catcccattc aaaatccttc tggtattatt cagatgggtc ttgctgagaa tcagctctca    180

ttcgatcttc ttgaatcatg gctcacaaga aaccaagatg taatccagtt tagagaaaat    240

ggaggatcta tgttcagaga cttggctctt ttccaagatt atcatggatt gcaggctttc    300

aagaacgtac tagtgtcatt catgggtgag atcagaagaa ggaaagtaaa atttgatcca    360

gagaagctag tactcacagc tggttcaact tcagcaaacg aaaccctcat attttgctta    420

gctgaacctg gagaagctct ccttcttcca actccttatt atccagggtt tgatagagat    480

ctaaaatgga gaacaggggc tgaaattgta cccatacact gctacagttc aaataacttc    540

agaataactg agtctgccct tgaagatgca tatgaagaag cccaacgact taatttaaga    600

gtcaagggtg tatttatcac aaatccttca aatccactag ggacaaccat gtcacgagac    660

gaattaaaca atcttatcac ctttgccatg gccaaaaata ttcatatagt tagcgacgaa    720

atatacgctg gaacagtttt cgattcgcca aaattcataa gcataatgga agctttaatt    780

gacagaaaac atgaaaaatc caaaatgtgg agtcaagttc acattgtgtc aagtctatca    840

aaagatctag gtctaccagg tttcagaatt gggatgattt attcaaacaa tgaaactctt    900

atagctgctg ctacaaaaat gtcaagtttt ggactcattt catctcaaac tcagtatcta    960

ctatctaaaa ttcttggaga taaaaaattt ataaaacgtt acattaaaga aaacaagaaa   1020

ggattgaaaa agaggaggga aatgcttgtt tccgggttag agaatagtgg gattgagtgt   1080

ttgaaaagta atgctggatt attttgtttt gtggacatga ggcatttgct aaattcaaac   1140

acatttgaag cagaaatgga actgtggaga aaaatactac taagtgatgt tggtttaaat   1200

gtgtctcctg gatcttcttg tcactgtagt gaacctggtt ggtttaaaat ttgttttgca   1260

aatattgccg aagaaactct tgatctcgcg atgcagagga ttaatgattt tgtcagttct   1320

atgaatcttc aacggcgaca gctgatcgcg gcggcgtcgg cgtctagctc aaggaggagg   1380

acacttgcga actgggttgt taagttatct tcaggtgaag gaaaaacata tcgttaa      1437
```

<210> SEQ ID NO 24
<211> LENGTH: 478
<212> TYPE: PRT
<213> ORGANISM: Nicotiana tabacum

<400> SEQUENCE: 24

```
Met Asp Ser Asp Arg Arg Asp Cys His Leu Asn Met Leu Ser Lys Met
1               5                   10                  15

Ala Met Cys Lys Ser His Gly Gln Asp Ser Ser Tyr Phe Ile Gly Trp
            20                  25                  30

Gln Glu Tyr Glu Lys Asn Pro Tyr His Pro Ile Gln Asn Pro Ser Gly
        35                  40                  45

Ile Ile Gln Met Gly Leu Ala Glu Asn Gln Leu Ser Phe Asp Leu Leu
    50                  55                  60

Glu Ser Trp Leu Thr Arg Asn Gln Asp Val Ile Gln Phe Arg Glu Asn
65                  70                  75                  80

Gly Gly Ser Met Phe Arg Asp Leu Ala Leu Phe Gln Asp Tyr His Gly
                85                  90                  95

Leu Gln Ala Phe Lys Asn Val Leu Val Ser Phe Met Gly Glu Ile Arg
            100                 105                 110

Arg Arg Lys Val Lys Phe Asp Pro Glu Lys Leu Val Leu Thr Ala Gly
        115                 120                 125

Ser Thr Ser Ala Asn Glu Thr Leu Ile Phe Cys Leu Ala Glu Pro Gly
    130                 135                 140
```

-continued

```
Glu Ala Leu Leu Leu Pro Thr Pro Tyr Tyr Pro Gly Phe Asp Arg Asp
145                 150                 155                 160

Leu Lys Trp Arg Thr Gly Ala Glu Ile Val Pro Ile His Cys Tyr Ser
                165                 170                 175

Ser Asn Asn Phe Arg Ile Thr Glu Ser Ala Leu Glu Asp Ala Tyr Glu
            180                 185                 190

Glu Ala Gln Arg Leu Asn Leu Arg Val Lys Gly Val Phe Ile Thr Asn
        195                 200                 205

Pro Ser Asn Pro Leu Gly Thr Thr Met Ser Arg Asp Glu Leu Asn Asn
    210                 215                 220

Leu Ile Thr Phe Ala Met Ala Lys Asn Ile His Ile Val Ser Asp Glu
225                 230                 235                 240

Ile Tyr Ala Gly Thr Val Phe Asp Ser Pro Lys Phe Ile Ser Ile Met
                245                 250                 255

Glu Ala Leu Ile Asp Arg Lys His Glu Lys Ser Lys Met Trp Ser Gln
            260                 265                 270

Val His Ile Val Ser Ser Leu Ser Lys Asp Leu Gly Leu Pro Gly Phe
        275                 280                 285

Arg Ile Gly Met Ile Tyr Ser Asn Asn Glu Thr Leu Ile Ala Ala Ala
    290                 295                 300

Thr Lys Met Ser Ser Phe Gly Leu Ile Ser Ser Gln Thr Gln Tyr Leu
305                 310                 315                 320

Leu Ser Lys Ile Leu Gly Asp Lys Lys Phe Ile Lys Arg Tyr Ile Lys
                325                 330                 335

Glu Asn Lys Lys Gly Leu Lys Lys Arg Arg Glu Met Leu Val Ser Gly
            340                 345                 350

Leu Glu Asn Ser Gly Ile Glu Cys Leu Lys Ser Asn Ala Gly Leu Phe
        355                 360                 365

Cys Phe Val Asp Met Arg His Leu Leu Asn Ser Asn Thr Phe Glu Ala
    370                 375                 380

Glu Met Glu Leu Trp Arg Lys Ile Leu Leu Ser Asp Val Gly Leu Asn
385                 390                 395                 400

Val Ser Pro Gly Ser Ser Cys His Cys Ser Glu Pro Gly Trp Phe Lys
                405                 410                 415

Ile Cys Phe Ala Asn Ile Ala Glu Glu Thr Leu Asp Leu Ala Met Gln
            420                 425                 430

Arg Ile Asn Asp Phe Val Ser Ser Met Asn Leu Gln Arg Arg Gln Leu
        435                 440                 445

Ile Ala Ala Ala Ser Ala Ser Ser Ser Arg Arg Arg Thr Leu Ala Asn
    450                 455                 460

Trp Val Val Lys Leu Ser Ser Gly Glu Gly Lys Thr Tyr Arg
465                 470                 475
```

<210> SEQ ID NO 25
<211> LENGTH: 645
<212> TYPE: DNA
<213> ORGANISM: Nicotiana tabacum

<400> SEQUENCE: 25

```
atgaacggtg gttcatgtgg tggtgctgat cgtgagtata ataacaataa caacaataat      60

gttgtaggtg gaggaggtgg cgggccttgt ggtgcatgca agtttcttag aagaaaatgt     120

gtgaggggat gcatatttgc accttatttt gattctgatc aaggcactgc tcatttcgct     180

gctgtacata aggtgtttgg tgctagcaat gcctctaaat tgctgctcag aattccagcg     240
```

```
cataaacgtc tggatgctgt cgttacactt tgctatgagg ctcttgctag agttagagac    300

cctatctatg gttgtgttgc tcacatcttt actcttcagc aacaggttgt aactttgcaa    360

gctgagttag catatgttca agcccgcctt tctaccctac cacacctacc tatgcgacaa    420

agtccaatta caccaacagg gctgcaatca tcttcagata tcttctgcac tacttcaagc    480

atatcatctt caagtaataa tatggaatat cctcaatttg acataactgc gggtttaagt    540

gattcgttcg atgaaaaaga actggagaac tttgagctcc atacattagc acgagagttg    600

gtttctagac acttacctgg agttagattt agaccttcac cataa                    645
```

<210> SEQ ID NO 26
<211> LENGTH: 214
<212> TYPE: PRT
<213> ORGANISM: Nicotiana tabacum

<400> SEQUENCE: 26

```
Met Asn Gly Gly Ser Cys Gly Gly Ala Asp Arg Glu Tyr Asn Asn Asn
1               5                   10                  15

Asn Asn Asn Asn Val Val Gly Gly Gly Gly Gly Gly Pro Cys Gly Ala
            20                  25                  30

Cys Lys Phe Leu Arg Arg Lys Cys Val Arg Gly Cys Ile Phe Ala Pro
        35                  40                  45

Tyr Phe Asp Ser Asp Gln Gly Thr Ala His Phe Ala Ala Val His Lys
    50                  55                  60

Val Phe Gly Ala Ser Asn Ala Ser Lys Leu Leu Leu Arg Ile Pro Ala
65                  70                  75                  80

His Lys Arg Leu Asp Ala Val Val Thr Leu Cys Tyr Glu Ala Leu Ala
                85                  90                  95

Arg Val Arg Asp Pro Ile Tyr Gly Cys Val Ala His Ile Phe Thr Leu
            100                 105                 110

Gln Gln Gln Val Val Thr Leu Gln Ala Glu Leu Ala Tyr Val Gln Ala
        115                 120                 125

Arg Leu Ser Thr Leu Pro His Leu Pro Met Arg Gln Ser Pro Ile Thr
    130                 135                 140

Pro Thr Gly Leu Gln Ser Ser Ser Asp Ile Phe Cys Thr Thr Ser Ser
145                 150                 155                 160

Ile Ser Ser Ser Ser Asn Asn Met Glu Tyr Pro Gln Phe Asp Ile Thr
                165                 170                 175

Ala Gly Leu Ser Asp Ser Phe Asp Glu Lys Glu Leu Glu Asn Phe Glu
            180                 185                 190

Leu His Thr Leu Ala Arg Glu Leu Val Ser Arg His Leu Pro Gly Val
        195                 200                 205

Arg Phe Arg Pro Ser Pro
    210
```

<210> SEQ ID NO 27
<211> LENGTH: 2205
<212> TYPE: DNA
<213> ORGANISM: Nicotiana tabacum

<400> SEQUENCE: 27

```
atgtcggata aaaaatctgt ctcgacgcca tttgaatgtt gcagaatctt gtttaagttt     60

ctgctgttta tggttattat cagtaatgtg gcgatccatg taacagcttt gagtgggcga    120

gaaggaataa ccccaagtac ggaatggggt ttggggcctc tggtgaagag aggagaaaga    180
```

-continued

```
aaactagtag tttcaactga aaatggggag gtctcttcag tcagagtagc tgatggaatc    240
accggttcct atcatcttca gttcatcaca ttggagccca attccctctt ccttcctgtt    300
gttctacatg cagatatggt cttctatgtc cacactgggt cgggaaggct gacttggatg    360
gatgaaactg aacaaaagtc agtggattta agaattggag atgttttcag gttgcccttt    420
ggaactattt tcttcataga gagcaactta gagcctgcgc gacagaaact tagagtttat    480
tccatcttta ccaattcagg ggatgatttg agagagccgt tgtccggacc acactctagc    540
atccgtgata tggttcttgg attcgatagg aaagttctcc aggcggcatt tcatgtacca    600
gaggatgtga tagatgaagt gttgaatggg acagaagtac cagccatcat acatggtgtg    660
cccaagacaa caaaaaagac cctgtgggaa atggaggctc aattcatgaa aagtcttcta    720
ggaaggggtg gtcacggttt ctttgactcc caaagcaata aaaagaagac tgaattgttc    780
aatattttca aagagaaacc agattttgag aattgcaatg gctggagcac tgtaattaca    840
cggaaaaaat tacccgcatt aaagggttcc cacattggta tttatgtagt gaacttaacc    900
aagggatcaa tgatggcgcc acactggaat ccaacggcaa ctgaaatagg aatagcattg    960
caaggagaag gaatggtaag ggtagtttgc tcaagcacgg gaacaaagca aggatgccaa   1020
aacatgaggt ttaaggtgga agaaggagat gtatttgcag tgccaaggtt tcgtcctatg   1080
gctcaaatgg ctttcaacaa caactcattt gtctttgttg gttttagtac aactacaaag   1140
agacatcatc ctcagtacct aacagggaag gcttcagtcc tccgaacact ggataggcaa   1200
atcttggcag cttcctttaa tgtgactaac acaacaatgg atcggattct ggaggcacag   1260
ggtgagtcag tcatactgga gtgtacttct tgtgctgaag aagaagtgag attaatggag   1320
gaagaaagga ggagggcaga ggaggaagaa aggagaaggg aagaagagga ggcaaggcag   1380
agggaggaag aaaggaggag ggaagaagag gaagctagaa ggaaggaaga ggaagaagca   1440
aggaaggctg aagaagaaag aagaaagaga gaggcagaag aagcaagaag acgagaagag   1500
gaggcaacaa gggagaaaga ggaacaaagg aggagacaag aagaagaagc caggagaagg   1560
gaagaggagg aagccagaag gcaagaagaa gaaatcagaa ggagacaaga agaaggggaa   1620
gctaggaaga gagaagagga agaagcagct agaaggcaac aggaggaaga agctgagaga   1680
gaggcagaag aagcgaggac aagagaagag gaagaggcag ctagaaggca gcagggggaa   1740
gaagcacaaa gggaggcaga ggaagcaaga aggagagagg aagaagcagc aaggaggagg   1800
gaggaacaag cgcagagaga ggcggaggaa gcaagtagga gagaggagga agcagcagct   1860
agaaggagac aggaacgaga ggaagcagaa agggaaagac aagcagagga agccaggagg   1920
gagggagagg aaacaaggag acatgaagaa gaagaagaag aagaagagga ggaggaggaa   1980
acaaggagag gagagagggg agaggaggag gaggaaggag gaagaaaaga agaggaggcg   2040
gcaagagagg ccgagaaaag aaggcaagaa gaagcccaga gacaacaaga agcagctagg   2100
agacaggaag aagaaatgga aagaaggcat caagaagaag aaaccgagga agaggagcag   2160
ggtccttacg cacggaggaa aagaacattc cttaaaacag catga                   2205
```

<210> SEQ ID NO 28
<211> LENGTH: 734
<212> TYPE: PRT
<213> ORGANISM: Nicotiana tabacum

<400> SEQUENCE: 28

```
Met Ser Asp Lys Lys Ser Val Ser Thr Pro Phe Glu Cys Cys Arg Ile
1               5                   10                  15
```

-continued

```
Leu Phe Lys Phe Leu Leu Phe Met Val Ile Ile Ser Asn Val Ala Ile
            20                  25                  30

His Val Thr Ala Leu Ser Gly Arg Glu Gly Ile Thr Pro Ser Thr Glu
        35                  40                  45

Trp Gly Leu Gly Pro Leu Val Lys Arg Gly Glu Arg Lys Leu Val Val
    50                  55                  60

Ser Thr Glu Asn Gly Glu Val Ser Ser Val Arg Val Ala Asp Gly Ile
65                  70                  75                  80

Thr Gly Ser Tyr His Leu Gln Phe Ile Thr Leu Glu Pro Asn Ser Leu
                85                  90                  95

Phe Leu Pro Val Val Leu His Ala Asp Met Val Phe Tyr Val His Thr
            100                 105                 110

Gly Ser Gly Arg Leu Thr Trp Met Asp Glu Thr Glu Gln Lys Ser Val
        115                 120                 125

Asp Leu Arg Ile Gly Asp Val Phe Arg Leu Pro Phe Gly Thr Ile Phe
    130                 135                 140

Phe Ile Glu Ser Asn Leu Glu Pro Ala Arg Gln Lys Leu Arg Val Tyr
145                 150                 155                 160

Ser Ile Phe Thr Asn Ser Gly Asp Asp Leu Arg Glu Pro Leu Ser Gly
                165                 170                 175

Pro His Ser Ser Ile Arg Asp Met Val Leu Gly Phe Asp Arg Lys Val
            180                 185                 190

Leu Gln Ala Ala Phe His Val Pro Glu Asp Val Ile Asp Glu Val Leu
        195                 200                 205

Asn Gly Thr Glu Val Pro Ala Ile Ile His Gly Val Pro Lys Thr Thr
    210                 215                 220

Lys Lys Thr Leu Trp Glu Met Glu Ala Gln Phe Met Lys Ser Leu Leu
225                 230                 235                 240

Gly Arg Gly Gly His Gly Phe Phe Asp Ser Gln Ser Asn Lys Lys Lys
                245                 250                 255

Thr Glu Leu Phe Asn Ile Phe Lys Glu Lys Pro Asp Phe Glu Asn Cys
            260                 265                 270

Asn Gly Trp Ser Thr Val Ile Thr Arg Lys Lys Leu Pro Ala Leu Lys
        275                 280                 285

Gly Ser His Ile Gly Ile Tyr Val Val Asn Leu Thr Lys Gly Ser Met
    290                 295                 300

Met Ala Pro His Trp Asn Pro Thr Ala Thr Glu Ile Gly Ile Ala Leu
305                 310                 315                 320

Gln Gly Glu Gly Met Val Arg Val Val Cys Ser Ser Thr Gly Thr Lys
                325                 330                 335

Gln Gly Cys Gln Asn Met Arg Phe Lys Val Glu Glu Gly Asp Val Phe
            340                 345                 350

Ala Val Pro Arg Phe Arg Pro Met Ala Gln Met Ala Phe Asn Asn Asn
        355                 360                 365

Ser Phe Val Phe Val Gly Phe Ser Thr Thr Thr Lys Arg His His Pro
    370                 375                 380

Gln Tyr Leu Thr Gly Lys Ala Ser Val Leu Arg Thr Leu Asp Arg Gln
385                 390                 395                 400

Ile Leu Ala Ala Ser Phe Asn Val Thr Asn Thr Thr Met Asp Arg Ile
                405                 410                 415

Leu Glu Ala Gln Gly Glu Ser Val Ile Leu Glu Cys Thr Ser Cys Ala
            420                 425                 430

Glu Glu Glu Val Arg Leu Met Glu Glu Glu Arg Arg Arg Ala Glu Glu
```

-continued

```
        435                 440                 445

Glu Glu Arg Arg Arg Glu Glu Glu Glu Ala Arg Gln Arg Glu Glu Glu
    450                 455                 460

Arg Arg Arg Glu Glu Glu Glu Ala Arg Arg Lys Glu Glu Glu Glu Ala
465                 470                 475                 480

Arg Lys Ala Glu Glu Glu Arg Arg Lys Arg Glu Ala Glu Glu Ala Arg
                485                 490                 495

Arg Arg Glu Glu Glu Ala Thr Arg Glu Lys Glu Glu Gln Arg Arg Arg
            500                 505                 510

Gln Glu Glu Glu Ala Arg Arg Arg Glu Glu Glu Glu Ala Arg Arg Gln
        515                 520                 525

Glu Glu Glu Ile Arg Arg Arg Gln Glu Glu Gly Glu Ala Arg Lys Arg
    530                 535                 540

Glu Glu Glu Glu Ala Ala Arg Arg Gln Gln Glu Glu Glu Ala Glu Arg
545                 550                 555                 560

Glu Ala Glu Glu Ala Arg Thr Arg Glu Glu Glu Glu Ala Ala Arg Arg
                565                 570                 575

Gln Gln Gly Glu Glu Ala Gln Arg Glu Ala Glu Glu Ala Arg Arg Arg
            580                 585                 590

Glu Glu Glu Ala Ala Arg Arg Arg Glu Glu Gln Ala Gln Arg Glu Ala
        595                 600                 605

Glu Glu Ala Ser Arg Arg Glu Glu Glu Ala Ala Ala Arg Arg Arg Gln
    610                 615                 620

Glu Arg Glu Glu Ala Glu Arg Glu Arg Gln Ala Glu Glu Ala Arg Arg
625                 630                 635                 640

Glu Gly Glu Glu Thr Arg Arg His Glu Glu Glu Glu Glu Glu Glu Glu
                645                 650                 655

Glu Glu Glu Glu Thr Arg Arg Gly Glu Arg Gly Glu Glu Glu Glu Glu
            660                 665                 670

Gly Gly Arg Lys Glu Glu Glu Ala Ala Arg Glu Ala Glu Lys Arg Arg
        675                 680                 685

Gln Glu Glu Ala Gln Arg Gln Gln Glu Ala Ala Arg Arg Gln Glu Glu
    690                 695                 700

Glu Met Glu Arg Arg His Gln Glu Glu Glu Thr Glu Glu Glu Glu Gln
705                 710                 715                 720

Gly Pro Tyr Ala Arg Arg Lys Arg Thr Phe Leu Lys Thr Ala
                725                 730
```

<210> SEQ ID NO 29
<211> LENGTH: 1302
<212> TYPE: DNA
<213> ORGANISM: Nicotiana tabacum

<400> SEQUENCE: 29

```
atgggcgtac cagaatcgga ggtggtgtca caaggtgagg ttgaatcacc attgcaacca      60

gatcaaaacc agcacaagaa ccatcagttc ccgtccctcg gtagacaagc atcgatctac     120

tccctcactc tcgacgaatt ccaacacacc ctatgtgaaa gtggcaagaa tttcgggtcg     180

atgaatatgg atgaattcct taacagcatt tggactgctg aagaaaacca agcccacgca     240

cacgcccatg cccatgccgc gcacgggcat gcgcacgcgc attctcatgc tcatagccaa     300

gcaccaagta caggggaagc cactagcaca ccacattttg cgataggaca gagcaatgtt     360

tcaatggaga aagctattgc caagcagcca agcttgccaa gacagggttc tcttacgctt     420

ccggaacctt tgtgtcggaa aactgtggat gaagtttggt cagaaattca taagagccaa     480
```

```
aaagagcaac atcagaataa tgggggcagt gtcccggaca cgggtaattc cgctcaacgg    540

caggttacat ttggcgaaat gacacttgag gatttcttgg tcaaagcagg ggtagtacgc    600

gaacaggaga atgcccctgc acctcctcaa cagcaatcat atatgatgta tcaaaacagc    660

aacaatcccg ctatggccaa tatggctcga cctgttattg gcttaggtgg agtcacgggc    720

agcgttggag ttggcattcc tagctatcca ccacttcctc agaccggggt ggttgaggcc    780

ccaatatacc cggtaagtat gaaaaggggt gccggattcc cacaacagcc aacggctgtt    840

tacggcggga gaatggggaa tggtggcggg gtcgggtatg ggcaagtaca aggagtggcc    900

gggatggggt cgccactaag tccagtgtcg tcggatggat tatgcgttaa tcaagtcgat    960

agcgggggtc aatacgggtt ggaaatggga atgagaggag gaagaaaacg cataatagat   1020

ggtccggtag agaaagtggt ggaaaggagg caaaggagaa tgatcaagaa tagagaatca   1080

gcagcaagat caagagcaag aaagcaggct tacacagtag aacttgaggc agaactgaac   1140

cagctaaaag aagagaatgc acatctgaaa caggccctgg cggagctcga gaggaaaagg   1200

aaacaacagt actttgacga agggaaaatg aaagtgcaaa cgaaagcgca aaaggcgact   1260

aacaaattga gaggtatgag gaggagtttg agttgccctt ga                      1302
```

<210> SEQ ID NO 30
<211> LENGTH: 433
<212> TYPE: PRT
<213> ORGANISM: Nicotiana tabacum

<400> SEQUENCE: 30

```
Met Gly Val Pro Glu Ser Glu Val Val Ser Gln Gly Glu Val Glu Ser
1               5                   10                  15

Pro Leu Gln Pro Asp Gln Asn Gln His Lys Asn His Gln Phe Pro Ser
            20                  25                  30

Leu Gly Arg Gln Ala Ser Ile Tyr Ser Leu Thr Leu Asp Glu Phe Gln
        35                  40                  45

His Thr Leu Cys Glu Ser Gly Lys Asn Phe Gly Ser Met Asn Met Asp
    50                  55                  60

Glu Phe Leu Asn Ser Ile Trp Thr Ala Glu Glu Asn Gln Ala His Ala
65                  70                  75                  80

His Ala His Ala His Ala Ala His Gly His Ala His Ala His Ser His
                85                  90                  95

Ala His Ser Gln Ala Pro Ser Thr Gly Glu Ala Thr Ser Thr Pro His
            100                 105                 110

Phe Ala Ile Gly Gln Ser Asn Val Ser Met Glu Lys Ala Ile Ala Lys
        115                 120                 125

Gln Pro Ser Leu Pro Arg Gln Gly Ser Leu Thr Leu Pro Glu Pro Leu
    130                 135                 140

Cys Arg Lys Thr Val Asp Glu Val Trp Ser Glu Ile His Lys Ser Gln
145                 150                 155                 160

Lys Glu Gln His Gln Asn Asn Gly Gly Ser Val Pro Asp Thr Gly Asn
                165                 170                 175

Ser Ala Gln Arg Gln Val Thr Phe Gly Glu Met Thr Leu Glu Asp Phe
            180                 185                 190

Leu Val Lys Ala Gly Val Val Arg Glu Gln Glu Asn Ala Pro Ala Pro
        195                 200                 205

Pro Gln Gln Gln Ser Tyr Met Met Tyr Gln Asn Ser Asn Asn Pro Ala
    210                 215                 220
```

-continued

```
Met Ala Asn Met Ala Arg Pro Val Ile Gly Leu Gly Gly Val Thr Gly
225                 230                 235                 240

Ser Val Gly Val Gly Ile Pro Ser Tyr Pro Pro Leu Pro Gln Thr Gly
                245                 250                 255

Val Val Glu Ala Pro Ile Tyr Pro Val Ser Met Lys Arg Gly Ala Gly
            260                 265                 270

Phe Pro Gln Gln Pro Thr Ala Val Tyr Gly Gly Arg Met Gly Asn Gly
        275                 280                 285

Gly Gly Val Gly Tyr Gly Gln Val Gln Gly Val Ala Gly Met Gly Ser
    290                 295                 300

Pro Leu Ser Pro Val Ser Ser Asp Gly Leu Cys Val Asn Gln Val Asp
305                 310                 315                 320

Ser Gly Gly Gln Tyr Gly Leu Glu Met Gly Met Arg Gly Gly Arg Lys
                325                 330                 335

Arg Ile Ile Asp Gly Pro Val Glu Lys Val Val Glu Arg Arg Gln Arg
            340                 345                 350

Arg Met Ile Lys Asn Arg Glu Ser Ala Ala Arg Ser Arg Ala Arg Lys
        355                 360                 365

Gln Ala Tyr Thr Val Glu Leu Glu Ala Glu Leu Asn Gln Leu Lys Glu
    370                 375                 380

Glu Asn Ala His Leu Lys Gln Ala Leu Ala Glu Leu Glu Arg Lys Arg
385                 390                 395                 400

Lys Gln Gln Tyr Phe Asp Glu Gly Lys Met Lys Val Gln Thr Lys Ala
                405                 410                 415

Gln Lys Ala Thr Asn Lys Leu Arg Gly Met Arg Arg Ser Leu Ser Cys
            420                 425                 430

Pro
```

<210> SEQ ID NO 31
<211> LENGTH: 1266
<212> TYPE: DNA
<213> ORGANISM: Nicotiana tabacum

<400> SEQUENCE: 31

```
atggaggaaa aagatgaact tgaggaagaa gaagaatatg ttgatgatga aatcaagaac     60

aatttaccag tccaaaactc atcttcaata agttggttca caaaaatgat atctttacaa    120

gtagagatct tcaccactat cttagtttcc cccattttct atatcctctc ttttgtatct    180

gacttcaact tcctccgccc tgaagaaacc gaaaagaacg tagctgtagc tgtaaatgct    240

gctgctacag taccttcaaa agtagtacat ggaagtactt tactgctcaa gaaatttggt    300

gttggaattc ttggagctgc ttatgttgga atggttttga caacgttgtt gattttgtcg    360

ggggttctgg gatttgggtt agtgagaatg tgggcggaag agcctgtggt attgagagag    420

aagctgtatt ttgattatgc agatgtttat cctaaggctg ttttttcttt tgctgaatat    480

ggtctggaga attataacca taattttatg atgttgaagc agaagaagaa ttttggtgtg    540

ccagttgggc atacaatgta tgtttctttg tttctactga tgcctgaatc tgatttcaac    600

agagatattg gtgttttcca gttggttgca gaagcgttat cagccgaggg gatcataatg    660

gcaagatcaa gtcatccacg tatgttgcga ttcagaagcc tgccaatccg tctcatgcga    720

gaatttatta tgagtgtgcc cctagtactt ggacttacag ctgaaacaca aaggatgatc    780

attccaatgt taaagcataa ggaaggtatt ccaagaacag aggcaatcaa aataactatg    840

atacctcgag ctggaacgct agccctgccg cagctttatc aatcggagat catattgaag    900
```

-continued

```
tctcatcctc cttggtataa agacttggca tacaagtgga aatggacatt ctccgtctgg    960

acctctatgt atatgtatgt tacactgctc ataattctac tcaactggtg cagaccgctc   1020

gtatttccag tgatcgcaac aagctttagg acacgcgttg atgagagttt aacagtggaa   1080

gcatcagaag aaccacaaga gaaagctcga gaagaaagtg atgtgtcgga gtcggtaaga   1140

agatggcggc agagcagaag aaagaggaag gcaatgcttc aacagagtgt ctcgccagag   1200

ttcgcggatg attctgcatc aagcatttct gtgactaggg aggatacagc tgagtcaagc   1260

gagtaa                                                              1266


<210> SEQ ID NO 32
<211> LENGTH: 421
<212> TYPE: PRT
<213> ORGANISM: Nicotiana tabacum

<400> SEQUENCE: 32

Met Glu Glu Lys Asp Glu Leu Glu Glu Glu Glu Glu Tyr Val Asp Asp
1               5                   10                  15

Glu Ile Lys Asn Asn Leu Pro Val Gln Asn Ser Ser Ser Ile Ser Trp
            20                  25                  30

Phe Thr Lys Met Ile Ser Leu Gln Val Glu Ile Phe Thr Thr Ile Leu
        35                  40                  45

Val Ser Pro Ile Phe Tyr Ile Leu Ser Phe Val Ser Asp Phe Asn Phe
    50                  55                  60

Leu Arg Pro Glu Glu Thr Glu Lys Asn Val Ala Val Ala Val Asn Ala
65                  70                  75                  80

Ala Ala Thr Val Pro Ser Lys Val Val His Gly Ser Thr Leu Leu Leu
                85                  90                  95

Lys Lys Phe Gly Val Gly Ile Leu Gly Ala Ala Tyr Val Gly Met Val
            100                 105                 110

Leu Thr Thr Leu Leu Ile Leu Ser Gly Val Leu Gly Phe Gly Leu Val
        115                 120                 125

Arg Met Trp Ala Glu Glu Pro Val Val Leu Arg Glu Lys Leu Tyr Phe
    130                 135                 140

Asp Tyr Ala Asp Val Tyr Pro Lys Ala Val Phe Ser Phe Ala Glu Tyr
145                 150                 155                 160

Gly Leu Glu Asn Tyr Asn His Asn Phe Met Met Leu Lys Gln Lys Lys
                165                 170                 175

Asn Phe Gly Val Pro Val Gly His Thr Met Tyr Val Ser Leu Phe Leu
            180                 185                 190

Leu Met Pro Glu Ser Asp Phe Asn Arg Asp Ile Gly Val Phe Gln Leu
        195                 200                 205

Val Ala Glu Ala Leu Ser Ala Glu Gly Ile Ile Met Ala Arg Ser Ser
    210                 215                 220

His Pro Arg Met Leu Arg Phe Arg Ser Leu Pro Ile Arg Leu Met Arg
225                 230                 235                 240

Glu Phe Ile Met Ser Val Pro Leu Val Leu Gly Leu Thr Ala Glu Thr
                245                 250                 255

Gln Arg Met Ile Ile Pro Met Leu Lys His Lys Glu Gly Ile Pro Arg
            260                 265                 270

Thr Glu Ala Ile Lys Ile Thr Met Ile Pro Arg Ala Gly Thr Leu Ala
        275                 280                 285

Leu Pro Gln Leu Tyr Gln Ser Glu Ile Ile Leu Lys Ser His Pro Pro
    290                 295                 300
```

```
Trp Tyr Lys Asp Leu Ala Tyr Lys Trp Lys Trp Thr Phe Ser Val Trp
305                 310                 315                 320

Thr Ser Met Tyr Met Tyr Val Thr Leu Leu Ile Ile Leu Leu Asn Trp
                325                 330                 335

Cys Arg Pro Leu Val Phe Pro Val Ile Ala Thr Ser Phe Arg Thr Arg
            340                 345                 350

Val Asp Glu Ser Leu Thr Val Glu Ala Ser Glu Glu Pro Gln Glu Lys
        355                 360                 365

Ala Arg Glu Glu Ser Asp Val Ser Glu Ser Val Arg Arg Trp Arg Gln
    370                 375                 380

Ser Arg Arg Lys Arg Lys Ala Met Leu Gln Gln Ser Val Ser Pro Glu
385                 390                 395                 400

Phe Ala Asp Asp Ser Ala Ser Ser Ile Ser Val Thr Arg Glu Asp Thr
                405                 410                 415

Ala Glu Ser Ser Glu
            420

<210> SEQ ID NO 33
<211> LENGTH: 597
<212> TYPE: DNA
<213> ORGANISM: Nicotiana tabacum

<400> SEQUENCE: 33

atgtataact caagcaacta cagctgtaat tacaacccca ttttctcatc taatttattc     60

aacatccctt ctccttgtat gcaatatgaa cacgaacttt tcttccaata ttaccatgat    120

caacttcaac agaatcttga cgatacctta gctgagatca gtactgagac tgccattatt    180

aacacggcag attccagcaa agacgaggct ataatcagta gaaatgaact tgaacaagat    240

caggaagcgc gtaagaataa aaagggtaaa gtaagcagca acaagagagt gtctaagaaa    300

gatagacaca gcaagattaa cactgctaaa ggcccgagag accgaagaat aagactttca    360

attgatattg ctcgcaattt tttcaattta caagacatgt tgaggttcga gaaggccagc    420

aaaactctgg agtggttgct tataaagtca aaatctgata tcaaggagct ctccaaaagt    480

cgaataagca aattaagatg tagtactgtt atgggtgcaa atagtgaaac ctccacttct    540

gaatgtgaag ttgtatcagg aattgatgaa tctccatcca atcaaggcaa atgctaa       597

<210> SEQ ID NO 34
<211> LENGTH: 198
<212> TYPE: PRT
<213> ORGANISM: Nicotiana tabacum

<400> SEQUENCE: 34

Met Tyr Asn Ser Ser Asn Tyr Ser Cys Asn Tyr Asn Pro Ile Phe Ser
1               5                   10                  15

Ser Asn Leu Phe Asn Ile Pro Ser Pro Cys Met Gln Tyr Glu His Glu
            20                  25                  30

Leu Phe Phe Gln Tyr Tyr His Asp Gln Leu Gln Gln Asn Leu Asp Asp
        35                  40                  45

Thr Leu Ala Glu Ile Ser Thr Glu Thr Ala Ile Ile Asn Thr Ala Asp
    50                  55                  60

Ser Ser Lys Asp Glu Ala Ile Ile Ser Arg Asn Glu Leu Glu Gln Asp
65                  70                  75                  80

Gln Glu Ala Arg Lys Asn Lys Lys Gly Lys Val Ser Ser Asn Lys Arg
                85                  90                  95

Val Ser Lys Lys Asp Arg His Ser Lys Ile Asn Thr Ala Lys Gly Pro
```

```
            100                 105                 110

Arg Asp Arg Arg Ile Arg Leu Ser Ile Asp Ile Ala Arg Asn Phe Phe
        115                 120                 125

Asn Leu Gln Asp Met Leu Arg Phe Glu Lys Ala Ser Lys Thr Leu Glu
    130                 135                 140

Trp Leu Leu Ile Lys Ser Lys Ser Asp Ile Lys Glu Leu Ser Lys Ser
145                 150                 155                 160

Arg Ile Ser Lys Leu Arg Cys Ser Thr Val Met Gly Ala Asn Ser Glu
                165                 170                 175

Thr Ser Thr Ser Glu Cys Glu Val Val Ser Gly Ile Asp Glu Ser Pro
            180                 185                 190

Ser Asn Gln Gly Lys Cys
        195


<210> SEQ ID NO 35
<211> LENGTH: 1038
<212> TYPE: DNA
<213> ORGANISM: Nicotiana tabacum

<400> SEQUENCE: 35

atgtatccgt caagcaacat ctgtaattac aaccccaata tttcctcctc aaataactta     60

tttcacattc catctcctaa ttctatgcaa tatgaacacg aacttttcca atatttccac    120

gaccatcatc tccttcaacc ccaacaacaa caactactct tgactacacc tgatcattac    180

atggcagcag attccaacaa agataccgta atcagtagta ctattaatca actggaaggt    240

cctaaagaag ttgaattaca aggcagctgc aagaacaaaa atggtgaaaa taagagagct    300

gttgcttaca agaaagatag acacagcaag attaatacag ctcacggccc tagagatcga    360

agaatgagac tttctctcga tgttgctcgc aaatttttca atttgcaaga cttgcttgga    420

ttcgataagg ccagcaaaac tgtggagtgg ttgcttacca agtccaaatc tgctatcaat    480

gagctcgtcc aaagtactgc tactggtgca attagtacat cctctacgac atccgagtgt    540

gaagtgatat caggaattga tgaatctaca accactaatg atattcagaa gcagccaaat    600

agaagtaaag taggggagaa gaaaaaggct aataaactag ctcgtagagc tgcatttaat    660

cctgtggcaa aggaatcaag gaaacaagct agagcgaggg caagggagag aacaaaaata    720

aagaaaagcc ttttaaatat tggtgatcag tctatggcgg ctgatgattt aaaacgatta    780

ggatgttgga gtccttttga aacaggtgaa gaatcaggta ttcaaggcta tagtactaat    840

catcaagtag aagaccaaca cactacgaac cacgaggagc atcttttggg gactaaagag    900

aatgttgatg gctgtaattt ggttgttact ggcaactgga acccatttac tatcttcaac    960

tatcaccaca atactgaaat ttctcacgag caacaattta caaacttcca gttttctggg   1020

aagttttggg aagtttag                                                 1038


<210> SEQ ID NO 36
<211> LENGTH: 345
<212> TYPE: PRT
<213> ORGANISM: Nicotiana tabacum

<400> SEQUENCE: 36

Met Tyr Pro Ser Ser Asn Ile Cys Asn Tyr Asn Pro Asn Ile Ser Ser
1               5                   10                  15

Ser Asn Asn Leu Phe His Ile Pro Ser Pro Asn Ser Met Gln Tyr Glu
            20                  25                  30

His Glu Leu Phe Gln Tyr Phe His Asp His His Leu Leu Gln Pro Gln
```

```
        35                  40                  45

Gln Gln Gln Leu Leu Leu Thr Thr Pro Asp His Tyr Met Ala Ala Asp
    50                  55                  60

Ser Asn Lys Asp Thr Val Ile Ser Ser Thr Ile Asn Gln Leu Glu Gly
65                  70                  75                  80

Pro Lys Glu Val Glu Leu Gln Gly Ser Cys Lys Asn Lys Asn Gly Glu
                85                  90                  95

Asn Lys Arg Ala Val Ala Tyr Lys Lys Asp Arg His Ser Lys Ile Asn
            100                 105                 110

Thr Ala His Gly Pro Arg Asp Arg Arg Met Arg Leu Ser Leu Asp Val
        115                 120                 125

Ala Arg Lys Phe Phe Asn Leu Gln Asp Leu Leu Gly Phe Asp Lys Ala
    130                 135                 140

Ser Lys Thr Val Glu Trp Leu Leu Thr Lys Ser Lys Ser Ala Ile Asn
145                 150                 155                 160

Glu Leu Val Gln Ser Thr Ala Thr Gly Ala Ile Ser Thr Ser Ser Thr
                165                 170                 175

Thr Ser Glu Cys Glu Val Ile Ser Gly Ile Asp Glu Ser Thr Thr Thr
            180                 185                 190

Asn Asp Ile Gln Lys Gln Pro Asn Arg Ser Lys Val Gly Glu Lys Lys
        195                 200                 205

Lys Ala Asn Lys Leu Ala Arg Arg Ala Ala Phe Asn Pro Val Ala Lys
    210                 215                 220

Glu Ser Arg Lys Gln Ala Arg Ala Arg Ala Arg Glu Arg Thr Lys Ile
225                 230                 235                 240

Lys Lys Ser Leu Leu Asn Ile Gly Asp Gln Ser Met Ala Ala Asp Asp
                245                 250                 255

Leu Lys Arg Leu Gly Cys Trp Ser Pro Phe Glu Thr Gly Glu Glu Ser
            260                 265                 270

Gly Ile Gln Gly Tyr Ser Thr Asn His Gln Val Glu Asp Gln His Thr
        275                 280                 285

Thr Asn His Glu Glu His Leu Leu Gly Thr Lys Glu Asn Val Asp Gly
    290                 295                 300

Cys Asn Leu Val Val Thr Gly Asn Trp Asn Pro Phe Thr Ile Phe Asn
305                 310                 315                 320

Tyr His His Asn Thr Glu Ile Ser His Glu Gln Gln Phe Thr Asn Phe
                325                 330                 335

Gln Phe Ser Gly Lys Phe Trp Glu Val
            340                 345


<210> SEQ ID NO 37
<211> LENGTH: 1014
<212> TYPE: DNA
<213> ORGANISM: Nicotiana tabacum

<400> SEQUENCE: 37

atgtatccgc caagcaatag ctgcaactac agccccattt tcaacatccc ttctccttgt      60

atgcaatatg gagacgaact attcttccaa tattatcatg acgattacct tcaagagcaa     120

caagtaccgt tgatagaaga tcagagtctt gacatcttag ctgagagcac tgagactgtt     180

actaataaca aagaaaccgt catcaattct gatcatagtg taaaagttta taacatagaa     240

actgttacaa acagtcaggg tttgggagga aatgaagaaa aaagagtaga aggccgcgaa     300

aacaaaagag atgatatgag cggcaccatt agtatcattc atggacggaa aaacaagaaa     360
```

```
tgttcccata aagatcgaca tagcaagatt agcactgctc gtggccttag agatcgaagg    420

atgagacttt cccttgatgc agctcgcaag tttttcagtt tacaagacat gttggggttc    480

gataaggcaa gtaaaactgt agaatggttg cttaccaaat cggagtctga aatcgaagag    540

ctagctaaag gcaataaaga aggagaatcc cttcctaaac aaagctgcag tactaccaat    600

ggaattggtg caattagtac tgcaatatcc tctatttctg agtgtgaggt tatatcagga    660

actgatgaat cttcttctat tactgataaa aagaagctgg aaactgctaa aggaccgttg    720

aaaaagaagg gtaaaactgc tcgtagagct acatttgatc ctcttattac aagggaatcg    780

aggaatcaag caagggttag ggctagagag cgaacaaaac taaagaaaag ccttagtaaa    840

tccaaagcca tgactcatga gaacagtgct gatgactgta atttggtggt taattttgga    900

gattggagtc aatttagcat cttcaactat cagcaaaatg cagttggaat ttcccatgat    960

cagcagcaat ttacagactt ccaattttgt ggtaataagc tgtgggaagt ctag         1014


<210> SEQ ID NO 38
<211> LENGTH: 337
<212> TYPE: PRT
<213> ORGANISM: Nicotiana tabacum

<400> SEQUENCE: 38

Met Tyr Pro Pro Ser Asn Ser Cys Asn Tyr Ser Pro Ile Phe Asn Ile
1               5                   10                  15

Pro Ser Pro Cys Met Gln Tyr Gly Asp Glu Leu Phe Phe Gln Tyr Tyr
            20                  25                  30

His Asp Asp Tyr Leu Gln Glu Gln Gln Val Pro Leu Ile Glu Asp Gln
        35                  40                  45

Ser Leu Asp Ile Leu Ala Glu Ser Thr Glu Thr Val Thr Asn Asn Lys
    50                  55                  60

Glu Thr Val Ile Asn Ser Asp His Ser Val Lys Val Tyr Asn Ile Glu
65                  70                  75                  80

Thr Val Thr Asn Ser Gln Gly Leu Gly Gly Asn Glu Glu Lys Arg Val
                85                  90                  95

Glu Gly Arg Glu Asn Lys Arg Asp Asp Met Ser Gly Thr Ile Ser Ile
            100                 105                 110

Ile His Gly Arg Lys Asn Lys Lys Cys Ser His Lys Asp Arg His Ser
        115                 120                 125

Lys Ile Ser Thr Ala Arg Gly Leu Arg Asp Arg Arg Met Arg Leu Ser
    130                 135                 140

Leu Asp Ala Ala Arg Lys Phe Phe Ser Leu Gln Asp Met Leu Gly Phe
145                 150                 155                 160

Asp Lys Ala Ser Lys Thr Val Glu Trp Leu Leu Thr Lys Ser Glu Ser
                165                 170                 175

Glu Ile Glu Glu Leu Ala Lys Gly Asn Lys Glu Gly Glu Ser Leu Pro
            180                 185                 190

Lys Gln Ser Cys Ser Thr Thr Asn Gly Ile Gly Ala Ile Ser Thr Ala
        195                 200                 205

Ile Ser Ser Ile Ser Glu Cys Glu Val Ile Ser Gly Thr Asp Glu Ser
    210                 215                 220

Ser Ser Ile Thr Asp Lys Lys Lys Leu Glu Thr Ala Lys Gly Pro Leu
225                 230                 235                 240

Lys Lys Lys Gly Lys Thr Ala Arg Arg Ala Thr Phe Asp Pro Leu Ile
                245                 250                 255

Thr Arg Glu Ser Arg Asn Gln Ala Arg Val Arg Ala Arg Glu Arg Thr
```

```
            260                 265                 270

Lys Leu Lys Lys Ser Leu Ser Lys Ser Lys Ala Met Thr His Glu Asn
        275                 280                 285

Ser Ala Asp Asp Cys Asn Leu Val Val Asn Phe Gly Asp Trp Ser Gln
    290                 295                 300

Phe Ser Ile Phe Asn Tyr Gln Gln Asn Ala Val Gly Ile Ser His Asp
305                 310                 315                 320

Gln Gln Gln Phe Thr Asp Phe Gln Phe Cys Gly Asn Lys Leu Trp Glu
                325                 330                 335

Val
```

<210> SEQ ID NO 39
<211> LENGTH: 867
<212> TYPE: DNA
<213> ORGANISM: Nicotiana tabacum

<400> SEQUENCE: 39

```
atgggcctct cacaatatcc agctccagca gatgcaggag tactgtgtgt gattcttgta     60

aacacagcca tatctatttc cattgtcaag gagatagtcc gatcgatcct tcacgttatt    120

ggcatccata tcgcatcatg ggaagattat tcttttgaag gatcatttga atgccgcgga    180

agcccatcag agtcatacat ggaggagttt agaagccgaa cacctgcatt tcgttatgac    240

tcggtgtgta tctctaacca ccctgagcaa gaatgctctg tgtgcctgac taaattcgag    300

cctgacacag agataaaccg tctctcctgt ggccatgttt tccataagct gtgtctagag    360

aagtggctca agtattggca tgtaacttgc cctctttgca ggaaacacat gatgcctcac    420

gagcaagagg acgatacatg tccaatgtca ttttccagct atgttgcgcg aactctccaa    480

aatgctaccg catttatgtt ggatcctcca aaaatgcact acttttggag gatccgacat    540

gtgcctgatg acattttcgg agaatctgag caacattgct ttccagtagc caactcagag    600

agtttcgagc caactgacat gctagtgcga gtcaacgcag ggttcctgtg gtatctgcac    660

ctgaaagaac ctgcatgtgt agttggtgag cacaagcagc tgtaccttac acttgatgtc    720

tttcgcaatg ctgacggtga agaaggcgtc gaggatggta atggtgccat agttggttgt    780

ggttgttcag ccatccttca gcagattctg cagaagaaat taatagatat gaacaagaaa    840

ttctggattg actatgaggt agagtag                                        867
```

<210> SEQ ID NO 40
<211> LENGTH: 288
<212> TYPE: PRT
<213> ORGANISM: Nicotiana tabacum

<400> SEQUENCE: 40

```
Met Gly Leu Ser Gln Tyr Pro Ala Pro Ala Asp Ala Gly Val Leu Cys
1               5                   10                  15

Val Ile Leu Val Asn Thr Ala Ile Ser Ile Ser Ile Val Lys Glu Ile
            20                  25                  30

Val Arg Ser Ile Leu His Val Ile Gly Ile His Ile Ala Ser Trp Glu
        35                  40                  45

Asp Tyr Ser Phe Glu Gly Ser Phe Glu Cys Arg Gly Ser Pro Ser Glu
    50                  55                  60

Ser Tyr Met Glu Glu Phe Arg Ser Arg Thr Pro Ala Phe Arg Tyr Asp
65                  70                  75                  80

Ser Val Cys Ile Ser Asn His Pro Glu Gln Glu Cys Ser Val Cys Leu
                85                  90                  95
```

-continued

```
Thr Lys Phe Glu Pro Asp Thr Glu Ile Asn Arg Leu Ser Cys Gly His
            100                 105                 110

Val Phe His Lys Leu Cys Leu Glu Lys Trp Leu Lys Tyr Trp His Val
        115                 120                 125

Thr Cys Pro Leu Cys Arg Lys His Met Met Pro His Glu Gln Glu Asp
    130                 135                 140

Asp Thr Cys Pro Met Ser Phe Ser Ser Tyr Val Ala Arg Thr Leu Gln
145                 150                 155                 160

Asn Ala Thr Ala Phe Met Leu Asp Pro Pro Lys Met His Tyr Phe Trp
                165                 170                 175

Arg Ile Arg His Val Pro Asp Asp Ile Phe Gly Glu Ser Glu Gln His
            180                 185                 190

Cys Phe Pro Val Ala Asn Ser Glu Ser Phe Glu Pro Thr Asp Met Leu
        195                 200                 205

Val Arg Val Asn Ala Gly Phe Leu Trp Tyr Leu His Leu Lys Glu Pro
    210                 215                 220

Ala Cys Val Val Gly Glu His Lys Gln Leu Tyr Leu Thr Leu Asp Val
225                 230                 235                 240

Phe Arg Asn Ala Asp Gly Glu Glu Gly Val Glu Asp Gly Asn Gly Ala
                245                 250                 255

Ile Val Gly Cys Gly Cys Ser Ala Ile Leu Gln Gln Ile Leu Gln Lys
            260                 265                 270

Lys Leu Ile Asp Met Asn Lys Lys Phe Trp Ile Asp Tyr Glu Val Glu
        275                 280                 285
```

<210> SEQ ID NO 41
<211> LENGTH: 2562
<212> TYPE: DNA
<213> ORGANISM: Nicotiana tabacum

<400> SEQUENCE: 41

```
atgaatcttc aggtggatga tcaaatgata ctcatttctc agtactatcc tggtatctac     60

actcaagagt taccagaaca aggggaggcg aaacaaagga ggagacgaaa gaagaacaaa    120

ggagaagcaa gtgaggttat gaggaaaaga aagcttagtg aagaacaagt gaatctgctt    180

gaacagagct ttgggaaaga gcacaaactg gagtccgaga ggaaagacaa gcttgcctct    240

gagctggggc ttgatcctag gcaagttgct gtctggtttc agaacagaag ggctagatgg    300

aagaacaaga agttggagga ggaatactct aagttgaagt ctgagcatga cactaacatt    360

gttcataatt gccgtcttga aaatgaggtt ttgaagctga aggaacagtt gtctgaagca    420

gagaaagaga tacaaaggtt gctgatggag agatgtgatg gggttaattc gagcaatagc    480

ccaactactt catcactctc aatggaagca gccaatatgg aacctccttt tcttggggaa    540

tttggaatgg aaggatttga caatacattt tatgtgccag aaaacactta ctctcaggga    600

ttggaatgga atggaccatt ttttgcacct cctgatattg attatgggat cattaggttc    660

cagacattac ccgaccccac tattcctggg cagtatgcga actacacatg ggtagtgaa     720

tcttatacac aattgcttca gtccgttagg cacaagctca acccttctgt tcatttttat    780

gtcattcgag gcattgcact agctatgcaa atatggttgt atgagtgttg ctctaccgtc    840

aacactgata tagctacaag gatttctaat tcaatctctc gcatacttag ctggtcagct    900

agtaaggaca agatatggtt atctgcaatt gaagatagaa tgatcaaacc atcatggatc    960

aagttcacca acataattga agcaccagag gagctttcaa gaatgaattt gccaaataaa   1020
```

-continued

```
gttgaataca ttcttgaaga agttgaaaca aagtccgagc atccgataga tgctccatct   1080

ccatccgttg gttcagatct tggaactttc aagaaagagg tttttgaaga actagataca   1140

gggcaggtga atgatataaa aattatggag aatgttcctg taggtgttga tttatcttcc   1200

caatttgaag gggcatttga tgaagagaat gcagagaagg aaactatgca tgtagaatct   1260

ccaaaacaga aagctacaat aagcattcca ggaaaacaaa aaaatgagga gaaggagaca   1320

aaaatacaat ctcacattca agaagagaac gttatacaac aaggagatga ttgttgtgaa   1380

gatttcagtg gtgaatcagc cgactacatt aatataggtg attcagacaa tgactctaga   1440

tctgaaaaaa gagaagtaac acttgatgat tttgagctgc cagagaactt ctcccagatt   1500

attaattctg gggggagaac ttctgttgga cctccaattt tcctcatcaa gcatccattt   1560

actggggtta ttggcgaaga tgttgatcct gacttattgg aagaattcaa taagtggtta   1620

tactttggta tcgatacagt ttcaaagagg aggaaggcgc cttattctgt aaaagataac   1680

cagcttaagc cgtggtatga ttttggagtg gagaaagttg ataaaaatga gaggttttat   1740

actttggtac accccgggca agtcctcaac gatacgcaca ttgatgttat tttatactat   1800

ttgagaaaga gaggaaagta tggtcgtcaa aacaaaatat ggtttacaat cattgattgt   1860

atgttcaaca ctagaattga acaaatttat cagaggtaca tcaatactcc tgccgataag   1920

aagcttgttg ttgtcaaatc ccaagacgtc gtatcagaat acatattggg gtacagatta   1980

ctcgcaaata ttgcattgga tcaagttgat tttgtgatta tgcccataaa cattgtgaaa   2040

aaattttatt ggttgttggt tgtgtttgac attaccgata gggttctata tgtttatgat   2100

tctatgttct cttcacgaaa tcacaacctt gttgaatttg ttgtcaacaa gtttgctgtt   2160

atgatccccc tctacttgtc atgcaccgac ttctatggca agcgtccaga catcaactac   2220

aagaacacaa aagcatacat tgaaaaatgt gttactgacc ctcttgacat tcagtggttg   2280

gtcggtgaga tactccatca aaatgaggga tcacttgact gtagtgtata cgtggctgca   2340

tttacagaat atgtcagcat tggagagcta gcagtttcaa aggaagacct ttctgatatt   2400

gatcaacatc gtagacgcta tggagcgcta ctttgggatt atgataggaa gaagcaagat   2460

actggtgcaa ttagtgagag cgaggtgact ggcagattag caagaagaaa aggtgcacca   2520

gctgtgaacg agagaacaca agtccggaag aagaagaatt ag                      2562
```

<210> SEQ ID NO 42
<211> LENGTH: 853
<212> TYPE: PRT
<213> ORGANISM: Nicotiana tabacum

<400> SEQUENCE: 42

```
Met Asn Leu Gln Val Asp Asp Gln Met Ile Leu Ile Ser Gln Tyr Tyr
1               5                   10                  15

Pro Gly Ile Tyr Thr Gln Glu Leu Pro Glu Gln Gly Glu Ala Lys Gln
            20                  25                  30

Arg Arg Arg Arg Lys Lys Asn Lys Gly Glu Ala Ser Glu Val Met Arg
        35                  40                  45

Lys Arg Lys Leu Ser Glu Glu Gln Val Asn Leu Leu Glu Gln Ser Phe
    50                  55                  60

Gly Lys Glu His Lys Leu Glu Ser Glu Arg Lys Asp Lys Leu Ala Ser
65                  70                  75                  80

Glu Leu Gly Leu Asp Pro Arg Gln Val Ala Val Trp Phe Gln Asn Arg
                85                  90                  95

Arg Ala Arg Trp Lys Asn Lys Lys Leu Glu Glu Glu Tyr Ser Lys Leu
```

-continued

```
            100                 105                 110

Lys Ser Glu His Asp Thr Asn Ile Val His Asn Cys Arg Leu Glu Asn
        115                 120                 125

Glu Val Leu Lys Leu Lys Glu Gln Leu Ser Glu Ala Glu Lys Glu Ile
    130                 135                 140

Gln Arg Leu Leu Met Glu Arg Cys Asp Gly Val Asn Ser Ser Asn Ser
145                 150                 155                 160

Pro Thr Thr Ser Ser Leu Ser Met Glu Ala Ala Asn Met Glu Pro Pro
                165                 170                 175

Phe Leu Gly Glu Phe Gly Met Glu Gly Phe Asp Asn Thr Phe Tyr Val
            180                 185                 190

Pro Glu Asn Thr Tyr Ser Gln Gly Leu Glu Trp Asn Gly Pro Phe Phe
        195                 200                 205

Ala Pro Pro Asp Ile Asp Tyr Gly Ile Ile Arg Phe Gln Thr Leu Pro
    210                 215                 220

Asp Pro Thr Ile Pro Gly Gln Tyr Ala Asn Tyr Thr Trp Gly Ser Glu
225                 230                 235                 240

Ser Tyr Thr Gln Leu Leu Gln Ser Val Arg His Lys Leu Asn Pro Ser
                245                 250                 255

Val His Phe Tyr Val Ile Arg Gly Ile Ala Leu Ala Met Gln Ile Trp
            260                 265                 270

Leu Tyr Glu Cys Cys Ser Thr Val Asn Thr Asp Ile Ala Thr Arg Ile
        275                 280                 285

Ser Asn Ser Ile Ser Arg Ile Leu Ser Trp Ser Ala Ser Lys Asp Lys
    290                 295                 300

Ile Trp Leu Ser Ala Ile Glu Asp Arg Met Ile Lys Pro Ser Trp Ile
305                 310                 315                 320

Lys Phe Thr Asn Ile Ile Glu Ala Pro Glu Glu Leu Ser Arg Met Asn
                325                 330                 335

Leu Pro Asn Lys Val Glu Tyr Ile Leu Glu Glu Val Glu Thr Lys Ser
            340                 345                 350

Glu His Pro Ile Asp Ala Pro Ser Pro Ser Val Gly Ser Asp Leu Gly
        355                 360                 365

Thr Phe Lys Lys Glu Val Phe Glu Glu Leu Asp Thr Gly Gln Val Asn
    370                 375                 380

Asp Ile Lys Ile Met Glu Asn Val Pro Val Gly Val Asp Leu Ser Ser
385                 390                 395                 400

Gln Phe Glu Gly Ala Phe Asp Glu Glu Asn Ala Glu Lys Glu Thr Met
                405                 410                 415

His Val Glu Ser Pro Lys Gln Lys Ala Thr Ile Ser Ile Pro Gly Lys
            420                 425                 430

Gln Lys Asn Glu Glu Lys Glu Thr Lys Ile Gln Ser His Ile Gln Glu
        435                 440                 445

Glu Asn Val Ile Gln Gln Gly Asp Asp Cys Cys Glu Asp Phe Ser Gly
    450                 455                 460

Glu Ser Ala Asp Tyr Ile Asn Ile Gly Asp Ser Asp Asn Asp Ser Arg
465                 470                 475                 480

Ser Glu Lys Arg Glu Val Thr Leu Asp Asp Phe Glu Leu Pro Glu Asn
                485                 490                 495

Phe Ser Gln Ile Ile Asn Ser Gly Gly Arg Thr Ser Val Gly Pro Pro
            500                 505                 510

Ile Phe Leu Ile Lys His Pro Phe Thr Gly Val Ile Gly Glu Asp Val
        515                 520                 525
```

```
Asp Pro Asp Leu Leu Glu Glu Phe Asn Lys Trp Leu Tyr Phe Gly Ile
    530                 535                 540

Asp Thr Val Ser Lys Arg Arg Lys Ala Pro Tyr Ser Val Lys Asp Asn
545                 550                 555                 560

Gln Leu Lys Pro Trp Tyr Asp Phe Gly Val Glu Lys Val Asp Lys Asn
                565                 570                 575

Glu Arg Phe Tyr Thr Leu Val His Pro Gly Gln Val Leu Asn Asp Thr
            580                 585                 590

His Ile Asp Val Ile Leu Tyr Tyr Leu Arg Lys Arg Gly Lys Tyr Gly
        595                 600                 605

Arg Gln Asn Lys Ile Trp Phe Thr Ile Ile Asp Cys Met Phe Asn Thr
    610                 615                 620

Arg Ile Glu Gln Ile Tyr Gln Arg Tyr Ile Asn Thr Pro Ala Asp Lys
625                 630                 635                 640

Lys Leu Val Val Val Lys Ser Gln Asp Val Val Ser Glu Tyr Ile Leu
                645                 650                 655

Gly Tyr Arg Leu Leu Ala Asn Ile Ala Leu Asp Gln Val Asp Phe Val
            660                 665                 670

Ile Met Pro Ile Asn Ile Val Lys Lys Phe Tyr Trp Leu Leu Val Val
        675                 680                 685

Phe Asp Ile Thr Asp Arg Val Leu Tyr Val Tyr Asp Ser Met Phe Ser
    690                 695                 700

Ser Arg Asn His Asn Leu Val Glu Phe Val Val Asn Lys Phe Ala Val
705                 710                 715                 720

Met Ile Pro Leu Tyr Leu Ser Cys Thr Asp Phe Tyr Gly Lys Arg Pro
                725                 730                 735

Asp Ile Asn Tyr Lys Asn Thr Lys Ala Tyr Ile Glu Lys Cys Val Thr
            740                 745                 750

Asp Pro Leu Asp Ile Gln Trp Leu Val Gly Glu Ile Leu His Gln Asn
        755                 760                 765

Glu Gly Ser Leu Asp Cys Ser Val Tyr Val Ala Ala Phe Thr Glu Tyr
    770                 775                 780

Val Ser Ile Gly Glu Leu Ala Val Ser Lys Glu Asp Leu Ser Asp Ile
785                 790                 795                 800

Asp Gln His Arg Arg Arg Tyr Gly Ala Leu Leu Trp Asp Tyr Asp Arg
                805                 810                 815

Lys Lys Gln Asp Thr Gly Ala Ile Ser Glu Ser Glu Val Thr Gly Arg
            820                 825                 830

Leu Ala Arg Arg Lys Gly Ala Pro Ala Val Asn Glu Arg Thr Gln Val
        835                 840                 845

Arg Lys Lys Lys Asn
    850
```

<210> SEQ ID NO 43
<211> LENGTH: 2790
<212> TYPE: DNA
<213> ORGANISM: Nicotiana tabacum

<400> SEQUENCE: 43

```
atgatagtag taagatggtg gatgacaaca ttccaattga cagagctgtt tgtgagttgt      60

ttagttcatt tgacttacgg gctttacata ttcagcacag cagtggccgg tgatgtttcc     120

cagactctga gcgattggct tttcaagcca aatttggaaa ctagccttaa aacagatgat     180

tcaaaaaaga ctaacactga tttgcctcct attgtgttgg ttcatggaat ctttggtttt     240
```

```
ggcaaaggga gattgggagg actttcatat ttcgctggtg cagagaaaaa ggatgaaagg    300
gttctagtac cggatttggg ttcacttact agcatttatg acagggcacg tgaattgttt    360
tattatttga aaggagggca ggttgattat ggggaggaac acagtaaggc ttgtgggcat    420
tcccaatttg gacgaattta tgaacaagga cactaccccg agtgggatga agatcatcct    480
attcattttg tgggccattc agctggagca caggttgttc gagtcttgca acagatgctg    540
gctgacaagg cattcaaagg ttacgacaac acttcagaga actgggtgtt aagcctaaca    600
tcattatctg gagcacttaa cgggacaacc cgaacttact ttgatggaat gcaacctgaa    660
gatgggaagt ccttaacgcc cgtatgtttg ctccaacttt gccgcattgg agtaataatt    720
tatgagtggc ttgacattcc cttgctgaag gactattaca actttggctt tgaccacttc    780
agtatgtcct ggaggaaaag tggtatccgg ggttttgttg attgcctttt agggaatggc    840
ggtccatttg cttcgggaga ttggatactt ccagatctta ctatccaggg gtcaatgaag    900
ttgaacagcc acttacgtac atttccgcaa acatactact tcagctatgc taccaagcgt    960
accacacaag taatgggtct tacagttcct tctggcgttc tagggataca tccgctgcta   1020
ttcatcagag tcctgcaaat gagccaatgg cggcatccac aagatgtttc tcctccgtac   1080
aagggctata gggatgaaga ttggtgggac aatgacggtg ctctcaacac catatctatg   1140
acgcacccac gcttgccggt tgaacacccg agtcaccttg tcgttaaaga ttctgattgt   1200
cagcccttgc aacctggcat ctggaatcat caagtttcct cttctgtgca gttgttatca   1260
ccaccattgg ctcgtaggct ttccgtgggg aaatgtgaaa gggaaatatc tgtcattctc   1320
agttatgtta cggaaagatc agctctcacc attagaaacc ccgatggaag ccaacaacaa   1380
accaccaaga tcctctttca ccaccagaag tgcgcatgcc ttccgtctta ctgtgaacgc   1440
ccacgtccaa tggaatttct gggaaggatt tcaagaaatg tagaaggaaa tgatactaag   1500
gctaggattt ctgcagctat tttactagtt tgcattatcc ttcctttgct agcctcagca   1560
tttcttgatc atcttcctga atttctagaa catgattcta gaaataaaga tgtaacaatc   1620
cgtggtgata ataatattgt tcgtgccaat gacaatgact ttactcttcc tcgctcacat   1680
gagaaaaaga atgaaagatc tttaagagaa aagaagtcaa agaagaagaa gcataagaag   1740
aagaagaaca agaagggaaa gaaatcacac aaagataaaa tttttgattt tgaccatatt   1800
tttggaggaa accaacaaga aggagatgaa ttttcccctt atttgcaacc atttgatgtg   1860
cctcaaacaa cagaagaaca agaacagacc gagaattatg atggattacg tgagggattt   1920
taccagaaaa catgtcctca agcagagaat attataagaa atggtctaat cagggccttt   1980
cagaatgact ctaccattgc tgctgcatta cctcgccttc tcttgcatga ttgctttgtc   2040
aatggatgtg atgggtcgat attactagat acaacaccca gtggtgcaag agtggagaag   2100
ttagcaggca caaatggtgc tacagtcaag ggatttgaac tcatagacga gatcaaagcc   2160
gagctcgaga gacaatgccc tggcattgtc tcctgctctg atattttggc atacttgtcg   2220
cgcgatgcct ttgttttatc aggcctcccc aattacaacg tgctaggtgg tcgacgcgat   2280
ggcatggaat ccaatgaagc aaacgttgtt ggaaacctac cacttcctgg cgacacagtg   2340
gatcaaatga ttgatctttt tcaaaagaaa ggcctaaatt cggaagattt ggttgtccta   2400
attggtgcac attcaattgg agtagcccat tgtttcaact tcctttacag attggacgaa   2460
ccagagaagg cacaaatgtt agatccaagg cttgctggag tcatgagatt tatttgtact   2520
aaccaaatga ataccttacc ttttgatccc acaacacagt acaagatgga ttcaattttc   2580
```

```
tacaagcaac taatgatgaa gaaagggttg attgaatcgg atcaaatact ggctcaagat   2640

attagaacga ggggcttggt gcaaaagttt ggtgatgatg aaatgggatg gtttgataag   2700

tttggtaagg ctatgaataa attgggagca attgaagtgc tcactggaaa ccaaggccag   2760

atcaggagac agtgtagagc tgttaactga                                     2790
```

<210> SEQ ID NO 44
<211> LENGTH: 929
<212> TYPE: PRT
<213> ORGANISM: Nicotiana tabacum

<400> SEQUENCE: 44

```
Met Ile Val Val Arg Trp Trp Met Thr Thr Phe Gln Leu Thr Glu Leu
1               5                   10                  15

Phe Val Ser Cys Leu Val His Leu Thr Tyr Gly Leu Tyr Ile Phe Ser
            20                  25                  30

Thr Ala Val Ala Gly Asp Val Ser Gln Thr Leu Ser Asp Trp Leu Phe
        35                  40                  45

Lys Pro Asn Leu Glu Thr Ser Leu Lys Thr Asp Asp Ser Lys Lys Thr
    50                  55                  60

Asn Thr Asp Leu Pro Pro Ile Val Leu Val His Gly Ile Phe Gly Phe
65                  70                  75                  80

Gly Lys Gly Arg Leu Gly Gly Leu Ser Tyr Phe Ala Gly Ala Glu Lys
                85                  90                  95

Lys Asp Glu Arg Val Leu Val Pro Asp Leu Gly Ser Leu Thr Ser Ile
            100                 105                 110

Tyr Asp Arg Ala Arg Glu Leu Phe Tyr Tyr Leu Lys Gly Gly Gln Val
        115                 120                 125

Asp Tyr Gly Glu Glu His Ser Lys Ala Cys Gly His Ser Gln Phe Gly
    130                 135                 140

Arg Ile Tyr Glu Gln Gly His Tyr Pro Glu Trp Asp Glu Asp His Pro
145                 150                 155                 160

Ile His Phe Val Gly His Ser Ala Gly Ala Gln Val Val Arg Val Leu
                165                 170                 175

Gln Gln Met Leu Ala Asp Lys Ala Phe Lys Gly Tyr Asp Asn Thr Ser
            180                 185                 190

Glu Asn Trp Val Leu Ser Leu Thr Ser Leu Ser Gly Ala Leu Asn Gly
        195                 200                 205

Thr Thr Arg Thr Tyr Phe Asp Gly Met Gln Pro Glu Asp Gly Lys Ser
    210                 215                 220

Leu Thr Pro Val Cys Leu Leu Gln Leu Cys Arg Ile Gly Val Ile Ile
225                 230                 235                 240

Tyr Glu Trp Leu Asp Ile Pro Leu Leu Lys Asp Tyr Tyr Asn Phe Gly
                245                 250                 255

Phe Asp His Phe Ser Met Ser Trp Arg Lys Ser Gly Ile Arg Gly Phe
            260                 265                 270

Val Asp Cys Leu Leu Gly Asn Gly Gly Pro Phe Ala Ser Gly Asp Trp
        275                 280                 285

Ile Leu Pro Asp Leu Thr Ile Gln Gly Ser Met Lys Leu Asn Ser His
    290                 295                 300

Leu Arg Thr Phe Pro Gln Thr Tyr Tyr Phe Ser Tyr Ala Thr Lys Arg
305                 310                 315                 320

Thr Thr Gln Val Met Gly Leu Thr Val Pro Ser Gly Val Leu Gly Ile
                325                 330                 335
```

```
His Pro Leu Leu Phe Ile Arg Val Leu Gln Met Ser Gln Trp Arg His
            340                 345                 350

Pro Gln Asp Val Ser Pro Pro Tyr Lys Gly Tyr Arg Asp Glu Asp Trp
        355                 360                 365

Trp Asp Asn Asp Gly Ala Leu Asn Thr Ile Ser Met Thr His Pro Arg
    370                 375                 380

Leu Pro Val Glu His Pro Ser His Leu Val Val Lys Asp Ser Asp Cys
385                 390                 395                 400

Gln Pro Leu Gln Pro Gly Ile Trp Asn His Gln Val Ser Ser Ser Val
                405                 410                 415

Gln Leu Leu Ser Pro Pro Leu Ala Arg Arg Leu Ser Val Gly Lys Cys
            420                 425                 430

Glu Arg Glu Ile Ser Val Ile Leu Ser Tyr Val Thr Glu Arg Ser Ala
        435                 440                 445

Leu Thr Ile Arg Asn Pro Asp Gly Ser Gln Gln Gln Thr Thr Lys Ile
    450                 455                 460

Leu Phe His His Gln Lys Cys Ala Cys Leu Pro Ser Tyr Cys Glu Arg
465                 470                 475                 480

Pro Arg Pro Met Glu Phe Leu Gly Arg Ile Ser Arg Asn Val Glu Gly
                485                 490                 495

Asn Asp Thr Lys Ala Arg Ile Ser Ala Ala Ile Leu Leu Val Cys Ile
            500                 505                 510

Ile Leu Pro Leu Leu Ala Ser Ala Phe Leu Asp His Leu Pro Glu Phe
        515                 520                 525

Leu Glu His Asp Ser Arg Asn Lys Asp Val Thr Ile Arg Gly Asp Asn
    530                 535                 540

Asn Ile Val Arg Ala Asn Asp Asn Asp Phe Thr Leu Pro Arg Ser His
545                 550                 555                 560

Glu Lys Lys Asn Glu Arg Ser Leu Arg Glu Lys Lys Ser Lys Lys Lys
                565                 570                 575

Lys His Lys Lys Lys Lys Asn Lys Lys Gly Lys Lys Ser His Lys Asp
            580                 585                 590

Lys Ile Phe Asp Phe Asp His Ile Phe Gly Gly Asn Gln Gln Glu Gly
        595                 600                 605

Asp Glu Phe Ser Pro Tyr Leu Gln Pro Phe Asp Val Pro Gln Thr Thr
    610                 615                 620

Glu Glu Gln Glu Gln Thr Glu Asn Tyr Asp Gly Leu Arg Glu Gly Phe
625                 630                 635                 640

Tyr Gln Lys Thr Cys Pro Gln Ala Glu Asn Ile Ile Arg Asn Gly Leu
                645                 650                 655

Ile Arg Ala Phe Gln Asn Asp Ser Thr Ile Ala Ala Ala Leu Pro Arg
            660                 665                 670

Leu Leu Leu His Asp Cys Phe Val Asn Gly Cys Asp Gly Ser Ile Leu
        675                 680                 685

Leu Asp Thr Thr Pro Ser Gly Ala Arg Val Glu Lys Leu Ala Gly Thr
    690                 695                 700

Asn Gly Ala Thr Val Lys Gly Phe Glu Leu Ile Asp Glu Ile Lys Ala
705                 710                 715                 720

Glu Leu Glu Arg Gln Cys Pro Gly Ile Val Ser Cys Ser Asp Ile Leu
                725                 730                 735

Ala Tyr Leu Ser Arg Asp Ala Phe Val Leu Ser Gly Leu Pro Asn Tyr
            740                 745                 750

Asn Val Leu Gly Gly Arg Arg Asp Gly Met Glu Ser Asn Glu Ala Asn
```

-continued

```
        755                 760                 765

Val Val Gly Asn Leu Pro Leu Pro Gly Asp Thr Val Asp Gln Met Ile
    770                 775                 780

Asp Leu Phe Gln Lys Lys Gly Leu Asn Ser Glu Asp Leu Val Val Leu
785                 790                 795                 800

Ile Gly Ala His Ser Ile Gly Val Ala His Cys Phe Asn Phe Leu Tyr
                805                 810                 815

Arg Leu Asp Glu Pro Glu Lys Ala Gln Met Leu Asp Pro Arg Leu Ala
            820                 825                 830

Gly Val Met Arg Phe Ile Cys Thr Asn Gln Met Asn Thr Leu Pro Phe
        835                 840                 845

Asp Pro Thr Thr Gln Tyr Lys Met Asp Ser Ile Phe Tyr Lys Gln Leu
    850                 855                 860

Met Met Lys Lys Gly Leu Ile Glu Ser Asp Gln Ile Leu Ala Gln Asp
865                 870                 875                 880

Ile Arg Thr Arg Gly Leu Val Gln Lys Phe Gly Asp Asp Glu Met Gly
                885                 890                 895

Trp Phe Asp Lys Phe Gly Lys Ala Met Asn Lys Leu Gly Ala Ile Glu
            900                 905                 910

Val Leu Thr Gly Asn Gln Gly Gln Ile Arg Arg Gln Cys Arg Ala Val
        915                 920                 925

Asn


<210> SEQ ID NO 45
<211> LENGTH: 2478
<212> TYPE: DNA
<213> ORGANISM: Nicotiana tabacum

<400> SEQUENCE: 45

gtatgtttca gtctcacaga gatcgttcat cgataccaca gccatgtgga agcagaaaaa      60

gagagctctg cagaagtttt ggacaccgag cactctaaat atgcaagctt catgacagtg     120

ggacaactgt tacaaacggt aggaaggcaa ctcgaggaac ctgctgttga tgatctcagt     180

gtaactgacc ttgtccattt ggaaaaccaa ctgccaactg ctctaatgca agtcagatct     240

agcaagacgc atttgatgat tgaatctatc aaaagtcttc gtgagaagga aaaactgctg     300

agtgaagaaa acaaacatct ggagaacaag tacactccag cttacaactt caaatcagca     360

atggctctac ctatcgacct cgaagccggc cttcaagatg aaaccaacaa cttggcgccc     420

ggggccggaa ggctacctga cgacggcaac gaggctcgaa tcgaagaacc cgaaattcga     480

gccgaagtac cattggatat caattcacaa atagctctag aagcgaatca gcgttctgaa     540

ccggaaagaa gcgttcaggg cggtgctcga cccatagccc gagacaccta cagcacgggg     600

gaaatcgggg tcagcttgcg tatgattttc gaaatgttac aagcccaaca agcagcgata     660

gctcagttgc agagccgaac tcatatgcaa agcgggccga actccaatcc gcttcttcga     720

gaagtcaccc ccagaacgga gcccgccgta gtgaaatcaa acgagcagga atcggggacc     780

gctcctgaaa ttgctaaatt gctcgaggaa ctcacaaaac gagtcgaagc caacgacaaa     840

aaagtggaaa cgtataacgc tagggtcgat caaatcccgg gggctccgcc aatgataaaa     900

gggctcgatt cgaaaaaatt catacaaaag ccttttccct cgagcgcggc cccaaaacca     960

atccccaaaa aattccgtat gcccgaaatt cccaaatata acggtacgac cgatcctaac    1020

gaacatgtca cctcctacac atgtgccatc aaaggcaacg atttggagga cgatgagatc    1080

gaatccgtgt tgttgaaaaa gttcggagag accctcgcaa agggagcaat gatctggtat    1140
```

```
cacaacttac caccaaattc cattgattct tttgccatgt tagcagattc gttcgtaaaa   1200

gcacatgctg gtgccataaa ggttgcaaca aggaaatcag acctcttcaa agtaaaacaa   1260

aggggtaacg aaatgctgag ggaattcgta tcccgatttc aaatggaacg tatggacttg   1320

ccaccggtca cagacgattg ggccgtacaa gctttcaccc aaggactgaa cgggctaagt   1380

tcgacagcat cacatcggat gaacaacggt tcagcacgtg atacggttcg gaacaaccga   1440

aggactgatc gggggcaaaa ttctcgggga cttatgagca agagcggctt tgataaatat   1500

gccgatccta tagaagtccc tcgattatcg gagtataact tcaacattga tacatccgcc   1560

atcgtatcgg ccatcggacg catcaaagac accagatggc ctcgacccat gcagaccgat   1620

cctgcccaaa ggaatcccaa tcaaatgtgc gaatatcatg gcacccatgg ccacagaacg   1680

gaagattgca ggcaactaag agaggaagtg gcccgcttat ttaacaaagg acaccttcgg   1740

gaatttctga gtgatagggc gaagaaccat tttaggaaca aggaattcgg caagcaaaac   1800

gagccagaag aaccgcaaca cgtcattcac atgatcatcg gcggcgtcga tgcccctcag   1860

ggaccgatgc ttaaacgcac taaaacatcg attgtgaggg aaaagcgatc tcgaactcaa   1920

gattatacac ccatagggac tttgtccttc agtgatgaag atacagaggg aatcatccaa   1980

ccccataacg atgcactggt aatatccgta ctcatgaata aaactaagat taagcgtgtg   2040

ttaattgatc caggtagctc ggccaatatc atcagatcga gggtcgtaga acagctcggc   2100

ctgcaagatc aggtcgtacc cgcaactctg gttctaaacg gattcaatat ggcatgtgaa   2160

accaccaaag gcgagattac cctaccgata aacgtggccg gaaccatcca ggaaacaaag   2220

tttcacgtga tcgaaggtga tatgagatat aacgcccttt tcggaaggcc gtggatccac   2280

agcatgagag ccgtaccctc gaccctacac caggtcctca aattcccaac atcgggaggt   2340

gtcaaaatag tgtacggaga acaaccggcc gcaaaggaaa tgttctccgt cgaagaagca   2400

aaatcaatat cctcgtcttc gccgataaaa ggatcaggtt cagaaggaga cacaatcgga   2460

gagcagagcg ccaaatag                                                 2478
```

```
<210> SEQ ID NO 46
<211> LENGTH: 825
<212> TYPE: PRT
<213> ORGANISM: Nicotiana tabacum

<400> SEQUENCE: 46

Val Cys Phe Ser Leu Thr Glu Ile Val His Arg Tyr His Ser His Val
1               5                   10                  15

Glu Ala Glu Lys Glu Ser Ser Ala Glu Val Leu Asp Thr Glu His Ser
            20                  25                  30

Lys Tyr Ala Ser Phe Met Thr Val Gly Gln Leu Leu Gln Thr Val Gly
        35                  40                  45

Arg Gln Leu Glu Glu Pro Ala Val Asp Asp Leu Ser Val Thr Asp Leu
    50                  55                  60

Val His Leu Glu Asn Gln Leu Pro Thr Ala Leu Met Gln Val Arg Ser
65                  70                  75                  80

Ser Lys Thr His Leu Met Ile Glu Ser Ile Lys Ser Leu Arg Glu Lys
                85                  90                  95

Glu Lys Leu Leu Ser Glu Glu Asn Lys His Leu Glu Asn Lys Tyr Thr
            100                 105                 110

Pro Ala Tyr Asn Phe Lys Ser Ala Met Ala Leu Pro Ile Asp Leu Glu
        115                 120                 125
```

-continued

```
Ala Gly Leu Gln Asp Glu Thr Asn Asn Leu Ala Pro Gly Ala Gly Arg
    130                 135                 140

Leu Pro Asp Asp Gly Asn Glu Ala Arg Ile Glu Glu Pro Glu Ile Arg
145                 150                 155                 160

Ala Glu Val Pro Leu Asp Ile Asn Ser Gln Ile Ala Leu Glu Ala Asn
                165                 170                 175

Gln Arg Ser Glu Pro Glu Arg Ser Val Gln Gly Gly Ala Arg Pro Ile
            180                 185                 190

Ala Arg Asp Thr Tyr Ser Thr Gly Glu Ile Gly Val Ser Leu Arg Met
        195                 200                 205

Ile Phe Glu Met Leu Gln Ala Gln Gln Ala Ala Ile Ala Gln Leu Gln
    210                 215                 220

Ser Arg Thr His Met Gln Ser Gly Pro Asn Ser Asn Pro Leu Leu Arg
225                 230                 235                 240

Glu Val Thr Pro Arg Thr Glu Pro Ala Val Val Lys Ser Asn Glu Gln
                245                 250                 255

Glu Ser Gly Thr Ala Pro Glu Ile Ala Lys Leu Leu Glu Glu Leu Thr
            260                 265                 270

Lys Arg Val Glu Ala Asn Asp Lys Lys Val Glu Thr Tyr Asn Ala Arg
        275                 280                 285

Val Asp Gln Ile Pro Gly Ala Pro Pro Met Ile Lys Gly Leu Asp Ser
    290                 295                 300

Lys Lys Phe Ile Gln Lys Pro Phe Pro Ser Ser Ala Ala Pro Lys Pro
305                 310                 315                 320

Ile Pro Lys Lys Phe Arg Met Pro Glu Ile Pro Lys Tyr Asn Gly Thr
                325                 330                 335

Thr Asp Pro Asn Glu His Val Thr Ser Tyr Thr Cys Ala Ile Lys Gly
            340                 345                 350

Asn Asp Leu Glu Asp Asp Glu Ile Glu Ser Val Leu Leu Lys Lys Phe
        355                 360                 365

Gly Glu Thr Leu Ala Lys Gly Ala Met Ile Trp Tyr His Asn Leu Pro
    370                 375                 380

Pro Asn Ser Ile Asp Ser Phe Ala Met Leu Ala Asp Ser Phe Val Lys
385                 390                 395                 400

Ala His Ala Gly Ala Ile Lys Val Ala Thr Arg Lys Ser Asp Leu Phe
                405                 410                 415

Lys Val Lys Gln Arg Gly Asn Glu Met Leu Arg Glu Phe Val Ser Arg
            420                 425                 430

Phe Gln Met Glu Arg Met Asp Leu Pro Pro Val Thr Asp Asp Trp Ala
        435                 440                 445

Val Gln Ala Phe Thr Gln Gly Leu Asn Gly Leu Ser Ser Thr Ala Ser
    450                 455                 460

His Arg Met Asn Asn Gly Ser Ala Arg Asp Thr Val Arg Asn Asn Arg
465                 470                 475                 480

Arg Thr Asp Arg Gly Gln Asn Ser Arg Gly Leu Met Ser Lys Ser Gly
                485                 490                 495

Phe Asp Lys Tyr Ala Asp Pro Ile Glu Val Pro Arg Leu Ser Glu Tyr
            500                 505                 510

Asn Phe Asn Ile Asp Thr Ser Ala Ile Val Ser Ala Ile Gly Arg Ile
        515                 520                 525

Lys Asp Thr Arg Trp Pro Arg Pro Met Gln Thr Asp Pro Ala Gln Arg
    530                 535                 540

Asn Pro Asn Gln Met Cys Glu Tyr His Gly Thr His Gly His Arg Thr
```

-continued

```
545                 550                 555                 560

Glu Asp Cys Arg Gln Leu Arg Glu Glu Val Ala Arg Leu Phe Asn Lys
                565                 570                 575

Gly His Leu Arg Glu Phe Leu Ser Asp Arg Ala Lys Asn His Phe Arg
            580                 585                 590

Asn Lys Glu Phe Gly Lys Gln Asn Glu Pro Glu Glu Pro Gln His Val
        595                 600                 605

Ile His Met Ile Ile Gly Gly Val Asp Ala Pro Gln Gly Pro Met Leu
    610                 615                 620

Lys Arg Thr Lys Thr Ser Ile Val Arg Glu Lys Arg Ser Arg Thr Gln
625                 630                 635                 640

Asp Tyr Thr Pro Ile Gly Thr Leu Ser Phe Ser Asp Glu Asp Thr Glu
                645                 650                 655

Gly Ile Ile Gln Pro His Asn Asp Ala Leu Val Ile Ser Val Leu Met
            660                 665                 670

Asn Lys Thr Lys Ile Lys Arg Val Leu Ile Asp Pro Gly Ser Ser Ala
        675                 680                 685

Asn Ile Ile Arg Ser Arg Val Val Glu Gln Leu Gly Leu Gln Asp Gln
    690                 695                 700

Val Val Pro Ala Thr Leu Val Leu Asn Gly Phe Asn Met Ala Cys Glu
705                 710                 715                 720

Thr Thr Lys Gly Glu Ile Thr Leu Pro Ile Asn Val Ala Gly Thr Ile
                725                 730                 735

Gln Glu Thr Lys Phe His Val Ile Glu Gly Asp Met Arg Tyr Asn Ala
            740                 745                 750

Leu Phe Gly Arg Pro Trp Ile His Ser Met Arg Ala Val Pro Ser Thr
        755                 760                 765

Leu His Gln Val Leu Lys Phe Pro Thr Ser Gly Gly Val Lys Ile Val
    770                 775                 780

Tyr Gly Glu Gln Pro Ala Ala Lys Glu Met Phe Ser Val Glu Glu Ala
785                 790                 795                 800

Lys Ser Ile Ser Ser Ser Ser Pro Ile Lys Gly Ser Gly Ser Glu Gly
                805                 810                 815

Asp Thr Ile Gly Glu Gln Ser Ala Lys
            820                 825


<210> SEQ ID NO 47
<211> LENGTH: 1152
<212> TYPE: DNA
<213> ORGANISM: Nicotiana tabacum

<400> SEQUENCE: 47

atgcagtctg tactctggaa cctaaggaag attgaaattc aagataaatt ctgcgatatt      60

gaaaggataa gtcctgcata cctcaacaca aatgacacgg caaagaaaat tcaagaagaa     120

atcaatggct tgcattgtaa actggaggag gctgagggat tattaagaat atttgaacca     180

gatacaaaaa aaattacatc actccatgag cttgatttgt gtgaaaaacg tcttcaggtt     240

gccttgaacc aagttaggca aagaatggaa caactctcca acaatcataa tacatcaagt     300

tatgaagata atatggagca aataaatgca ctccttcaat acatagacaa cacacaaact     360

gaggacacaa aaccctcgtt ggaggaatct ccctatgact tatggctaga gcttgaagat     420

tatagttaca caaactatat taatgacaac aacaatagtc atctctatgc tgcctcagaa     480

acatcttctc ttactcaaag ttctatgagc ctttcttctc caattattta tgatgcaata     540
```

```
tcccaaacaa gtataagtgg tgtgactaat tatcataaag aagggacttt tagttcttta    600

actgatgaga attttaagca atcacaacat tcaaccagaa ccttcccaac tctcacttta    660

caaacttcat tcaaatttgc caagcctgaa atggaaactc ccacatctgc actacggccg    720

gtagcgccat atctgcatgt tgaagcaaca gcagcgtgta gccagcaacc agtttcaagt    780

gattattata aagagaacaa tgaactcgac tgcagatttc aacctaaagt tacaacgtct    840

aactatcaaa tgtcccaaaa acgtactgca gaaggaagtt ttagttcctt aactgatgaa    900

agctttaagc aatcacaatg ttcaaccagg atcttcccac ctatcgctcc attacaaact    960

tcattctcat ttgccacgcc tgaaatggaa actccaacct cagcattgcg gccggtggca   1020

ccatatctgc aggctgaagc agcagcatcc tctaaccagc agctaccttc taataatatt   1080

gaagaagaga accatgaaat ctcttggttt cagcctcaaa tgaaaaagtc gaagtatcat   1140

catttagctt ga                                                       1152


<210> SEQ ID NO 48
<211> LENGTH: 383
<212> TYPE: PRT
<213> ORGANISM: Nicotiana tabacum

<400> SEQUENCE: 48

Met Gln Ser Val Leu Trp Asn Leu Arg Lys Ile Glu Ile Gln Asp Lys
1               5                   10                  15

Phe Cys Asp Ile Glu Arg Ile Ser Pro Ala Tyr Leu Asn Thr Asn Asp
            20                  25                  30

Thr Ala Lys Lys Ile Gln Glu Glu Ile Asn Gly Leu His Cys Lys Leu
        35                  40                  45

Glu Glu Ala Glu Gly Leu Leu Arg Ile Phe Glu Pro Asp Thr Lys Lys
    50                  55                  60

Ile Thr Ser Leu His Glu Leu Asp Leu Cys Glu Lys Arg Leu Gln Val
65                  70                  75                  80

Ala Leu Asn Gln Val Arg Gln Arg Met Glu Gln Leu Ser Asn Asn His
                85                  90                  95

Asn Thr Ser Ser Tyr Glu Asp Asn Met Glu Gln Ile Asn Ala Leu Leu
            100                 105                 110

Gln Tyr Ile Asp Asn Thr Gln Thr Glu Asp Thr Lys Pro Ser Leu Glu
        115                 120                 125

Glu Ser Pro Tyr Asp Leu Trp Leu Glu Leu Glu Asp Tyr Ser Tyr Thr
    130                 135                 140

Asn Tyr Ile Asn Asp Asn Asn Asn Ser His Leu Tyr Ala Ala Ser Glu
145                 150                 155                 160

Thr Ser Ser Leu Thr Gln Ser Ser Met Ser Leu Ser Ser Pro Ile Ile
                165                 170                 175

Tyr Asp Ala Ile Ser Gln Thr Ser Ile Ser Gly Val Thr Asn Tyr His
            180                 185                 190

Lys Glu Gly Thr Phe Ser Ser Leu Thr Asp Glu Asn Phe Lys Gln Ser
        195                 200                 205

Gln His Ser Thr Arg Thr Phe Pro Thr Leu Thr Leu Gln Thr Ser Phe
    210                 215                 220

Lys Phe Ala Lys Pro Glu Met Glu Thr Pro Thr Ser Ala Leu Arg Pro
225                 230                 235                 240

Val Ala Pro Tyr Leu His Val Glu Ala Thr Ala Ala Cys Ser Gln Gln
                245                 250                 255

Pro Val Ser Ser Asp Tyr Tyr Lys Glu Asn Asn Glu Leu Asp Cys Arg
```

260 265 270

Phe Gln Pro Lys Val Thr Thr Ser Asn Tyr Gln Met Ser Gln Lys Arg
275 280 285

Thr Ala Glu Gly Ser Phe Ser Ser Leu Thr Asp Glu Ser Phe Lys Gln
290 295 300

Ser Gln Cys Ser Thr Arg Ile Phe Pro Pro Ile Ala Pro Leu Gln Thr
305 310 315 320

Ser Phe Ser Phe Ala Thr Pro Glu Met Glu Thr Pro Thr Ser Ala Leu
325 330 335

Arg Pro Val Ala Pro Tyr Leu Gln Ala Glu Ala Ala Ala Ser Ser Asn
340 345 350

Gln Gln Leu Pro Ser Asn Asn Ile Glu Glu Glu Asn His Glu Ile Ser
355 360 365

Trp Phe Gln Pro Gln Met Lys Lys Ser Lys Tyr His His Leu Ala
370 375 380

<210> SEQ ID NO 49
<211> LENGTH: 813
<212> TYPE: DNA
<213> ORGANISM: Nicotiana tabacum

<400> SEQUENCE: 49
atgggaactg gtacttatgg agaagtggga cgtacaatac atcaaagatc aggaacacat 60
atacctcaaa ttctcgatcc gcctttgcta ggggatagtg attgcaagcg agaaggcaaa 120
catgtagaat ttatgcctcc aatcatgggt gaaaacttaa aagcagctaa tcaatttgaa 180
ctgatggccc cgtcaattgc attcaaatca tatccctatt cggaggtacc acaatattct 240
ggtggcaatg tggctgctgc atgtggtgaa tctttggtac atcaaaatat agaaagatca 300
gtgcataatg gtagaatgat tttgccaatt gaagtgaagg aggagcctat gtatgtaaat 360
gccaaacaat accatggaat tctaaggcga aggcaacttc gtgcaaaggc tgtgttggag 420
caaaaagtgg ttaaatctag aaagccttat cttcatgaat ctcggcaccg gcatgcgatg 480
agaagagcta gagatggtgg aggccgattt ctcaacacaa aaaagaagat ccaacttcct 540
gctaataata atattaatac aactactcca agtagtaaag gcaaaggttg tgcagcctcg 600
gaagtcagtt ccatggactc tgatttctct caaaattact tgctcaattc tggacatatt 660
ggatcatcca atgctacttc tgttgaagga ttccagttcc aaggaataca taatacagat 720
aatcctcaat tgggttgtca ttatcagtgg aatctcaatg acaaccattg ctattgcatg 780
cagtcaggag cttctaatct ccaaccattt tga 813

<210> SEQ ID NO 50
<211> LENGTH: 270
<212> TYPE: PRT
<213> ORGANISM: Nicotiana tabacum

<400> SEQUENCE: 50

Met Gly Thr Gly Thr Tyr Gly Glu Val Gly Arg Thr Ile His Gln Arg
1 5 10 15

Ser Gly Thr His Ile Pro Gln Ile Leu Asp Pro Pro Leu Leu Gly Asp
20 25 30

Ser Asp Cys Lys Arg Glu Gly Lys His Val Glu Phe Met Pro Pro Ile
35 40 45

Met Gly Glu Asn Leu Lys Ala Ala Asn Gln Phe Glu Leu Met Ala Pro
50 55 60

-continued

```
Ser Ile Ala Phe Lys Ser Tyr Pro Tyr Ser Glu Val Pro Gln Tyr Ser
65                  70                  75                  80

Gly Gly Asn Val Ala Ala Ala Cys Gly Glu Ser Leu Val His Gln Asn
                85                  90                  95

Ile Glu Arg Ser Val His Asn Gly Arg Met Ile Leu Pro Ile Glu Val
            100                 105                 110

Lys Glu Glu Pro Met Tyr Val Asn Ala Lys Gln Tyr His Gly Ile Leu
        115                 120                 125

Arg Arg Arg Gln Leu Arg Ala Lys Ala Val Leu Glu Gln Lys Val Val
    130                 135                 140

Lys Ser Arg Lys Pro Tyr Leu His Glu Ser Arg His Arg His Ala Met
145                 150                 155                 160

Arg Arg Ala Arg Asp Gly Gly Gly Arg Phe Leu Asn Thr Lys Lys Lys
                165                 170                 175

Ile Gln Leu Pro Ala Asn Asn Asn Ile Asn Thr Thr Thr Pro Ser Ser
            180                 185                 190

Lys Gly Lys Gly Cys Ala Ala Ser Glu Val Ser Ser Met Asp Ser Asp
        195                 200                 205

Phe Ser Gln Asn Tyr Leu Leu Asn Ser Gly His Ile Gly Ser Ser Asn
    210                 215                 220

Ala Thr Ser Val Glu Gly Phe Gln Phe Gln Gly Ile His Asn Thr Asp
225                 230                 235                 240

Asn Pro Gln Leu Gly Cys His Tyr Gln Trp Asn Leu Asn Asp Asn His
                245                 250                 255

Cys Tyr Cys Met Gln Ser Gly Ala Ser Asn Leu Gln Pro Phe
            260                 265                 270
```

<210> SEQ ID NO 51
<211> LENGTH: 762
<212> TYPE: DNA
<213> ORGANISM: Nicotiana tabacum

<400> SEQUENCE: 51

```
atgggagctg gtgcttttgg agaagccgga cgtacaatat atcaaaagtc cgatagtgat      60

tgcaagcgag atggcaaacg tgtagaattt atgcctccaa tcatgggtga aaacttaaga     120

gcagctaatc aatttgaact gatgcccccc tcaattgcat tcagatcata tccctattca     180

gaagtaccac aatattctgg tggcaatgtg gctgctgcat ttggcgaatc tacggtacat     240

caaaatatag aaagatcagt gcataatggt agaatgattt tgccacttga agtgaaggag     300

gagcctatgt atgtaaatgc caaacaatac catggaattc taaggcgaag gcaactccgt     360

gcaaaggctg tgttggagca aaaggtggtc aaatctagaa agccttatct tcatgaatct     420

cggcaccggc atgcgatgag aagagctaga gatggtggcg gccgatttct caacacaaag     480

aagaagatcc aacttactac taataataat aataataatg ggaatactaa tgcaactcca     540

agtagtaaag gcaaaggttc ttcagcctca gaagtcagtt ccatggactc ttattctgga     600

catattggat catccaatag tactgctcat gtccagggat ttcagttcca aggaatacat     660

aatacagaaa atcctcaact gggttgtcat tatcagtgga atctcaatga taaccattgc     720

aattgcatgc agtcaggagc ttctaatatc caaccatttt ga                        762
```

<210> SEQ ID NO 52
<211> LENGTH: 253
<212> TYPE: PRT
<213> ORGANISM: Nicotiana tabacum

<400> SEQUENCE: 52

Met Gly Ala Gly Ala Phe Gly Glu Ala Gly Arg Thr Ile Tyr Gln Lys
1               5                   10                  15

Ser Asp Ser Asp Cys Lys Arg Asp Gly Lys Arg Val Glu Phe Met Pro
            20                  25                  30

Pro Ile Met Gly Glu Asn Leu Arg Ala Ala Asn Gln Phe Glu Leu Met
        35                  40                  45

Pro Pro Ser Ile Ala Phe Arg Ser Tyr Pro Tyr Ser Glu Val Pro Gln
    50                  55                  60

Tyr Ser Gly Gly Asn Val Ala Ala Ala Phe Gly Glu Ser Thr Val His
65                  70                  75                  80

Gln Asn Ile Glu Arg Ser Val His Asn Gly Arg Met Ile Leu Pro Leu
                85                  90                  95

Glu Val Lys Glu Glu Pro Met Tyr Val Asn Ala Lys Gln Tyr His Gly
            100                 105                 110

Ile Leu Arg Arg Arg Gln Leu Arg Ala Lys Ala Val Leu Glu Gln Lys
        115                 120                 125

Val Val Lys Ser Arg Lys Pro Tyr Leu His Glu Ser Arg His Arg His
    130                 135                 140

Ala Met Arg Arg Ala Arg Asp Gly Gly Gly Arg Phe Leu Asn Thr Lys
145                 150                 155                 160

Lys Lys Ile Gln Leu Thr Thr Asn Asn Asn Asn Asn Asn Gly Asn Thr
                165                 170                 175

Asn Ala Thr Pro Ser Ser Lys Gly Lys Gly Ser Ser Ala Ser Glu Val
            180                 185                 190

Ser Ser Met Asp Ser Tyr Ser Gly His Ile Gly Ser Ser Asn Ser Thr
        195                 200                 205

Ala His Val Gln Gly Phe Gln Phe Gln Gly Ile His Asn Thr Glu Asn
    210                 215                 220

Pro Gln Leu Gly Cys His Tyr Gln Trp Asn Leu Asn Asp Asn His Cys
225                 230                 235                 240

Asn Cys Met Gln Ser Gly Ala Ser Asn Ile Gln Pro Phe
                245                 250

<210> SEQ ID NO 53
<211> LENGTH: 753
<212> TYPE: DNA
<213> ORGANISM: Nicotiana tabacum

<400> SEQUENCE: 53
atgcaatatg aacacgaatt tttcttccaa tattaccatg atcaacttca acagaatctt 60
gatgatacct tagctgagat cagtactgag actgccatta ttaacacggc agattccaac 120
aaagacgacg ctttaataag tagaaatgaa cttgaacaag aggaaggatg tgagaataaa 180
aagggtaaaa taagcagcaa caagagagtg tctaagaaag atagacacag tgcaaatagt 240
gaatcctcta cttctgaatg tgaagttgta tcagaaattg atgaatctcc atctaatcat 300
aaggcaaatg ctaaaggaaa ttcttgcaac aaggagaagg agaagaagaa gaaggagaag 360
gagaaatcag ttcgtcgagc tgcattttat catccatttg caaaagaatc aaggaaacaa 420
gcaagagaga gggcaaggga gagaacaaaa ctaaagaaaa acttttgtaa atctcatcat 480
ttgaacttaa gatcttggaa tttctccgaa gggggcgaag aatcagcggg atatattagc 540
atgaatcttc cttgtcaaga aatgcaagct gaaatagttg aagaactcac ctcccacaat 600
gagaagcagc ttttattagg gattaaagaa aacattgcta atgattgtaa tttggtggct 660
actggcaatt ggagcccaaa tgccattttc aactatcaac aaaatgctgg aattcctcat 720
gagcatcaaa ttacagacat tccgttttca tga 753

<210> SEQ ID NO 54
<211> LENGTH: 250
<212> TYPE: PRT
<213> ORGANISM: Nicotiana tabacum

<400> SEQUENCE: 54

```
Met Gln Tyr Glu His Glu Phe Phe Phe Gln Tyr Tyr His Asp Gln Leu
1               5                   10                  15

Gln Gln Asn Leu Asp Asp Thr Leu Ala Glu Ile Ser Thr Glu Thr Ala
            20                  25                  30

Ile Ile Asn Thr Ala Asp Ser Asn Lys Asp Asp Ala Leu Ile Ser Arg
        35                  40                  45

Asn Glu Leu Glu Gln Glu Glu Gly Cys Glu Asn Lys Lys Gly Lys Ile
    50                  55                  60

Ser Ser Asn Lys Arg Val Ser Lys Lys Asp Arg His Ser Ala Asn Ser
65                  70                  75                  80

Glu Ser Ser Thr Ser Glu Cys Glu Val Val Ser Glu Ile Asp Glu Ser
                85                  90                  95

Pro Ser Asn His Lys Ala Asn Ala Lys Gly Asn Ser Cys Asn Lys Glu
            100                 105                 110

Lys Glu Lys Lys Lys Lys Glu Lys Glu Lys Ser Val Arg Arg Ala Ala
        115                 120                 125

Phe Tyr His Pro Phe Ala Lys Glu Ser Arg Lys Gln Ala Arg Glu Arg
    130                 135                 140

Ala Arg Glu Arg Thr Lys Leu Lys Lys Asn Phe Cys Lys Ser His His
145                 150                 155                 160

Leu Asn Leu Arg Ser Trp Asn Phe Ser Glu Gly Gly Glu Glu Ser Ala
                165                 170                 175

Gly Tyr Ile Ser Met Asn Leu Pro Cys Gln Glu Met Gln Ala Glu Ile
            180                 185                 190

Val Glu Glu Leu Thr Ser His Asn Glu Lys Gln Leu Leu Leu Gly Ile
        195                 200                 205

Lys Glu Asn Ile Ala Asn Asp Cys Asn Leu Val Ala Thr Gly Asn Trp
    210                 215                 220

Ser Pro Asn Ala Ile Phe Asn Tyr Gln Gln Asn Ala Gly Ile Pro His
225                 230                 235                 240

Glu His Gln Ile Thr Asp Ile Pro Phe Ser
                245                 250
```

<210> SEQ ID NO 55
<211> LENGTH: 1422
<212> TYPE: DNA
<213> ORGANISM: Arabidopsis thaliana

<400> SEQUENCE: 55
atgatgaagc atatagtaca tctgggctcc acctcaaatc ttacagtagc agctagaggc 60
catggtcact cgcttcaagg acaagctcta gctcatcaag gtgttgtcat caaaatggag 120
tcacttcgaa gtcctgatat caggatttat aaggggaagc aaccatatgt tgatgtctca 180
ggtggtgaaa tatggataaa cattctacgc gagactctaa aatacggtct ttcaccaaag 240
tcctggacag actaccttca tttgaccgtt ggaggtacac tatctaatgc tggaatcagc 300

```
ggtcaagcat tcaagcatgg accccaaatc aacaacgtct accagctaga gattgttaca    360

gggaaaggag aagtcgtaac ctgttctgag aagcggaatt ctgaactttt cttcagtgtt    420

cttggcgggc ttggacagtt tggcataatc acccgggcac ggatctctct tgaaccagca    480

ccgcatatgg ttaaatggat cagggtactc tactctgact tttctgcatt ttcaagggac    540

caagaatatc tgatttcgaa ggagaaaact tttgattacg ttgaaggatt tgtgataatc    600

aatagaacag accttctcaa taattggcga tcgtcattca gtcccaacga ttccacacag    660

gcaagcagat tcaagtcaga tgggaaaact ctttattgcc tagaagtggt caaatatttc    720

aacccagaag aagctagctc tatggatcag gaaactggca agttactttc agagttaaat    780

tatattccat ccactttgtt ttcatctgaa gtgccatata tcgagtttct ggatcgcgtg    840

catatcgcag agagaaaact aagagcaaag ggtttatggg aggttccaca tccctggctg    900

aatctcctga ttcctaagag cagcatatac caatttgcta cagaagtttt caacaacatt    960

ctcacaagca acaacaacgg tcctatcctt atttatccag tcaatcaatc caagtggaag   1020

aaacatacat ctttgataac tccaaatgaa gatatattct atctcgtagc ctttctcccc   1080

tctgcagtgc caaattcctc agggaaaaac gatctagagt accttttgaa acaaaaccaa   1140

agagttatga acttctgcgc agcagcaaac ctcaacgtga agcagtattt gccccattat   1200

gaaactcaaa aagagtggaa atcacacttt ggcaaaagat gggaaacatt tgcacagagg   1260

aaacaagcct acgaccctct agcgattcta gcacctggcc aaagaatatt ccaaaagaca   1320

acaggaaaat tatctcccat ccaactcgca aagtcaaagg caacaggaag tcctcaaagg   1380

taccattacg catcaatact gccgaaacct agaactgtat aa                      1422


<210> SEQ ID NO 56
<211> LENGTH: 473
<212> TYPE: PRT
<213> ORGANISM: Arabidopsis thaliana

<400> SEQUENCE: 56

Met Met Lys His Ile Val His Leu Gly Ser Thr Ser Asn Leu Thr Val
1               5                   10                  15

Ala Ala Arg Gly His Gly His Ser Leu Gln Gly Gln Ala Leu Ala His
            20                  25                  30

Gln Gly Val Val Ile Lys Met Glu Ser Leu Arg Ser Pro Asp Ile Arg
        35                  40                  45

Ile Tyr Lys Gly Lys Gln Pro Tyr Val Asp Val Ser Gly Gly Glu Ile
    50                  55                  60

Trp Ile Asn Ile Leu Arg Glu Thr Leu Lys Tyr Gly Leu Ser Pro Lys
65                  70                  75                  80

Ser Trp Thr Asp Tyr Leu His Leu Thr Val Gly Gly Thr Leu Ser Asn
                85                  90                  95

Ala Gly Ile Ser Gly Gln Ala Phe Lys His Gly Pro Gln Ile Asn Asn
            100                 105                 110

Val Tyr Gln Leu Glu Ile Val Thr Gly Lys Gly Glu Val Val Thr Cys
        115                 120                 125

Ser Glu Lys Arg Asn Ser Glu Leu Phe Phe Ser Val Leu Gly Gly Leu
    130                 135                 140

Gly Gln Phe Gly Ile Ile Thr Arg Ala Arg Ile Ser Leu Glu Pro Ala
145                 150                 155                 160

Pro His Met Val Lys Trp Ile Arg Val Leu Tyr Ser Asp Phe Ser Ala
                165                 170                 175
```

-continued

```
Phe Ser Arg Asp Gln Glu Tyr Leu Ile Ser Lys Glu Lys Thr Phe Asp
            180                 185                 190

Tyr Val Glu Gly Phe Val Ile Ile Asn Arg Thr Asp Leu Leu Asn Asn
        195                 200                 205

Trp Arg Ser Ser Phe Ser Pro Asn Asp Ser Thr Gln Ala Ser Arg Phe
    210                 215                 220

Lys Ser Asp Gly Lys Thr Leu Tyr Cys Leu Glu Val Val Lys Tyr Phe
225                 230                 235                 240

Asn Pro Glu Glu Ala Ser Ser Met Asp Gln Glu Thr Gly Lys Leu Leu
                245                 250                 255

Ser Glu Leu Asn Tyr Ile Pro Ser Thr Leu Phe Ser Ser Glu Val Pro
            260                 265                 270

Tyr Ile Glu Phe Leu Asp Arg Val His Ile Ala Glu Arg Lys Leu Arg
        275                 280                 285

Ala Lys Gly Leu Trp Glu Val Pro His Pro Trp Leu Asn Leu Leu Ile
    290                 295                 300

Pro Lys Ser Ser Ile Tyr Gln Phe Ala Thr Glu Val Phe Asn Asn Ile
305                 310                 315                 320

Leu Thr Ser Asn Asn Asn Gly Pro Ile Leu Ile Tyr Pro Val Asn Gln
                325                 330                 335

Ser Lys Trp Lys Lys His Thr Ser Leu Ile Thr Pro Asn Glu Asp Ile
            340                 345                 350

Phe Tyr Leu Val Ala Phe Leu Pro Ser Ala Val Pro Asn Ser Ser Gly
        355                 360                 365

Lys Asn Asp Leu Glu Tyr Leu Leu Lys Gln Asn Gln Arg Val Met Asn
    370                 375                 380

Phe Cys Ala Ala Ala Asn Leu Asn Val Lys Gln Tyr Leu Pro His Tyr
385                 390                 395                 400

Glu Thr Gln Lys Glu Trp Lys Ser His Phe Gly Lys Arg Trp Glu Thr
                405                 410                 415

Phe Ala Gln Arg Lys Gln Ala Tyr Asp Pro Leu Ala Ile Leu Ala Pro
            420                 425                 430

Gly Gln Arg Ile Phe Gln Lys Thr Thr Gly Lys Leu Ser Pro Ile Gln
        435                 440                 445

Leu Ala Lys Ser Lys Ala Thr Gly Ser Pro Gln Arg Tyr His Tyr Ala
    450                 455                 460

Ser Ile Leu Pro Lys Pro Arg Thr Val
465                 470
```

<210> SEQ ID NO 57
<211> LENGTH: 1659
<212> TYPE: DNA
<213> ORGANISM: Nicotiana tabacum

<400> SEQUENCE: 57

```
atgaagtcac caccaactca tgtcttcttt aaacataaaa gtatgcttct taggttgctt      60

atattcatac taggcatttg ctcaataaac agaactaacc tttgttgtga ccaacctttt     120

gccaccccaa tatcttcttc ttcttctacc ccttcaagtt tttcagtgat tcaatcatca     180

ttgaaacagt taaatattga agggtatttt agtttcaaga atttcgatca cgcggccaaa     240

gactttggca acagatatca cttcttgcca tcggcagttc tgtatccaaa atcagtttct     300

gatatatcat ctaccataaa acatgttttt gacatgggtg ttactacaga cctaactgtt     360

gctgctagag gccatggcca ttctttagaa ggccaagctc aagcttacca aggagtagtg     420
```

```
atcaatatgg aatcgcttcg agcgccagca atgcgtttcc acacagggaa tcaagaactg    480

ccttttgttg atgtctctgc aggagaactt tggataaaca tcctgcatga aagtcttaaa    540

cttggattaa caccaaaatc ttggactgat tatcttcacc tcaccgttgg agggactttg    600

tcgaatgccg gaatcagtgg tcaagcattc aaacatggac cacagatcaa taatgtttac    660

caacttgagg ttgtcactgg taaaggagag gtgattactt gttcagagga gaagaatgct    720

gacctgttct atggtgtatt aggaggacta ggccagtttg gtatcatcac aagggctaga    780

attgctcttg aaccagcacc taaaaaggta aagtggatca gagtgctgta ttcagatttc    840

tccacatttt cctatgatca agaacacttg atatcatccg agaactcttt tgactatata    900

gaaggatttg tcattatcaa tagaacagga ttgttaaaca actggaggtc tactttcaat    960

cctaaagatc cacttctagc caaagagttc agttctgagg gaaaagttct gtactgccta   1020

gaagttgcca aatacttcaa tccagaagag acaaccaaaa ctgatcagaa tgttgatgtt   1080

cttttatcaa agttgaatta tatccaatcg acgctgttcc aatcagaagt atcctacgtg   1140

gatttcctcg acagagttca cgtatccgag atgaaacttc aagagaaggg gttatgggat   1200

attcctcatc catggctaaa ccttctaatt ccaaagagca agattcatga ctttgcacga   1260

gaagtttttg ggaagatact taccgacact agccacggtc ctatactcat ctacccagtc   1320

aacaaatcaa agtggagaaa aggaacatca gtagttacac ctgaagaaga tgttatgtat   1380

ctaatagcat ttctatcttc tgccatgcca tcttcaacag gaaaggacgg cgtagaatat   1440

attctaaata agaataagaa gatactaaac ttttgcagaa aagcacatat tggaatgaaa   1500

cagtatttgc cacactacac aacgcaggaa gactggaaag gtcactttgg tccccagtgg   1560

gaaacattta aaaggaggaa atctacatat gacccctttgg ctatcctagc tcctggccag   1620

agaattttta gaagagcatc aggcgttcaa caacaatga                           1659
```

<210> SEQ ID NO 58
<211> LENGTH: 552
<212> TYPE: PRT
<213> ORGANISM: Nicotiana tabacum

<400> SEQUENCE: 58

```
Met Lys Ser Pro Pro Thr His Val Phe Phe Lys His Lys Ser Met Leu
1               5                   10                  15

Leu Arg Leu Leu Ile Phe Ile Leu Gly Ile Cys Ser Ile Asn Arg Thr
            20                  25                  30

Asn Leu Cys Cys Asp Gln Pro Phe Ala Thr Pro Ile Ser Ser Ser Ser
        35                  40                  45

Ser Thr Pro Ser Ser Phe Ser Val Ile Gln Ser Ser Leu Lys Gln Leu
    50                  55                  60

Asn Ile Glu Gly Tyr Phe Ser Phe Lys Asn Phe Asp His Ala Ala Lys
65                  70                  75                  80

Asp Phe Gly Asn Arg Tyr His Phe Leu Pro Ser Ala Val Leu Tyr Pro
                85                  90                  95

Lys Ser Val Ser Asp Ile Ser Ser Thr Ile Lys His Val Phe Asp Met
            100                 105                 110

Gly Val Thr Thr Asp Leu Thr Val Ala Ala Arg Gly His Gly His Ser
        115                 120                 125

Leu Glu Gly Gln Ala Gln Ala Tyr Gln Gly Val Val Ile Asn Met Glu
    130                 135                 140

Ser Leu Arg Ala Pro Ala Met Arg Phe His Thr Gly Asn Gln Glu Leu
145                 150                 155                 160
```

```
Pro Phe Val Asp Val Ser Ala Gly Glu Leu Trp Ile Asn Ile Leu His
                165                 170                 175

Glu Ser Leu Lys Leu Gly Leu Thr Pro Lys Ser Trp Thr Asp Tyr Leu
            180                 185                 190

His Leu Thr Val Gly Gly Thr Leu Ser Asn Ala Gly Ile Ser Gly Gln
        195                 200                 205

Ala Phe Lys His Gly Pro Gln Ile Asn Asn Val Tyr Gln Leu Glu Val
    210                 215                 220

Val Thr Gly Lys Gly Glu Val Ile Thr Cys Ser Glu Glu Lys Asn Ala
225                 230                 235                 240

Asp Leu Phe Tyr Gly Val Leu Gly Gly Leu Gly Gln Phe Gly Ile Ile
                245                 250                 255

Thr Arg Ala Arg Ile Ala Leu Glu Pro Ala Pro Lys Lys Val Lys Trp
            260                 265                 270

Ile Arg Val Leu Tyr Ser Asp Phe Ser Thr Phe Ser Tyr Asp Gln Glu
        275                 280                 285

His Leu Ile Ser Ser Glu Asn Ser Phe Asp Tyr Ile Glu Gly Phe Val
    290                 295                 300

Ile Ile Asn Arg Thr Gly Leu Leu Asn Asn Trp Arg Ser Thr Phe Asn
305                 310                 315                 320

Pro Lys Asp Pro Leu Leu Ala Lys Glu Phe Ser Ser Glu Gly Lys Val
                325                 330                 335

Leu Tyr Cys Leu Glu Val Ala Lys Tyr Phe Asn Pro Glu Glu Thr Thr
            340                 345                 350

Lys Thr Asp Gln Asn Val Asp Val Leu Leu Ser Lys Leu Asn Tyr Ile
        355                 360                 365

Gln Ser Thr Leu Phe Gln Ser Glu Val Ser Tyr Val Asp Phe Leu Asp
    370                 375                 380

Arg Val His Val Ser Glu Met Lys Leu Gln Glu Lys Gly Leu Trp Asp
385                 390                 395                 400

Ile Pro His Pro Trp Leu Asn Leu Leu Ile Pro Lys Ser Lys Ile His
                405                 410                 415

Asp Phe Ala Arg Glu Val Phe Gly Lys Ile Leu Thr Asp Thr Ser His
            420                 425                 430

Gly Pro Ile Leu Ile Tyr Pro Val Asn Lys Ser Lys Trp Arg Lys Gly
        435                 440                 445

Thr Ser Val Val Thr Pro Glu Glu Asp Val Met Tyr Leu Ile Ala Phe
    450                 455                 460

Leu Ser Ser Ala Met Pro Ser Ser Thr Gly Lys Asp Gly Val Glu Tyr
465                 470                 475                 480

Ile Leu Asn Lys Asn Lys Lys Ile Leu Asn Phe Cys Arg Lys Ala His
                485                 490                 495

Ile Gly Met Lys Gln Tyr Leu Pro His Tyr Thr Thr Gln Glu Asp Trp
            500                 505                 510

Lys Gly His Phe Gly Pro Gln Trp Glu Thr Phe Lys Arg Arg Lys Ser
        515                 520                 525

Thr Tyr Asp Pro Leu Ala Ile Leu Ala Pro Gly Gln Arg Ile Phe Arg
    530                 535                 540

Arg Ala Ser Gly Val Gln Gln Gln
545                 550
```

<210> SEQ ID NO 59
<211> LENGTH: 1632

<212> TYPE: DNA
<213> ORGANISM: Nicotiana tabacum

<400> SEQUENCE: 59
atgaaattac catcccattt tttatttaag caaaatgact tgctcctgaa attgcttata 60
ttcatactct gcagttgttc aagcaacaaa aataaactct gctgtaatta tcatcagttt 120
gccacccctg cagtttctac cccctcaagt ttctcactga attatttatc attgaaacaa 180
ttacaacttg aaggttacct taaatttgac aacttagaac atgcagccaa agactttggt 240
aatagatgcc acttccttcc attagcagtt ttgtacccaa aatcagtttc tgatatctct 300
tccactataa aacatgtctt tgaaataggt tccaaaactg atttaactgt tgctgctaga 360
ggccatggcc attctctaga aggtcaagct caagcttatc aaggagtagt gattagtatg 420
gaatcactac aaacaccagc aatgaaattc aagactggag aattgcctta tgttgatgtt 480
tctgctggag agctttggat taatatcctg aaagaaagtc ttaaacttgg gcttgcacct 540
aaatcttgga ctgattatct tcacctcaca gttggcggca ctttgtctaa tgctggaatc 600
agtggacaag ctttccgcca cggaccgcag atcaataacg tccaacaact tgaagttgtc 660
actggtaaag gagaggtgat tacttgttca gaggagcaga atgcagactt gtttcatggt 720
gtactaggag gactggggca atttggtatt attaccagag caaggattgc tcttgaaaca 780
gcacctaaac aggtcaagtg gattagagtg ctgtattcag atttttccat attttccaat 840
gatcaagagc acttgatatc aactcaggat acatttgact atattgaagg ttttgtcact 900
atcaaccaaa ctggattatt aaataactgg aggtctgctt tcaatcctaa agatccagtt 960
ctagccagca atttcagttc tgagggtaga gttttgttct gcttagaaat tgccaaatac 1020
ttcaatccag aagtcacaga tagtattgat cagaacattg atgtgatctt atcaaagttg 1080
aattatatcc gatccacgct gttcctatca gaagtctcct acacagaatt cctcgacagg 1140
gtgcatgtct ctgagatgaa actccaagaa aatgtttctc atccatggct aaatcttcta 1200
ataccaaaaa gcaggattct tgaatttgca caacaagttt ttggcaagat tcttactgac 1260
actagcaatg gtcctttact catctaccct gtcaacaaat caaagtggag aaaaggaaca 1320
tccatggtta cccctgacga agatgttttt tatctgatcg cgttcctatc ttctgctatg 1380
tcatcttcaa caggaaacga tggactaaga catattcttg ctcagagcaa aaggatactg 1440
aacttttgtg aagaaacaaa tatcggaatg aaacaatatt taccaaatta caagactaag 1500
gaagagtgga aggatcactt tggtcatcaa tgggaagcat ttgctagaag gaaatctaca 1560
tatgaccctt tggcaatact tgctcctggc cagagaattt tcagaagggc agaagcctgt 1620
gaacaacaat aa 1632

<210> SEQ ID NO 60
<211> LENGTH: 543
<212> TYPE: PRT
<213> ORGANISM: Nicotiana tabacum

<400> SEQUENCE: 60

Met Lys Leu Pro Ser His Phe Leu Phe Lys Gln Asn Asp Leu Leu Leu
1 5 10 15

Lys Leu Leu Ile Phe Ile Leu Cys Ser Cys Ser Ser Asn Lys Asn Lys
20 25 30

Leu Cys Cys Asn Tyr His Gln Phe Ala Thr Pro Ala Val Ser Thr Pro
35 40 45

Ser Ser Phe Ser Leu Asn Tyr Leu Ser Leu Lys Gln Leu Gln Leu Glu

-continued

```
    50                  55                  60

Gly Tyr Leu Lys Phe Asp Asn Leu Glu His Ala Ala Lys Asp Phe Gly
65                  70                  75                  80

Asn Arg Cys His Phe Leu Pro Leu Ala Val Leu Tyr Pro Lys Ser Val
                85                  90                  95

Ser Asp Ile Ser Ser Thr Ile Lys His Val Phe Glu Ile Gly Ser Lys
            100                 105                 110

Thr Asp Leu Thr Val Ala Ala Arg Gly His Gly His Ser Leu Glu Gly
        115                 120                 125

Gln Ala Gln Ala Tyr Gln Gly Val Val Ile Ser Met Glu Ser Leu Gln
    130                 135                 140

Thr Pro Ala Met Lys Phe Lys Thr Gly Glu Leu Pro Tyr Val Asp Val
145                 150                 155                 160

Ser Ala Gly Glu Leu Trp Ile Asn Ile Leu Lys Glu Ser Leu Lys Leu
                165                 170                 175

Gly Leu Ala Pro Lys Ser Trp Thr Asp Tyr Leu His Leu Thr Val Gly
            180                 185                 190

Gly Thr Leu Ser Asn Ala Gly Ile Ser Gly Gln Ala Phe Arg His Gly
        195                 200                 205

Pro Gln Ile Asn Asn Val Gln Gln Leu Glu Val Val Thr Gly Lys Gly
    210                 215                 220

Glu Val Ile Thr Cys Ser Glu Glu Gln Asn Ala Asp Leu Phe His Gly
225                 230                 235                 240

Val Leu Gly Gly Leu Gly Gln Phe Gly Ile Ile Thr Arg Ala Arg Ile
                245                 250                 255

Ala Leu Glu Thr Ala Pro Lys Gln Val Lys Trp Ile Arg Val Leu Tyr
            260                 265                 270

Ser Asp Phe Ser Ile Phe Ser Asn Asp Gln Glu His Leu Ile Ser Thr
        275                 280                 285

Gln Asp Thr Phe Asp Tyr Ile Glu Gly Phe Val Thr Ile Asn Gln Thr
    290                 295                 300

Gly Leu Leu Asn Asn Trp Arg Ser Ala Phe Asn Pro Lys Asp Pro Val
305                 310                 315                 320

Leu Ala Ser Asn Phe Ser Ser Glu Gly Arg Val Leu Phe Cys Leu Glu
                325                 330                 335

Ile Ala Lys Tyr Phe Asn Pro Glu Val Thr Asp Ser Ile Asp Gln Asn
            340                 345                 350

Ile Asp Val Ile Leu Ser Lys Leu Asn Tyr Ile Arg Ser Thr Leu Phe
        355                 360                 365

Leu Ser Glu Val Ser Tyr Thr Glu Phe Leu Asp Arg Val His Val Ser
    370                 375                 380

Glu Met Lys Leu Gln Glu Asn Val Ser His Pro Trp Leu Asn Leu Leu
385                 390                 395                 400

Ile Pro Lys Ser Arg Ile Leu Glu Phe Ala Gln Gln Val Phe Gly Lys
                405                 410                 415

Ile Leu Thr Asp Thr Ser Asn Gly Pro Leu Leu Ile Tyr Pro Val Asn
            420                 425                 430

Lys Ser Lys Trp Arg Lys Gly Thr Ser Met Val Thr Pro Asp Glu Asp
        435                 440                 445

Val Phe Tyr Leu Ile Ala Phe Leu Ser Ser Ala Met Ser Ser Ser Thr
    450                 455                 460

Gly Asn Asp Gly Leu Arg His Ile Leu Ala Gln Ser Lys Arg Ile Leu
465                 470                 475                 480
```

Asn Phe Cys Glu Glu Thr Asn Ile Gly Met Lys Gln Tyr Leu Pro Asn
485 490 495

Tyr Lys Thr Lys Glu Glu Trp Lys Asp His Phe Gly His Gln Trp Glu
500 505 510

Ala Phe Ala Arg Arg Lys Ser Thr Tyr Asp Pro Leu Ala Ile Leu Ala
515 520 525

Pro Gly Gln Arg Ile Phe Arg Arg Ala Glu Ala Cys Glu Gln Gln
530 535 540

<210> SEQ ID NO 61
<211> LENGTH: 960
<212> TYPE: DNA
<213> ORGANISM: Nicotiana tabacum

<400> SEQUENCE: 61
atgagaaact cttcactaat gtgcaaacaa gtatggccaa ctttgcgaaa tttgcctcaa 60
aaggacaagg ttgtgtttgt gatgggagtc accggcgccg gaaaatcaag actgtcaata 120
gacttagcca ctcaattcag aggagaaata gtgaactccg acaaaataca agtgtacaaa 180
ggtcttgata ttgccactaa caaaatcaca caagaagaac gttgtggtgt accacaccat 240
ctcctaggcg taattgatcc ttacaaagaa ttcaccacca aaaacttctg caacatggct 300
tcacttgcag ttaactctat aaccgaccgc ggtaaacttc cgatcatcgt tggaggttcc 360
aattcgttta tcgaggcgct tgtccacgac aactctcata attttcgtac gaggtatgat 420
tgttgtttcc tatgggtcga tgtgtccatg aacgtactaa attcattttt gtacgaacga 480
gtggacaaaa tgatggagca aggtatgact gacgaagtaa gaagcatgtt caatccaaaa 540
aacacagatt ataccaaagg catacgtaaa gcaattggcg taccagaatt cgatagttat 600
tttcgagctg aattatcaaa ttctgttgac gtggagacgc gcgagaggct actaaaagaa 660
gctattaatg aagtgaagat caataactgt atactagcaa gtaagcaact agagaaaata 720
aagagactca taaatgttaa gggatggaaa attcaaagat tagatgcaac agaagttttt 780
aggaggaaac agagaaatgc agaggaagaa gccgaggaaa tttggaagaa tatggtgatg 840
ggacagagca taaagattgt gggtaaattt ttatgcgaaa ataatcggag caaaatggtt 900
tacagaaatg atgtgacagc cattaagaga gcagcagcgt cggccatagc tcaatattag 960

<210> SEQ ID NO 62
<211> LENGTH: 319
<212> TYPE: PRT
<213> ORGANISM: Nicotiana tabacum

<400> SEQUENCE: 62

Met Arg Asn Ser Ser Leu Met Cys Lys Gln Val Trp Pro Thr Leu Arg
1 5 10 15

Asn Leu Pro Gln Lys Asp Lys Val Val Phe Val Met Gly Val Thr Gly
20 25 30

Ala Gly Lys Ser Arg Leu Ser Ile Asp Leu Ala Thr Gln Phe Arg Gly
35 40 45

Glu Ile Val Asn Ser Asp Lys Ile Gln Val Tyr Lys Gly Leu Asp Ile
50 55 60

Ala Thr Asn Lys Ile Thr Gln Glu Glu Arg Cys Gly Val Pro His His
65 70 75 80

Leu Leu Gly Val Ile Asp Pro Tyr Lys Glu Phe Thr Thr Lys Asn Phe
85 90 95

-continued

```
Cys Asn Met Ala Ser Leu Ala Val Asn Ser Ile Thr Asp Arg Gly Lys
            100                 105                 110

Leu Pro Ile Ile Val Gly Gly Ser Asn Ser Phe Ile Glu Ala Leu Val
        115                 120                 125

His Asp Asn Ser His Asn Phe Arg Thr Arg Tyr Asp Cys Cys Phe Leu
    130                 135                 140

Trp Val Asp Val Ser Met Asn Val Leu Asn Ser Phe Leu Tyr Glu Arg
145                 150                 155                 160

Val Asp Lys Met Met Glu Gln Gly Met Thr Asp Glu Val Arg Ser Met
                165                 170                 175

Phe Asn Pro Lys Asn Thr Asp Tyr Thr Lys Gly Ile Arg Lys Ala Ile
            180                 185                 190

Gly Val Pro Glu Phe Asp Ser Tyr Phe Arg Ala Glu Leu Ser Asn Ser
        195                 200                 205

Val Asp Val Glu Thr Arg Glu Arg Leu Leu Lys Glu Ala Ile Asn Glu
    210                 215                 220

Val Lys Ile Asn Asn Cys Ile Leu Ala Ser Lys Gln Leu Glu Lys Ile
225                 230                 235                 240

Lys Arg Leu Ile Asn Val Lys Gly Trp Lys Ile Gln Arg Leu Asp Ala
                245                 250                 255

Thr Glu Val Phe Arg Arg Lys Gln Arg Asn Ala Glu Glu Glu Ala Glu
            260                 265                 270

Glu Ile Trp Lys Asn Met Val Met Gly Gln Ser Ile Lys Ile Val Gly
        275                 280                 285

Lys Phe Leu Cys Glu Asn Asn Arg Ser Lys Met Val Tyr Arg Asn Asp
    290                 295                 300

Val Thr Ala Ile Lys Arg Ala Ala Ala Ser Ala Ile Ala Gln Tyr
305                 310                 315
```

<210> SEQ ID NO 63
<211> LENGTH: 930
<212> TYPE: DNA
<213> ORGANISM: Nicotiana tabacum

<400> SEQUENCE: 63

```
atggaagctg ctcaacaaca aaaccagcag cactatcttc accaacaaca tttatcaatt      60

ggacaggtgg caaacaacat tgaagatggt gttggtggta atagcagcaa aaacaacagc     120

agcagtttca tgtgcaggca aagtagtacg aggtggacac ccacaactga ccagataaga     180

attttgaagg acctttacta caacaatgga gttaggtctc caactgctga acagattcag     240

aggatctctg ctaagttaag acagtacggt aagattgaag gcaagaatgt gttttattgg     300

tttcagaacc ataaagctcg tgaaaggcaa aagaagaggc ttattgctgc tgctgccact     360

gataacaaca ataatatccc catgcaaatg agaggtgttt ggagatctgc tgatgatccc     420

attcaccaca agtataacaa cactacaggt attcactgtc catcagcttc ttctcatggt     480

gtactagcag ttggacagaa tggaaactat ggttatggaa ctgtagctat ggagaagagc     540

tttagggact gttcaatatc accaggtggt aactccaacg gatcaatggg tcatcaaaac     600

attacatggg ttggagttga tccctacact tctcatcaag catacccttt tcttgaaaag     660

actaaacatt ttgatgaaac cctagacgat tatgaggaac tgcaacaaga agaagaaaat     720

taccaaagag cctctgcttt agaaactctc ccactttttc ccatgcacga agagaacatt     780

tccagtttct gcaacatcaa acatgaatct tcaggcggat tctacacaga atggtatcgt     840

tcagatgatc ataacttggc tgctgcggcc agagcttctc ttgaactcag tctcaactct     900
```

ttcattggca gatctcctaa ttccccttaa 930

<210> SEQ ID NO 64
<211> LENGTH: 309
<212> TYPE: PRT
<213> ORGANISM: Nicotiana tabacum

<400> SEQUENCE: 64

Met Glu Ala Ala Gln Gln Gln Asn Gln Gln His Tyr Leu His Gln Gln
1 5 10 15

His Leu Ser Ile Gly Gln Val Ala Asn Asn Ile Glu Asp Gly Val Gly
20 25 30

Gly Asn Ser Ser Lys Asn Asn Ser Ser Ser Phe Met Cys Arg Gln Ser
35 40 45

Ser Thr Arg Trp Thr Pro Thr Thr Asp Gln Ile Arg Ile Leu Lys Asp
50 55 60

Leu Tyr Tyr Asn Asn Gly Val Arg Ser Pro Thr Ala Glu Gln Ile Gln
65 70 75 80

Arg Ile Ser Ala Lys Leu Arg Gln Tyr Gly Lys Ile Glu Gly Lys Asn
85 90 95

Val Phe Tyr Trp Phe Gln Asn His Lys Ala Arg Glu Arg Gln Lys Lys
100 105 110

Arg Leu Ile Ala Ala Ala Ala Thr Asp Asn Asn Asn Asn Ile Pro Met
115 120 125

Gln Met Arg Gly Val Trp Arg Ser Ala Asp Asp Pro Ile His His Lys
130 135 140

Tyr Asn Asn Thr Thr Gly Ile His Cys Pro Ser Ala Ser Ser His Gly
145 150 155 160

Val Leu Ala Val Gly Gln Asn Gly Asn Tyr Gly Tyr Gly Thr Val Ala
165 170 175

Met Glu Lys Ser Phe Arg Asp Cys Ser Ile Ser Pro Gly Gly Asn Ser
180 185 190

Asn Gly Ser Met Gly His Gln Asn Ile Thr Trp Val Gly Val Asp Pro
195 200 205

Tyr Thr Ser His Gln Ala Tyr Pro Phe Leu Glu Lys Thr Lys His Phe
210 215 220

Asp Glu Thr Leu Asp Asp Tyr Glu Glu Leu Gln Gln Glu Glu Glu Asn
225 230 235 240

Tyr Gln Arg Ala Ser Ala Leu Glu Thr Leu Pro Leu Phe Pro Met His
245 250 255

Glu Glu Asn Ile Ser Ser Phe Cys Asn Ile Lys His Glu Ser Ser Gly
260 265 270

Gly Phe Tyr Thr Glu Trp Tyr Arg Ser Asp Asp His Asn Leu Ala Ala
275 280 285

Ala Ala Arg Ala Ser Leu Glu Leu Ser Leu Asn Ser Phe Ile Gly Arg
290 295 300

Ser Pro Asn Ser Pro
305

<210> SEQ ID NO 65
<211> LENGTH: 822
<212> TYPE: DNA
<213> ORGANISM: Nicotiana tabacum

<400> SEQUENCE: 65

-continued

```
atggaagctg cccaacaaca aaaccagcag cactatcttc accaacaaca tttatcaatt     60
ggacaggtga caaacaacat tattgaagat ggtgttggtg gtaatagcag caaaaacaac    120
agcagcagtt tcatgtgcag gcaaagtagt acgaggtgga cacccacaac tgaccagata    180
agaatcttga aggatcttta ctacaacaat ggagttaggt ctccaactgc tgaacagatt    240
cagaggatct ctgctaagtt aagacagtac ggtaagattg aaggcaagaa tgtgttttat    300
tggtttcaga accataaagc tcgtgaaagg caaaagaaga ggcttattgc tgctgctgct    360
actgatagca acaataatat tcccatgcac atgagaggtg tttggagatc tgctgatgat    420
cctatccacc acaagtataa caacactaca ggtattcact gtccatcagc ttcttctcat    480
ggtgtactgg ccgttggaca gaatggaaac tatggttatg gaactttagc tatggaaaag    540
agctttagga ctaaacattt tgatgaaacc ctagtagacg attatgagga actgcaacaa    600
gaagaagaaa attaccaaag agcctctgct ttagaaactc tcccactttt tcccatgcat    660
gaagagaaca tctccagttt ctgcaacatc aaacatgaat cttcaggcgg attctacaca    720
gaatggtacc gttcagatga tcataacttg gctgctgcgg ccagagcttc tcttgaactt    780
agtctcaact ctttcattgg cagatctcct aattcccctt aa                       822
```

```
<210> SEQ ID NO 66
<211> LENGTH: 273
<212> TYPE: PRT
<213> ORGANISM: Nicotiana tabacum

<400> SEQUENCE: 66

Met Glu Ala Ala Gln Gln Gln Asn Gln Gln His Tyr Leu His Gln Gln
1               5                   10                  15

His Leu Ser Ile Gly Gln Val Thr Asn Asn Ile Ile Glu Asp Gly Val
            20                  25                  30

Gly Gly Asn Ser Ser Lys Asn Asn Ser Ser Ser Phe Met Cys Arg Gln
        35                  40                  45

Ser Ser Thr Arg Trp Thr Pro Thr Thr Asp Gln Ile Arg Ile Leu Lys
    50                  55                  60

Asp Leu Tyr Tyr Asn Asn Gly Val Arg Ser Pro Thr Ala Glu Gln Ile
65                  70                  75                  80

Gln Arg Ile Ser Ala Lys Leu Arg Gln Tyr Gly Lys Ile Glu Gly Lys
                85                  90                  95

Asn Val Phe Tyr Trp Phe Gln Asn His Lys Ala Arg Glu Arg Gln Lys
            100                 105                 110

Lys Arg Leu Ile Ala Ala Ala Ala Thr Asp Ser Asn Asn Asn Ile Pro
        115                 120                 125

Met His Met Arg Gly Val Trp Arg Ser Ala Asp Asp Pro Ile His His
    130                 135                 140

Lys Tyr Asn Asn Thr Thr Gly Ile His Cys Pro Ser Ala Ser Ser His
145                 150                 155                 160

Gly Val Leu Ala Val Gly Gln Asn Gly Asn Tyr Gly Tyr Gly Thr Leu
                165                 170                 175

Ala Met Glu Lys Ser Phe Arg Thr Lys His Phe Asp Glu Thr Leu Val
            180                 185                 190

Asp Asp Tyr Glu Glu Leu Gln Gln Glu Glu Glu Asn Tyr Gln Arg Ala
        195                 200                 205

Ser Ala Leu Glu Thr Leu Pro Leu Phe Pro Met His Glu Glu Asn Ile
    210                 215                 220

Ser Ser Phe Cys Asn Ile Lys His Glu Ser Ser Gly Gly Phe Tyr Thr
```

225 230 235 240

Glu Trp Tyr Arg Ser Asp Asp His Asn Leu Ala Ala Ala Ala Arg Ala
245 250 255

Ser Leu Glu Leu Ser Leu Asn Ser Phe Ile Gly Arg Ser Pro Asn Ser
260 265 270

Pro

<210> SEQ ID NO 67
<211> LENGTH: 291
<212> TYPE: DNA
<213> ORGANISM: Arabidopsis thaliana

<400> SEQUENCE: 67
atggattcga agagttttct gctactacta ctactcttct gcttcttgtt ccttcatgat 60
gcttctgatc tcactcaagc tcatgctcac gttcaaggac tttccaaccg caagatgatg 120
atgatgaaaa tggaaagtga atgggttgga gcaaatggag aagcagagaa ggcaaagacg 180
aagggtttag gactacatga agagttaagg actgttcctt cgggacctga cccgttgcac 240
catcatgtga acccaccaag acagccaaga aacaactttc agctcccttg a 291

<210> SEQ ID NO 68
<211> LENGTH: 96
<212> TYPE: PRT
<213> ORGANISM: Arabidopsis thaliana

<400> SEQUENCE: 68

Met Asp Ser Lys Ser Phe Leu Leu Leu Leu Leu Leu Phe Cys Phe Leu
1 5 10 15

Phe Leu His Asp Ala Ser Asp Leu Thr Gln Ala His Ala His Val Gln
20 25 30

Gly Leu Ser Asn Arg Lys Met Met Met Met Lys Met Glu Ser Glu Trp
35 40 45

Val Gly Ala Asn Gly Glu Ala Glu Lys Ala Lys Thr Lys Gly Leu Gly
50 55 60

Leu His Glu Glu Leu Arg Thr Val Pro Ser Gly Pro Asp Pro Leu His
65 70 75 80

His His Val Asn Pro Pro Arg Gln Pro Arg Asn Asn Phe Gln Leu Pro
85 90 95

<210> SEQ ID NO 69
<211> LENGTH: 396
<212> TYPE: DNA
<213> ORGANISM: Nicotiana tabacum

<400> SEQUENCE: 69
atgtgtattc catatcttga tccgtttgtt tcttactcac ttatagatca acaacttgca 60
tctactgcat ttctgttcgc ttctgaaatg actaatttca ctgccaaacg tttcaccctc 120
ttcctcttgc tgtgtgtttt ggttgtgcaa gaatctcatg ggtgcactag tagctcaaaa 180
tgcatttcac aaaaggaagt tgcttctgtg agaatactaa acagaaaggt tttaggaagc 240
cagcgggctg cttttggaaa gggcttaaat ggaaactaca atcattcagg gaagattaat 300
gacaagtttg ctgattggga gcttagggga attccagctg gtcctgatcc attgcaccac 360
aatggtgcta atccgaagaa accccggact ccataa 396

<210> SEQ ID NO 70
<211> LENGTH: 131

<212> TYPE: PRT
<213> ORGANISM: Nicotiana tabacum

<400> SEQUENCE: 70

Met Cys Ile Pro Tyr Leu Asp Pro Phe Val Ser Tyr Ser Leu Ile Asp
1               5                   10                  15

Gln Gln Leu Ala Ser Thr Ala Phe Leu Phe Ala Ser Glu Met Thr Asn
            20                  25                  30

Phe Thr Ala Lys Arg Phe Thr Leu Phe Leu Leu Leu Cys Val Leu Val
        35                  40                  45

Val Gln Glu Ser His Gly Cys Thr Ser Ser Ser Lys Cys Ile Ser Gln
    50                  55                  60

Lys Glu Val Ala Ser Val Arg Ile Leu Asn Arg Lys Val Leu Gly Ser
65                  70                  75                  80

Gln Arg Ala Ala Phe Gly Lys Gly Leu Asn Gly Asn Tyr Asn His Ser
                85                  90                  95

Gly Lys Ile Asn Asp Lys Phe Ala Asp Trp Glu Leu Arg Gly Ile Pro
            100                 105                 110

Ala Gly Pro Asp Pro Leu His His Asn Gly Ala Asn Pro Lys Lys Pro
        115                 120                 125

Arg Thr Pro
    130

<210> SEQ ID NO 71
<211> LENGTH: 1158
<212> TYPE: DNA
<213> ORGANISM: Nicotiana tabacum

<400> SEQUENCE: 71
atgttaggat cctttggttc atcatctcaa tctcatgatg aagaagctga tgatcaacgg 60
cggagatgca gttccacttc ccctgcaatc caaatccggc aactactcat tagctgcgcg 120
gagttaatct cacggtccga tttctcggcg gcaaacagac tcctcaccat tttatcaact 180
aactcttccc cttttgccac taatttcttg acacctaatg catcatctaa tgttgttgaa 240
agttcaaatg attcagctct acttcagtca tcctatcttt ccctaaacca agtgacccct 300
tttattagat ttagtcagct aactgctaat caagcgattt tagaagctat taacgataac 360
caacaagcga tccacatcgt tgattttgat attaatcacg gtgttcaatg gccaccgtta 420
atgcaagcac tagctgatcg ttaccctcct ccaactcttc ggattaccgg tactggaaat 480
gacctcgata cccttcgtag aaccggagat cgtttagcta aatttgctca ctctttaggc 540
cttagatttc agtttcaccc tcttttgatc accaataata atgacaatga tcatgaccct 600
tcaatcattt cttctattgt tcttctccct gatgagacat tagcaatcaa ctgtgtattt 660
tatcttcaca ggctcttaaa agaccgcgaa atgttaagga tttttttgca taggattaaa 720
tccatgaacc ctaaagttgt aacactggcc gagagagaag caaatcataa tcacccactt 780
tttttgcaaa gatttgtgga ggctttggat tattatgcag ctgtctttga ttcattggaa 840
gcaactttgc cgccgagcag tagagagagg atgacagtgg agcaagtttg gttcggaaga 900
gaaattatag atatagtagc agcagaagga gataagagaa gagaaagaca cgagagattc 960
agatcatggg aagtaatgtt gaggagctgt ggatttagca atgttgcttt aagtcctttt 1020
gcactttcac aagctaaact tctcttgaga cttcattacc cttctgaagg ataccagctt 1080
agtgtttcga gtacgagtaa ttctttcttc ttgggttggc aaaatcaacc cctttttttcc 1140 atatcttctt ggcgttaa 1158

<210> SEQ ID NO 72
<211> LENGTH: 385
<212> TYPE: PRT
<213> ORGANISM: Nicotiana tabacum

<400> SEQUENCE: 72

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Ala Thr Asn Phe Leu Thr Pro Asn Ala Ser Ser Asn Val Val Glu
65                  70                  75                  80

Ser Ser Asn Asp Ser Ala Leu Leu Gln Ser Ser Tyr Leu Ser Leu Asn
                85                  90                  95

Gln Val Thr Pro Phe Ile Arg Phe Ser Gln Leu Thr Ala Asn Gln Ala
            100                 105                 110

Ile Leu Glu Ala Ile Asn Asp Asn Gln Gln Ala Ile His Ile Val Asp
        115                 120                 125

Phe Asp Ile Asn His Gly Val Gln Trp Pro Pro Leu Met Gln Ala Leu
    130                 135                 140

Ala Asp Arg Tyr Pro Pro Pro Thr Leu Arg Ile Thr Gly Thr Gly Asn
145                 150                 155                 160

Asp Leu Asp Thr Leu Arg Arg Thr Gly Asp Arg Leu Ala Lys Phe Ala
                165                 170                 175

His Ser Leu Gly Leu Arg Phe Gln Phe His Pro Leu Leu Ile Thr Asn
            180                 185                 190

Asn Asn Asp Asn Asp His Asp Pro Ser Ile Ile Ser Ser Ile Val Leu
        195                 200                 205

Leu Pro Asp Glu Thr Leu Ala Ile Asn Cys Val Phe Tyr Leu His Arg
    210                 215                 220

Leu Leu Lys Asp Arg Glu Met Leu Arg Ile Phe Leu His Arg Ile Lys
225                 230                 235                 240

Ser Met Asn Pro Lys Val Val Thr Leu Ala Glu Arg Glu Ala Asn His
                245                 250                 255

Asn His Pro Leu Phe Leu Gln Arg Phe Val Glu Ala Leu Asp Tyr Tyr
            260                 265                 270

Ala Ala Val Phe Asp Ser Leu Glu Ala Thr Leu Pro Pro Ser Ser Arg
        275                 280                 285

Glu Arg Met Thr Val Glu Gln Val Trp Phe Gly Arg Glu Ile Ile Asp
    290                 295                 300

Ile Val Ala Ala Glu Gly Asp Lys Arg Arg Glu Arg His Glu Arg Phe
305                 310                 315                 320

Arg Ser Trp Glu Val Met Leu Arg Ser Cys Gly Phe Ser Asn Val Ala
                325                 330                 335

Leu Ser Pro Phe Ala Leu Ser Gln Ala Lys Leu Leu Leu Arg Leu His
            340                 345                 350

Tyr Pro Ser Glu Gly Tyr Gln Leu Ser Val Ser Ser Thr Ser Asn Ser
        355                 360                 365

Phe Phe Leu Gly Trp Gln Asn Gln Pro Leu Phe Ser Ile Ser Ser Trp 370 375 380

Arg
385

<210> SEQ ID NO 73
<211> LENGTH: 1224
<212> TYPE: DNA
<213> ORGANISM: Nicotiana tabacum

<400> SEQUENCE: 73
atgttaggat cctttggttc atcatctcaa tctcatgatg aagaaactga tgatcaacgg 60
cggagattca gttccacttc ccctgcaatc caaatccggc aactactcat tagctgcgcg 120
gagttaatct cgcggtccga tttctcggcc gcaaacagac tcctcaccat tttatcaact 180
aactcttccc cttttggtga ttcaactgaa agattagtcc atcagttcac tcgcgcactt 240
tctcttcgcc tcaaccgtta tatctcttca gccactaatt tcttgacacc atctaatgtt 300
gttgaaagtt caaatgattc agctctactt cagtcatcct atctttccct aaaccaagtg 360
actcctttca ttagatttag tcagctaact gctaatcaag cgattttgga agctattaac 420
gataaccaac aagcgatcca catcgttgat tttgatatta atcacggtgt tcaatggcca 480
ccgttaatgc aagcactagc tgatcgttac cctcctccaa ctcttcggat taccggtact 540
ggaaatgacc ttgataccct tcgtagaacc ggagatcgtt tagctaaatt tgctcactct 600
ttaggcctta gatttcagtt tcaccctctt ttgattacca ataataatga caatgatcat 660
gacccttcaa taatttcttc tattgttctt ctccctgatg agacattagc tatcaactgt 720
gtattttatc ttcacaggct cttgaaagac cgcgaaaagt taaggatttt tttgcatagg 780
attaaatcca tgaaccctaa agttgtaacg ctggccgaga gagaagcaaa tcataatcac 840
ccactttttt tgcaaagatt tgtggaggct ttggattatt atgcagctgt gtttgattca 900
ttggaagcaa ctttgccacc gagcagtaga gagaggatga cagtggaaca agtttggttc 960
gggagagaaa taattgatat agtagcagca gaaggagata agagaagaga aagacacgag 1020
agattcagat catgggaagt aatgttgagg agctgtggat ttagcaatgt tgctttaagc 1080
ccttttgcac tctcacaagc taaacttctc ttgagacttc attacccatc tgaaggatac 1140
cagcttagtg tttcgagtac gagtaattct ttcttcttgg gttggcaaaa tcaacccctt 1200
ttttccatat cttcttggcg ttaa 1224

<210> SEQ ID NO 74
<211> LENGTH: 407
<212> TYPE: PRT
<213> ORGANISM: Nicotiana tabacum

<400> SEQUENCE: 74

Met Leu Gly Ser Phe Gly Ser Ser Ser Gln Ser His Asp Glu Glu Thr
1 5 10 15

Asp Asp Gln Arg Arg Arg Phe Ser Ser Thr Ser Pro Ala Ile Gln Ile
20 25 30

Arg Gln Leu Leu Ile Ser Cys Ala Glu Leu Ile Ser Arg Ser Asp Phe
35 40 45

Ser Ala Ala Asn Arg Leu Leu Thr Ile Leu Ser Thr Asn Ser Ser Pro
50 55 60

Phe Gly Asp Ser Thr Glu Arg Leu Val His Gln Phe Thr Arg Ala Leu
65 70 75 80

Ser Leu Arg Leu Asn Arg Tyr Ile Ser Ser Ala Thr Asn Phe Leu Thr

-continued

```
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255

Phe Leu His Arg Ile Lys Ser Met Asn Pro Lys Val Val Thr Leu Ala
            260                 265                 270

Glu Arg Glu Ala Asn His Asn His Pro Leu Phe Leu Gln Arg Phe Val
        275                 280                 285

Glu Ala Leu Asp Tyr Tyr Ala Ala Val Phe Asp Ser Leu Glu Ala Thr
    290                 295                 300

Leu Pro Pro Ser Ser Arg Glu Arg Met Thr Val Glu Gln Val Trp Phe
305                 310                 315                 320

Gly Arg Glu Ile Ile Asp Ile Val Ala Ala Glu Gly Asp Lys Arg Arg
                325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Phe Leu Gly Trp Gln Asn Gln Pro Leu
385                 390                 395                 400

Phe Ser Ile Ser Ser Trp Arg
                405
```

<210> SEQ ID NO 75
<211> LENGTH: 1014
<212> TYPE: DNA
<213> ORGANISM: Nicotiana tabacum

<400> SEQUENCE: 75

```
atggggagag ctccatgttg tgataaagca aatgtgaaga gagggccatg gtctcctgaa     60

gaagatgcta aactcaaaga tttcattcac aaatatggaa ctggtggaaa ttggattgct    120

cttcctcaaa aagctggtct aaagagatgt gggaagagtt gtagattgag atggctaaat    180

tatttaaggc ctaacattaa acatggtgat ttttctgagg aagaagatag agttatttgc    240

accttgtatt ccaccattgg aagcaggtgg tcaataatag cagctcaatt accgggaaga    300
```

-continued

```
actgacaatg atatcaagaa ttactggaat actaagctca agaaaaaacc tatgggatta    360

atgcaatcaa ctaaccaaag aaaatcacca tattttccag ctactaattc tcttcaaacc    420

caaccccaga taaattcaag tctttttaga gacttatatt acaccccaaa taataggcct    480

aatattacag gcctaaatca tcagtccatt tcttctgccc accagacaaa ttttctctac    540

actaataata acatgaactt tcctaatttg ggtgctacaa ataatcaata tccttataat    600

atccaaagtc ataatttact tatgtttgga gaagcaagtt gttcttcatc agatggaagt    660

tgcagccaaa tgagttttgg taaagaaatc aagagagaag aaattatgag taatagttta    720

caacaaggtc aaatttcaag tgttaatgct tttgaagaaa accaccagaa ttttactctt    780

gattatggca atagtagtag taattgggtg gatcaaaaac caaatgtgta ttttggtact    840

actactactc aagtacttca gtatgataat gttgaagaag ttaagcagca gctaacaagt    900

tgtaccaatg gcaacaatgg tagtactatt ggatgtaaca acaacaacag tatgttcgtg    960

ttcaatgatg agaattataa caagtcaaat gagatagaga tgttctatta ctga         1014
```

<210> SEQ ID NO 76
<211> LENGTH: 337
<212> TYPE: PRT
<213> ORGANISM: Nicotiana tabacum

<400> SEQUENCE: 76

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240

Gln Gln Gly Gln Ile Ser Ser Val Asn Ala Phe Glu Glu Asn His Gln
```

```
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Asn Gly
    290                 295                 300

Asn Asn Gly Ser Thr Ile Gly Cys Asn Asn Asn Asn Ser Met Phe Val
305                 310                 315                 320

Phe Asn Asp Glu Asn Tyr Asn Lys Ser Asn Glu Ile Glu Met Phe Tyr
                325                 330                 335

Tyr
```

<210> SEQ ID NO 77
<211> LENGTH: 1011
<212> TYPE: DNA
<213> ORGANISM: Nicotiana tabacum

<400> SEQUENCE: 77

```
atggggagag ctccatgttg tgataaagca aatgtgaaga gagggccatg gtctcctgaa      60

gaagatgcta aactcaaaga tttcattcac aaatatggaa ctggtggaaa ttggattgct     120

cttccccaaa aagcaggtct aaagagatgt gggaagagtt gtagattgag atggctaaat     180

tatctaaggc ctaatatcaa acatggtgat ttttcggagg aagaagatag agttatttgc     240

agcttgtatt ccaccattgg aagcaggtgg tcaataatag cagctcaatt accaggaagg     300

actgacaatg atatcaagaa ttactggaat actaaactca agaaaaagct tatgggatta     360

atgcaatcaa caaaccaaag aaaatcacca tattttccag ctactaattc tcttcaaacc     420

caaccccaga taaattcaag tctttttaga gacttatatt acaacccaaa taataggcct     480

attattacag gcctaaatca gtccatttct tctgcccacc agccaaattt tctctacact     540

aatagtaaca tgaattttcc taatttgggt gctacaaata gtcaatatcc ttataatatt     600

caaagtcata atttacttat gtttggagaa gcaagttgtt cttcatcaga tggaagttgt     660

agccaaatga gttttggcaa agaaatcaag agagaggaaa ttatgagtaa ttgtttacaa     720

caaggtcaaa tttcaagtgt taatgctttt gaagaaaatc agaatttcac tcttgattat     780

ggtaacagta gtagtaattg ggtggatcaa aaaccaaatg tgtattttgg aaatactact     840

actactactc aagtacttca gtatgatgtt gaagaagtta agcagcagct aacaagttgt     900

accaatggca acaatggcag tactattgga tgtaacaaca acaacagtat gttcgtgttc     960

aatgatgaga attataacaa gtcaaatgag atagggatgt tctattactg a             1011
```

<210> SEQ ID NO 78
<211> LENGTH: 336
<212> TYPE: PRT
<213> ORGANISM: Nicotiana tabacum

<400> SEQUENCE: 78

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
```

-continued

```
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Asn Pro Asn Asn Arg Pro
145                 150                 155                 160

Ile Ile Thr Gly Leu Asn Gln Ser Ile Ser Ser Ala His Gln Pro Asn
                165                 170                 175

Phe Leu Tyr Thr Asn Ser Asn Met Asn Phe Pro Asn Leu Gly Ala Thr
            180                 185                 190

Asn Ser Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Cys Leu Gln
225                 230                 235                 240

Gln Gly Gln Ile Ser Ser Val Asn Ala Phe Glu Glu Asn Gln Asn Phe
                245                 250                 255

Thr Leu Asp Tyr Gly Asn Ser Ser Ser Asn Trp Val Asp Gln Lys Pro
            260                 265                 270

Asn Val Tyr Phe Gly Asn Thr Thr Thr Thr Thr Gln Val Leu Gln Tyr
        275                 280                 285

Asp Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Gly Met Phe Tyr Tyr
                325                 330                 335
```

<210> SEQ ID NO 79
<211> LENGTH: 495
<212> TYPE: DNA
<213> ORGANISM: Bacillus amyloliquefaciens

<400> SEQUENCE: 79

```
atgaaaagga atcagcttca catgatgaaa atgggaggta ttgctttgaa aaaacgatta      60

tcgtggattt ccgtttgttt actggtgctt gtctccgcgg cggggatgct gttttcaaca     120

gctgccaaaa cggaaacatc ttctcacaag gcacacacag aagcacaggt tatcaacacg     180

tttgacgggg ttgcggatta tcttcagaca tatcataagc tacctgataa ttacattaca     240

aaatcagaag cacaagccct cggctgggtg gcatcaaaag ggaaccttgc agacgtcgct     300

ccggggaaaa gcatcggcgg agacatcttc tcaaacaggg aaggcaaact cccgggcaaa     360

agcggacgaa catggcgtga agcggatatt aactatacat caggcttcag aaattcagac     420

cggattcttt actcaagcga ctggctgatt tacaaaacaa cggaccatta tcagaccttt     480

acaaaaatca gataa                                                      495
```

<210> SEQ ID NO 80
<211> LENGTH: 164
<212> TYPE: PRT
<213> ORGANISM: Bacillus amyloliquefaciens

<400> SEQUENCE: 80

```
Met Lys Arg Asn Gln Leu His Met Met Lys Met Gly Gly Ile Ala Leu
1               5                   10                  15

Lys Lys Arg Leu Ser Trp Ile Ser Val Cys Leu Leu Val Leu Val Ser
            20                  25                  30

Ala Ala Gly Met Leu Phe Ser Thr Ala Ala Lys Thr Glu Thr Ser Ser
        35                  40                  45

His Lys Ala His Thr Glu Ala Gln Val Ile Asn Thr Phe Asp Gly Val
    50                  55                  60

Ala Asp Tyr Leu Gln Thr Tyr His Lys Leu Pro Asp Asn Tyr Ile Thr
65                  70                  75                  80

Lys Ser Glu Ala Gln Ala Leu Gly Trp Val Ala Ser Lys Gly Asn Leu
                85                  90                  95

Ala Asp Val Ala Pro Gly Lys Ser Ile Gly Gly Asp Ile Phe Ser Asn
            100                 105                 110

Arg Glu Gly Lys Leu Pro Gly Lys Ser Gly Arg Thr Trp Arg Glu Ala
        115                 120                 125

Asp Ile Asn Tyr Thr Ser Gly Phe Arg Asn Ser Asp Arg Ile Leu Tyr
    130                 135                 140

Ser Ser Asp Trp Leu Ile Tyr Lys Thr Thr Asp His Tyr Gln Thr Phe
145                 150                 155                 160

Thr Lys Ile Arg
```

<210> SEQ ID NO 81
<211> LENGTH: 1290
<212> TYPE: DNA
<213> ORGANISM: Arabidopsis thaliana

<400> SEQUENCE: 81

```
atgaacaaca acattttcag tactactacc accatcaatg acgactacat gttattccct      60

tataatgacc attattcctc acaaccattg ctccctttta gcccttcttc ttccattaac     120

gacatcttga ttcactccac ctctaacaca tcaaacaatc atcttgacca tcatcatcaa     180

ttccaacaac cttctccttt ttctcacttc gaatttgccc cggactgcgc cctcctcacc     240

tctttccacc cagaaaacaa tggccatgat gataaccaaa ccatcccaaa cgacaatcat     300

catccatcac ttcactttcc cttgaacaac accattgtag aacaacccac tgagccctcg     360

gaaactataa accttataga agattcccag agaatctcaa cttctcaaga cccaaaaatg     420

aaaaaagcca agaaacccag cagaacggac aggcacagca agatcaaaac ggccaaaggg     480

acacgagatc gtaggatgag actctcgcta gatgtcgcca aagagttgtt tggcttacaa     540

gacatgcttg gatttgacaa agccagcaaa accgttgaat ggttgcttac acaagcaaaa     600

cctgagatca taaagatcgc gacaaccctt tctcaccatg gctgcttcag cagcggcgat     660

gagtctcata tccgatccat ggacacatct tctgatctat gtgaacttgc atccatgtgg     720

acggtcgacg atagaggcag caatactaac acgaccgaaa caagaggaaa caaggtcgat     780

gggagatcga tgagagggaa gagaaagagg ccagaaccgc gaacgcccat tttaaagaag     840

ttgtccaagg aggagagagc gaaagctaga gaaagagcaa agggtagaac aatggagaaa     900

atgatgatga agatgaaagg aagatcacaa ttagtgaaag ttgtggaaga agacgctcat     960
```

```
gatcatggtg agataataaa gaataataat agaagccaag tgaatcggag ttcttttgag   1020

atgacacact gcgaagacaa gatcgaagaa ctttgcaaga acgatcgttt tgcagtttgc   1080

aacgaattta tcatgaataa gaaagatcac atttcaaatg aatcttatga cttagtcaac   1140

tacaaaccga actcatcatt cccagtgatt aaccaccatc gcagccaagg agcagctaat   1200

tccattgagc agcatcagtt tacggatctt cattactcct tcggcgcgaa accaagagac   1260

ctcatgcaca actatcaaaa catgtattga                                    1290
```

<210> SEQ ID NO 82
<211> LENGTH: 429
<212> TYPE: PRT
<213> ORGANISM: Arabidopsis thaliana

<400> SEQUENCE: 82

```
Met Asn Asn Asn Ile Phe Ser Thr Thr Thr Thr Ile Asn Asp Asp Tyr
1               5                   10                  15

Met Leu Phe Pro Tyr Asn Asp His Tyr Ser Ser Gln Pro Leu Leu Pro
            20                  25                  30

Phe Ser Pro Ser Ser Ser Ile Asn Asp Ile Leu Ile His Ser Thr Ser
        35                  40                  45

Asn Thr Ser Asn Asn His Leu Asp His His His Gln Phe Gln Gln Pro
    50                  55                  60

Ser Pro Phe Ser His Phe Glu Phe Ala Pro Asp Cys Ala Leu Leu Thr
65                  70                  75                  80

Ser Phe His Pro Glu Asn Asn Gly His Asp Asp Asn Gln Thr Ile Pro
                85                  90                  95

Asn Asp Asn His His Pro Ser Leu His Phe Pro Leu Asn Asn Thr Ile
            100                 105                 110

Val Glu Gln Pro Thr Glu Pro Ser Glu Thr Ile Asn Leu Ile Glu Asp
        115                 120                 125

Ser Gln Arg Ile Ser Thr Ser Gln Asp Pro Lys Met Lys Lys Ala Lys
    130                 135                 140

Lys Pro Ser Arg Thr Asp Arg His Ser Lys Ile Lys Thr Ala Lys Gly
145                 150                 155                 160

Thr Arg Asp Arg Arg Met Arg Leu Ser Leu Asp Val Ala Lys Glu Leu
                165                 170                 175

Phe Gly Leu Gln Asp Met Leu Gly Phe Asp Lys Ala Ser Lys Thr Val
            180                 185                 190

Glu Trp Leu Leu Thr Gln Ala Lys Pro Glu Ile Ile Lys Ile Ala Thr
        195                 200                 205

Thr Leu Ser His His Gly Cys Phe Ser Ser Gly Asp Glu Ser His Ile
    210                 215                 220

Arg Ser Met Asp Thr Ser Ser Asp Leu Cys Glu Leu Ala Ser Met Trp
225                 230                 235                 240

Thr Val Asp Asp Arg Gly Ser Asn Thr Asn Thr Thr Glu Thr Arg Gly
                245                 250                 255

Asn Lys Val Asp Gly Arg Ser Met Arg Gly Lys Arg Lys Arg Pro Glu
            260                 265                 270

Pro Arg Thr Pro Ile Leu Lys Lys Leu Ser Lys Glu Glu Arg Ala Lys
        275                 280                 285

Ala Arg Glu Arg Ala Lys Gly Arg Thr Met Glu Lys Met Met Met Lys
    290                 295                 300

Met Lys Gly Arg Ser Gln Leu Val Lys Val Val Glu Glu Asp Ala His
```

```
305                 310                 315                 320

Asp His Gly Glu Ile Ile Lys Asn Asn Asn Arg Ser Gln Val Asn Arg
                325                 330                 335

Ser Ser Phe Glu Met Thr His Cys Glu Asp Lys Ile Glu Glu Leu Cys
            340                 345                 350

Lys Asn Asp Arg Phe Ala Val Cys Asn Glu Phe Ile Met Asn Lys Lys
        355                 360                 365

Asp His Ile Ser Asn Glu Ser Tyr Asp Leu Val Asn Tyr Lys Pro Asn
    370                 375                 380

Ser Ser Phe Pro Val Ile Asn His His Arg Ser Gln Gly Ala Ala Asn
385                 390                 395                 400

Ser Ile Glu Gln His Gln Phe Thr Asp Leu His Tyr Ser Phe Gly Ala
                405                 410                 415

Lys Pro Arg Asp Leu Met His Asn Tyr Gln Asn Met Tyr
            420                 425
```

<210> SEQ ID NO 83
<211> LENGTH: 299
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
atgtatccgc caagcaacag ctgcaactac agccccattt tcaacatccc ttctccttgt     60

atgcaatatg gagacgaact attcttccaa tattatcctg accatttcct tcaacagcaa    120

caagtgcctt tgatagaaga tcagagtgtt gacatcttag ctgattgcac tgagaatgtt    180

actaacgaag aaactgtcat caatactgat actgtaaaag ttctttatga cacaggagct    240

gttacaaaca gtcagtgttg gggaggaaat gaagaagtag aagaaggccg cgaaaacaa     299
```

<210> SEQ ID NO 84
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
atggctcgct ccttgtgttt catggcattt gcagtcttgg caatgatgct ctttgttgcc     60

tatgaggtgc aagctagaga atgcaaaaca gaaagcaata cattccctgg attatgcatt    120

accaaaccac catgcagaaa agcttgtatc agtgagggat ttactgatgg tcattgtagc    180

aaaatcctca gaaggtgcct atgcactaag ccatgtgtgt ttgatgagaa gatgatcaaa    240

acaggagctg aaacttttgc tgaggaagca aaaactttgg ctgcagcttt gcttgaagaa    300

gagataatgg ataactaa                                                  318
```

<210> SEQ ID NO 85
<211> LENGTH: 300
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
atggcaggga aggttgagaa agtgcttgca gtagtgatgc ttgcaatgct tctgttttcg     60
```

```
gagcatttaa tggctgctaa tcatgaaatt aaaacaactg aagataactc tactattagc    120

cctttctgct tagtaaaatg tttatttgga tgtagggggt tgccacctgt acaagcatcc    180

atttgtgctg ctcaatgtta tttaaagtgc cgtgaccaag atgcggccaa tattgctgaa    240

actaagggca taattggtga gactgcatac aaccagtatg atgttggatg tgcccttggc    300


<210> SEQ ID NO 86
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 86

atgtatccgt caagcaacag ctgtaattac agcctcaata tttcctcctc aaataactta     60

tttcacattc catctccgaa ttctatgcaa tatgaacacg aacttttcca atattttcat    120

gaccatcatc tccttcaacc ccaacaacaa caacaacaac aacaactctt gactacacct    180

gatcattata tggcagcaga ttccaacaaa gacaccgtaa tcagtagtac taatcaagat    240

cctgaagaag ttgaattaca aggccgctgc aagaacaaaa aaggtgacaa taagagacgt    300


<210> SEQ ID NO 87
<211> LENGTH: 362
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 87

atggaaaagg ttcatgagaa accgctatct ctttataatg gatcattatc tgtttttaga     60

ttaggagatt tggctgtgaa aataacaaag gtgaaaaagg gatcattaaa taatgataat    120

ctttcacccc caacttcatt gttagttgtt tcaccaatca taccaggaac ttatccagtt    180

ttactctttt ttcatggctt cgttctcaag cctatatggt acaagtctct ccttcaacat    240

atttcttccc acggctatat agttgttgct ccacaggttt ctcaaagcga agaagtgaaa    300

aaagcagcca aagttacaga atggttaagt aaagccctcg aatccgtact gccggagaaa    360

gt                                                                   362


<210> SEQ ID NO 88
<211> LENGTH: 300
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 88

atgtgtttgt taataaaggt ggcgaatcca ggagaatccg gcgagcatga cagaattcca     60

tcaacgggag gtgattcaga aagtacaact actaccacag aaggaggaat tccgcagcta    120

tatgaacaat tacaatcaca atcacaatca tttgaagaaa tgttgcggca acaaatacaa    180

caagaaacag agtatttgat gtcttcatct gcaactccta tgttttcacg gtatagtcag    240

acaagggaga tgtcggcaat ggtaacggcg ttaacgcatg tggtatcagg acggagagag    300


<210> SEQ ID NO 89
<211> LENGTH: 300
```

<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 89
atggcacatt tcttctctat aaattcaacg ttagcaggaa cgaataaagc atccaaaaca 60
aatttcacat attcaactca agaaacagaa aaaccaaaaa taaagatcat cttactcttg 120
ttttctcttg cattagttcc cttgtcagcg atggcaactt gcaccactga tactccaaac 180
caagcactat tgagggatgt acacgatata gatggtaacc cccttcaagt aaaagccagg 240
tacttcatat ttccagttat tggcggtggt ggtgtacggc ttgctaatct tggagatcaa 300

<210> SEQ ID NO 90
<211> LENGTH: 348
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 90
atggctgagc aacaccagcg ccaccagcaa cagcagcagc agcagcagat gcaagtgggc 60
cacccgacgg aggcaatcaa gagccttctt cctcaaaggg gtccctctaa atcccaagtc 120
cttgctgtcg tcactctctt ccctgttggt ggggccctcc tctgccttgc tggactgacg 180
ctcgccggaa ctctgatcgg gcttgcagtc gctacgccgg ttttcttact gttcagcccg 240
gttttggtcc ccgctgccct gacaatcgcg ttggccgtca ctggattctt gacttccggc 300
gcctttggaa taacggcgct gtcgtcgctc tcgtggatca ttaactat 348

<210> SEQ ID NO 91
<211> LENGTH: 300
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 91
atgaacggtg gttcatgtgg tggtgctgat cgtgagtata ataacaataa caacaataat 60
gttgtaggtg gaggaggtgg cgggccttgt ggtgcatgca agtttcttag aagaaaatgt 120
gtgaggggat gcatatttgc accttatttt gattctgatc aaggcactgc tcatttcgct 180
gctgtacata aggtgtttgg tgctagcaat gcctctaaat tgctgctcag aattccagcg 240
cataaacgtc tggatgctgt cgttacactt tgctatgagg ctcttgctag agttagagac 300

<210> SEQ ID NO 92
<211> LENGTH: 300
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 92
atgtcggata aaaaatctgt ctcgacgcca tttgaatgtt gcagaatctt gtttaagttt 60
ctgctgttta tggttattat cagtaatgtg gcgatccatg taacagcttt gagtgggcga 120
gaaggaataa ccccaagtac ggaatggggt ttggggcctc tggtgaagag aggagaaaga 180
aaactagtag tttcaactga aaatggggag gtctcttcag tcagagtagc tgatggaatc 240
accggttcct atcatcttca gttcatcaca ttggagccca attccctctt ccttcctgtt 300

<210> SEQ ID NO 93
<211> LENGTH: 293
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 93
atgggcgtac cagaatcgga ggtggtgtca caaggtgagg ttgaatcacc attgcaacca 60
gatcaaaacc agcacaagaa ccatcagttc ccgtccctcg gtagacaagc atcgatctac 120
tccctcactc tcgacgaatt ccaacacacc ctatgtgaaa gtggcaagaa tttcgggtcg 180
atgaatatgg atgaattcct aacagcattt ggactgctga agaaaaccaa gcccacgcac 240
acgcccatgc ccatgccgcg cacgggcatg cgcacgcgca ttctcatgct cat 293

<210> SEQ ID NO 94
<211> LENGTH: 300
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 94
atggaggaaa aagatgaact tgaggaagaa gaagaatatg ttgatgatga aatcaagaac 60
aatttaccag tccaaaactc atcttcaata agttggttca caaaaatgat atctttacaa 120
gtagagatct tcaccactat cttagtttcc cccattttct atatcctctc ttttgtatct 180
gacttcaact tcctccgccc tgaagaaacc gaaaagaacg tagctgtagc tgtaaatgct 240
gctgctacag taccttcaaa agtagtacat ggaagtactt tactgctcaa gaaatttggt 300

<210> SEQ ID NO 95
<211> LENGTH: 300
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 95
atgtataact caagcaacta cagctgtaat tacaacccca ttttctcatc taatttattc 60
aacatccctt ctccttgtat gcaatatgaa cacgaacttt tcttccaata ttaccatgat 120
caacttcaac agaatcttga cgatacctta gctgagatca gtactgagac tgccattatt 180
aacacggcag attccagcaa agacgaggct ataatcagta gaaatgaact tgaacaagat 240
caggaagcgc gtaagaataa aaagggtaaa gtaagcagca acaagagagt gtctaagaaa 300

<210> SEQ ID NO 96
<211> LENGTH: 300
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 96
atgggaactg gtacttatgg agaagtggga cgtacaatac atcaaagatc aggaacacat 60

```
atacctcaaa ttctcgatcc gcctttgcta ggggatagtg attgcaagcg agaaggcaaa    120

catgtagaat ttatgcctcc aatcatgggt gaaaacttaa aagcagctaa tcaatttgaa    180

ctgatggccc cgtcaattgc attcaaatca tatccctatt cggaggtacc acaatattct    240

ggtggcaatg tggctgctgc atgtggtgaa tctttggtac atcaaaatat agaaagatca    300


<210> SEQ ID NO 97
<211> LENGTH: 320
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 97

aggacaaggt tgtgtttgtg atgggagtca ccggcgccgg aaaatcaaga ctgtcaatag     60

acttagccac tcaattcaga ggagaaatag tgaactccga caaaatacaa gtgtacaaag    120

gtcttgatat tgccactaac aaaatcacac aagaagaacg ttgtggtgta ccacaccatc    180

tcctaggcgt aattgatcct tacaaagaat tcaccaccaa aaacttctgc aacatggctt    240

cacttgcagt taactctata accgaccgcg gtaaacttcc gatcatcgtt ggaggttcca    300

attcgtttat cgaggcgctt                                                320


<210> SEQ ID NO 98
<211> LENGTH: 297
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 98

gaagatggtg ttggtggtaa tagcagcaaa aacaacagca gcagtttcat gtgcaggcaa     60

agtagtacga ggtggacacc cacaactgac cagataagaa tcttgaagga tctttactac    120

aacaatggag ttaggtctcc aactgctgaa cagattcaga ggatctctgc taagttaaga    180

cagtacggta agattgaagg caagaatgtg ttttattggt ttcagaacca taaagctcgt    240

gaaaggcaaa agaagaggct tattgctgct gctgctactg atagcaacaa taatatt       297


<210> SEQ ID NO 99
<211> LENGTH: 339
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 99

tctaatgttg ttgaaagttc aaatgattca gctctacttc agtcatccta tctttcccta     60

aaccaagtga ctcctttcat tagatttagt cagctaactg ctaatcaagc gattttggaa    120

gctattaacg ataaccaaca agcgatccac atcgttgatt ttgatattaa tcacggtgtt    180

caatggccac cgttaatgca agcactagct gatcgttacc ctcctccaac tcttcggatt    240

accggtactg gaaatgacct tgataccctt cgtagaaccg gagatcgttt agctaaattt    300

gctcactctt taggccttag atttcagttt caccctctt                           339


<210> SEQ ID NO 100
<211> LENGTH: 480
```

<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 100

```
actgacaatg atatcaagaa ttactggaat actaagctca agaaaaaacc tatgggatta     60
atgcaatcaa ctaaccaaag aaaatcacca tattttccag ctactaattc tcttcaaacc    120
caaccccaga taaattcaag tctttttaga gacttatatt acaccccaaa taataggcct    180
aatattacag gcctaaatca tcagtccatt tcttctgccc accagacaaa ttttctctac    240
actaatagta acatgaattt tcctaatttg ggtgctacaa atagtcaata tccttataat    300
attcaaagtc ataatttact tatgtttgga gaagcaagtt gttcttcatc agatggaagt    360
tgtagccaaa tgagttttgg caaagaaatc aagagagagg aaattatgag taattgttta    420
caacaaggtc aaatttcaag tgttaatgct tttgaagaaa atcagaattt cactcttgat    480
```

<210> SEQ ID NO 101
<211> LENGTH: 900
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 101

```
atgaattcaa agaaaaacaa ctcaccaaga aaaaggttga gaaaatatca tacaagaaaa     60
gctcctatta ttagctctta tatggacatg gctgaagcta gaagagaaat tgttcatgct    120
ttacaacttc atcgatcttc atcttcatct ccaactccgt ctattaatag cccaaagaag    180
tacacattat tgggtcaagg agttgtaagc tctcaacaat attactatta ctcaatagtg    240
gaatctatgc ctattcctga accaacatgg tctacaacgg ctccggcaat acttaatgca    300
atgggaactg gtacttatgg agaagtggga cgtacaatac atcaaagatc aggaacacat    360
atacctcaaa ttctcgatcc gcctttgcta ggggatagtg attgcaagcg agaaggcaaa    420
catgtagaat ttatgcctcc aatcatgggt gaaaacttaa aagcagctaa tcaatttgaa    480
ctgatggccc cgtcaattgc attcaaatca tatccctatt cggaggtacc acaatattct    540
ggtggcaatg tggctgctgc atgtggtgaa tctttggtac atcaaaatat agaaagatca    600
atgtctgatc cccttgtgat tggtagagtg attggggaag ttgttgatta tttcactcca    660
agtgttaaga tgtctgttac ttataacagc agcaagcatg tttataatgg gcatgaactc    720
tttccttcct cagtcacctc taaacctagg gttgaagttc atggaggtga tttgagatct    780
ttctttacaa tgatcatgat agacccagat gttcctggtc ctagtgatcc atatctcagg    840
gaacacctac actggattgt cacagacatt ccaggcacta cagattgctc gtttgggaaa    900
```

<210> SEQ ID NO 102
<211> LENGTH: 150
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 102

```
caccacatag attgaacgga gggaataata gtgtagcccc attgggaaac accatattta     60
tataggtaga agaaatactc cagatttaac tagaatttct actgacaaaa gatcttttac    120
```

actatcaatc acttaaaaga taactacagg 150

<210> SEQ ID NO 103
<211> LENGTH: 141
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 103
cactaagctt tcttttcctc ataacctcac ttgcttctcc tttgttcttc tttcgtctcc 60
tcctttgttt cgcctcccct tgttctggta actcttgagt gtagatacca ggatagtact 120
gagaaatgag tatcatttga t 141

<210> SEQ ID NO 104
<211> LENGTH: 150
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 104
catgaaccaa cacaatagga ggcaaatcag tgttagtctt ttttgaatca tctgttttaa 60
ggctagtttc caaatttggc ttgaaaagcc aatcgctcag agtctgggaa acatcaccgg 120
ccactgaaac agctctgtca attggaatgt 150

<210> SEQ ID NO 105
<211> LENGTH: 165
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 105
gttatcacaa ttcacaaggg aaagttcata acatgaccac tgtcgaatca aaaagggaaa 60
gttcatatat aatacgctta ggctttgggt ttttcaaatg aagggtagag ttcttcataa 120
acgaaattcc acattgttac ttcatatttc acatattccc gaata 165

<210> SEQ ID NO 106
<211> LENGTH: 153
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 106
ttctccttat acctcctgag taccataatt tacactcatc tatgtccaat gccttacatc 60
ccacccatct aatttcctga acacaagcta cactaatctt ctaatgagcg caaaatacaa 120
cacaaaatta ttgctcgcta gtcaaagata ata 153

<210> SEQ ID NO 107
<211> LENGTH: 180
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 107
tgggacattt gatagttaga cgttgtaact ttaggttgaa atctgcagtc gagttcattg 60
ttctctttat aataatcact tgaaactggt tgctggctac acgctgctgt tgcttcaaca 120
tgcagatatg gcgctaccgg ccgtagtgca gatgtgggag tttccatttc aggcttggca 180

<210> SEQ ID NO 108
<211> LENGTH: 560
<212> TYPE: DNA
<213> ORGANISM: Nicotiana tabacum

<400> SEQUENCE: 108
attactctta actttaaata gatttcttat atatgggttc aaaaatgtct gatccccttg 60
tgattggtag agtgattggg gaagttgttg attatttcac tccaagtgtt aagatgtctg 120
ttacttataa cagcagcaag catgtttata atgggcatga actctttcct tcctcagtca 180
cctctaaacc tagggttgaa gttcatggag gtgatttgag atctttcttt acaatgatca 240
tgatagaccc agatgttcct ggtcctagtg atccatatct cagggaacac ctacactgga 300
ttgtcacaga cattccaggc actacagatt gctcgtttgg gaaagaaata gttggctatg 360
aaatgccaag gccaaatatt ggaattcaca ggtttgtatt tctgctgttc aagcagaaga 420
agaggcaaac agtattgact gcacctctct ccagggatcg atttaatacg cgtaaattcg 480
cagaagaaaa tgagcttggg tctcctgttg cagcagtttt cttcaattgc cagagggaaa 540
ctgctgccag aaggcgttga 560

<210> SEQ ID NO 109
<211> LENGTH: 522
<212> TYPE: DNA
<213> ORGANISM: Nicotiana tabacum

<400> SEQUENCE: 109
atggctcaaa tgacagatcc ccttgtgatt agtagggtgg ttggagatgt tgttgattat 60
ttctctccaa gtgttaagat gtgtgttatt tataacccca gtaagcatgt ctataatggg 120
catgaactct ttccatccct tgttacctct aaacctaagg ttgaagttca tggaggtgac 180
atgagatcct tctttacact gatcatgact gaccctgatg ttcctggtcc tagcgatcca 240
tatcttaggg agcacttaca ttgggtaatt acagacattc caggcactac agattcctcg 300
tttggaaaag aagtggtggg ctatgaaatg ccaatgccta acattggaat ccataggttt 360
gtgtttctgc tcttcaagca gaagaagagg caaacagtga gcgcaccatt atccagggac 420
cgattcaata cgcggaaata cgcagaagaa aatgagcttg gctctccagt tgctgctgtt 480
ttcttcaact gccaaaggga aaccgcggcc agaaagcgtt ga 522

<210> SEQ ID NO 110
<211> LENGTH: 453
<212> TYPE: DNA
<213> ORGANISM: Nicotiana tabacum

<400> SEQUENCE: 110
atggctcaaa tgagtacaga tccccttgtg attggcaggg tggttggaga tgttgttgat 60
tatttctccc caagtgttaa aatgtctgtt atttgtaacc ccagcaaaca tgtctataat 120
gggcatgaac tctttccatc ctctgttacc tctaaaccta aggttgaagt taacggaggt 180
gacatgacat ccttctttac attgatcatg actgaccctg atgttcctgg tcctagtgat 240

```
ccatatatta gggagcactt gcactggaaa agaattaagt ggtgggctat gaaatgccaa    300

tgccaaataa aggaatccat aggtttgtgt ttgtgctgtt caagcagaag aaaaggcaaa    360

cagtatgcat tatccaggga ccgattcaat accaatacag ctgctgctgt tttcttcaat    420

tgccaaaggg aaaccgcggc cagaaggcgt tga                                 453
```

<210> SEQ ID NO 111
<211> LENGTH: 3155
<212> TYPE: DNA
<213> ORGANISM: Artificial Sequence
<220> FEATURE:
<223> OTHER INFORMATION: Description of Artificial Sequence: Synthetic construct for transforming plants

<400> SEQUENCE: 111

```
aagcttccag aaggtaatta tccaagatgt agcatcaaga atccaatgtt tacgggaaaa     60

actatggaag tattatgtga gctcagcaag aagcagatca atatgcggca catatgcaac    120

ctatgttcaa aaatgaagaa tgtacagata caagatccta tactgccaga atacgaagaa    180

gaatacgtag aaattgaaaa agaagaacca ggcgaagaaa agaatcttga agacgtaagc    240

actgacgaca acaatgaaaa gaagaagata aggtcggtga ttgtgaaaga gacatagagg    300

acacatgtaa ggtggaaaat gtaagggcgg aaagtaacct tatcacaaag gaatcttatc    360

ccccactact tatcctttta tatttttccg tgtcattttt gcccttgagt tttcctatat    420

aaggaaccaa gttcggcatt tgtgaaaaca agaaaaaatt tggtgtaagc tattttcttt    480

gaagtactga ggatacaact tcagagaaat ttgtaagttt gtggatcctg caggctagcg    540

tgcactctag actcgacgaa ctgacgagct cgaatttccc cgatcgttca aacatttggc    600

aataaagttt cttaagattg aatcctgttg ccggtcttgc gatgattatc atataatttc    660

tgttgaatta cgttaagcat gtaataatta acatgtaatg catgacgtta tttatgagat    720

gggtttttat gattagagtc ccgcaattat acatttaata cgcgatagaa aacaaaatat    780

agcgcgcaaa ctatgataaa ttatcgcgcg cggtgtcatc tatgttacta gatcgggaat    840

tcctcgagca actattttta tgtatgcaag agtcagcata tgtataattg attcagaatc    900

gttttgacga gttcggatgt agtagtagcc attatttaat gtacatacta atcgtgaata    960

gtgaatatga tgaaacattg tatcttattg tataaatatc cataaacaca tcatgaaaga   1020

cactttcttt cacggtctga attaattatg atacaattct aatagaaaac gaattaaatt   1080

acgttgaatt gtatgaaatc taattgaaca agccaaccac gacgacgact aacgttgcct   1140

ggattgactc ggtttaagtt aaccactaaa aaaacggagc tgtcatgtaa cacgcggatc   1200

gagcaggtca cagtcatgaa gccatcaaag caaaagaact aatccaaggg ctgagatgat   1260

taattagttt aaaaattagt taacacgagg gaaaaggctg tctgacagcc aggtcacgtt   1320

atctttacct gtggtcgaaa tgattcgtgt ctgtcgattt taattatttt tttgaaaggc   1380

cgaaaataaa gttgtaagag ataaacccgc ctatataaat tcatatattt tcctctccgc   1440

tttgaattgt ctcgttgtcc tcctcacttt catcagccgt tttgaatctc cggcgacttg   1500

acagagaaga acaaggaaga agactaagag agaaagtaag agataatcca ggagattcat   1560

tctccgtttt gaatcttcct caatctcatc ttcttccgct ctttctttcc aaggtaatag   1620

gaactttctg gatctacttt atttgctgga tctcgatctt gttttctcaa tttccttgag   1680

atctggaatt cgtttaattt ggatctgtga acctccacta aatcttttgg ttttactaga   1740

atcgatctaa gttgaccgat cagttagctc gattatagct accagaattt ggcttgacct   1800
```

-continued

```
tgatggagag atccatgttc atgttacctg ggaaatgatt tgtatatgtg aattgaaatc   1860

tgaactgttg aagttagatt gaatctgaac actgtcaatg ttagattgaa tctgaacact   1920

gtttaaggtt agatgaagtt tgtgtataga ttcttcgaaa ctttaggatt tgtagtgtcg   1980

tacgttgaac agaaagctat ttctgattca atcagggttt atttgactgt attgaactct   2040

ttttgtgtgt ttgcagctca taaaaggtac caaacaatga ttgaacaaga tggattgcac   2100

gcaggttctc cggccgcttg ggtggagagg ctattcggct atgactgggc acaacagaca   2160

atcggctgct ctgatgccgc cgtgttccgg ctgtcagcgc aggggcgccc ggttcttttt   2220

gtcaagaccg acctgtccgg tgccctgaat gaactgcagg acgaggcagc gcggctatcg   2280

tggctggcca cgacgggcgt tccttgcgca gctgtgctcg acgttgtcac tgaagcggga   2340

agggactggc tgctattggg cgaagtgccg gggcaggatc tcctgtcatc tcaccttgct   2400

cctgccgaga aagtatccat catggctgat gcaatgcggc ggctgcatac gcttgatccg   2460

gctacctgcc cattcgacca ccaagcgaaa catcgcatcg agcgagcacg tactcggatg   2520

gaagccggtc ttgtcgatca ggatgatctg gacgaagagc atcaggggct cgcgccagcc   2580

gaactgttcg ccaggctcaa ggcgcgcatg cccgacggcg aggatctcgt cgtgacccat   2640

ggcgatgcct gcttgccgaa tatcatggtg gaaaatggcc gcttttctgg attcatcgac   2700

tgtggccggc tgggtgtggc ggaccgctat caggacatag cgttggctac ccgtgatatt   2760

gctgaagagc ttggcggcga atgggctgac cgcttcctcg tgctttacgg tatcgccgct   2820

cccgattcgc agcgcatcgc cttctatcgc cttcttgacg agttcttttg agcgggactc   2880

tggcgatcgc cccgatcgtt caaacatttg gcaataaagt ttcttaagat tgaatcctgt   2940

tgccggtctt gcgatgatta tcatataatt tctgttgaat tacgttaagc atgtaataat   3000

taacatgtaa tgcatgacgt tatttatgag atgggttttt atgattagag tcccgcaatt   3060

atacatttaa tacgcgatag aaaacaaaat atagcgcgca aactaggata aattatcgcg   3120

cgcggtgtca tctatgttac tagatcggga ctagt                              3155
```

<210> SEQ ID NO 112
<211> LENGTH: 11801
<212> TYPE: DNA
<213> ORGANISM: Artificial Sequence
<220> FEATURE:
<223> OTHER INFORMATION: Description of Artificial Sequence: Synthetic construct for transforming plants

<400> SEQUENCE: 112

```
tgagcgtcgc aaaggcgctc ggtcttgcct tgctcgtcgg tgatgtactt caccagctcc     60

gcgaagtcgc tcttcttgat ggagcgcatg gggacgtgct tggcaatcac gcgcaccccc    120

cggccgtttt agcggctaaa aaagtcatgg ctctgccctc gggcggacca cgcccatcat    180

gaccttgcca agctcgtcct gcttctcttc gatcttcgcc agcagggcga ggatcgtggc    240

atcaccgaac cgcgccgtgc gcgggtcgtc ggtgagccag agtttcagca ggccgcccag    300

gcggcccagg tcgccattga tgcgggccag ctcgcggacg tgctcatagt ccacgacgcc    360

cgtgattttg tagccctggc cgacggccag caggtaggcc gacaggctca tgccggccgc    420

cgccgccttt tcctcaatcg ctcttcgttc gtctggaagg cagtacacct tgataggtgg    480

gctgcccttc ctggttggct tggtttcatc agccatccgc ttgccctcat ctgttacgcc    540

ggcggtagcc ggccagcctc gcagagcagg attcccgttg agcaccgcca ggtgcgaata    600

agggacagtg aagaaggaac acccgctcgc gggtgggcct acttcaccta tcctgcccgg    660
```

-continued

```
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
atagtcctgt cgggtttcgc cacctctgac ttgagcgtcg atttttgtga tgctcgtcag    960
gggggcggag cctatggaaa aacgccagca acgcggcctt tttacggttc ctggcctttt   1020
gctggccttt tgctcacatg ttctttcctg cgttatcccc tgattctgtg gataaccgta   1080
ttaccgcctt tgagtgagct gataccgctc gccgcagccg aacgaccgag cgcagcgagt   1140
cagtgagcga ggaagcggaa gagcgccaga aggccgccag agaggccgag cgcggccgtg   1200
aggcttggac gctagggcag ggcatgaaaa agcccgtagc gggctgctac gggcgtctga   1260
cgcggtggaa agggggaggg gatgttgtct acatggctct gctgtagtga gtgggttgcg   1320
ctccggcagc ggtcctgatc aatcgtcacc ctttctcggt ccttcaacgt tcctgacaac   1380
gagcctcctt ttcgccaatc catcgacaat caccgcgagt ccctgctcga acgctgcgtc   1440
cggaccggct tcgtcgaagg cgtctatcgc ggcccgcaac agcggcgaga gcggagcctg   1500
ttcaacggtg ccgccgcgct cgccggcatc gctgtcgccg gcctgctcct caagcacggc   1560
cccaacagtg aagtagctga ttgtcatcag cgcattgacg gcgtccccgg ccgaaaaacc   1620
cgcctcgcag aggaagcgaa gctgcgcgtc ggccgtttcc atctgcggtg cgcccggtcg   1680
cgtgccggca tggatgcgcg cgccatcgcg gtaggcgagc agcgcctgcc tgaagctgcg   1740
ggcattcccg atcagaaatg agcgccagtc gtcgtcggct ctcggcaccg aatgcgtatg   1800
attctccgcc agcatggctt cggccagtgc gtcgagcagc gcccgcttgt tcctgaagtg   1860
ccagtaaagc gccggctgct gaacccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tcttttctct taggtttacc   2460
cgccaatata tcctgtcaaa cactgatagt ttaaactgaa ggcgggaaac gaagcttcca   2520
gaaggtaatt atccaagatg tagcatcaag aatccaatgt ttacgggaaa aactatggaa   2580
gtattatgtg agctcagcaa gaagcagatc aatatgcggc acatatgcaa cctatgttca   2640
aaaatgaaga atgtacagat acaagatcct atactgccag aatacgaaga agaatacgta   2700
gaaattgaaa aagaagaacc aggcgaagaa aagaatcttg aagacgtaag cactgacgac   2760
aacaatgaaa agaagaagat aaggtcggtg attgtgaaag agacatagag gacacatgta   2820
aggtggaaaa tgtaagggcg gaaagtaacc ttatcacaaa ggaatcttat cccccactac   2880
ttatcctttt atatttttcc gtgtcatttt tgcccttgag ttttcctata taaggaacca   2940
agttcggcat ttgtgaaaac aagaaaaaat ttggtgtaag ctattttctt tgaagtactg   3000
aggatacaac ttcagagaaa tttgtaagtt tgtggatcct gcaggctagc gtgcactcta   3060
```

gactcgacga actgacgagc tcgaatttcc ccgatcgttc aaacatttgg caataaagtt 3120
tcttaagatt gaatcctgtt gccggtcttg cgatgattat catataattt ctgttgaatt 3180
acgttaagca tgtaataatt aacatgtaat gcatgacgtt atttatgaga tgggttttta 3240
tgattagagt cccgcaatta tacatttaat acgcgataga aaacaaaata tagcgcgcaa 3300
actatgataa attatcgcgc gcggtgtcat ctatgttact agatcgggaa ttcctcgagc 3360
aactattttt atgtatgcaa gagtcagcat atgtataatt gattcagaat cgttttgacg 3420
agttcggatg tagtagtagc cattatttaa tgtacatact aatcgtgaat agtgaatatg 3480
atgaaacatt gtatcttatt gtataaatat ccataaacac atcatgaaag acactttctt 3540
tcacggtctg aattaattat gatacaattc taatagaaaa cgaattaaat tacgttgaat 3600
tgtatgaaat ctaattgaac aagccaacca cgacgacgac taacgttgcc tggattgact 3660
cggtttaagt taaccactaa aaaaacggag ctgtcatgta acacgcggat cgagcaggtc 3720
acagtcatga agccatcaaa gcaaaagaac taatccaagg gctgagatga ttaattagtt 3780
taaaaattag ttaacacgag ggaaaaggct gtctgacagc caggtcacgt tatctttacc 3840
tgtggtcgaa atgattcgtg tctgtcgatt ttaattattt ttttgaaagg ccgaaaataa 3900
agttgtaaga gataaacccg cctatataaa ttcatatatt ttcctctccg ctttgaattg 3960
tctcgttgtc ctcctcactt tcatcagccg ttttgaatct ccggcgactt gacagagaag 4020
aacaaggaag aagactaaga gagaaagtaa gagataatcc aggagattca ttctccgttt 4080
tgaatcttcc tcaatctcat cttcttccgc tctttctttc caaggtaata ggaactttct 4140
ggatctactt tatttgctgg atctcgatct tgttttctca atttccttga gatctggaat 4200
tcgtttaatt tggatctgtg aacctccact aaatcttttg gttttactag aatcgatcta 4260
agttgaccga tcagttagct cgattatagc taccagaatt tggcttgacc ttgatggaga 4320
gatccatgtt catgttacct gggaaatgat ttgtatatgt gaattgaaat ctgaactgtt 4380
gaagttagat tgaatctgaa cactgtcaat gttagattga atctgaacac tgtttaaggt 4440
tagatgaagt ttgtgtatag attcttcgaa actttaggat ttgtagtgtc gtacgttgaa 4500
cagaaagcta tttctgattc aatcagggtt tatttgactg tattgaactc tttttgtgtg 4560
tttgcagctc ataaaaggta ccaaacaatg attgaacaag atggattgca cgcaggttct 4620
ccggccgctt gggtggagag gctattcggc tatgactggg cacaacagac aatcggctgc 4680
tctgatgccg ccgtgttccg gctgtcagcg caggggcgcc cggttctttt tgtcaagacc 4740
gacctgtccg gtgccctgaa tgaactgcag gacgaggcag cgcggctatc gtggctggcc 4800
acgacgggcg ttccttgcgc agctgtgctc gacgttgtca ctgaagcggg aagggactgg 4860
ctgctattgg gcgaagtgcc ggggcaggat ctcctgtcat ctcaccttgc tcctgccgag 4920
aaagtatcca tcatggctga tgcaatgcgg cggctgcata cgcttgatcc ggctacctgc 4980
ccattcgacc accaagcgaa acatcgcatc gagcgagcac gtactcggat ggaagccggt 5040
cttgtcgatc aggatgatct ggacgaagag catcaggggc tcgcgccagc cgaactgttc 5100
gccaggctca aggcgcgcat gcccgacggc gaggatctcg tcgtgaccca tggcgatgcc 5160
tgcttgccga atatcatggt ggaaaatggc cgcttttctg gattcatcga ctgtggccgg 5220
ctgggtgtgg cggaccgcta tcaggacata gcgttggcta cccgtgatat tgctgaagag 5280
cttggcggcg aatgggctga ccgcttcctc gtgctttacg gtatcgccgc tcccgattcg 5340
cagcgcatcg ccttctatcg ccttcttgac gagttctttt gagcgggact ctggcgatcg 5400

-continued ccccgatcgt tcaaacattt ggcaataaag tttcttaaga ttgaatcctg ttgccggtct 5460
tgcgatgatt atcatataat ttctgttgaa ttacgttaag catgtaataa ttaacatgta 5520
atgcatgacg ttatttatga gatgggtttt tatgattaga gtcccgcaat tatacattta 5580
atacgcgata gaaaacaaaa tatagcgcgc aaactaggat aaattatcgc gcgcggtgtc 5640
atctatgtta ctagatcggg actagtttac accacaatat atcctgccac cagccagcca 5700
acagctcccc gaccggcagc tcggcacaaa atcaccactc gatacaggca gcccatcagt 5760
ccgggacggc gtcagcggga gagccgttgt aaggcggcag actttgctca tgttaccgat 5820
gctattcgga agaacggcaa ctaagctgcc gggtttgaaa cacggatgat ctcgcggagg 5880
gtagcatgtt gattgtaacg atgacagagc gttgctgcct gtgatcaaat atcatctccc 5940
tcgcagagat ccgaattatc agccttctta ttcatttctc gcttaaccgt gacaggctgt 6000
cgatcttgag aactatgccg acataatagg aaatcgctgg ataaagccgc tgaggaagct 6060
gagtggcgct atttctttag aagtgaacgt tgacgatatc aactccccta tccattgctc 6120
accgaatggt acaggtcggg gacccgaagt tccgactgtc ggcctgatgc atccccggct 6180
gatcgacccc agatctgggg ctgagaaagc ccagtaagga aacaactgta ggttcgagtc 6240
gcgagatccc ccggaaccaa aggaagtagg ttaaacccgc tccgatcagg ccgagccacg 6300
ccaggccgag aacattggtt cctgtaggca tcgggattgg cggatcaaac actaaagcta 6360
ctggaacgag cagaagtcct ccggccgcca gttgccaggc ggtaaaggtg agcagaggca 6420
cgggaggttg ccacttgcgg gtcagcacgg ttccgaacgc catggaaacc gcccccgcca 6480
ggcccgctgc gacgccgaca ggatctagcg ctgcgtttgg tgtcaacacc aacagcgcca 6540
cgcccgcagt tccgcaaata gcccccagga ccgccatcaa tcgtatcggg ctacctagca 6600
gagcggcaga gatgaacacg accatcagcg gctgcacagc gcctaccgtc gccgcgaccc 6660
cgcccggcag gcggtagacc gaaataaaca acaagctcca gaatagcgaa atattaagtg 6720
cgccgaggat gaagatgcgc atccaccaga ttcccgttgg aatctgtcgg acgatcatca 6780
cgagcaataa acccgccggc aacgcccgca gcagcatacc ggcgacccct cggcctcgct 6840
gttcgggctc cacgaaaacg ccggacagat gcgccttgtg agcgtccttg gggccgtcct 6900
cctgtttgaa gaccgacagc ccaatgatct cgccgtcgat gtaggcgccg aatgccacgg 6960
catctcgcaa ccgttcagcg aacgcctcca tgggcttttt ctcctcgtgc tcgtaaacgg 7020
acccgaacat ctctggagct ttcttcaggg ccgacaatcg gatctcgcgg aaatcctgca 7080
cgtcggccgc tccaagccgt cgaatctgag ccttaatcac aattgtcaat tttaatcctc 7140
tgtttatcgg cagttcgtag agcgcgccgt gcgtcccgag cgatactgag cgaagcaagt 7200
gcgtcgagca gtgcccgctt gttcctgaaa tgccagtaaa gcgctggctg ctgaaccccc 7260
agccggaact gaccccacaa ggccctagcg tttgcaatgc accaggtcat cattgaccca 7320
ggcgtgttcc accaggccgc tgcctcgcaa ctcttcgcag gcttcgccga cctgctcgcg 7380
ccacttcttc acgcgggtgg aatccgatcc gcacatgagg cggaaggttt ccagcttgag 7440
cgggtacggc tcccggtgcg agctgaaata gtcgaacatc cgtcgggccg tcggcgacag 7500
cttgcggtac ttctcccata tgaatttcgt gtagtggtcg ccagcaaaca gcacgacgat 7560
ttcctcgtcg atcaggacct ggcaacggga cgttttcttg ccacggtcca ggacgcggaa 7620
gcggtgcagc agcgacaccg attccaggtg cccaacgcgg tcggacgtga agcccatcgc 7680
cgtcgcctgt aggcgcgaca ggcattcctc ggccttcgtg taataccggc cattgatcga 7740
ccagcccagg tcctggcaaa gctcgtagaa cgtgaaggtg atcggctcgc cgataggggt 7800

-continued gcgcttcgcg tactccaaca cctgctgcca caccagttcg tcatcgtcgg cccgcagctc 7860
gacgccggtg taggtgatct tcacgtcctt gttgacgtgg aaaatgacct tgttttgcag 7920
cgcctcgcgc gggatttttct tgttgcgcgt ggtgaacagg gcagagcggg ccgtgtcgtt 7980
tggcatcgct cgcatcgtgt ccggccacgg cgcaatatcg aacaaggaaa gctgcatttc 8040
cttgatctgc tgcttcgtgt gtttcagcaa cgcggcctgc ttggcctcgc tgacctgttt 8100
tgccaggtcc tcgccggcgg tttttcgctt cttggtcgtc atagttcctc gcgtgtcgat 8160
ggtcatcgac ttcgccaaac ctgccgcctc ctgttcgaga cgacgcgaac gctccacggc 8220
ggccgatggc gcgggcaggg cagggggagc cagttgcacg ctgtcgcgct cgatcttggc 8280
cgtagcttgc tggaccatcg agccgacgga ctggaaggtt tcgcggggcg cacgcatgac 8340
ggtgcggctt gcgatggttt cggcatcctc ggcggaaaac cccgcgtcga tcagttcttg 8400
cctgtatgcc ttccggtcaa acgtccgatt cattcaccct ccttgcggga ttgccccgac 8460
tcacgccggg gcaatgtgcc cttattcctg atttgacccg cctggtgcct tggtgtccag 8520
ataatccacc ttatcggcaa tgaagtcggt cccgtagacc gtctggccgt ccttctcgta 8580
cttggtattc cgaatcttgc cctgcacgaa taccagcgac cccttgccca aatacttgcc 8640
gtgggcctcg gcctgagagc caaaacactt gatgcggaag aagtcggtgc gctcctgctt 8700
gtcgccggca tcgttgcgcc acatctaggt actaaaacaa ttcatccagt aaaatataat 8760
attttatttt ctcccaatca ggcttgatcc ccagtaagtc aaaaaatagc tcgacatact 8820
gttcttcccc gatatcctcc ctgatcgacc ggacgcagaa ggcaatgtca taccacttgt 8880
ccgccctgcc gcttctccca agatcaataa agccacttac tttgccatct ttcacaaaga 8940
tgttgctgtc tcccaggtcg ccgtgggaaa agacaagttc ctcttcgggc ttttccgtct 9000
ttaaaaaatc atacagctcg cgcggatctt taaatggagt gtcttcttcc cagttttcgc 9060
aatccacatc ggccagatcg ttattcagta agtaatccaa ttcggctaag cggctgtcta 9120
agctattcgt atagggacaa tccgatatgt cgatggagtg aaagagcctg atgcactccg 9180
catacagctc gataatcttt tcagggcttt gttcatcttc atactcttcc gagcaaagga 9240
cgccatcggc ctcactcatg agcagattgc tccagccatc atgccgttca aagtgcagga 9300
cctttggaac aggcagcttt ccttccagcc atagcatcat gtccttttcc cgttccacat 9360
cataggtggt ccctttatac cggctgtccg tcatttttaa atataggttt tcattttctc 9420
ccaccagctt atataccta gcaggagaca ttccttccgt atcttttacg cagcggtatt 9480
tttcgatcag tttttttcaat tccggtgata ttctcatttt agccatttat tatttccttc 9540
ctcttttcta cagtatttaa agatacccca agaagctaat tataacaaga cgaactccaa 9600
ttcactgttc cttgcattct aaaaccttaa ataccagaaa acagcttttt caaagttgtt 9660
ttcaaagttg gcgtataaca tagtatcgac ggagccgatt ttgaaaccac aattatgggt 9720
gatgctgcca acttactgat ttagtgtatg atggtgtttt tgaggtgctc cagtggcttc 9780
tgtgtctatc agctgtccct cctgttcagc tactgacggg gtggtgcgta acggcaaaag 9840
caccgccgga catcagcgct atctctgctc tcactgccgt aaaacatggc aactgcagtt 9900
cacttacacc gcttctcaac ccggtacgca ccagaaaatc attgatatgg ccatgaatgg 9960
cgttggatgc cgggcaacag cccgcattat gggcgttggc ctcaacacga ttttacgtca 10020
cttaaaaaac tcaggccgca gtcggtaacc tcgcgcatac agccgggcag tgacgtcatc 10080
gtctgcgcgg aaatggacga acagtggggc tatgtcgggg ctaaatcgcg ccagcgctgg 10140

```
ctgttttacg cgtatgacag tctccggaag acggttgttg cgcacgtatt cggtgaacgc  10200

actatggcga cgctggggcg tcttatgagc ctgctgtcac cctttgacgt ggtgatatgg  10260

atgacggatg gctggccgct gtatgaatcc cgcctgaagg gaaagctgca cgtaatcagc  10320

aagcgatata cgcagcgaat tgagcggcat aacctgaatc tgaggcagca cctggcacgg  10380

ctgggacgga agtcgctgtc gttctcaaaa tcggtggagc tgcatgacaa agtcatcggg  10440

cattatctga acataaaaca ctatcaataa gttggagtca ttacccaatt atgatagaat  10500

ttacaagcta taaggttatt gtcctgggtt tcaagcatta gtccatgcaa gtttttatgc  10560

tttgcccatt ctatagatat attgataagc gcgctgccta tgccttgccc cctgaaatcc  10620

ttacatacgg cgatatcttc tatataaaag atatattatc ttatcagtat tgtcaatata  10680

ttcaaggcaa tctgcctcct catcctcttc atcctcttcg tcttggtagc tttttaaata  10740

tggcgcttca tagagtaatt ctgtaaaggt ccaattctcg ttttcatacc tcggtataat  10800

cttacctatc acctcaaatg gttcgctggg tttatcgcac ccccgaacac gagcacggca  10860

cccgcgacca ctatgccaag aatgcccaag gtaaaaattg ccggccccgc catgaagtcc  10920

gtgaatgccc cgacggccga agtgaagggc aggccgccac ccaggccgcc gccctcactg  10980

cccggcacct ggtcgctgaa tgtcgatgcc agcacctgcg gcacgtcaat gcttccgggc  11040

gtcgcgctcg ggctgatcgc ccatcccgtt actgccccga tcccggcaat ggcaaggact  11100

gccagcgctg ccatttttgg ggtgaggccg ttcgcggccg aggggcgcag cccctggggg  11160

gatgggaggc ccgcgttagc gggccgggag ggttcgagaa ggggggcac cccccttcgg  11220

cgtgcgcggt cacgcgcaca gggcgcagcc ctggttaaaa acaaggttta taaatattgg  11280

tttaaaagca ggttaaaaga caggttagcg gtggccgaaa aacgggcgga aacccttgca  11340

aatgctggat tttctgcctg tggacagccc ctcaaatgtc aataggtgcg cccctcatct  11400

gtcagcactc tgcccctcaa gtgtcaagga tcgcgcccct catctgtcag tagtcgcgcc  11460

cctcaagtgt caataccgca gggcacttat ccccaggctt gtccacatca tctgtgggaa  11520

actcgcgtaa aatcaggcgt tttcgccgat ttgcgaggct ggccagctcc acgtcgccgg  11580

ccgaaatcga gcctgcccct catctgtcaa cgccgcgccg ggtgagtcgg cccctcaagt  11640

gtcaacgtcc gcccctcatc tgtcagtgag ggccaagttt tccgcgaggt atccacaacg  11700

ccggcggccg cggtgtctcg cacacggctt cgacggcgtt tctggcgcgt ttgcagggcc  11760

atagacggcc gccagcccag cggcgagggc aaccagcccg g                       11801
```

```
<210> SEQ ID NO 113
<211> LENGTH: 2499
<212> TYPE: DNA
<213> ORGANISM: Nicotiana tabacum

<400> SEQUENCE: 113

tctaggagca aaaaaaaaaa aaaaaaaaaa aacaagtagt agtagtagta gtaaatggaa     60

aaatagagag gcaatttttt ttagtatctt actttatcca ttagcactta aaaaacatag    120

gtttacatgc tctcattgtc acgccaggcc gctaattaaa tggtacattt catcatcccc    180

attttttggc ctcatagtta attatcacaa tttctgaaag caacatcaga acaaccccac    240

atttcttgtg gtcctataat tactgctaga tagtccaaac ccatctgcct atttagggct    300

tgtgaatgag gattgaaaat ggtagagaat atttgcaaag gcatcatgca tatatggaaa    360

agactaaaga gagagttagt gccttgcaaa gcggattctc acagttgtag aaaaggactc    420

accattttca agaatactcc cggcatgaag atggacaatt taatataaaa aacaaagaaa    480
```

```
atagtaatta agtgcgttga gatgaatgaa atttatccgc tcttaattga atatggggaa    540
ttgaaagaaa tttctgataa taaattaatg agtcttacat gacgtggatc cgacttaatc    600
tagtctattt aaactaagaa tagataagaa tagagaatat agacaaaaga gaggctcatt    660
ggctagggtt tcaagggagt tccttgaaca taagtggcaa gtacaagcac aaagccaatt    720
tccatggact aaagatgaat aagatgtgtc gtgtggtatg gtgggaaggt gaggaggtat    780
ggggtaattg gagatgctaa acctctctaa aagctctttt gctccaaata tctaaatcca    840
tctctatcac ttttggcgac tgccccaaaa tttgcaactt atgaattaaa gttttaatat    900
ttttaagtta ataaattctg aattaataat ttaacatatt caataaactt tttaaaacaa    960
attacgtata taccatcaaa ctggctgcac catgatcact ttctaaactc acaatgacat   1020
atggatttaa tcaggcacaa agtcatgttg atagaaagag atagtacgga gaatgaagaa   1080
aaaaggtagg ggagagagat ggggtgagtg gggaaaagat agggttctct ttttagtgaa   1140
agcgacaggg tctgagaacc ctaggtcaaa agttgcataa acctctatac aggcttcttc   1200
actcccttac tactaatata ctctcattaa ggcttgaggt ttaattcatt aaaattgtgg   1260
tttaattatt gtatcccctc aaacgaaata attgtccttg tcgaggttag acaatgttgc   1320
gtactatttt caaacgcagt cagccattat tctcctatcc tttacagtcg agattcaaag   1380
acagaaagta gcatgcaagc tgttattaat ttactttgat taggactttg ccaagaaaat   1440
gaagaacctt ttcttttttc ttttaattta gttatcttac aacatgtaat ttttcctagc   1500
aagcaaatac ggtaactttt ttttttattc tcatttaatt tgttggagct attgctactt   1560
tgatgacttc aaccaaatcc tggttggtag gcggagggtg ctgacgatgg aaactacccc   1620
tcttgtccaa atacgataac ctaaaaaata gaataatagc ttattgtact gtgctgcaaa   1680
aattgcattg tcagtataca taattaaaat ctattttgaa tgtgtggagg gcaaagaggg   1740
gtgactggtc tagggttgta gaaatcaggt gggagagaga atggtatttg tctctgtgtc   1800
agctgatatc acgtgaagag gcacaataag aagtccttcg tatccattca cttcccaaaa   1860
ataccggcat tactacaaat atagtactag cacttgcttt ctctatcccc atctttgcta   1920
tttcctttcc ctttccaact ttttggcttt agaattgcaa agatggaggg aattgtggtt   1980
ctttgtatct gtaaaatttt tcctccaagc tccagttgta gctagcttaa tgcgtggacg   2040
cgcgcgcaca cactagaaat ctgcaatcta tatatatatt cacaaggcac tcacatatca   2100
aaaaccacat agacattgta tagagagagc tgtcgttctc aagcagaaaa aatgatatga   2160
tttcatcagc atgtggtcaa ccaaatagtt caattctagt ctttgcttcc tctttctaat   2220
tactgtataa atagagccac aaggacatag aattgagaaa ataaaagaca ataaaaacaa   2280
atctagctac ttaagcgaat gatgatgact ctctctcagt agtcttaact cttaataccc   2340
ttgttttcct tcttgtgctg cagtttgatt ggttaattaa cctaatcaaa agatgtttta   2400
actgtgtttt atccgtcttt ctcaagatct atcttagtcc caccacatag ctccctcaag   2460
ctacagctgc aaaatatata ctatatatat atataacaa                          2499
```

<210> SEQ ID NO 114
<211> LENGTH: 2500
<212> TYPE: DNA
<213> ORGANISM: Nicotiana tabacum

<400> SEQUENCE: 114

```
tgacattgct ttggtggttt aagttctcag ccagtatatg cattgtccta ataggtctca     60
```

-continued

```
catggaagca gcactgagag ttgtaagata cataaaagaa gctcctggct taggtctctt    120
cttgcctgta aaatcttcag atcaactaag tgctttttgt gactcagatt ggggagcatg    180
tatacaaatt agaaggttag ttacagggta cttggtaaag tttgaaagtg ctcttatatc    240
ctggaagtct aagaagcaga gtactgtgtc taggagctct aatgaagctg agtttataag    300
tatggcttca tgtgcagcag aagttacctg gccggtagga ctgttcagtg aacttggtgt    360
caaggttaaa cttcctataa acttggtatg tgatagtaaa gctgcaatcc aaattgcagc    420
aaatccaatc ttccatgaaa gaacaaaaca tattgatata gactgtcact ttgtaaagga    480
aaagctaagt ctaaggatgc taaaaactga gtatgtcaac atgaggatca actggcagat    540
atacttacaa aaggattgtg aagagctcaa catgtacatt tgctgaacaa gctagggttg    600
aagaatctgt atcaaccatc agcttgagag ggagtgttaa tcaacatggt taccactagt    660
ttatttataa agtgtaaatg ctaaaccata gctagtgagt tagttaatag ttagttgagt    720
ttgttataaa tattagtcag ctgtacagtt taacatagct tctctttcag aaatgaaaat    780
tgctcttctc tcatttcctc tcttctagat tcttcttctc cctccttctc ttagctcaga    840
tctctcttat gacagctaac aataaatacg aatatttctt gtaacggttg ctcattgaat    900
gttgtctttc tcaaccgata tctttctttc aagttttccc cccgattcga gtatttttga    960
aactcactca gcaccggtca catattcgta atcggtgcca gctatttgct tactcatatc   1020
ttatttgact tcattgtcac gtgtcagaca gaagtatgtg cgcatatacc atcaagtctc   1080
aatttgaaat aaaatcaact taagcagtta aaagtcaaat ctcttttagt tcggtcttta   1140
aaataataat ttaaataatg aacctataaa acacgcaact cacactgaat ataggggcag   1200
acataaaagc cgaaagactg aattccgaac cggaccgaat tatttcggta tttcgatatc   1260
ggtttattca gtatttcggt actatttcgg tataggattt ttagttattc ggtatttcgg   1320
tacgatcctc ggtattgaaa tttcgatatt tcggtatacc gaaataccga ataatttaag   1380
tacaccttcc ttcactgccc agcccgttat caattttcag cccaagtttc taacttgtta   1440
tttctttccc ttagccagta gcctactaag attaagccca acgccccaac ctaacattag   1500
aaattattat aattagaaaa gtataaagaa agtactcaca ttctactgct atgctcatgt   1560
agtgatttct attagaaatt attagaagtg aaggtactgc ccacattttc ttgttgctat   1620
actcattatc acgcaattag aaattttcta atgaattaga attcagtagt tcagcacaga   1680
ggcggatgta gcgtattacc tacgggttca actgaaccta taactttcga cacagagtaa   1740
aaatttatat gtaaaaattc tttaaaattg taaaaatcgt agatatgaac ccataacttt   1800
aaaaatataa tgggtaacat taaaattgaa cccatagaat ttaaatcctg gattcgcctc   1860
tggttcagca ttgtttagtt cacaaaaata tggtacgatg ccgaaccgta tcgaaaccat   1920
accgaaccaa acaagaagat atcgaacaat accgaactac tttggtacag tatttggtat   1980
gcacacttga tatatcgaat accgaaatac cgaaccgtaa ttttcgaata ccgtaccgaa   2040
ataccgaaca ctcacccata actaaacatt aaaaagctag aactcaggtg tttaatgact   2100
aaacggaagt aagatctaga taatccgtca ctctgttgat ttgtaaggct atcgacatgc   2160
aaaagtggaa gcaaaatgga gccgaaattt taacaaaaat gctgaaccaa taccatgaaa   2220
ttgatgaatg gtgggaccct atttcactct tttagaattt gcgtaagacc agaaaataac   2280
ttcaatcgaa atcaaaataa ataccaaccc ttttaggccc caaatcacta cgtgtgattt   2340
gcaaacgtca ttagccttat gtaaacagtg acctcatgcc aacatattat cgcagcctat   2400
aaatcttagt ttacatttca ttttctttca aacacacaca cctcacaata gaactaagtt   2460
```

gtaagagttt cattttcttt gttctttctc acaaaccaaa 2500

<210> SEQ ID NO 115
<211> LENGTH: 2500
<212> TYPE: DNA
<213> ORGANISM: Nicotiana tabacum

<400> SEQUENCE: 115
tgccagacag tctaaaattc aaaaatagga cagcccacat cccctccacc ccactagatc 60
tcactacttc ttaattagga cttgtggggg ggagtagagg gatttgcaaa ggcggccgcg 120
gcatgcatat acggaaaaga gaagttagtg gtttgcaaag atgattgtgg aaaagggctt 180
acctaacaat gaagaagagg aagagggtag atggataata ataactcaaa aatagaaaga 240
agagggacaa gtgggggctc aatggctaag gttttaaggg aggtcttgga aacatcatta 300
gcaagtacat gcagtattac caccctacat cagactgtgg ggtctgatgg aatattcttc 360
tactatactc ttttaaatag agggaattaa tgagccttta taatgttgaa atttataaga 420
aaatagtata actttttaaa tctcttaatt atgtatcaaa tcaaatctca tatttaccct 480
ttagtggatc tattcactga agtctgaata aatcgtacca gtaattcata ccgaatgtgt 540
aaataatttg aaagaaagat agacaaggcc tcaatgkcta gggatttgtt agcatcaata 600
gcaagtataa gcagaaatat ataccaccaa ggagtgaggt ggaagaatta agatttactc 660
taatgaaata tatatatcaa gattgagtca tgtgaatgaa gaatttctta gtaccttaaa 720
ttaagcgaat atcacataac agaggtgtaa aaaaacgaaa gatggacaag ctaagtggct 780
ctcaatggct ggggttttaa gggatcggag gtcttgttaa catcagacgg aagtacaatt 840
agagtatata tgctactcta ataatacttg gctacaaaca taaaaaaata tctctatcac 900
tatctctcaa ctcgccatat agacttaatt ggcacaaagt catgctgatg gaaagagata 960
taaggagaat gggaagacaa aaaaaaaagt ggggatagaa agagtgtcca agtagctaga 1020
agggggtggg ggtggggggt gggggagttg ttgttttagt tgtggaagag ataggtttct 1080
ctttttagtg aaagtgacat atatagctag actgagaacc ctggtcaaaa gttgctttgc 1140
cttaacgttt ctaaatgcct gacctctgag aggctatctt ctcctctcat tctctcgacc 1200
cttactgttc atataccccc aaatttgagg tctaatttat ccacactatg gtttcttact 1260
gttgtcttct tctctgaaac aatattgctt gtcgatcttg gacttggcca cgtcaacgtg 1320
taacttcagc aactagggtg actccaagtc atagacagat ctaggtcgac ttctgtgaat 1380
ttaactaaac aaattattta atttcgactc aaaatagata tgtactatat atatatatag 1440
taaacttatt gtgaacttac taacttaaaa ttttcaagtt tgcagtattt tttggaataa 1500
gaaaggggaa aaagaggcag aaaaccccat atttcttcct ctttggagtt gacgctaaag 1560
ggataaagct aacatgcaag ctcttaacaa ataacatact cagtataatc tcacaaatgg 1620
ggtatagaga ggataaaacg tacacaaatc ttaacaatat acacagtgta attccataag 1680
tgagttctgt ggacggtagt agcttacccc ttgcctttaa catgcaagct cttaagcttt 1740
gtatttttat tttgttcttt ctttttggag aggaagaagt ggtggttgaa gactagagat 1800
aaggaagaaa agagaaggat ttttgtcagt tgctatcacg tgaactgaag gggcacaatt 1860
agagagaagt ctatatgctt cacttcccat aaaatcagtt gtaactacaa caagtactaa 1920
gagtgtcccc tccattttct ttctttccct caattccctt tcatactttt aaagcttaat 1980
tccacagcta gaaaaagaag cctttctttt tctctagagg tatttagcaa agatggaagg 2040

```
acaatattac agctctcttt gtctctacag gtaacaaacc attgcctgtc tttctcaatc   2100

tccagtattt ccagctatct tataatgctt tgagtactcc cacaaaacac atgcattata   2160

gccactagct acatatatat atatatttgt aaaaccacac attaatttag ctgtcattct   2220

caaccaaaaa gctatgttat catcaacata ttgacaaatt acctataatt ccttcccctc   2280

tagctatatg atctatctca ctttattatg cacttaaaaa gttatgttgt ccctctcaaa   2340

agtcttaatt aattaacctt gttttgcatc ttgctgcagc tagctagctt attaaattga   2400

caaactcaga agatgttgtg gttctttcaa cttcaataaa aagctaagag tagtacttgt   2460

gcttgtatat ccgtccttct caagctcaag tcccacttca                         2500
```

<210> SEQ ID NO 116
<211> LENGTH: 3433
<212> TYPE: DNA
<213> ORGANISM: Nicotiana tabacum
<220> FEATURE:
<221> NAME/KEY: modified_base
<222> LOCATION: (3171)..(3178)
<223> OTHER INFORMATION: a, c, t or g

<400> SEQUENCE: 116

```
gttggagcta aaaataagag aaatggacaa gtgtcaaatt ctagcgtcca tggtagcgcg     60

acgcactatt gtggcgctag aaatagaaga ccaaaatttc caatgttggc gtcgaccttg    120

cgttgcggta ttttttctat ttcgctaggg acaagattat ttcaacaaaa ggggttctaa    180

acctaatttg gaggatatct aacatacttt gaaggcgaat tcacgtaagg gaatacaaac    240

cacgcttgga aggggctttc aactagtttt tcttctcttc ttttctcttc ctttcatctc    300

attatgtatt agttctaggg ttgttggtac ttacattaac gttatagttt gaagcttgga    360

ttatcttatt attttatcat attggtttat ttattcaatc ttgcgcttga taatttaatt    420

ttaattgatt gatcaccaat taaatactat ctacgaattt aggattgaaa tcgggagaga    480

aaattttaga ttgcatatag gattgagtag agtaagatct tgaacctgaa ttacgaggga    540

acgaatttgc gattaggata taaggatata cctaatcgtc ttgcttggtt actatacggg    600

aattattaat acgttcttat taatcctaat ccactggaat ataggcgttg agttagcttg    660

aacaggcgag tagtacttcg ggagaatact acgagtaata ttaaattgtc aatcaataaa    720

ctagataaat ttataagata gtttaagtaa aaaactcaat gagattgtta gttgacccat    780

aactctgaaa tattttctcc cattagattg tctttaagct tgccggcata gtttttctag    840

ttttctagtt tacaactcta gattagttat agttaacaat cacactttag aaaatcgctt    900

gagtagatta attgttaatt tagttgatag ttaatcataa gtcatcgagg gaacgatact    960

ctacttatca ctttattact tatcgaccac gtatacttga gtgcgtttgg gagcaacaaa   1020

tttttgacgc cgttgccggg acgttagttg atgttttcaa ctagtgaaca aaatgcaaat   1080

atgttatgca attcggtgcc atttacacgt ctatgaggag ttatattaaa gaactttatg   1140

taggatgttg gttggatcct acaagctaaa attatggcta agaaaattgt gaattactaa   1200

taaacttgta ataagataaa aaataatttc ctagaacgta atagaattga agtgagatta   1260

gaccgacacc tcttcgtcgg aaaactatgt tatatatgta ggttatttta tatatatata   1320

tatatatata tataattttc ttggcgttta atttttata ttttgattct tcctactaat    1380

aattctaact ctatcactga attaaacgta caggattcat ttcttataca aaagaggttg   1440

atcattatta ggtctgggca ctgtcagagg ctgaccgata tgagtagttc ttcacatgct   1500

tggcagcaat ttgaactgtg attgcttgag gggcgaaaaa gagagtagaa tctaagttcg   1560
```

```
gtaattttta tctgaattct gtatttgtct taaaaattta ttgagtatgc ataaaattat   1620

tattttaaac tcagtaattt aaaaaattta gaattcgaac tcataaattt caaattggga   1680

ctccacctct gattgtttgt aagtggagtt taggggcaga actagctcaa aaagttcggg   1740

ttcgattgaa ctcagtaaat ttgattcaaa gtctatatat ttattgaaaa atcaactaaa   1800

tatgtatata tacaataaat ttcaaattca taaaaattta aatcctgaat taacctaata   1860

gtaaaaccgc agactctaac tagtggtcta gtttagagag tcaaattatg gtttttaaca   1920

accttaaaca agcacaaata cttttccact attggttcaa ttttggttgt taacaacctt   1980

gattggtaat tacgtacttg catgggcatt tgaaaattaa gttacgtacg tgtaaaacgt   2040

tttagagtag tccgtactaa ttaagaacac aaacactgct tgagattttg tggcggaagt   2100

ttgttttgac ttagcatggg taggcccacg aattccccat tttgaataaa agacaacctg   2160

tgctagtcga ttagctatta tttaattact agaatattac ttactccctc ctttttaatt   2220

tagacgattt agtttgactt ggcacaaagt ttaaagaaaa aaaaaagact tttgaaatat   2280

gtggtgttaa aatcttaatg ggcaaaagct aagtggagtc atgatatttg tgtgactata   2340

aaaacttctc attaagaata aagtgagtaa aataaaaaat taaagtcaaa ttatttctaa   2400

atatagaaat atatcattct tttttgaacg gactaatacg gaaagtgtgt catttaaatt   2460

aaaataaata aagtaatatt tatcatatga ttttaacatg taaatatcat acaagtaatc   2520

taatcgtcaa gcgcggatct aataaataag ggacgggtat tttgtttagg ctgtgtatat   2580

ataatttttt aaaatctact aaaaaagaac aaataataga tttgtaaatt agagggatat   2640

ggtagaatct aactataaac ccttaaagtt caaatcttgt atctgcttgt ggtaatagtg   2700

tatatatatt ttttacacgt ttttgttgta tagaactcaa actaaaaagg gcattccagt   2760

gcacaaagca tctcctattc acacacaatt cggtgaaggg ccgcactgta tgcaaggggt   2820

gtgatatcgg cagtctatcc tgatgcaagc atcaatggtt gattccacgg ctcgaatccg   2880

ttacctatag gtcatacgga gataacttta ccgttactcc aagtccccct tctacataaa   2940

acttgcatca atagctgatt tcacgactcg aacccataac ctagttgata cgaagataac   3000

tttaccgttg cttcaaggtc cgtctacaca aaactgatca aattattttc ataaataaag   3060

aagctatcat ttctctataa atagaactag agtccttgca tattccaaca taagtatcag   3120

ttccaggaaa atcaagacat aatctgttag cttttctctt tgccattctc nnnnnnnnat   3180

ggattcctta ccagtctcct ccattgaatc tctagtcatt gagatcaaga aagagatgtt   3240

ctcaaaccaa gaatttaaca cttttgtcac cccaatatct gcctatgaca ctgcttggtt   3300

ggccatgatt tcttataata atcaagaaga agccattaat ggtcattctt tttctggccc   3360

tatgtttaag agttgtttaa attggattct caacaaccaa aatgagcaag gatttttgggg   3420

agaatccaat ggt                                                      3433
```

<210> SEQ ID NO 117
<211> LENGTH: 2512
<212> TYPE: DNA
<213> ORGANISM: Nicotiana tabacum

<400> SEQUENCE: 117

```
aagctggtac ccttatgttt agtccaagaa aaataaccat acccaaatat aagggtttgt     60

tgaagacgga aatatataaa caaataaaca aatatcatca tatctccgat agtttaaaat    120

tttagattgg atatttcaca caatttatca aaattttcaa aaaaaaattc tactttttct    180
```

-continued

```
tgcttggaac ttggaagggg aaggggtggt ggtggagata gggcggggca tcttctatct    240
agtctatgtg attaatataa caaaacaaaa agggcgaggc aaaaacatgg atgaatggtg    300
gtccttttct atatttatat ggattgttac gatacgtcga tttcactttg caaaatacca    360
attagattca tttagttatc tttttgatca ctctgctttt actatcatat atatatagga    420
gtccttccac gtttcgcatg tgtcattgtt tatattttcc atggtcttcc ttccaaatgg    480
ctaaaaaaat ttgacacagt ggtcccaaaa gtttatagaa atagaattca acagtgaggc    540
atatacctat gaattctatt ttacatcttc atcgtataaa atagaatgtg ttataaactt    600
tacctcgtga tgcttacaag gggtgaaaat ataaaagcac tttatagatt tacaagagtc    660
acaccttgat ttatcctaag attttatttt tttacatgcc aaacaatgaa gtatgggaga    720
tccaattgga ataacatcaa atttaataaa attcgaaata gtcagagagc tgtctactga    780
ggtatattga aacttatttt tttttaatag aaaatatcaa atacttagca atatattaaa    840
atgtttcata aattacattg tttaaaccaa gcgttgaaac atatgctgat acgaggtagg    900
cttattgatg aatttataag ggcctcattg gaaaagacga tccaaagcaa tgggctaaaa    960
aattggccca ttttctgcca cccagtgtat ggttattact agtttcaccc acacagattt   1020
gcacttcatt agaggacaat gttgctgaat ttgaaacata agtccattta tctccactgt   1080
acagtccttc ctggagtcca atcctgacca tatcttcatg attttatgta atgtggtgaa   1140
taagcaaagt ttcatgttat gctttgtctc attttatagc aaattcattt cctcataaaa   1200
tttacttcaa aaaagtttcg tttgattttc agaaatcaaa atatgctttt cggtaaccaa   1260
atggttttca attttgttta cgaagaactt aaaactttcc aacaccctac atctatgatt   1320
gcaagttaaa attgcagaaa tatgacactt tttggagtgg tctttatcgt ttaacttcac   1380
ttgcacttta agggcaaaag ttaaaagtgt ttccatgaag caagcgaggg ataacactta   1440
ttaaacttga aattctactc atagaccaaa acaaggacaa aaattcaaga ctatctatgt   1500
gggtaaacgt acgaaaattg ggcttctcca gattagagcc ggaccttgtg gaaagacaga   1560
gaaattcgag gcccacttcc agtttctaag gagattaagc ctatcaaacg atggtccaga   1620
acgaaatatg tctttcttta ttctctacta tatagctgac tcagaatcgt tagaatttgc   1680
aatttcctca taataaaatg tgaggcagta tagattcgaa aacctttgtt gaagattatt   1740
gactcagcta cgcgaaacaa actgtagtat ccaatgtacc gattaacaag cgactggtta   1800
actatgaatt tgttagctcg acaaaatcac cggttaataa tgagtttgtg agttcgataa   1860
aatctaattt tctgatagaa attttatata ttatgcagaa atttaataaa agtagactta   1920
acttatatat tttagcattg actcttttga agtaaaatcc attccatcta aattatgact   1980
tccctacatc gagtaagtaa gttgcgtctg tatcctcatt ttacccactt ttcgctatgc   2040
aattattcaa ggatctttac acaaatagca agccaatatt aattatttat tttttttagt   2100
catatatata aattatacat atattatata cccattaatt atttttaatt taagtgatag   2160
attggacgac tatttggatt aattcttcgt tattcaagat aatagatgtc gtctctaata   2220
catgagctag aagataataa ggattactag gccgaaaggc tgatggaaat gaacaagaag   2280
ataagctcct aaatggaaac agtacggaaa aagtcaaaga gcagtgcatg ggaggaatca   2340
tcagtcagaa aaggaagcca cgtgtcaagt agaaacaagc acgtgtccat gcaaaagcca   2400
cgtaactccc ttccatcaca tcttccttct tcaaaacctc gtgttttact ctctcttttc   2460
tcactgccag tgatcgtcag gactgtgcat gtttgtttaa aaactaaagg ca           2512
```

<210> SEQ ID NO 118
<211> LENGTH: 941
<212> TYPE: DNA
<213> ORGANISM: Nicotiana tabacum

<400> SEQUENCE: 118

```
tttaaaacgc caaaaaataa gggacggcca tggcgtagca atgactattg ttccgtaggt     60

catttgtgaa ggaccgacaa aattttaggc gatccgggtc cgatttttcg gttctgctca    120

agaaaactcg atctgcacga atagcttata atcaaaccct tttttttttt tcaagaatgt    180

ctaattgatc ctaaaaagac aaccttatat gttccaccat ggcaggatcg gccttattac    240

taagggtttg ccaatagaca cgtttttaac attcaagtaa aaaaaacatt tattcttaat    300

aacccaccta ctatagtacg ttatttggca gtagactacg ttgtacattt gggaccattt    360

ggaacactcg tctttcacga gtcactaatt tttgtgttga atgcataaaa tttgtttttt    420

tctttttcga aattgaacaa ttttatcttc gatcacacct atagtatatt attaccttat    480

tgttagaaaa tattttattt tattattgac tcctaataaa aagtggggta aatttgggtc    540

ttttttttaa agaatgtgaa ctactcattt cactttggtt agaacaaata tgagaagatt    600

tgctaatgac agcaaaatga atagaccaaa agcgtaacga atattaaaaa taaacaattc    660

cgaataactg gttactgaaa attgtggaac tctacatagc cgttgtgagt atggtattgt    720

ttgttcttgt gggcagaata actagttacg gaaaatttat gaatttgctt cacattattt    780

ttttcatttt cttttttgct tcaaaagata agtacaagtt tttatactct tatttcattg    840

cctataaata cctctattga gttactgctc attcacaact ctaaatagca atctttctta    900

ttattaaaat tcctatcctt ttttactcat tcagagaaac g                        941
```

<210> SEQ ID NO 119
<211> LENGTH: 3013
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 119

```
tttaaaacgc caaaaaataa gggacggcca tggcgtagca atgactattg ttccgtaggt     60

catttgtgaa ggaccgacaa aattttaggc gatccgggtc cgatttttcg gttctgctca    120

agaaaactcg atctgcacga atagcttata atcaaaccct tttttttttt tcaagaatgt    180

ctaattgatc ctaaaaagac aaccttatat gttccaccat ggcaggatcg gccttattac    240

taagggtttg ccaatagaca cgtttttaac attcaagtaa aaaaaacatt tattcttaat    300

aacccaccta ctatagtacg ttatttggca gtagactacg ttgtacattt gggaccattt    360

ggaacactcg tctttcacga gtcactaatt tttgtgttga atgcataaaa tttgtttttt    420

tctttttcga aattgaacaa ttttatcttc gatcacacct atagtatatt attaccttat    480

tgttagaaaa tattttattt tattattgac tcctaataaa aagtggggta aatttgggtc    540

ttttttttaa agaatgtgaa ctactcattt cactttggtt agaacaaata tgagaagatt    600

tgctaatgac agcaaaatga atagaccaaa agcgtaacga atattaaaaa taaacaattc    660

cgaataactg gttactgaaa attgtggaac tctacatagc cgttgtgagt atggtattgt    720

ttgttcttgt gggcagaata actagttacg gaaaatttat gaatttgctt cacattattt    780

ttttcatttt cttttttgct tcaaaagata agtacaagtt tttatactct tatttcattg    840

cctataaata cctctattga gttactgctc attcacaact ctaaatagca atctttctta    900
```

```
ttattaaaat tcctatccta atttactcaa acagagaaac gatgtatccg ccaagcaaca    960

gctgcaacta cagccccatt ttcaacatcc cttctccttg tatgcaatat ggagacgaac   1020

tattcttcca atattatcct gaccatttcc ttcaacagca acaagtgcct ttgatagaag   1080

atcagagtgt tgacatctta gctgattgca ctgagaatgt tactaacgaa gaaactgtca   1140

tcaatactga tactgtaaaa gttctttatg acacaggagc tgttacaaac agtcagtgtt   1200

ggggaggaaa tgaagaagta gaagaaggcc gcgaaaacaa aagaaatgac atgagaagca   1260

ccattagtat tattcatgta cggaaaaaca agaaatgttc caataaagat cgacatagca   1320

agattaacac tgctcgtggc ctcagagacc gaaggatgag actttccctt gatgcagctc   1380

gcaagttttt cagtttacaa gacatgttgg ggttcgataa ggcaagtaaa actgtagaat   1440

ggttgcttat caaatcggag tctgaaatcg aagagctagc caaaggcaat aaaggaggag   1500

gcattcctaa acaaagctgc agtactacta atggaattgg tgcaattagt actgcaatat   1560

cctctatttc tgagtgtgag gttatatcag gaactgatga atctttctct attacttata   1620

aaaagaagct gaaaactgct aaaggagcct cgaaaaagac ggctaaaact gctcgtagag   1680

ctgcatttga tcgtcttatt acaagggaaa cgaggaatca agcaagggct agggctagag   1740

agagaacaaa aataaagaaa agcctcggta aatccaaaga gaacagtgct gattactgta   1800

atttggtgga taattatgga gattggagtc aatttagtat cttcaactat cagaaaaatg   1860

cagttggaat ttcccatgat caggtgggtt caataattaa acaacatgat tttttaggat   1920

ttcaataggc tcgctccttg tgtaacatgg cataagcagt cttggcaatg atgctctttg   1980

ttgcctatgg tttgtctcca tttattcctc taatacccca taaaaataat aaaatataaa   2040

ttacatctac atgactggtt ttgaattatg ataatgaaca tgaagttaca cttcttatga   2100

ttttttcaag tacattgtgt tttgattacc gcataaatat ttaagcatgg tcatcttttt   2160

tttgattcat ttgttgttag agtgactaat taatctgtag tatatgtctg gaggcttgag   2220

gaatctgaaa aaatgtgcgt gtttgcatag ttctttcaaa atagtatagg acaatatatt   2280

cttttaaaaa aaggagtccg gtgcacaaag catgtcgcat tgttccgagt aaaagctgca   2340

cccaaagagt gtgatgcaga caacctactc taatacaagc attaatgaac gcgttgctcc   2400

aaggctccgg ccccttcaat atatttcttt atgaaccgtg aatttattca tgtttaaaag   2460

ctttctttca attccatctt ttcttttgtt ctaacatttg ttagtaaacg tgaatgaatg   2520

tagaggttca agctagagaa tgcaaaacag aaagcaatac attccctgga ttatgcatta   2580

ccaaaccacc atgcagaaaa gcttgtatca gtgagggatt tactgatggt cattgtagca   2640

aaatcctcag aaggtgccta tgcactaagc catgtgtgtt tgatgagaag atgatcaaaa   2700

caggagctga aacttttgct gaggaagcaa aaactttggc tgcagctttg cttgaagaag   2760

agataatgga taactaatta gagattagag gaaaggatta attcagtgtc acacataata   2820

aagttgctgc ctttcttaaa aggatagcta atgtattggc ttttagtagc ctttgttacc   2880

ctaaaataag tgtgacatgt caatcctttt gatctagtac caagtttatg tatgttttaa   2940

tgaaaaatga tcttctatgg tcattgcaat cccattatat tccaagaaca aaacttcatt   3000

attttcttgg tcc                                                      3013
```

<210> SEQ ID NO 120
<211> LENGTH: 120
<212> TYPE: DNA
<213> ORGANISM: Artificial Sequence
<220> FEATURE:

<223> OTHER INFORMATION: Description of Artificial Sequence:
      Synthetic polynucleotide

<400> SEQUENCE: 120
tagcaatctt tcttattatt aaaattccta tcctttttta ctcattcaga gaaacgatgg     60
ctcgctcctt gtgtttcatg gcatttgcag tcttggcaat gatgctcttt gttgcctatg    120

<210> SEQ ID NO 121
<211> LENGTH: 5668
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 121
tttaaaacgc caaaaaataa gggacggcca tggcgtagca atgactattg ttccgtaggt     60
catttgtgaa ggaccgacaa aattttaggc gatccgggtc cgatttttcg gttctgctca    120
agaaaactcg atctgcacga atagcttata atcaaaccct tttttttttt tcaagaatgt    180
ctaattgatc ctaaaaagac aaccttatat gttccaccat ggcaggatcg gccttattac    240
taagggtttg ccaatagaca cgtttttaac attcaagtaa aaaaaacatt tattcttaat    300
aacccaccta ctatagtacg ttatttggca gtagactacg ttgtacattt gggaccattt    360
ggaacactcg tctttcacga gtcactaatt tttgtgttga atgcataaaa tttgtttttt    420
tctttttcga aattgaacaa ttttatcttc gatcacacct atagtatatt attaccttat    480
tgttagaaaa tattttattt tattattgac tcctaataaa aagtggggta aatttgggtc    540
ttttttttaa agaatgtgaa ctactcattt cactttggtt agaacaaata tgagaagatt    600
tgctaatgac agcaaaatga atagaccaaa agcgtaacga atattaaaaa taaacaattc    660
cgaataactg gttactgaaa attgtggaac tctacatagc cgttgtgagt atggtattgt    720
ttgttcttgt gggcagaata actagttacg gaaaatttat gaatttgctt cacattattt    780
ttttcatttt ctttttgct tcaaaagata agtacaagtt tttatactct tatttcattg    840
cctataaata cctctattga gttactgctc attcacaact ctaaatagca atctttctta    900
ttattaaaat tcctatccta atttactcaa acagagaaac gtctaggagc aaaaaaaaaa    960
aaaaaaaaaa aaacaagtag tagtagtagt agtaaatgga aaaatagaga ggcaattttt   1020
tttagtatct tactttatcc attagcactt aaaaaacata ggtttacatg ctctcattgt   1080
cacgccaggc cgctaattaa atggtacatt tcatcatccc cattttttgg cctcatagtt   1140
aattatcaca atttctgaaa gcaacatcag aacaacccca catttcttgt ggtcctataa   1200
ttactgctag atagtccaaa cccatctgcc tatttagggc ttgtgaatga ggattgaaaa   1260
tggtagagaa tatttgcaaa ggcatcatgc atatatggaa aagactaaag agagagttag   1320
tgccttgcaa agcggattct cacagttgta gaaaaggact caccattttc aagaatactc   1380
ccggcatgaa gatggacaat ttaatataaa aaacaaagaa aatagtaatt aagtgcgttg   1440
agatgaatga aatttatccg ctcttaattg aatatgggga attgaaagaa atttctgata   1500
ataaattaat gagtcttaca tgacgtggat ccgacttaat ctagtctatt taaactaaga   1560
atagataaga atagagaata tagacaaaag agaggctcat tggctagggt ttcaagggag   1620
ttccttgaac ataagtggca agtacaagca caaagccaat ttccatggac taaagatgaa   1680
taagatgtgt cgtgtggtat ggtgggaagg tgaggaggta tggggtaatt ggagatgcta   1740
aacctctcta aaagctcttt tgctccaaat atctaaatcc atctctatca cttttggcga   1800

```
ctgccccaaa atttgcaact tatgaattaa agttttaata tttttaagtt aataaattct   1860
gaattaataa tttaacatat tcaataaact ttttaaaaca aattacgtat ataccatcaa   1920
actggctgca ccatgatcac tttctaaact cacaatgaca tatggattta atcaggcaca   1980
aagtcatgtt gatagaaaga gatagtacgg agaatgaaga aaaaaggtag gggagagaga   2040
tggggtgagt ggggaaaaga tagggttctc tttttagtga aagcgacagg gtctgagaac   2100
cctaggtcaa aagttgcata aacctctata caggcttctt cactccctta ctactaatat   2160
actctcatta aggcttgagg tttaattcat taaaattgtg gtttaattat tgtatcccct   2220
caaacgaaat aattgtcctt gtcgaggtta gacaatgttg cgtactattt tcaaacgcag   2280
tcagccatta ttctcctatc ctttacagtc gagattcaaa gacagaaagt agcatgcaag   2340
ctgttattaa tttactttga ttaggacttt gccaagaaaa tgaagaacct tttctttttt   2400
cttttaattt agttatctta caacatgtaa tttttcctag caagcaaata cggtaacttt   2460
ttttttatt ctcatttaat ttgttggagc tattgctact ttgatgactt caaccaaatc   2520
ctggttggta ggcggagggt gctgacgatg gaaactaccc ctcttgtcca aatacgataa   2580
cctaaaaaat agaataatag cttattgtac tgtgctgcaa aaattgcatt gtcagtatac   2640
ataattaaaa tctattttga atgtgtggag ggcaaagagg ggtgactggt ctagggttgt   2700
agaaatcagg tgggagagag aatggtattt gtctctgtgt cagctgatat cacgtgaaga   2760
ggcacaataa gaagtccttc gtatccattc acttcccaaa aataccggca ttactacaaa   2820
tatagtacta gcacttgctt tctctatccc catctttgct atttcctttc cctttccaac   2880
tttttggctt tagaattgca aagatggagg gaattgtggt tctttgtatc tgtaaaattt   2940
ttcctccaag ctccagttgt agctagctta atgcgtggac gcgcgcgcac acactagaaa   3000
tctgcaatct atatatatat tcacaaggca ctcacatatc aaaaaccaca tagacattgt   3060
atagagagag ctgtcgttct caagcagaaa aaatgatatg atttcatcag catgtggtca   3120
accaaatagt tcaattctag tctttgcttc ctctttctaa ttactgtata aatagagcca   3180
caaggacata gaattgagaa aataaaagac aataaaaaca aatctagcta cttaagcgaa   3240
tgatgatgac tctctctcag tagtcttaac tcttaatacc cttgttttcc ttcttgtgct   3300
gcagtttgat tggttaatta acctaatcaa aagatgtttt aactgtgttt tatccgtctt   3360
tctcaagatc tatcttagtc ccaccacata gctccctcaa gctacagctg caaaatatat   3420
actatatata tatataacaa atgtatccgt caagcaacag ctgtaattac agcctcaata   3480
tttcctcctc aaataactta tttcacattc catctccgaa ttctatgcaa tatgaacacg   3540
aacttttcca atattttcat gaccatcatc tccttcaacc ccaacaacaa caacaacaac   3600
aacaactctt gactacacct gatcattata tggcagcaga ttccaacaaa gacaccgtaa   3660
tcagtagtac taatcaagat cctgaagaag ttgaattaca aggccgctgc aagaacaaaa   3720
aaggtgacaa taagagacgt gttgcttaca agaaagatag acacagcaag attaacactg   3780
ctcacggccc tagagaccga agaatgagac tttctctcga tgtagctcgc aaatttttca   3840
atttgcaaga cttgcttgga ttcgataagg ctagcaaaac tgtggagtgg ttgctaacaa   3900
agtccaaatg tgctgtcaat gagctcgtcc aaggcataaa taaagaaaat tgcgctactg   3960
ctaatattgg tgcaattagt acatgctcta ctacatctga gtgtgaagtt gtatcaggaa   4020
ttgatgaatc tacaaccact aatgatattc agaagcagtc aaatagaggt aaagtagggg   4080
agaagaagaa ggctaataaa ctagttcgta gagctgcatt taatcctgtg gcaaaggaat   4140
```

-continued caagaaagca agctagagcg agggcaaggg agagaacaaa aataaagaaa agctttttaa 4200
atattggtga tcagtctatg gcggctgatg atttaaaacg attaggatgt tggagtcttt 4260
ttgaaacagg tgaagaatca ggtattcaag gtactaatca tcaaattgaa gaacacacca 4320
cgcaccacga ggagcctctt ttggggacta atgagaatgt tgatgattgt aatttggttg 4380
ttaccggcaa ctggaaccca tataccatct tcaattatca ccacagtact gaaatttctc 4440
acgaggtagg ttttacactt catttaaatc caagagtaat tcttttagag ttcaagattc 4500
tgatattttt tttggtggcg agaccctttc ttatatcaaa gcaaccttca aggtacatac 4560
aagattggat aaaccaattc tgagctcgct ccttgtgtaa catggcataa gcagtcttgg 4620
caatgatgct ctttgttgcc tatggtttgt ctccatttat tcctctaata ccccataaaa 4680
ataataaaat ataaattaca tctacatgac tggttttgaa ttatgataat gaacatgaag 4740
ttacacttct tatgattttt tcaagtacat tgtgttttga ttaccgcata aatatttaag 4800
catggtcatc ttttttttga ttcatttgtt gttagagtga ctaattaatc tgtagtatat 4860
gtctggaggc ttgaggaatc tgaaaaaatg tgcgtgtttg catagttctt tcaaaatagt 4920
ataggacaat atattctttt aaaaaaagga gtccggtgca caaagcatgt cgcattgttc 4980
cgagtaaaag ctgcacccaa agagtgtgat gcagacaacc tactctaata caagcattaa 5040
tgaacgcgtt gctccaaggc tccggcccct tcaatatatt tctttatgaa ccgtgaattt 5100
attcatgttt aaaagctttc tttcaattcc atcttttctt ttgttctaac atttgttagt 5160
aaacgtgaat gaatgtagag gttcaagcta gagaatgcaa aacagaaagc aatacattcc 5220
ctggattatg cattaccaaa ccaccatgca gaaaagcttg tatcagtgag ggatttactg 5280
atggtcattg tagcaaaatc ctcagaaggt gcctatgcac taagccatgt gtgtttgatg 5340
agaagatgat caaaacagga gctgaaactt ttgctgagga agcaaaaact ttggctgcag 5400
ctttgcttga agaagagata atggataact aattagagat tagaggaaag gattaattca 5460
gtgtcacaca taataaagtt gctgcctttc ttaaaaggat agctaatgta ttggctttta 5520
gtagcctttg ttaccctaaa ataagtgtga catgtcaatc cttttgatct agtaccaagt 5580
ttatgtatgt tttaatgaaa aatgatcttc tatggtcatt gcaatcccat tatattccaa 5640
gaacaaaact tcattatttt cttggtcc 5668

<210> SEQ ID NO 122
<211> LENGTH: 130
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 122
gacctaggat cccaccacat agattgaacg gagggaataa tagtgtagcc ccattgggaa 60
acaccatatt tatataggta gaagaaatac tccagattta actagaattt ctactgacaa 120
aagatctttt 130

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 123
ttttcgaggc tcctttagca 20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 124
catgttgggg ttcgataagg 20

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 125 cctttttac tcattcagag aaacga 26

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 126
gtgtgacact gaattaatcc tttcc 25

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 127
aggcttgctg aagcaaaaga 20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 128
tcggcgaaat tacagtctca 20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 129
ttgtgtcatg gtgcaatcaa 20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 130
tccaacttag gcctcacacc 20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 131
ttgcaatgct tctgttttcg 20

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 132
atattggccg catcttggt 19

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 133
ttctcttccc gagaaacagt g 21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 134
cggagttgga gatgaagatg a 21

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 135
cctgtggcaa aggaatcaag 20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 136
tgcgtggtgt gttcttcaat 20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 137
gggtgctttg aagtcccttt 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 138
gaatcctgct ccaaacaagc 20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 139
tgggcagcag aaataagaga 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 140
gctgatcttg ttgtggcttg 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 141
caccataagc acaggtgcaa 20

```
<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 142

tccgccttgc tttatgaaaa                                               20


<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 143

tcctctttgc catttctctc a                                             21


<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 144

ggccagaaaa agaatgacca                                               20


<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 145

gggtccctct aaatcccaag                                               20


<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 146

ccggaagtca agaatccagt                                               20


<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 147

tggacatgag gcatttgcta                                               20
```

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 148
gcatcgcgag atcaagagtt 20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 149
aagcccgcct ttctacctta 20

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 150
tcttgatcat cgaacgaatc ac 22

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 151
ccaattccct cttccttcct 20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 152
atccatccaa gtcagccttc 20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 153
tggttgaggc cccaatatac 20

<210> SEQ ID NO 154

-continued

<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 154
ccccgctatc gacttgatta 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 155
cggaagagcc tgtggtatga 20

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 156
tgaaatcaga ttcaggcatc a 21

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 157
agatcaggaa gcgcgtaaga 20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 158
cagagttttg ctggccttct 20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 159
gtggcaaagg aatcaaggaa 20

<210> SEQ ID NO 160
<211> LENGTH: 20

<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 160
atgggttcca gttgccagta 20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 161
cggtccttta gcagtttcca 20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 162
catgttgggg ttcgataagg 20

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 163
atctggagta tttcttctac ct 22

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 164
cttaaactct ctgccgaata aa 22

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 165
tccttctttc tgtctgtttc tctt 24

<210> SEQ ID NO 166
<211> LENGTH: 21
<212> TYPE: DNA

```
<213> ORGANISM: Artificial Sequence
<220> FEATURE:
<223> OTHER INFORMATION: Description of Artificial Sequence:
      Synthetic oligonucleotide

<400> SEQUENCE: 166

gtcctcactg ctgtctttct c                                          21


<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 167

gcacttctgg tggtgaaaga                                            20


<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 168

gtcattctca gttatgttac ggaaag                                     26


<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 169

agctgctcca taaccgaaat                                            20


<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 170

cgaccctgaa tttcctctag tt                                         22


<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 171

ggatgtaagg cattggacat aga                                        23


<210> SEQ ID NO 172
<211> LENGTH: 22
<212> TYPE: DNA
<213> ORGANISM: Artificial Sequence
```

<220> FEATURE:
<223> OTHER INFORMATION: Description of Artificial Sequence:
Synthetic oligonucleotide

<400> SEQUENCE: 172
gagttcccta tcaaccgaaa ca 22

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 173
ggcgagtcat taacctccta ttt 23

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 174
gtcttagcgt ccaagtgcta at 22

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 175
gctgaagaac ctttgccttt ac 22

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 176
gccgatttct caacacaaag aa 22

<210> SEQ ID NO 177
<211> LENGTH: 2399
<212> TYPE: DNA
<213> ORGANISM: Nicotiana tabacum

<400> SEQUENCE: 177
ttagcactta aaaaacatag gtttacatgc tctcattgtc acgccaggcc gctaattaaa 60
tggtacattt catcatcccc attttttggc ctcatagtta attatcacaa tttctgaaag 120
caacatcaga acaaccccac atttcttgtg gtcctataat tactgctaga tagtccaaac 180
ccatctgcct atttagggct tgtgaatgag gattgaaaat ggtagagaat atttgcaaag 240
gcatcatgca tatatggaaa agactaaaga gagagttagt gccttgcaaa gcggattctc 300
acagttgtag aaaaggactc accattttca agaatactcc cggcatgaag atggacaatt 360

```
taatataaaa aacaaagaaa atagtaatta agtgcgttga gatgaatgaa atttatccgc    420
tcttaattga atatggggaa ttgaaagaaa tttctgataa taaattaatg agtcttacat    480
gacgtggatc cgacttaatc tagtctattt aaactaagaa tagataagaa tagagaatat    540
agacaaaaga gaggctcatt ggctagggtt tcaagggagt tccttgaaca taagtggcaa    600
gtacaagcac aaagccaatt tccatggact aaagatgaat aagatgtgtc gtgtggtatg    660
gtgggaaggt gaggaggtat ggggtaattg gagatgctaa acctctctaa aagctctttt    720
gctccaaata tctaaatcca tctctatcac ttttggcgac tgccccaaaa tttgcaactt    780
atgaattaaa gttttaatat ttttaagtta ataaattctg aattaataat ttaacatatt    840
caataaactt tttaaaacaa attacgtata taccatcaaa ctggctgcac catgatcact    900
ttctaaactc acaatgacat atggatttaa tcaggcacaa agtcatgttg atagaaagag    960
atagtacgga gaatgaagaa aaaaggtagg ggagagagat ggggtgagtg gggaaaagat   1020
agggttctct ttttagtgaa agcgacaggg tctgagaacc ctaggtcaaa agttgcataa   1080
acctctatac aggcttcttc actcccttac tactaatata ctctcattaa ggcttgaggt   1140
ttaattcatt aaaattgtgg tttaattatt gtatcccctc aaacgaaata attgtccttg   1200
tcgaggttag acaatgttgc gtactatttt caaacgcagt cagccattat tctcctatcc   1260
tttacagtcg agattcaaag acagaaagta gcatgcaagc tgttattaat ttactttgat   1320
taggactttg ccaagaaaat gaagaacctt ttcttttttc ttttaattta gttatcttac   1380
aacatgtaat ttttcctagc aagcaaatac ggtaactttt ttttttattc tcatttaatt   1440
tgttggagct attgctactt tgatgacttc aaccaaatcc tggttggtag gcggagggtg   1500
ctgacgatgg aaactacccc tcttgtccaa atacgataac ctaaaaaata gaataatagc   1560
ttattgtact gtgctgcaaa aattgcattg tcagtataca taattaaaat ctattttgaa   1620
tgtgtggagg gcaaagaggg gtgactggtc tagggttgta gaaatcaggt gggagagaga   1680
atggtatttg tctctgtgtc agctgatatc acgtgaagag gcacaataag aagtccttcg   1740
tatccattca cttcccaaaa ataccggcat tactacaaat atagtactag cacttgcttt   1800
ctctatcccc atctttgcta tttcctttcc ctttccaact ttttggcttt agaattgcaa   1860
agatggaggg aattgtggtt ctttgtatct gtaaaatttt tcctccaagc tccagttgta   1920
gctagcttaa tgcgtggacg cgcgcgcaca cactagaaat ctgcaatcta tatatatatt   1980
cacaaggcac tcacatatca aaaaccacat agacattgta tagagagagc tgtcgttctc   2040
aagcagaaaa aatgatatga tttcatcagc atgtggtcaa ccaaatagtt caattctagt   2100
ctttgcttcc tctttctaat tactgtataa atagagccac aaggacatag aattgagaaa   2160
ataaaagaca ataaaaacaa atctagctac ttaagcgaat gatgatgact ctctctcagt   2220
agtcttaact cttaataccc ttgttttcct tcttgtgctg cagtttgatt ggttaattaa   2280
cctaatcaaa agatgtttta actgtgtttt atccgtcttt ctcaagatct atcttagtcc   2340
caccacatag ctccctcaag ctacagctgc aaaatatata ctatatatat atataacaa    2399
```

<210> SEQ ID NO 178
<211> LENGTH: 300
<212> TYPE: DNA
<213> ORGANISM: Nicotiana tabacum

<400> SEQUENCE: 178

```
tctttgcttc ctctttctaa ttactgtata aatagagcca caaggacata gaattgagaa     60
```

aataaaagac aataaaaaca aatctagcta cttaagcgaa tgatgatgac tctctctcag 120
tagtcttaac tcttaatacc cttgttttcc ttcttgtgct gcagtttgat tggttaatta 180
acctaatcaa aagatgtttt aactgtgttt tatccgtctt tctcaagatc tatcttagtc 240
ccaccacata gctccctcaa gctacagctg caaaatatat actatatata tatataacaa 300

<210> SEQ ID NO 179
<211> LENGTH: 1901
<212> TYPE: DNA
<213> ORGANISM: Nicotiana tabacum

<400> SEQUENCE: 179
aatctagtct atttaaacta agaatagata agaatagaga atatagacaa aagagaggct 60
cattggctag ggtttcaagg gagttccttg aacataagtg gcaagtacaa gcacaaagcc 120
aatttccatg gactaaagat gaataagatg tgtcgtgtgg tatggtggga aggtgaggag 180
gtatggggta attggagatg ctaaacctct ctaaaagctc ttttgctcca aatatctaaa 240
tccatctcta tcacttttgg cgactgcccc aaaatttgca acttatgaat taaagtttta 300
atatttttaa gttaataaat tctgaattaa taatttaaca tattcaataa actttttaaa 360
acaaattacg tatataccat caaactggct gcaccatgat cactttctaa actcacaatg 420
acatatggat ttaatcaggc acaaagtcat gttgatagaa agagatagta cggagaatga 480
agaaaaaagg taggggagag agatggggtg agtggggaaa agataggggtt ctctttttag 540 tgaaagcgac agggtctgag aaccctaggt caaaagttgc ataaacctct atacaggctt 600
cttcactccc ttactactaa tatactctca ttaaggcttg aggtttaatt cattaaaatt 660
gtggtttaat tattgtatcc cctcaaacga aataattgtc cttgtcgagg ttagacaatg 720
ttgcgtacta ttttcaaacg cagtcagcca ttattctcct atcctttaca gtcgagattc 780
aaagacagaa agtagcatgc aagctgttat taatttactt tgattaggac tttgccaaga 840
aaatgaagaa ccttttcttt tttcttttaa tttagttatc ttacaacatg taatttttcc 900
tagcaagcaa atacggtaac tttttttttt attctcattt aatttgttgg agctattgct 960
actttgatga cttcaaccaa atcctggttg gtaggcggag ggtgctgacg atggaaacta 1020
cccctcttgt ccaaatacga taacctaaaa aatagaataa tagcttattg tactgtgctg 1080
caaaaattgc attgtcagta tacataatta aaatctattt tgaatgtgtg gagggcaaag 1140
aggggtgact ggtctagggt tgtagaaatc aggtgggaga gagaatggta tttgtctctg 1200
tgtcagctga tatcacgtga agaggcacaa taagaagtcc ttcgtatcca ttcacttccc 1260
aaaaataccg gcattactac aaatatagta ctagcacttg ctttctctat ccccatcttt 1320
gctatttcct ttccctttcc aactttttgg ctttagaatt gcaaagatgg agggaattgt 1380
ggttctttgt atctgtaaaa tttttcctcc aagctccagt tgtagctagc ttaatgcgtg 1440
gacgcgcgcg cacacactag aaatctgcaa tctatatata tattcacaag gcactcacat 1500
atcaaaaacc acatagacat tgtatagaga gagctgtcgt tctcaagcag aaaaaatgat 1560
atgatttcat cagcatgtgg tcaaccaaat agttcaattc tagtctttgc ttcctctttc 1620
taattactgt ataaatagag ccacaaggac atagaattga gaaaataaaa gacaataaaa 1680
acaaatctag ctacttaagc gaatgatgat gactctctct cagtagtctt aactcttaat 1740
acccttgttt tccttcttgt gctgcagttt gattggttaa ttaacctaat caaaagatgt 1800
tttaactgtg ttttccgtct ttctcaagat ctatcttagt cccaccacat agctccctca 1860
agctacagct gcaaaatata tactatatat atatataaca a 1901

<210> SEQ ID NO 180
<211> LENGTH: 2500
<212> TYPE: DNA
<213> ORGANISM: Nicotiana tabacum

<400> SEQUENCE: 180

```
atgtttagtc caagaaaaat aaccataccc aaatataagg gtttgttgaa gacggaaata     60
tataaacaaa taaacaaata tcatcatatc tccgatagtt taaaatttta gattggatat    120
ttcacacaat ttatcaaaat tttcaaaaaa aaattctact ttttcttgct tggaacttgg    180
aaggggaagg ggtggtggtg gagatagggc ggggcatctt ctatctagtc tatgtgatta    240
atataacaaa acaaaaaggg cgaggcaaaa acatggatga atggtggtcc ttttctatat    300
ttatatggat tgttacgata cgtcgatttc actttgcaaa ataccaatta gattcattta    360
gttatctttt tgatcactct gcttttacta tcatatatat ataggagtcc ttccacgttt    420
cgcatgtgtc attgtttata ttttccatgg tcttccttcc aaatggctaa aaaaatttga    480
cacagtggtc ccaaaagttt atagaaatag aattcaacag tgaggcatat acctatgaat    540
tctattttac atcttcatcg tataaaatag aatgtgttat aaactttacc tcgtgatgct    600
tacaaggggt gaaaatataa aagcacttta tagatttaca agagtcacac cttgatttcc    660
taagatttta tttttttaca tgccaaacaa tgaagtatgg gagatccaat tggaataaca    720
tcaaatttaa taaaattcga aatagtcaga gagctgtcta ctgaggtata ttgaaactta    780
ttttttttta atagaaaata tcaaatactt agcaatatat taaaatgttt cataaattac    840
attgtttaaa ccaagcgttg aaacatatgc tgatacgagg taggcttatt gatgaattta    900
taagggcctc attggaaaag acgatccaaa gcaatgggct aaaaaattgg cccattttct    960
gccacccagt gtatggttat tactagtttc acccacacag atttgcactt cattagagga   1020
caatgttgct gaatttgaaa cataagtcca tttatctcca ctgtacagtc cttcctggag   1080
tccaatcctg accatatctt catgatttta tgtaatgtgg tgaataagca aagtttcatg   1140
ttatgctttg tctcatttta tagcaaattc atttcctcat aaaatttact tcaaaaaagt   1200
ttcgtttgat tttcagaaat caaaatatgc ttttcggtaa ccaaatggtt ttcaattttg   1260
tttacgaaga acttaaaact ttccaacacc ctacatctat gattgcaagt taaaattgca   1320
gaaatatgac actttttgga gtggtcttta tcgtttaact tcacttgcac tttaagggca   1380
aaagttaaaa gtgtttccat gaagcaagcg agggaaaccc tacacttatt aaacttgaaa   1440
ttctactcat agaccaaaac aaggacaaaa attcaagact atctatgtgg gtaaacgtac   1500
gaaaattggg cttctccaga ttagagccgg accttgtgga aagacagaga aattcgaggc   1560
ccacttccag tttctaagga gattaagcct atcaaacgat ggtccagaac gaaatatgtc   1620
tttctttatt ctctactata tagctgactc agaatcgtta gaatttgcaa tttcctcata   1680
ataaaatgtg aggcagtata gattcgaaaa cctttgttga agattattga ctcagctacg   1740
cgaaacaaac tgtagtatcc aatgtaccga ttaacaagcg actggttaac tatgaatttg   1800
ttagctcgac aaaatcaccg gttaataatg agtttgtgag ttcgataaaa tctaattttc   1860
tgatagaaat tttatatatt atgcagaaat ttaataaaag tagacttaac ttatatattt   1920
tagcattgac tcttttgaag taaaatccat tccatctaaa ttatgacttc cctacatcga   1980
gtaagtaagt tgcgtctgta tcctcatttt acccactttt cgctatgcaa ttattcaagg   2040
atctttacac aaatagcaag ccaatattaa ttatttattt tttttagtca tatatataaa   2100
```

ttatacatat attatatacc cattaattat ttttaattta agtgatagat tggacgacta 2160
tttggattaa ttcttcgtta ttcaagataa tagatgtcgt ctctaataca tgagctagaa 2220
gataataagg attactaggc cgaaaggctg atggaaatga acaagaagat aagctcctaa 2280
atggaaacag tacggaaaaa gtcaaagagc agtgcatggg aggaatcatc agtcagaaaa 2340
ggaagccacg tgtcaagtag aaacaagcac gtgtccatgc aaaagccacg taactccctt 2400
ccatcacatc ttccttcttc aaaacctcgt gttttactct ctcttttctc actgccagtg 2460
atcgtcagga ctgtgcatgt ttgtttaaaa actaaaggca 2500

<210> SEQ ID NO 181
<211> LENGTH: 528
<212> TYPE: DNA
<213> ORGANISM: Nicotiana tabacum

<400> SEQUENCE: 181
atgggttcaa aaatgtctga tccccttgtg attgggagag tgattgggga agttgttgat 60
tatttcactc caagtgttaa gatgtctgtt acttataaca gcagcaagca tgtttataat 120
gggcatgaac tctttccttc ctcagtcacc tctaaaccta gggttgaagt tcatggaggt 180
gatttgagat ctttctttac aatgatcatg atagacccag atgttcctgg tcctagtgat 240
ccatatctca gggaacacct acactggatt gtcacagaca ttccaggcac tacagattgc 300
tcgtttggga aagaaatagt tggctatgaa atgccaaggc caaatattgg aattcacagg 360
tttgtatttc tgctgttcaa gcagaagaag aggcaaacag tattgactgc acctctctcc 420
agggatcgat ttaatacgcg taaattcgca gaagaaaatg agcttgggtc tcctgttgca 480
gcagttttct tcaattgcca gagggaaact gctgccagaa ggcgttga 528

<210> SEQ ID NO 182
<211> LENGTH: 1728
<212> TYPE: DNA
<213> ORGANISM: Arabidopsis thaliana

<400> SEQUENCE: 182
atgggattga cctcatcctt acggttccat agacaaaaca acaagacttt cctcggaatc 60
ttcatgatct tggttctaag ctgtatacca ggtagaacca atctttgttc caatcattct 120
gttagtaccc caaaagaatt accttcttca aatccttcag atattcgttc ctcattagtt 180
tcactagatt tggagggtta tataagcttc gacgatgtcc acaatgtggc caaggacttt 240
ggcaacagat accagttacc acctttggca attctacatc caaggtcagt ttttgatatt 300
tcatcgatga tgaagcatat agtacatctg ggctccacct caaatcttac agtagcagct 360
agaggccatg gtcactcgct tcaaggacaa gctctagctc atcaaggtgt tgtcatcaaa 420
atggagtcac ttcgaagtcc tgatatcagg atttataagg ggaagcaacc atatgttgat 480
gtctcaggtg gtgaaatatg gataaacatt ctacgcgaga ctctaaaata cggtctttca 540
ccaaagtcct ggacagacta ccttcatttg accgttggag gtacactatc taatgctgga 600
atcagcggtc aagcattcaa gcatggaccc caaatcaaca acgtctacca gctagagatt 660
gttacaggga aaggagaagt cgtaacctgt tctgagaagc ggaattctga acttttcttc 720
agtgttcttg gcgggcttgg acagtttggc ataatcaccc gggcacggat ctctcttgaa 780
ccagcaccgc atatggttaa atggatcagg gtactctact ctgacttttc tgcattttca 840
agggaccaag aatatctgat ttcgaaggag aaaacttttg attacgttga aggatttgtg 900
ataatcaata gaacagacct tctcaataat tggcgatcgt cattcagtcc caacgattcc 960

-continued

```
acacaggcaa gcagattcaa gtcagatggg aaaactcttt attgcctaga agtggtcaaa   1020

tatttcaacc cagaagaagc tagctctatg gatcaggaaa ctggcaagtt actttcagag   1080

ttaaattata ttccatccac tttgttttca tctgaagtgc catatatcga gtttctggat   1140

cgcgtgcata tcgcagagag aaaactaaga gcaaagggtt tatgggaggt tccacatccc   1200

tggctgaatc tcctgattcc taagagcagc atataccaat ttgctacaga agttttcaac   1260

aacattctca caagcaacaa caacggtcct atccttattt atccagtcaa tcaatccaag   1320

tggaagaaac atacatcttt gataactcca aatgaagata tattctatct cgtagccttt   1380

ctcccctctg cagtgccaaa ttcctcaggg aaaaacgatc tagagtacct tttgaaacaa   1440

aaccaaagag ttatgaactt ctgcgcagca gcaaacctca acgtgaagca gtatttgccc   1500

cattatgaaa ctcaaaaaga gtggaaatca cactttggca aaagatggga aacatttgca   1560

cagaggaaac aagcctacga ccctctagcg attctagcac ctggccaaag aatattccaa   1620

aagacaacag gaaaattatc tcccatccaa ctcgcaaagt caaaggcaac aggaagtcct   1680

caaaggtacc attacgcatc aatactgccg aaacctagaa ctgtataa                1728
```

<210> SEQ ID NO 183
<211> LENGTH: 1644
<212> TYPE: DNA
<213> ORGANISM: Nicotiana tabacum

<400> SEQUENCE: 183

```
atgaaattac caccccattt tttatttaag caaaatgact tgctcctgaa attgcttata     60

ttcatactat gcagttgttc aagcaacaaa aataaactct gctgtaacaa tcatcagttt    120

gccacccctg cagtttctac ctcctcaagt ttctcactga actatttatc attgaaacaa    180

ttacaacttg aagggtacct taattttgac aacttagaac atgcagccaa agactttggt    240

aatagatgcc acttcctccc attagcagtt ctgtacccaa aatcagtttc tgacatctct    300

tccactataa aacttatctt tgaaatgggt tccaaaactg gcataactgt tgctgctaga    360

ggccatggcc attctttaga aggccagtct caagcttatc aaggactagt gattagtatg    420

gaatcactac aaacaccagc aatgaaattc aagactggag aagtacctta tgttgatgta    480

tctgctggag agctttggat aaacatcctg catgaaagtc ttaaacttgg gattgcgcct    540

aaatcttgga ctgattatat tcacctcaca gttggtggca ctttgtctaa tgctggaatc    600

agtggacaag ctttccggca tggaccccag atcaataacg tccaacaact tgaagttgtc    660

actggtaaag gagaggtgat tacttgttcg gaggagaaga atgcagactt gtttcatggt    720

gtactaggtg gactggggca atttggtatt attaccagag caaggattgc tcttgaaaca    780

gcacctaaac aggtcaagtg gattagagtg ctgtattcag attttgccat attttccaat    840

gatcaagagc atttgatatc aactcaggat acatttgatt atattgaagg gtttgtcatt    900

atcaaccaaa ctggattatt gaatagctgg aggtctagtt tcaatcgtaa agattcagtt    960

ctagccagca atttcagttc tgagggtaga gttttgttct gcctagaagt tgccaaatac   1020

ttcaatccag aagacacaga tagtattgat cagaacattg atatcctctt atcaaagttg   1080

aactttatgc gatccacgct gttcctatca gaagtctcct acgtggaatt cctcgacaga   1140

gtgcatgtct ctgagatgga actccaagaa aaagggttgt gggatgttcc tcatccatgg   1200

ctaaatcttc taataccaaa aagcaggatt cttgaatttg cacaagaagt tttggcaag    1260

attcttactg acactagcaa tggtccttta ctcatctacc ctgtcaacaa atcaaagtgg   1320
```

-continued

```
agaaaaggaa catccatggt taccccctgac gaagatgttt tctacctgat cgcattccta   1380

tcttccgcca tgccatcttc aacaggcagc gatggactaa gacatattct tgctcagaac   1440

aaaaggatac taaatttttg tgaaaaaata aatattggaa tgaaacaata tttgccaaat   1500

tacaagactc aggaagagtg gaaagatcac tttggcccac aatggatacc atttgctaga   1560

aggaaatcca catatgaccc tttggcaatg cttgctcctg gccagagaat tttcagaagg   1620

gcagaagcct gtgaacaaca ataa                                          1644


<210> SEQ ID NO 184
<211> LENGTH: 1659
<212> TYPE: DNA
<213> ORGANISM: Nicotiana tabacum

<400> SEQUENCE: 184

atgaagtcac caccaactca tgtcttcttt aaacataaaa gtatgcttct taggttgctt     60

atattcatac taggcatttg ctcaataaac agaactaacc tttgttgtga ccaacctttt    120

gccaccccaa tatcttcttc ttcttctacc ccttcaagtt tttcagtgat tcaatcatca    180

ttgaaacagt taaatattga agggtatttt agtttcaaga atttcgatca cgcggccaaa    240

gactttggca acagatatca cttcttgcca tcggcagttc tgtatccaaa atcagtttct    300

gatatatcat ctaccataaa acatgttttt gacatgggtg ttactacaga cctaactgtt    360

gctgctagag gccatggcca ttctttagaa ggccaagctc aagcttacca aggagtagtg    420

atcaatatgg aatcgcttcg agcgccagca atgcgtttcc acacagggaa tcaagaactg    480

ccttttgttg atgtctctgc aggagaactt tggataaaca tcctgcatga aagtcttaaa    540

cttggattaa caccaaaatc ttggactgat tatcttcacc tcaccgttgg agggactttg    600

tcgaatgccg gaatcagtgg tcaagcattc aaacatggac cacagatcaa taatgtttac    660

caacttgagg ttgtcactgg taaaggagag gtgattactt gttcagagga gaagaatgct    720

gacctgttct atggtgtatt aggaggacta ggccagtttg gtatcatcac aagggctaga    780

attgctcttg aaccagcacc taaaaaggta aagtggatca gagtgctgta ttcagatttc    840

tccacatttt cctatgatca agaacacttg atatcatccg agaactcttt tgactatata    900

gaaggatttg tcattatcaa tagaacagga ttgttaaaca actggaggtc tactttcaat    960

cctaaagatc cacttctagc caaagagttc agttctgagg gaaaagttct gtactgccta   1020

gaagttgcca aatacttcaa tccagaagag acaaccaaaa ctgatcagaa tgttgatgtt   1080

cttttatcaa agttgaatta tatccaatcg acgctgttcc aatcagaagt atcctacgtg   1140

gatttcctcg acagagttca cgtatccgag atgaaacttc aagagaaggg gttatgggat   1200

attcctcatc catggctaaa ccttctaatt ccaaagagca agattcatga ctttgcacga   1260

gaagtttttg ggaagatact taccgacact agccacggtc ctatactcat ctacccagtc   1320

aacaaatcaa agtggagaaa aggaacatca gtagttacac ctgaagaaga tgttatgtat   1380

ctaatagcat ttctatcttc tgccatgcca tcttcaacag gaaaggacgg cgtagaatat   1440

attctaaata agaataagaa gatactaaac ttttgcagaa aagcacatat tggaatgaaa   1500

cagtatttgc cacactacac aacgcaggaa gactggaaag gtcactttgg tccccagtgg   1560

gaaacattta aaaggaggaa atctacatat gaccctttgg ctatcctagc tcctggccag   1620

agaattttta gaagagcatc aggcgttcaa caacaatga                          1659


<210> SEQ ID NO 185
<211> LENGTH: 1593
```

-continued

<212> TYPE: DNA
<213> ORGANISM: Nicotiana tabacum

<400> SEQUENCE: 185
atgaaatcac caccaactca tgtcttcttt aaacataaaa gtatgtttct taggtttctt 60
atattcatat taggcatttg ctcaataaac aaaactaacc tctgttgtga ccaaactttt 120
gccaccccaa tatcttcttc ttcttctatc ccttcaaatt tttcagtgat tcaatcatca 180
ctgaaacagt taaatattga agggtatttt agtttcaaga atttcgatca cgcggccaag 240
gactttggca acagatatca tttcttaccg tcggcagttc tgtatccaaa atcagtttct 300
gatatatcat ctaccataaa acatgtgttt gacatgggta gcaatacaga cctaactgtt 360
gctgctagag gtcatggtca ttctctagaa ggccaagctc aagcttacca aggagtagtg 420
atcaatatgg aatctcgagc gctgactttt gttgatgttt ctgctggtga actttggata 480
aacatcctgc atgaaagtct taaacttgga ttaacaccaa aatcttggac tgattatctt 540
cacctaaccg ttggagggac tttgtcgaat gccggaatca gtggtcaagc attcaaacat 600
ggaccacaga tcaataatgt ttaccaactt gaggttgtca ctggtaaagg agaggtgatt 660
acttgttcag aggagcagaa tgctgacctg ttctatggtg tattaggagg actaggccag 720
tttggtatca tcacaagggc taggattgct cttgaaccag cacctaaaaa ggtacaggta 780
aagtggatca gagtgctgta ttcagatttc tccacatttt cctatgatca agaacacttg 840
atatcattgg agaattcttt cgactatata gaaggatttg tcattatcaa tagaacagga 900
ttgttaaaca actggaggtc tactttcaat cctaaagatc cacttctagc caaaagttct 960
ctactgccta gaagttgcca aatacttcaa tccagaagac agaatgttga tgctctttta 1020
tcaaagttga attatatcca atcgacgttg ttccaatcag aagtctcgta tgttgatttt 1080
ctcgacagag tccatgtatc cgagatgaaa ctccaagaga aggggttatg ggatgttcct 1140
catccatggc taaaccttct aattccaaag accaggattc atgacttcgc acaagaagtt 1200
tttgggaaga tacttaccga cactagccac ggtcctatac tcatctaccc agtcaacaaa 1260
tcaaagtgga gaaaaggaac atcactagtt acacccgaag aagatgttat gtacttaata 1320
gcatttctat cttctgccat gccatcttca acaggaaagg acggcgtaga atatattcta 1380
aataagaata agaagatact aaacttttgc agaaaagcac atattggaat gaaacagtat 1440
ttgccacact acacaacaca ggaagactgg aaaagtcact ttggtttcca atgggaaaca 1500
tttaatagga ggaaatccac atatgaccct ttggctatcc tagctcctgg ccatagaatt 1560
tttagaagag catcaggcgt tcaacaacaa tga 1593

<210> SEQ ID NO 186
<211> LENGTH: 1632
<212> TYPE: DNA
<213> ORGANISM: Nicotiana tabacum

<400> SEQUENCE: 186
atgaaattac catcccattt tttatttaag caaaatgact tgctcctgaa attgcttata 60
ttcatactct gcagttgttc aagcaacaaa aataaactct gctgtaatta tcatcagttt 120
gccacccctg cagtttctac cccctcaagt ttctcactga attatttatc attgaaacaa 180
ttacaacttg aaggttacct taaatttgac aacttagaac atgcagccaa agactttggt 240
aatagatgcc acttccttcc attagcagtt ttgtacccaa aatcagtttc tgatatctct 300
tccactataa aacatgtctt tgaaataggt tccaaaactg atttaactgt tgctgctaga 360

```
ggccatggcc attctctaga aggtcaagct caagcttatc aaggagtagt gattagtatg    420

gaatcactac aaacaccagc aatgaaattc aagactggag aattgcctta tgttgatgtt    480

tctgctggag agctttggat taatatcctg aaagaaagtc ttaaacttgg gcttgcacct    540

aaatcttgga ctgattatct tcacctcaca gttggcggca ctttgtctaa tgctggaatc    600

agtggacaag ctttccgcca cggaccgcag atcaataacg tccaacaact tgaagttgtc    660

actggtaaag gagaggtgat tacttgttca gaggagcaga atgcagactt gtttcatggt    720

gtactaggag gactggggca atttggtatt attaccagag caaggattgc tcttgaaaca    780

gcacctaaac aggtcaagtg gattagagtg ctgtattcag atttttccat attttccaat    840

gatcaagagc acttgatatc aactcaggat acatttgact atattgaagg ttttgtcact    900

atcaaccaaa ctggattatt aaataactgg aggtctgctt tcaatcctaa agatccagtt    960

ctagccagca atttcagttc tgagggtaga gttttgttct gcttagaaat tgccaaatac   1020

ttcaatccag aagtcacaga tagtattgat cagaacattg atgtgatctt atcaaagttg   1080

aattatatcc gatccacgct gttcctatca gaagtctcct acacagaatt cctcgacagg   1140

gtgcatgtct ctgagatgaa actccaagaa aatgtttctc atccatggct aaatcttcta   1200

ataccaaaaa gcaggattct tgaatttgca caacaagttt ttggcaagat tcttactgac   1260

actagcaatg gtcctttact catctaccct gtcaacaaat caaagtggag aaaaggaaca   1320

tccatggtta cccctgacga agatgttttt tatctgatcg cgttcctatc ttctgctatg   1380

tcatcttcaa caggaaacga tggactaaga catattcttg ctcagagcaa aaggatactg   1440

aacttttgtg aagaaacaaa tatcggaatg aaacaatatt taccaaatta caagactaag   1500

gaagagtgga aggatcactt tggtcatcaa tgggaagcat ttgctagaag gaaatctaca   1560

tatgaccctt tggcaatact tgctcctggc cagagaattt tcagaagggc agaagcctgt   1620

gaacaacaat aa                                                       1632
```

<210> SEQ ID NO 187
<211> LENGTH: 1572
<212> TYPE: DNA
<213> ORGANISM: Nicotiana tabacum

<400> SEQUENCE: 187

```
atggctaaac tttattccct aggttactta gttatattct tcaccattag ccgtttagtg     60

tccatcatag gtaaaccttc aattacaaat gaagttcttt cccaccttga tattgcaaca    120

agacttagtg taaatatttc agatgccact atagcaactt ccactgattt tggaaaactt    180

gttcaagaaa tcccagctgc agttctttac ccttcctcca ttcatgacat tgttaagctc    240

ataaactact ccaacaatgg cgccatttct gccccttttg gcgtcgcggc gagaggacat    300

ggccattcag tgaggggaca agccatgtca ccaaatgggg ttgtggtggt catgagttct    360

ttgaataata ataataataa taataatgga aaaattgggg ttttttggga gagtagttta    420

gggttttatt atgcagatgt gggaggtgag cagcttcgga ttgatgtttt gcatgccact    480

ttagagcatg gacttgcacc tgtctcttgg actgattatt tatatctctc cgttggagga    540

actctctcta atgctggaat tagtggccaa actttcaaat atggtcctca gattagtaat    600

gttcttgaaa tggatgttat cacaggtaaa ggggaacttg tcacttgttc caagcggaca    660

aattcggagc tgtttttttgc agttttagga agtctaggcc agtttgggat cataatcaga    720

gcaagaattg tcttagagaa agcaccaaca agagtactcg ggttagagt attgtatagg     780

gatttttcaa aattcacaag agaccaagaa aaactgatct ccattaatga tggcatggac    840
```

```
tatgtggaag gctctctaat gatgaatcaa agtcctccaa ataattggag atcttctttt    900

ttctcaactt ccaaccaatc taaaatactt tccttgatat ccaaatatgg aattatctac    960

tgtttggaaa tggtcaagta ctatgatgat cagactgcta atacagttga taaggaattg   1020

cagaagatga tgagaggttt gaactttgtg tttggacaca tattcaagaa agatacagcc   1080

tttgtacatt ttctgaatag agtgagaagt ggtgagctaa tgttgcaatc aaagggaatg   1140

tgggatgttc ctcacccttg gctcaatctc tttgtaccaa agtccagtat tatggacttt   1200

aatgttggtg tctttttgga catcattctc agacaaaaca agtccacagg acctattctt   1260

gtgtacccaa caaccagaaa aagatgggat gatcggatgt ctgttgtgat accagaagag   1320

gacacattct actgcgtagg gctattgcat tctagtagat tcaatgactg ggaagttttg   1380

gatggacaaa atgaagaaat cataaactgc tgtgaaaaag ctggtctcaa cgtcaagcag   1440

tatcttccgc attacaaaac caaggaagct tggatgaatc attttggcaa aaaatggaaa   1500

atatttcaac aaaggaaaag tcagtttgat ccaaagatga ttctgtcacc aggacaaaag   1560

attttcattt ag                                                       1572
```

<210> SEQ ID NO 188
<211> LENGTH: 1563
<212> TYPE: DNA
<213> ORGANISM: Nicotiana tabacum

<400> SEQUENCE: 188

```
atggctaaac tttattccct aggttactta attattttct tcaccattag ccctttagtg     60

tccatcatag gtaaaccttc aattccatat gaagttcttt tccaccttga tattgcaaca    120

agacttagtg taaatatttc agatgccact atagcaactt ccactgattt tggaaaactt    180

gttcaaaaaa tcccagctgc agttctttac ccttcctcca tacatgacat tattaagctc    240

attaactact ccaacaatgg cgccatttct gtccctttttg gtgtcgcggc gagaggacat   300

ggccattcag tgaggggaca agccatgtcg ccaaatgggg ttgtggtggt catgagttct    360

ttgaagaata ataacaatgg aaaaaattagg gttttatggg agagttgttt agggttttat   420

tatgcagatg tgggaggtga gcagctttgg attgatgttt tgcatgccac tttagagcat    480

ggacttgcac ctgtctcttg gactgattat ttgtatctct ctgttggagg aactctctct    540

aatgctggaa ttagtggcca aactttcaaa tacggtcctc agattagcaa tgttcttgaa    600

atggatgtta tcacaggtaa agggcaactt gtcacttgtt ccaagcagac aaattcggag    660

ctgttttttg cagttttagg gggtctaggc cagtttggaa tcataaccag agcaaggatt    720

gtcttagaga aagcaccaac aagagtgaaa tgggttagag tgttctatag tgatttttca    780

aaattcacaa aagaccaaga aaaactgatc tccattaata atggcatgga ctatgtggaa    840

ggctctctaa tgatgaatca aagtcctcca aataattgga gatcttcctt tttctcaact    900

tccaaccaat ctaaaataat ttccttgata tccaaatatg gaattatcta ctgtttggaa    960

atggtcaagt actatgatga tcagtgtgct aatactgttg ataaggaatt gcagaagatg   1020

atgagaggtt tgaactttct gtctggacac atattcaaga aagatacaac atttgtacat   1080

tttctgaata gagtaagaag tggtgagcta aggctgcaat caaatggaat gtgggatgtt   1140

cctcaccctt ggctcaatct ctttgtacca aaatccagta ttatggactt taatgttggt   1200

gtcttcttgg acattattct cagacaaaac aagaccacag gacctattct tgtgtaccca   1260

acaaccagaa aaagatggga tgatcggatg tctgttgtga taccagaaga ggacacattc   1320
```

tactgcgtag ggctattgca ttctagtgga ttcaatgact gggaagtttt ggatggacaa 1380
aatgaagaaa tcataaacta ctgtgaaaaa gctggtctca acatcaagca gtatcttcca 1440
cattacaaat ccaaggaagc ttggatgaac cattttggca aaaaatggaa aatatttcaa 1500
caaaggaaaa gtcagtttga tccaaagatg attctgtcac caggacaaaa gattttcatt 1560
tag 1563

<210> SEQ ID NO 189
<211> LENGTH: 1593
<212> TYPE: DNA
<213> ORGANISM: Nicotiana tabacum

<400> SEQUENCE: 189
atgacgtgcc aaagctttgt tttcaccaga aaaaagaacg ttctgttcct aagaagcttc 60
acaattttag tgctaagctg ggtaattatc aaaccaaatt tttgtttttc cagtgtcctg 120
tcctcattga aagcccttca tttagaaggc catattactt tcgaaaacaa tgagtttgca 180
gcccgagatt tcggcaatca aattcatgtc caccctttag cagtagtcca tccgaaatcc 240
gttgctgata tttcagaaat aataaaacat gtttggcaaa tgggtccgag ttctgaattg 300
accgtggcag cacgaggcca cggtcattcg cttcagggcc aggcacaagc gcgacgagga 360
gttataatca atatggagtc attccagggt caaggaatgc aggtccacag gggccaattc 420
ccttatgtag atgtctcagc tggtgaattg tggattaata tattgcatga aaccttgaaa 480
tatggattag caccaaaatc ttggactgat tacctccatc ttactgttgg aggtacactg 540
tctaatgctg gcatcagtgg gcaagcattt cgacacggcc ctcagatcag taatgtccat 600
cagctggagg ttgttacagg aaaaggagaa gtcttaattt gttcgaagga acagaatgca 660
gacctattcc atgctgtttt gggaggactt ggacagtttg gcataataac tagagcaaga 720
atctctctgg aacgagcccc aaaaatggtg aaatggataa gagtgttgta ctctgatttc 780
tccacatttg ctagagacca agagcatttg atatctgctg caaaaacatt tgattacata 840
gaagggctgg tgataaagaa caaaacaggt ctaatgaata actggagagc atcttttgac 900
cctcaagatc ctgttcaagc tagccatttt gtatcagatg gaagaacact ctattgcctt 960
gaacttacca aaaatttata ccccgaaaaa tcggatacag taaaccagga aattaaagac 1020
ttattatcgc aactaagtta tatcccatca acactattta tgtcagaagt tccatacata 1080
gaatttttgg acagagttca tgcatcagag ctaaaacttc gatcgaaagg actatgggat 1140
ctcccacacc catggctcaa tcttctagtt cccaaaagca aaatacaaca ctttgctaag 1200
gaagtttttg gcaacatcct aagagatact aacaatggcc ctgttcttgt ctaccccatt 1260
cataaatcaa agttggataa cagaacctca tttgtttctc caaacgatga tattatctac 1320
ctagtggcat tttatccca tgcaaatcct tcatccaatg gaactgacag tttagaatat 1380
gtcttaactc agaacaaaag aatattagac ttctgtgatg tggcacacct aggagtcaag 1440
caatatttgc ctcattacac aacacaagaa cagtggagga cccactttgg tccaaaatgg 1500
gaagtattta tacagaggaa atctgcttat gaccctttag ctatgcttgc tcctggtcag 1560
agaattttcc aaaaggcagt atcagtttca taa 1593

<210> SEQ ID NO 190
<211> LENGTH: 1593
<212> TYPE: DNA
<213> ORGANISM: Nicotiana tabacum

<400> SEQUENCE: 190

```
atgacgtgcc aaagctttgt tttcaccaga aaaaagaacg ttctgttcct aagaagcttc      60
acaattttag tgctaagctg ggtaattatc aaaccagaat tttgtttttc cagtgtccta     120
tcctcattga aagcccttca tttacaaggc catattactt tcgaaaacaa tgagtttgca     180
gcccgagatt tcggcaacca aattcatgtc caccctttag cagtagtcca tcccaaatcc     240
gttgctgata tttcagaaat aattaaacat gtctggcaaa tgggtccggg ttctgaatta     300
accgtagccg cgcgaggcca cggtcattcg cttcagggcc aggcgcaagc gcgacgtgga     360
gttataatca acatggagtc actacagggt caggaaatgc aggtctacag ggtcaattc      420
ccttatgtag atgtctcagc tggtgaattg tggattaata tattgcatga aactttgaaa     480
tatggattag caccaaaatc ttggactgac tacctccatc ttactgttgg aggtacactg     540
tctaatgctg gcatcagtgg acaggcattt cgacacggcc ctcagatcag taatgtccac     600
cagctggagg ttgttacagg aaaaggagaa gtcttaattt gttcaaagga acagaatgct     660
gacctattcc atgctgtttt gggaggactt ggacagtttg gcataataac tagagcaaga     720
atctctctgg aacgagcccc aaaaatggtg aaatggataa gagtgttgta ctctgatttc     780
tccacatttg ccagagacca agagcatttg atatctgcag ctaaaacatt tgattacata     840
gaagggctgg tgataaagaa caaaacaggt ctaatgaata actggagagc atcttttgac     900
cctcaagatc ctgttcaagc cagccacttt gtatcagatg gaagaacact ctattgcctt     960
gaactaacca aaaatttata ccccgaaaaa tccgatacag taaaccaggt aattgaagat    1020
ttattatccc aactaagtta tattccatca acgttattta tgtcagaagt tccatacata    1080
gaatttttgg acagagttca tgcttcagag ctaaaacttc gatcgaaagg actttgggat    1140
ctcccacacc catggctcaa tcttctagtt cctaaaagca aaatacaaca cttcgctaag    1200
gaagtttttg gcaacatcct taaagatact aacaatggcc ctgttcttgt ctaccccatt    1260
cataaatcaa agttggataa cagaacctca tttgtttctc caaatgaaga tattatctac    1320
ctggtggcct ttttatccca tgcaaatcct tcatccagtg gaactgacag tttagaacat    1380
gtcttaactc agaacaaaag aatattagat ttctgtgatg tggcacacct aggagtcaag    1440
caatatttgc ctcattacac aacacaagaa cagtggagga cccactttgg tccaaaatgg    1500
gaagtatttg tacagagaaa atctgcttat gaccctttag ctatgctagc acctggtcag    1560
agaattttcc aaaaggcagt atcagtttca taa                                 1593
```

<210> SEQ ID NO 191
<211> LENGTH: 1533
<212> TYPE: DNA
<213> ORGANISM: Nicotiana tabacum

<400> SEQUENCE: 191

```
atgtctaagc ttctttctcc tagttataac ttcattattt tctttattat cagtcgttta      60
atgtctatta taggaaagtt aaagccatgg aataatcctt ctattcctta tgaaattctt     120
tcccttgata tagcttctaa acttagtaca aattcagatt ccattagtga aacctccaca     180
gattttggga aaattgttca agaaatccca gctgctgttc tttatccttc ttctattatt     240
gatatagttg agttaattaa attttcctat ggtctttcta tcccttttca tatagcagca     300
agaggtcatg gccattccat tagaggacaa gccatggcac aaaatggtgt tgttgtggaa     360
atgaattctc tgaataacaa caacaacaac aataatatta ataataataa aaatggaagt     420
tgtggaatta gggtttcttg ggattcttct ttagggtttt acgctgatgt aggaggcgag     480
```

-continued

```
cagttatgga ttgatgttct ttgtgctacc ctcgagcatg ggctttcgcc tgtctcgtgg    540

actgattact tgtaccttac ggttggaggt actctctcta atgcaggaat tagtggccaa    600

actttccgac atggccctca aattagtaat gtccatgaaa tggacgttat tacaggtaca    660

ggtaaagggg aatttgtgac ttgctccaaa cacaagaatt cagaactgtt ctttgcagtg    720

aaatgggtga gaatgctata tgtagatttc tcaaaattca caaaagacca agaacatttg    780

atttcaattg atggcctgga ttatgttgaa ggatctctaa tgatggaaca aagcagtcta    840

aataattgga gatcttcatt tttctcacca tctaatcaga ccaaaatagc ttcgttgtta    900

tcacaaaatg gcattattta ttgcctagaa atggtcaagt actatgatga tcagactgct    960

aatactgttg acgaggaatt gaagaagttg gtaaaaggtt tgaacttttt gcctggattt   1020

atcttcaaga aagatgtcac atttgtggat tttttgaata gagtaagaag tggagagcta   1080

gagctacaat caaaaggaca atgggatgtt ccacatccat ggcttaatct ctttgtacca   1140

aaatccaata tcatggattt caatgctggt gtttttgtgg acattattct cagacaaaac   1200

aagacaacag gacctatcct tgtctaccca acaagcagga aaagatggga tgagaggatg   1260

tctgcagtga taccagaaga ggagacattt tactgtgtgg ggctattgca ttcaagtgga   1320

tttaatgact ggaaaaattt ggatgatcaa aatgaagaaa tcttgaatta ctgtgataaa   1380

gctggcctca agataaagca atatcttcca cattataaaa caaaggagga ttggataaaa   1440

cattttggca aaaagtggaa tatttttcaa caaaggaaaa gtcagtttga tccaaagatg   1500

attctatcac caggacaaag aatttttaat tag                                1533
```

<210> SEQ ID NO 192
<211> LENGTH: 1524
<212> TYPE: DNA
<213> ORGANISM: Nicotiana tabacum

<400> SEQUENCE: 192

```
atgtctaagc ttctttctcc tagttataac ttcattattt tcttcattat tagtcgttta     60

gtgtctatca taggaaagtt aaagccatgg aataatcctt caattccttg tgaaattctt    120

tcccttgata tatcttctaa acttagtaca aattcagatt ccattatgga aacttccaca    180

gattttggga aaattgttca agaaatccca gctgctgttc tttatccttc ttctattaat    240

gatatagttg agttaactaa atttcctat ggtctttcta tcccttttca tatagcagca    300

agaggtcatg gccattccat taggggacaa gccatggcac aaaatggtgt tgttgtggaa    360

atgaattctc tgaataataa taataataat aataataata ataataataa taacaacaac    420

ggaaatagtg gaattagggt ttcttgggat tcttctttag ggttttacgc tgatgtagga    480

ggcgaacagt tatggattga tgttcttcga gctaccctcg agcatggcct ttcgcctgtc    540

acgtggactg attacttgta cctcactgtt ggtggtactc tctctaatgc aggaattagt    600

ggccaaactt tccgacatgg tcctcaaatt agtaacgtcc atgaaatgga cattattaca    660

ggtacttcag aactgttctt tgcagtttta ggaggtttgg gacagtttgg aataataacc    720

agggcaagaa ttgtcttaga taaagcacca acaagagtga aatgggtgag aatgctatat    780

gcagatttct caaaattcac aaaagaccaa gaacatttga tttcaattta tggcctggat    840

tatgttgaag gatcactgat gatggaacaa agctctctaa ataactggag atcttcattt    900

ttctcacctt ctaatcagac caaaatagct tccttattat cccaaaatgg cattatttat    960

tgcctagaaa tggtcaagta ctatgatgat cagactgcta atactgttga tgaggaattg   1020

aagaagttgg taaaaggttt gaactttttg cctggattta tattcaagaa agatgtcaca   1080
```

```
tttgtggatt ttctgaatag agttagaaga ggagagttag agctaaaatc aaaaggacaa   1140

tgggatgttc cacatccatg gctcaacaat gctggtgttt ttgtggacat tattctcaga   1200

caaaacaaga caacaggacc tatccttgtc tacccaacaa gcaggaaaag atgggatgac   1260

aggatgtctg cagtgatacc agaagaggag acattttact gtgtggggct attacattca   1320

agtggattta atgactggaa aagtttggat gatcaaaatg aagaaatctt gaagtattgt   1380

gataaagctg gcttaaagat aaagcaatat cttccacatt ataaaacaaa gcattttggc   1440

aaaaagtgga atatttttca acaaagaaaa agtcagtttg atccaaagat gattctatca   1500

ccaggacaaa gaatttttaa ttag                                          1524
```

<210> SEQ ID NO 193
<211> LENGTH: 1404
<212> TYPE: DNA
<213> ORGANISM: Nicotiana tabacum

<400> SEQUENCE: 193

```
atggctacta aacttttgtt gacacttgct atatgtcggc ttattgtaac cgttgggttt     60

acgtttgacc cgaccgagct tttacggctc gggctcaacg gaaacctcag cgtagcggca    120

gccgatttag aaaccgcctc cgtggacttc ggccggttgc atagagccga gccgatggcg    180

gttcttcacc cagctacagc cgaggacgta gcgcggcttg tgaaagcggc gtatgactcg    240

gctcgtggct tcaccgtgtc ggctagagga cacggacatt ctataaatgg tcaggctatg    300

acaacaaaag gagttgtgat tccaatgctg gtattagtgg acaagctttc aatcatggcc    360

ctcaaattaa caatgttcat gagcttgatg ttgttacagg ttaagggtga gctattaaca    420

tgttcagaaa aagaaaactc cgagctgttt catgctgctc ttggtggatt aggacaattt    480

gggatcataa caagggcaag aattgcactt gaacaagctc cccaaagggt aaggtggatc    540

cgagttttat attcgaattt ttcaacattt accgaagacc aagaatatct aatatctcta    600

caggcaaaac cagcttccca aaaatttgac tatgttgaag gatttgttat agttgatgaa    660

ggcctcatta acaactggag atcttctttc ttctccccaa gtaaccctgt gaagatttct    720

tctcttaagg ctgacggagg agttttatat tgcttagaaa tcaccaaaaa ttatcacctt    780

tcaaatgctg atatcgttga tcaggagata gagactttgt taaaaaagct aaaatatata    840

ccagcatcag ttttcacaac agaccttcct tacgtggatt tcttggaccg ggttcacaag    900

gcagagttga aactccggtc taaagggttg tgggaagtgc cacacccatg gctaaaccta    960

tttgttccaa aatcaagaat tgtggacttc gataaaggag tttttaaggg cattttgggg   1020

aataagacca gtggtcccat actcatctac cccatgaaca agaacaagtg ggacgagagg   1080

agttcagtag tgacaccaga ggaggaggtt ttttacttag tgggatttct gaggtcggca   1140

ttgacaaaca gtgacgagac acagacatta gagtacctca gcaatcaaaa ctacgaaata   1200

ttgaagtttt gtgaagatgc aaatatcaaa atcaaacaat acctgcctca ttacacaaca   1260

caaagagaat ggagggacca ttttggagat aagtattgga ccagatttca gcaaaggaaa   1320

ttagagtttg acccaagaca tattttagct accggccaac gtattttcat gccttctttt   1380

aatcctaata ctgcctcttg gtga                                          1404
```

<210> SEQ ID NO 194
<211> LENGTH: 1404
<212> TYPE: DNA
<213> ORGANISM: Nicotiana tabacum

<400> SEQUENCE: 194
atggctacta aacttttgtt gacacttgct atatgtcggc ttattgtaac cgtcgggttt 60
aggtttgacc cgactgagct tttacggctc gggctcaacg gaaacctcag cgtggcggta 120
gccgatttag aaactgcgtc cgtggacttc ggcgggttgc atagagctga gccgatggcg 180
gttcttaacc cggctacagc cgaggacgta gcgcggcttg tgaaagccgc gtacgactcg 240
gctcatgggt ttaccgtgtc ggctagagga cacggacatt ctataaatgg acaggctatg 300
ataacaaatg gtgttgtgat cccaatgctg gtattagtgg acaagctttc aatcatggcc 360
ctcaaattaa caatgttcat gagcttgatg ttgttacagg ttaagggtga gctattaaca 420
tgttcagaaa aagaaaactc cgagctgttt catgctgctc ttggtggatt aggacaattt 480
gggattataa caagggcaag aattgcactt gaacaagctc cccaaagggt gaggtggatc 540
cgagttttat attcaaattt ttcaacattt accgaagacc aagaatatct aatatctcta 600
catggaaaac cagcttccca aaaatttgac tatgttgaag gatttgttat agttgatgaa 660
ggcctcatta acaactggag atcttctttt ttctccccaa gtaaccctgt caagatttct 720
tctcttaagt ctgaaggagg agttttatat tgcttagaaa tcaccaaaaa ttatcacctt 780
tcaaatgctg atatcgttga ccaggagata gagacattgt taaagaagct aaaatatata 840
ccagcatcag tttttacaac agaccttcct tacgtggatt tcttggaccg ggttcacaag 900
gcagagttga aactccggtc taaaggattg tgggaagtgc cacacccatg gctaaaccta 960
tttgtcccaa aatcaagaat tgcagacttc gataaaggag tttttaaggg cattttgggg 1020
aataagacca gtggtcccat actcatctac cccatgaaca agaacaagtg ggacgagagg 1080
agttcagtag tgacgccaga agaggaagtg ttttacttag tgggatttct gaggtcagca 1140
ttgacaaatg gtgacgagac acaaacatta gagtacctca gcaatcaaaa ctaccaaata 1200
ttgaagtttt gtgaagatgc aaagatcaaa atcaaacaat acctgcctca ttacacaaca 1260
caaagagaat ggagggacca ttttggagat aaatattgga ccagatttca gcaaaggaaa 1320
ttagattttg acccaagaca tattttagcc accggccaac gcattttcat gccttctttt 1380
aatcctaata ctgcctcttg gtga 1404

<210> SEQ ID NO 195
<211> LENGTH: 1671
<212> TYPE: DNA
<213> ORGANISM: Nicotiana tabacum

<400> SEQUENCE: 195
atgggaaatc aagttttcct atttgcttgc acaatggctc ttctagcttc ttattcctca 60
ttggtttcag ctgaagttgt taaccattct tttcatgtac caaattcagc aaaaaagatg 120
ttagcgtgtt tagttgaaag atttgtggct gagaatgacg ctgattcaat acctgaacct 180
gaaaaaatcg acgacggcgt tttgaaagac ttggacattg aaggaagcat tgattatgga 240
ctcacggtta ccggtttagc cggtaaagat tttggcggca tgtatgcagt gaagccgtta 300
gccgttatac gtccggccgg tgccgatgac gtcgcgcggg tgattaggca agcgttacac 360
tcaccatcat taacggtagc ggcgaggggt aacggtcatt ccattaacgg ccaagctatg 420
gcccaccatg gactcgttat caatatgaaa tcaatgggcg ataataacag aatcgacgtc 480
agcgtctccg ccatgtacgc cgacgtaggt ggcggagcat tatgggctga tgtcttgaaa 540
cgctgcgttt tgggatatgg cttggctcct acctcgtgga cggattatct tgatttaacg 600
gtcggaggta ctttgtctaa cgccggcgtc agtggccaag ctttccgtta tggaccccaa 660

```
acgtcaaccg taacggaatt ggaagtggtt accggaaacg gagagagaac cgtctgctca    720

aactctcaaa attctgaact cttcttctct gttcttggcg gacttggtca gtttggtatc    780

atcactagag ctcggatttt gcttcaaccc gccccggata tggtaaggtg gataagagtg    840

gtatacagtg aattcgacga gtttactcgt gatgctgagt tactggtaat gagtccggaa    900

tcgttcgatt atgtggaagg atttgtgttt gtgaatagtg atgacccggt aaatgggtgg    960

ccgtcggtgc cattggattc aaatcattca tttgacccga cccatttacc aacaaacact   1020

ggcccggttc tctattgcct tgaagtggcc ctgcattatc acaaccatga ccatccctcc   1080

actgtaaata tgatggtgga gaaattgttt ggacgatcga gatttatcga acacttgagg   1140

tttgagattg acttgaatta tatggatttc ttgttacgag taaaacgcgt agaacaaatg   1200

gctagggata atggtatatg ggatgcacct catccatggc ttaacatgtt cgtttccaag   1260

agagacattg ccgcgttcaa tcgaattgtg ttccaaaaca tcttaaaaga tggtatcaat   1320

ggtcctatgt tgacatatcc tctcatccga agcaagtggg ataatcgatc atcagtggtg   1380

ttaccccaag gtgaaatatt ttacttagtg gctctgcttc ggtttagcca tgcacatcca   1440

aaagagtctg aaataaacga gatggtagca cagaaccaag agatcttgca aacttgcata   1500

aacaatgggt ttgatttcaa gttgtacctt ccgcattaca agtcaacaga ggaatggaag   1560

aagcactttg gggatcaatg gggaagattt gtagagagaa agagccagtt tgatccaaag   1620

gctatccttg cacctggcca aaaaatattt actagaaacc atctactcta a            1671
```

<210> SEQ ID NO 196
<211> LENGTH: 1671
<212> TYPE: DNA
<213> ORGANISM: Nicotiana tabacum

<400> SEQUENCE: 196

```
atggggcatc aacttttcct gtttgcttgt accatggctc ttcttgcttc ttattcctca     60

ttggtttcag ctgaagttgt tggccattct tttcatgtac caatttcagc aaaaaggatg    120

ttagcgtgtt tagttgagag atttgttgct gagaatgaag ctgattcaat acctgaacct    180

gaaaaaattg acgacggcgt tttgaaaaac ttggacattg aaggaagcat tgattatgga    240

ctcacggtaa ccggtttagc cggtaaagat tttggcggca tgtatgcagt gaagccgtta    300

gcggttgtac gtccggccgg tgccgatgac gttgcgcggg tgattaggca agcgttacac    360

tcaccaacat taacggtagc ggcgaggggt aacggtcatt ccattaacgg tcaagctatg    420

gcccatcatg gactcgttat cgacatgaaa tcattgggcg ataataacag aatcgacgtc    480

aacgtctcca ccatgtatgc cgacgtgggt ggcggagcat tatgggctga cgtcttgaaa    540

cgctgcgttt tgggttacgg cttggctcct atctcgtgga cggattatct tgatttaaca    600

gtcggaggta ctctgtctaa cgccggcgtc agtggccaag ctttccgtta tggaccccaa    660

acgtcaactg taacggaatt ggaagtggtt accggcaacg gagagagaac cgtctgctca    720

aactctcaaa attctgaact cttcttctct gttcttgggg gacttggtca gtttggtatc    780

atcactagag ctcgggttat gcttcaaccc gccccggata tggtgaggtg gataagagtg    840

gtatacagtg aattcgacga gtttactcgt gatgcggagt tactggtaat gagtccggaa    900

tcgttcgatt atgtggaagg atttgtgttt gtaaacagtg atgacccggt aaatgggtgg    960

ccgtcggtgc cattggattc aaatcattca tttgacccga cccagttacc cacaaacact   1020

ggcccggttc tctattgcct tgaagtggcc ctgcattatc acaaccatga ccatcccacc   1080
```

-continued

```
actgtaaata tgatggtgga gaaattgtta gcgcgattga ggtttatcga gcacttgagg   1140
tttgaggccg acatgactta catggatttc ttgttacgag taaagcgcgt agaacaaatg   1200
gctagggata atggtatatg ggatgcgcct catccatggc ttaacatgtt cgtttccaag   1260
agagacattg gcacgttcaa tcgaattgtg ttccaaaaca tcttaaaaga tggtatcaat   1320
ggccctatgt tgacatatcc tctcatccgt agcaagtgga ataatcgatc gtcagtggtg   1380
ttacccaaag gtgaaatatt ttacttagtg gctctgcttc ggtttagcca tgcacatcca   1440
aaagagtctg aaataaatga gatggtggca cagaaccaag agatcttgca aacttgcata   1500
aataatggat ttgatttcaa gttgtacctt ccgcattaca aatccacaga ggaatggaag   1560
aagcattttg gagatcaatg gggaagattt gtcgagagaa agagccagtt tgatccaaag   1620
gctgtccttg cgcctggcca aaaaatattt actagaaacc atcaacgcta a            1671
```